United States Patent
Kratz et al.

(10) Patent No.: US 11,384,104 B2
(45) Date of Patent: Jul. 12, 2022

(54) DELIVERY SYSTEMS FOR CONTROLLED DRUG RELEASE

(71) Applicant: CENTURION BIOPHARMA CORPORATION, Los Angeles, CA (US)

(72) Inventors: Felix Kratz, Ehrenkirchen (DE); Khalid Abu Ajaj, Berlin (DE); André Warnecke, Freiburg (DE); Stephan David Koester, Gundelfingen (DE); Friederike I. Nollmann, Freiburg (DE); Simon Waltzer, Freiburg (DE); Olga Fuchs, Herbolzheim (DE); Javier García Fernandez, Freiburg (DE)

(73) Assignee: CENTURION BIOPHARMA CORPORATION, Los Angeles, CA (US)

( * ) Notice: Subject to any disclaimer, the term of this patent is extended or adjusted under 35 U.S.C. 154(b) by 325 days.

(21) Appl. No.: 15/735,885

(22) PCT Filed: Jun. 17, 2016

(86) PCT No.: PCT/US2016/038223
§ 371 (c)(1),
(2) Date: Dec. 12, 2017

(87) PCT Pub. No.: WO2016/205738
PCT Pub. Date: Dec. 22, 2016

(65) Prior Publication Data
US 2019/0002484 A1    Jan. 3, 2019

Related U.S. Application Data

(60) Provisional application No. 62/261,563, filed on Dec. 1, 2015, provisional application No. 62/261,213, filed on Nov. 30, 2015, provisional application No. 62/182,219, filed on Jun. 19, 2015.

(51) Int. Cl.
| | | |
|---|---|---|
| *A61K 47/68* | (2017.01) | |
| *C07H 15/26* | (2006.01) | |
| *C07H 19/06* | (2006.01) | |
| *C07K 5/06* | (2006.01) | |
| *A61K 45/06* | (2006.01) | |
| *C07F 9/6558* | (2006.01) | |
| *C07K 5/072* | (2006.01) | |
| *C07K 5/062* | (2006.01) | |

(52) U.S. Cl.
CPC ...... *C07F 9/65586* (2013.01); *A61K 47/6889* (2017.08); *C07H 15/26* (2013.01); *C07H 19/06* (2013.01); *C07K 5/06052* (2013.01); *C07K 5/06104* (2013.01); *C07K 5/06191* (2013.01); *A61K 45/06* (2013.01)

(58) Field of Classification Search
CPC . C07F 9/65586; A61K 47/6889; A61K 45/06; C07H 15/26; C07H 19/06; C07K 5/06052; C07K 5/06104; C07K 5/06191
See application file for complete search history.

(56) References Cited

U.S. PATENT DOCUMENTS

| | | | |
|---|---|---|---|
| 4,125,704 A | 11/1978 | Henry et al. | |
| 4,699,880 A | 10/1987 | Goldstein | |
| 4,816,397 A | 3/1989 | Boss et al. | |
| 4,816,567 A | 3/1989 | Cabilly et al. | |
| 4,946,778 A | 8/1990 | Ladner et al. | |
| 4,966,999 A | 10/1990 | Coughlin et al. | |
| 5,225,539 A | 7/1993 | Winter | |
| 5,476,786 A | 12/1995 | Huston | |
| 5,514,548 A | 5/1996 | Krebber et al. | |
| 6,884,869 B2 | 4/2005 | Senter | |
| 7,387,771 B1 | 6/2008 | Kratz | |
| 8,703,724 B2 | 4/2014 | Kratz | |
| 2012/0195832 A1 | 8/2012 | Kratz | |
| 2014/0221429 A1* | 8/2014 | Al-Resayes | A61K 31/444 514/332 |

(Continued)

FOREIGN PATENT DOCUMENTS

| | | |
|---|---|---|
| EP | 0 239 400 B1 | 9/1987 |
| EP | 0 125 023 B1 | 6/1991 |

(Continued)

OTHER PUBLICATIONS

Rodrigues et al. (Bioorganic & Medicinal Chemistry (2006), vol. 14, pp. 4110-4117) (Year: 2006).*
Rodrgues et al (Year: 2006).*
Berge, et al., "Pharmaceutical Salts", J. Pharm. Sci. 66(1): 1-19 (1977).
Bird, et al., "Single-Chain Antigen-Einding Proteins", Science 242: 423-426 (1988).

(Continued)

*Primary Examiner* — Jeffrey S Lundgren
*Assistant Examiner* — Ibrahim D Bori
(74) *Attorney, Agent, or Firm* — Haley Guiliano LLP

(57) ABSTRACT

The present invention provides a compound having the structure of Formula (I) or a pharmaceutically acceptable salt, hydrate, solvate, or isomer thereof, for the controlled delivery and release of Agent.

Formula (I)

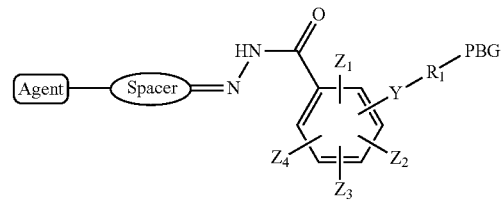

36 Claims, 8 Drawing Sheets

(56) References Cited

U.S. PATENT DOCUMENTS

2020/0385403 A1 12/2020 Kratz
2020/0385421 A1 12/2020 Kratz

FOREIGN PATENT DOCUMENTS

| EP | 0 519 596 A1 | 12/1992 |
|---|---|---|
| EP | 0 120 694 B1 | 7/1993 |
| EP | 0 194 276 B1 | 8/1993 |
| EP | 0 451 216 B1 | 1/1996 |
| EP | 2289558 | 3/2011 |
| WO | WO-86/01533 A1 | 3/1986 |
| WO | WO-93/06213 A1 | 4/1993 |
| WO | WO-01/62726 A2 | 8/2001 |
| WO | WO2002088172 | 11/2002 |
| WO | WO-2005/055939 A2 | 6/2005 |
| WO | WO-2013/124068 A1 | 8/2013 |
| WO | WO2016205378 | 12/2016 |
| WO | WO2019108974 | 6/2019 |
| WO | WO2019108975 | 6/2019 |

OTHER PUBLICATIONS

Chari, et al., "Antibody-Drug Conjugates: An Emerging Concept in Cancer Therapy", Angewandte Reviews 53: 3796-3827 (2014).
Cross, et al., "Rules for the Nomenclature of Organic Chemistry—Section E: Stereochemistry", Pure and Applied Chemistry 45: 11-30 (1976).
Dao, et al., "Design, synthesis, and initial biological evaluation of a steroidal anti-estrogen-doxorubicin bioconjugate for targeting estrogen receptor-positive breast cancer cells", Bioconjugate Chemistry 23: 785-795 (2012).
Daugherty, et al., "Polymerase chain reaction facilitates the cloning, CDR-grafting, and rapid expression of a murine monoclonal antibody directed against the CD18 component of leukocyte integrins", Nucleic Acids Research 19(9): 2471-2476 (1991).
Kamman, et al., "Rapid insertional mutagenesis of DNA by polymerase chain reaction (PCR)", Nucleic Acids Research 17(13): 5404 (1989).
Kratz, et al., "Preparation, characterization and in vitro efficacy of albumin conjugates of doxorubicin", Biological & Pharmaceutical Bulletin 21(1): 56-61 (1998).
Kratz, et al., "Prodrug strategies in anticancer chemotherapy", ChemMedChem 3(1): 20-53 (2008).
Kratz, et al., "Transferrin conjugates of doxorubicin: Synthesis, characterization, cellular uptake, and in vitro efficacy", J. Pharm. Sci. 87(3): 338-346 (1998).
Lau, et al., "Novel doxorubincon-monoclonal anti-carcinoembryonic antigen antibody immunoconjugate activity in vitro", Bioorganic & Medicinal Chemistry 3(10): 1305-1312 (1995).
Lewis, et al., "Immunoglobulin complementarity-determining region grafting by recombinant polymerase chain reaction to generate humanized monoclonal antibodies", Gene 101: 297-302 (1991).
Newman, et al., ""Primatization" of Recombinant Antibodies for Immunotherapy of Human Diseases: A Macaque/Human Chimeric Antibody Against Human CD4", Biotechnology 10: 1455-1460 (1992).
Panowski, et al., "Site-specific antibody drug conjugates for cancer therapy", mAbs 6(1): 34-45 (2014).
Ponta, et al., "Tumor-preferential sustained drug release enhances antitumor activity of block copolymer micelles", J. Drug Targeting 22(7): 619-628 (2014).
Rea, et al., "Site-specifically radioiodinated antibody for targeting tumors", Cancer Research (Suppl.) 50: 857s-861s (1990).
Rodrigues, et al., "Correlation of the acid-sensitivity of polyethylene glycol daunorubicin conjugates with their invitro antiproliferative activity", Bioorganic & Medicinal Chemistry 14(12): 4110-4117 (2006).
Sato, et al., "Reshaping a Human Antibody to Inhibit the Interleukin 6-dependent Tumor Cell Growth", Cancer Research 53: 851-856 (1993).
Chen, et al., "Tubulin Inhibitor-Based Antibody-Drug Conjugates for Cancer Therapy," Molecules, 22(8):1281-1309 (2017).
Nollmann, et al., "Abstract 1657: Structure-activity relationship studies and biological evaluation of novel maytansinoids, a class of highly selective tubulin inhibitors," Cancer Research, 78(13) (2018) (4 pages).
Nollmann, et al., "Abstract 2661: Novel albumin-binding maytansinoids inducing long-term partial and complete tumor regressions in several human cancer xenograft models in nude mice," Cancer Research, 78(13) (2018) (4pages).
Temming, et al., "Evaluation of RGD-targeted albumin carriers for specific delivery of auristatin E to tumor blood vessels," Bioconjugate Chemistry, 17(6):1385-1394 (2006).
E.A. Perez et al., "Phase II trial of dolastatin-10 in patients with advanced breast cancer," Invest. New Drugs, 23:257-261 (2005).
F. Kratz, "Albumin as a drug carrier: Design of prodrugs, drug conjugates and nanoparticles," J. Control. Release, 132:171-183 (2008).
F. Kratz, U. Beyer, "Serum Proteins as Drug Carriers of Anticancer Agents: A Review," Drug Delivery, 5:281-299 (1998).
M. von Mehren et al., "Phase II trial of dolastatin-10, a novel anti-tubulin agent, in metastatic soft tissue sarcomas," Sarcoma, 8:107-111 (2004).
Pyataev, et al. "Targeted Delivery of Antitumor Chemotherapeutics: Advanced Technologies and Development Prospects," Povolzhskiy Onkologicheskiy Vestnik, 2012, No. 2, pp. 60-71. (English Abstract Only).
R.S. Marks et al., "A Phase II Study of the Dolastatin 15 Analogue LU103793 in the Treatment of Advanced Non-Small-Cell Lung Cancer," Am. J. Clin. Oncol., 26:336-337 (2003).
U.S. Appl. No. 16/768,418, filed May 29, 2020, Felix Kratz.
U.S. Appl. No. 16/768,436, filed May 29, 2020, Felix Kratz.

* cited by examiner

DELIVERY SYSTEMS FOR CONTROLLED DRUG RELEASE

RELATED APPLICATION

This application is a national stage application under 35 U.S.C. § 371 of International Application No. PCT/US2016/038223, filed Jun. 17, 2016, which claims the benefit of and priority from U.S. Provisional Patent Applications 62/182,219, filed Jun. 19, 2015, 62/261,213, filed Nov. 30, 2015, and 62/261,563, filed Dec. 1, 2015. The contents and disclosures of each of the foregoing applications are incorporated herein by reference in their entirety.

BACKGROUND OF THE INVENTION

Many drugs, particularly cancer therapeutics, have a narrow therapeutic window, wherein their side effects limit their beneficial effects. Systemic administration of such drugs often results in a limited therapeutic effect because the dose required to elicit a more robust effect results in unacceptable side effects to the patient. This is particularly critical in the case of those drugs which possess a high cytotoxic potential, such as cytostatic agents, virostatic agents or immunosuppressive agents. Numerous research endeavors have looked into delivering a particular drug at a particular site of action. Often, this approach results in a higher concentration of the drug at the site of action than would be achieved by systemic administration, while limiting the side effects.

Drug delivery in oncology is of particular interest owing to the narrow therapeutic window of agents used in such indication. Numerous research efforts have concentrated on conjugating anticancer drugs with a wide spectrum of low- and high-molecular-weight carriers including sugars, growth factors, vitamins, peptides, antibodies, polysaccharides, lectins, serum proteins, and synthetic polymers. In most such drug delivery systems, the drug is bound to the carrier through a spacer that incorporates a pre-determined breaking point that allows the bound drug to be released at the cellular target site. (Kratz et al., ChemMedChem, 3:20-53 (2008)). Conjugates are known in which cytostatic agents are bound to serum proteins, predominantly to specific carrier molecules such as human serum albumin and human serum transferin, and then administered. In some instances, conjugates comprise a therapeutically effective substance, and, upon administration, result in the transport of the therapeutically effective substance to the target site where it is released (U.S. Pat. No. 7,387,771). In other instances, conjugates comprising a therapeutically effective substance, a spacer molecule and a protein-binding molecule, bind covalently to circulating serum albumin upon administration, which result in the transport of the therapeutically effective substance to the target site where it is released (U.S. Pat. No. 7,387,771). In yet other instances, antibody drug conjugates (ADC) can transport the drug to the target site for local release (Kratz et al., ChemMedChem, 3:20-53 (2008); Panowski et al., mAbs, 6, 34-45 (2014); Chari et al., Angewandte Chem. Int. Ed., 53, 3796-3827 (2014)).

However, when designing drug delivery systems, the appropriate balance should be struck between preserving the targeting properties of the drug carrier while enabling a controlled release of the drug. The drug delivery construct should have sufficient stability in the bloodstream, and yet allow effective release of the drug at the tumor site by enzymatic cleavage, reduction or, in a pH-dependent manner (Kratz et al., ChemMedChem, 3:20-53 (2008)). For example, Gemcitabine (Gemzar®) is an anticancer nucleoside chemotherapeutic agents that is widely used to treat solid tumors. Unfortunately, at its recommended dose of ~1000 mg/m$^2$ approximately 90% are deactivated by cytidine deaminase to the inactive uridine metabolite and excreted in the urine. A further disadvantage resulting in chemo-resistance is the low expression level of the human equilibrative nucleoside transporter 1 (hENT1) on the cell surface of cancer cells thus preventing substantial uptake of gemcitabine.

Therefore, there is still a need for efficient drug delivery and release systems in order to achieve more effective and controlled delivery and release of the drug.

SUMMARY OF THE INVENTION

The present invention provides delivery systems for the effective and controlled delivery and release of therapeutic agents.

The present invention relates to a drug delivery system that comprises a hydrazone moiety that is cleaved in an acidic environment in a controlled manner, to provide controlled release of therapeutic agents. The present invention relates to a drug delivery system that comprises an amide bond, a carbamate bond, and/or an ester bond that is cleaved enzymatically, e.g., by esterases or amidases and/or hydrolytically, to provide controlled release of therapeutic agents. In some embodiments, the present invention relates to a drug delivery system that comprises an amide bond that is cleaved enzymatically, e.g., by esterases or amidases and/or hydrolytically, to provide controlled release of therapeutic agents. In other embodiments, the present invention relates to a drug delivery system that comprises a carbamate bond that is cleaved enzymatically and/or hydrolytically. In yet other embodiments, the present invention relates to a drug delivery system that comprises an ester bond that is cleaved enzymatically and/or hydrolytically.

The present invention relates to a drug delivery system that comprises (i) a hydrazone moiety that is cleaved in an acidic environment in a controlled manner, and optionally (ii) an amide bond, a carbamate bond, and/or an ester bond that is cleaved enzymatically, e.g., by esterases or amidases and/or hydrolytically, to provide controlled release of therapeutic agents. In some embodiments, the present invention relates to a drug delivery system that comprises a (i) hydrazone moiety that is cleaved in an acidic environment in a controlled manner, and optionally (ii) an amide bond that is cleaved enzymatically, e.g., by esterases or amidases and/or hydrolytically, to provide controlled release of therapeutic agents. In some embodiments, the present invention relates to a drug delivery system that comprises a (i) hydrazone moiety that is cleaved in an acidic environment in a controlled manner, and optionally (ii) a carbamate bond that is cleaved enzymatically and/or hydrolytically, to provide controlled release of therapeutic agents. In some embodiments, the present invention relates to a drug delivery system that comprises a (i) hydrazone moiety that is cleaved in an acidic environment in a controlled manner, and optionally (ii) an ester bond that is cleaved enzymatically and/or hydrolytically, to provide controlled release of therapeutic agents. In some embodiments, the present invention relates to a drug delivery system that comprises (i) a hydrazone moiety that is cleaved in an acidic environment in a controlled manner, and optionally (ii) an amide bond that is selectively cleaved by carboxylesterase 1 and/or 2, to provide controlled release of therapeutic agents. In some embodiments, the present invention relates to a drug delivery system that comprises a (i) hydrazone moiety that is cleaved in an acidic environment in a controlled manner, and (ii) an amide bond that is selectively cleaved by carboxylesterase 2, to provide controlled release of therapeutic agents.

The present invention provides a compound having the structure represented by Formula (I):

Formula (I)

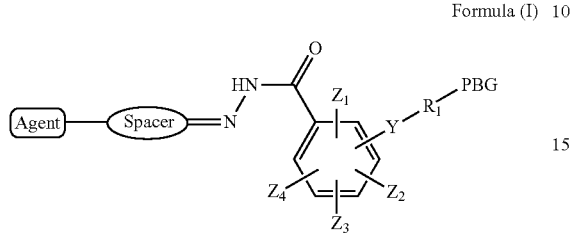

or a pharmaceutically acceptable salt, hydrate, solvate, or isomer thereof;
wherein:
Agent is selected from the group consisting of a cytostatic agent, a cytotoxic agent, a cytokine, an immunosuppressive agent, an antirheumatic, an antiphlogistic, an antibiotic, an analgesic, a virostatic agent, an anti-inflammatory agent, an antimicotic agent, a transcription factor inhibitor, a cell cycle modulator, an MDR modulator, a proteasome or protease inhibitor, an apoptosis modulator, an enzyme inhibitor, a signal transduction inhibitor, a protease inhibitor, an angiogenesis inhibitor, a hormone or hormone derivative, an antibody or a fragment thereof, a therapeutically or diagnostically active peptide, a radioactive substance, a light emitting substance, a light absorbing substance, and a derivative of any of the foregoing;
Spacer is absent,

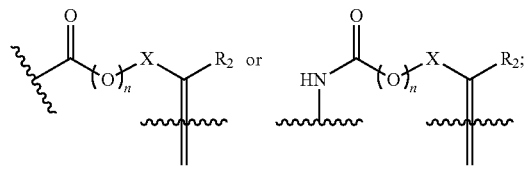

n is 0 or 1;
X is selected from the group consisting of: optionally substituted $C_1$-$C_{18}$ alkyl wherein optionally up to six carbon atoms in said $C_1$-$C_{18}$ alkyl are each independently replaced with —$OCH_2CH_2$—; optionally substituted $C_1$-$C_{18}$ alkyl-NH—C(O)—$R_5$— wherein optionally up to six carbon atoms in said $C_1$-$C_{18}$ alkyl are each independently replaced with —$OCH_2CH_2$—; optionally substituted $C_1$-$C_{18}$ alkyl-C(O)—NH—$R_5$— wherein optionally up to six carbon atoms in said $C_1$-$C_{18}$ alkyl are each independently replaced with —$OCH_2CH_2$—; optionally substituted aryl; optionally substituted heteroaryl; and optionally substituted cycloalkyl;
$R_5$ is selected from the group consisting of an optionally substituted aryl, optionally substituted heteroaryl, and optionally substituted cycloalkyl;
Y is absent or selected from the group consisting of optionally substituted $C_1$-$C_6$ alkyl, —NH—C(O)—, —C(O)—NH—, —C(O)—O—, and —O—C(O)—;
$R_1$ is absent or selected from the group consisting of optionally substituted $C_1$-$C_{18}$ alkyl wherein optionally up to six carbon atoms in said $C_1$-$C_{18}$ alkyl are each independently replaced with —$OCH_2CH_2$—; optionally substituted $C_1$-$C_{18}$ alkyl-NH—C(O)$R_5$— wherein optionally up to six carbon atoms in said $C_1$-$C_{18}$ alkyl are each independently replaced with —$OCH_2CH_2$—; and optionally substituted $C_1$-$C_{18}$ alkyl-C(O)—NH—$R_5$— wherein optionally up to six carbon atoms in said $C_1$-$C_{18}$ alkyl are each independently replaced with —$OCH_2CH_2$—,
or $R_1$ is a naturally or non-naturally occurring amino acid, or $R_1$ has the following formula:

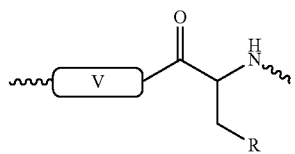

wherein:
$\boxed{V}$ is absent, or is selected from the group consisting of:

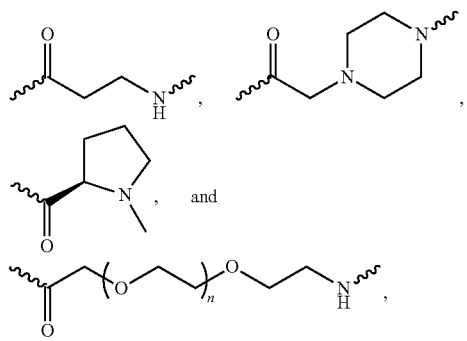

R is: $\sim$ $OPO_3M_1$ wherein $M_1$=$Mg^{2+}$, 2 $Na^+$, $2K^+$, $2H^+$, $2NH_4^+$
or
$\sim$ $SO_3M_2$ wherein $M_2$=$Na^+$, $K^+$, $H^+$, $NH_4^+$
$R_2$ is selected from the group consisting of optionally substituted $C_1$-$C_{12}$ alkyl, optionally substituted aryl, and optionally substituted heteroaryl;
$Z_1$, $Z_2$, $Z_3$ and $Z_4$ are each independently selected from the group consisting of —H, an electron-withdrawing group, and a water-soluble group;
PBG is a protein-binding group selected from the group consisting of an optionally substituted maleimide group, an optionally substituted haloacetamide group, an optionally substituted haloacetate group, an optionally substituted pyridylthio group, an optionally substituted isothiocyanate group, an optionally substituted vinylcarbonyl group, an optionally substituted aziridine group, an optionally substituted disulfide group, an optionally substituted acetylene group, an optionally substituted N-hydroxysuccinimide ester group, an antibody or fragment thereof, and a derivatized antibody of derivatized fragment thereof;
wherein when Spacer is absent, Agent is linked to the nitrogen adjacent to Spacer by a double bond; and
wherein at least one of $Z_1$, $Z_2$, $Z_3$ and $Z_4$ is an electron-withdrawing group.

In some embodiments, PBG is a protein-binding group selected from the group consisting of an optionally substituted maleimide group, an optionally substituted haloacetamide group, an optionally substituted haloacetate group, an optionally substituted pyridylthio group, an optionally substituted isothiocyanate group, an optionally substituted vinylcarbonyl group, an optionally substituted aziridine group, an optionally substituted disulfide group, an optionally substituted acetylene group, and an optionally substituted N-hydroxysuccinimide ester group.

In some embodiments, the PBG is associated with an antibody or fragment thereof. In some embodiments, the PBG is covalently bound to an antibody or fragment thereof. In some embodiments, the PBG is associated with albumin. In other embodiments, the PBG is covalently bound to endogenous or exogeneous albumin. In other embodiments, the PGB is covalently bound to the cysteine-34 of endogenous or exogenous albumin.

The present invention provides a compound having the structure represented by Formula (I):

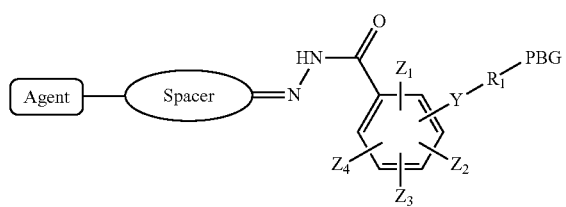

Formula (I)

or a pharmaceutically acceptable salt, hydrate, solvate, or isomer thereof; wherein Agent is selected from the group consisting of a cytostatic agent, a cytotoxic agent, a cytokine, an immunosuppressive agent, an antirheumatic, an antiphlogistic, an antibiotic, an analgesic, a virostatic agent, an anti-inflammatory agent, an antimicotic agent, a transcription factor inhibitor, a cell cycle modulator, an MDR modulator, a proteasome or protease inhibitor, an apoptosis modulator, an enzyme inhibitor, a signal transduction inhibitor, a protease inhibitor, an angiogenesis inhibitor, a hormone or hormone derivative, an antibody or a fragment thereof, a therapeutically or diagnostically active peptide, a radioactive substance, a light emitting substance, a light absorbing substance, and a derivative of any of the foregoing;

Spacer is absent,

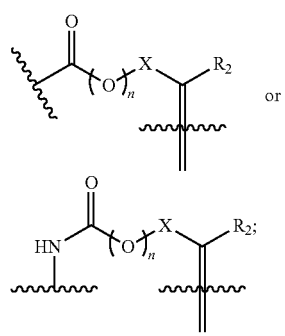

n is 0 or 1;

X is selected from the group consisting of optionally substituted $C_1$-$C_{18}$ alkyl wherein optionally up to six carbon atoms in said $C_1$-$C_{18}$ alkyl are each independently replaced with —OCH$_2$CH$_2$—; optionally substituted $C_1$-$C_{18}$ alkyl-NH—C(O)—$R_5$— wherein optionally up to six carbon atoms in said $C_1$-$C_{18}$ alkyl are each independently replaced with —OCH$_2$CH$_2$—, optionally substituted $C_1$-$C_{18}$ alkyl-C(O)—NH—$R_5$— wherein optionally up to six carbon atoms in said $C_1$-$C_{18}$ alkyl are each independently replaced with —OCH$_2$CH$_2$—; optionally substituted aryl; optionally substituted heteroaryl; and optionally substituted cycloalkyl;

$R_5$ is selected from the group consisting of from an optionally substituted aryl, optionally substituted heteroaryl, and optionally substituted cycloalkyl;

Y is absent or selected from the group consisting of optionally substituted $C_1$-$C_6$ alkyl, —NH—C(O)—, —C(O)—NH—, —C(O)—O—, and —O—C(O)—;

$R_1$ is absent or selected from the group consisting of optionally substituted $C_1$-$C_{18}$ alkyl wherein optionally up to six carbon atoms in said $C_1$-$C_{18}$ alkyl are each independently replaced with —OCH$_2$CH$_2$—; optionally substituted $C_1$-$C_{18}$ alkyl-NH—C(O)$R_5$— wherein optionally up to six carbon atoms in said $C_1$-$C_{18}$ alkyl are each independently replaced with —OCH$_2$CH$_2$—, and optionally substituted $C_1$-$C_{18}$ alkyl-C(O)—NH—$R_5$— wherein optionally up to six carbon atoms in said $C_1$-$C_{18}$ alkyl are each independently replaced with —OCH$_2$CH$_2$—;

$R_2$ is selected from the group consisting of —H, optionally substituted $C_1$-$C_{12}$ alkyl, optionally substituted aryl, and optionally substituted heteroaryl;

$Z_1$, $Z_2$, $Z_3$ and $Z_4$ are each independently selected from the group consisting of —H or an electron-withdrawing group;

PBG is a protein-binding group selected from the group consisting of an optionally substituted maleimide group, an optionally substituted haloacetamide group, an optionally substituted haloacetate group, an optionally substituted pyridylthio group, an optionally substituted isothiocyanate group, an optionally substituted vinylcarbonyl group, an optionally substituted aziridine group, an optionally substituted disulfide group, an optionally substituted acetylene group, an optionally substituted N-hydroxysuccinimide ester group, and an antibody or fragment thereof;

wherein when Spacer is absent, Agent is linked to the nitrogen adjacent to Spacer by a double bond; and wherein at least one of $Z_1$, $Z_2$, $Z_3$ and $Z_4$ is an electron-withdrawing group.

In some embodiments, PBG is a protein-binding group selected from the group consisting of an optionally substituted maleimide group, an optionally substituted haloacetamide group, an optionally substituted haloacetate group, an optionally substituted pyridylthio group, an optionally substituted isothiocyanate group, an optionally substituted vinylcarbonyl group, an optionally substituted aziridine group, an optionally substituted disulfide group, an optionally substituted acetylene group, and an optionally substituted N-hydroxysuccinimide ester group.

In some embodiments, the PBG is associated with an antibody or fragment thereof. In some embodiments, the PBG is covalently bound to an antibody or fragment thereof. In some embodiments, the PBG is associated with albumin. In other embodiments, the PBG is covalently bound to endogenous or exogenous albumin. In other embodiments, the PGB is covalently bound to the cysteine-34 of endogenous or exogenous albumin.

In certain embodiments, the invention provides a compound represented by Formula (II):

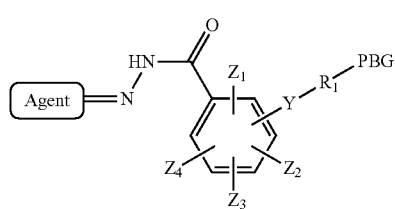

Formula (II)

or a pharmaceutically acceptable salt, hydrate, solvate, or isomer thereof;

wherein Agent, PBG, Y, $R_1$, $Z_1$, $Z_2$, $Z_3$ and $Z_4$ are as defined for a compound of Formula (I).

In certain embodiments, the invention provides a compound having the structure represented by Formula (III):

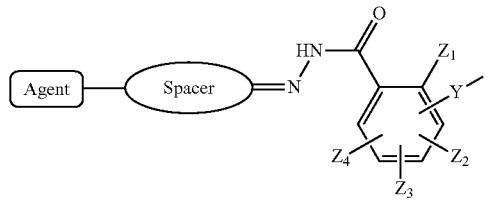

Formula (III)

or a pharmaceutically acceptable salt, hydrate, solvate, or isomer thereof;

wherein Agent, Spacer, PBG, Y, $R_1$, $Z_2$, $Z_3$ and $Z_4$ are as defined for a compound of Formula (I); and wherein $Z_1$ is an electron withdrawing group.

In certain embodiments, the invention provides a compound having the structure represented by Formula (IV):

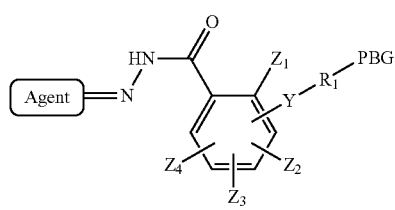

Formula (IV)

or a pharmaceutically acceptable salt, hydrate, solvate, or isomer thereof;

wherein Agent, PBG, Y, $R_1$, $Z_2$, $Z_3$ and $Z_4$ are as defined for a compound of Formula (I); and wherein $Z_1$ is an electron withdrawing group.

In certain embodiments, the invention provides a compound having the structure represented by Formula (V):

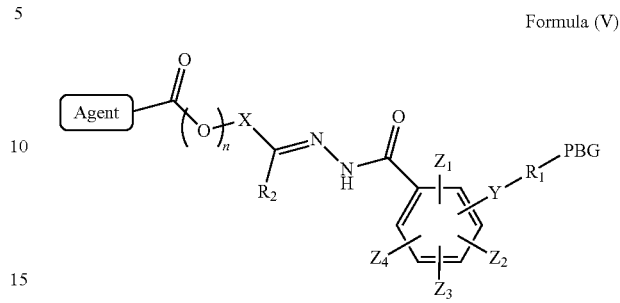

Formula (V)

or a pharmaceutically acceptable salt, hydrate, solvate, or isomer thereof;

wherein Agent, PBG, n, Y, $R_1$, $R_2$, $Z_1$, $Z_2$, $Z_3$ and $Z_4$ are as defined for a compound of Formula (I).

In certain embodiments, the invention provides a compound having the structure represented by Formula (VI):

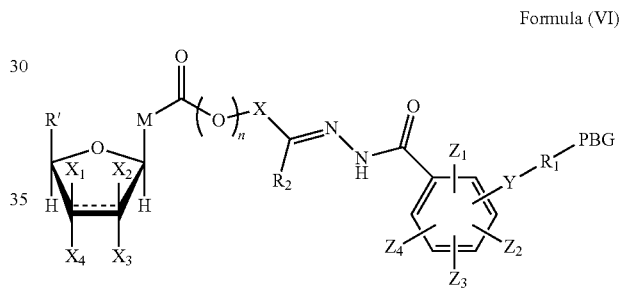

Formula (VI)

or a pharmaceutically acceptable salt, hydrate, solvate, or isomer thereof;

wherein:

M is a pyrimidine or purine group that contains at least one primary or secondary amino group and optionally contains one or more substituents selected from halogen.

$X_1$ and $X_2$ are each independently selected from the group consisting of —H, —OH, $C_1$-$C_6$ alkyl, halogen, and —$N_3$.

$X_3$ and $X_4$ are each independently, as valence permits, absent or selected from the group consisting of —H, —OH, $C_1$-$C_6$ alkyl, halogen, and —$N_3$.

R' is —$R_3$ or —$CH_2R_3$;

wherein each occurrence of $R_3$ is independently selected from the group consisting of —OH, —$CH_3$, —OP(O)(OH)$_2$, —P(O)(OH)OP(O)(OH)$_2$, —OP(O)(OH)OP(O)(OH)OP(O)(OH)$_2$, —OP(O)(OH)(NH$_2$), an amino acid, an acyl group, and a pharmaceutically acceptable salt thereof, wherein the salt contains an alkali metal ion, an alkaline metal ion, an ammonium or an alkyl substituted ammonium ion; and wherein X, n, $Z_1$, $Z_2$, $Z_3$, $Z_4$, Y, $R_1$, $R_2$ and PBG are as defined for a compound of Formula (V).

In certain embodiments, the invention provides a compound having the structure represented by Formula (VI):

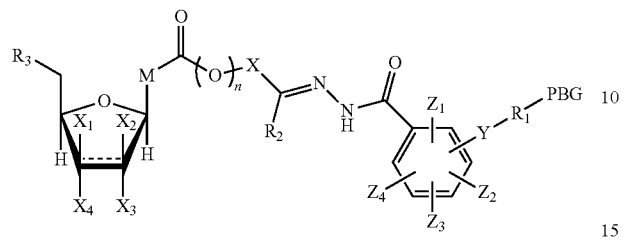

Formula (VI)

or a pharmaceutically acceptable salt, hydrate, solvate, or isomer thereof; wherein M is a pyrimidine or purine group that contains at least one primary or secondary amino group.

$X_1$ and $X_2$ are each independently selected from the group consisting of —H, —OH, $C_1$-$C_6$ alkyl, halogen, and —$N_3$.

$X_3$ and $X_4$ are each independently, as valence permits, absent or selected from the group consisting of —H, —OH, $C_1$-$C_6$ alkyl, halogen, and —$N_3$.

$R_3$ is selected from —OH, —OP(O)(OH)$_2$, —P(O)(OH) OP(O)(OH)$_2$, —OP(O)(OH)OP(O)(OH)OP(O)(OH)$_2$, —OP(O)(OH)(NH$_2$), an amino acid, an acyl group, and a pharmaceutically acceptable salt thereof, wherein the salt contains an alkali metal ion, an alkaline metal ion, an ammonium or an alkyl substituted ammonium ion; and wherein X, n, $Z_1$, $Z_2$, $Z_3$, $Z_4$, Y, $R_1$, $R_2$ and PBG are as defined for a compound of Formula (V).

In certain embodiments, the invention provides a compound having the structure represented by Formula (VII):

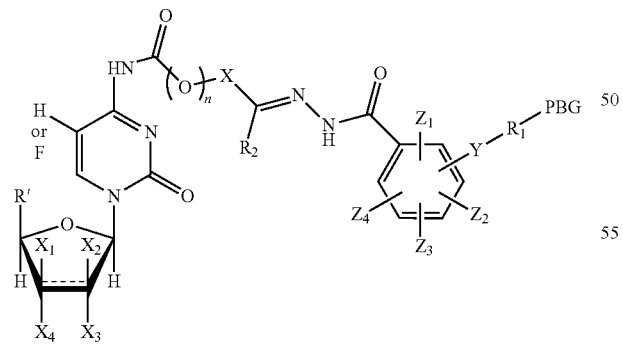

Formula (VII)

or a pharmaceutically acceptable salt, hydrate, solvate, or isomer thereof;

wherein R' is —$R_3$ or —CH$_2$$R_3$; and X, $X_1$, $X_2$, $X_3$, $X_4$, n, Y, $R_1$, $R_2$, $R_3$, $Z_1$, $Z_2$, $Z_3$, $Z_4$ and PBG are as defined for a compound of Formula (VI).

In certain embodiments, the invention provides a compound having the structure represented by Formula (VII):

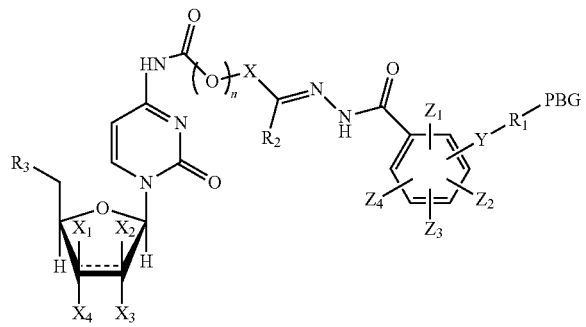

Formula (VII)

or a pharmaceutically acceptable salt, hydrate, solvate, or isomer thereof;

wherein X, $X_1$, $X_2$, $X_3$, $X_4$, n, Y, $R_1$, $R_2$, $R_3$, $Z_1$, $Z_2$, $Z_3$, $Z_4$ and PBG are as defined for a compound of Formula (V).

In certain embodiments, the invention provides a compound having a structure represented by Formula (VIII):

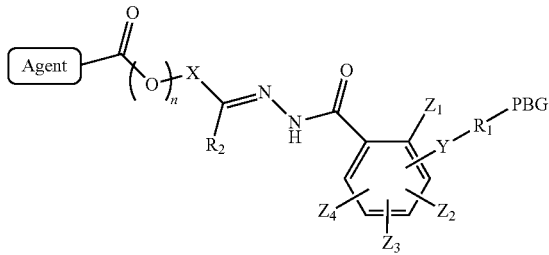

Formula (VIII)

or pharmaceutically acceptable salt, hydrate, solvate, or isomer thereof; wherein $Z_1$ is an electron withdrawing group; and wherein Agent, X, n, $R_2$, PBG, Y, $R_1$, $Z_2$, $Z_3$ and $Z_4$ are as defined for a compound of Formula (V).

In certain embodiments, the invention provides a compound having the structure represented by Formula (IX):

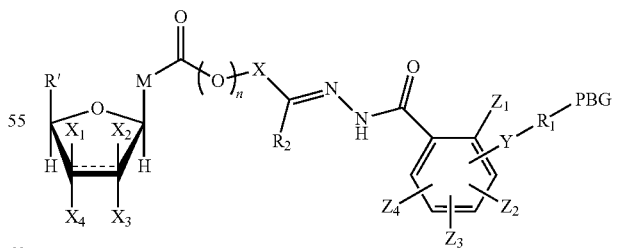

Formula (IX)

or a pharmaceutically acceptable salt, hydrate, solvate, or isomer thereof;

wherein:

M is a pyrimidine or purine group that contains at least one primary or secondary amino group and optionally contains one or more substituents selected from halogen;

$X_1$ and $X_2$ are each independently selected from the group consisting of —H, —OH, $C_1$-$C_6$ alkyl, halogen, and —$N_3$;

$X_3$ and $X_4$ are each independently, as valence permits, absent or selected from the group consisting of —H, —OH, $C_1$-$C_6$ alkyl, halogen, and —$N_3$;

R' is —$R_3$ or —$CH_2R_3$;

wherein each occurence of $R_3$ is independently selected from the group consisting of —OH, —$CH_3$, —OP(O)(OH)$_2$, —P(O)(OH)OP(O)(OH)$_2$, —OP(O)(OH)OP(O)(OH)OP(O)(OH)$_2$, —OP(O)(OH)(NH$_2$), an amino acid, an acyl group, and a pharmaceutically acceptable salt thereof, wherein the salt contains an alkali metal ion, an alkaline metal ion, an ammonium or an alkyl substituted ammonium ion; and wherein X, n, Y, $Z_1$, $Z_2$, $Z_3$, $Z_4$, $R_1$, $R_2$ and PBG are as defined for a compound of Formula (VIII).

In certain embodiments, the invention provides a compound having the structure represented by Formula (IX):

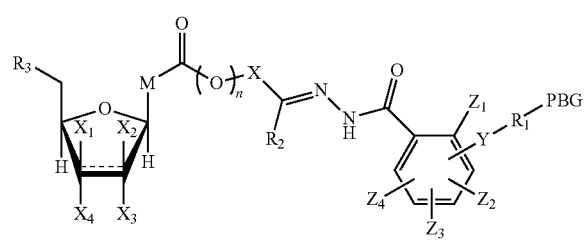

Formula (IX)

or a pharmaceutically acceptable salt, hydrate, solvate, or isomer thereof; wherein M is a pyrimidine or purine group that contains at least one primary or secondary amino group;

$X_1$ and $X_2$ are each independently selected from the group consisting of —H, —OH, $C_1$-$C_6$ alkyl, halogen, and —$N_3$;

$X_3$ and $X_4$ are each independently, as valence permits, absent or selected from the group consisting of —H, —OH, $C_1$-$C_6$ alkyl, halogen, and —$N_3$;

$R_3$ is selected from —OH, —OP(O)(OH)$_2$, —P(O)(OH)OP(O)(OH)$_2$, —OP(O)(OH)OP(O)(OH)OP(O)(OH)$_2$, —OP(O)(OH)(NH$_2$), an amino acid, an acyl group, and a pharmaceutically acceptable salt thereof, wherein the salt contains an alkali metal ion, an alkaline metal ion, an ammonium or an alkyl substituted ammonium ion; and wherein X, n, Y, $Z_1$, $Z_2$, $Z_3$, $Z_4$, $R_1$, $R_2$ and PBG are as defined for a compound of Formula (VIII).

In some embodiments, $X_1$, $X_2$, $X_3$, and $X_4$ are each independently selected from the group consisting of —H, —OH, —$CH_3$, —F, —Cl, —Br, —I, and —$N_3$.

In certain embodiments, the invention provides a compound having the structure represented by Formula (X):

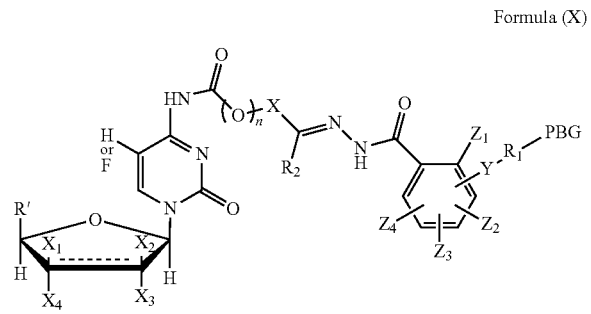

Formula (X)

or a pharmaceutically acceptable salt, hydrate, solvate, or isomer thereof;

wherein R' is —$R_3$ or —$CH_2R_3$; and $X_1$, $X_2$, $X_3$, $X_4$, $R_3$, X, n, Y, $Z_1$, $Z_2$, $Z_3$, $Z_4$, $R_1$ and $R_2$ are as defined for a compound of Formula (IX).

In certain embodiments, the invention provides a compound having the structure represented by Formula (X):

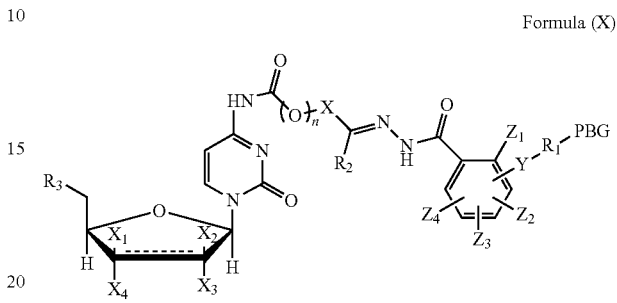

Formula (X)

or a pharmaceutically acceptable salt, hydrate, solvate, or isomer thereof;

wherein $X_1$, $X_2$, $X_3$, $X_4$, $R_3$, X, n, Y, $Z_1$, $Z_2$, $Z_3$, $Z_4$, $R_1$ and $R_2$ are as defined for a compound of Formula (IX).

In some embodiments, Agent is selected from the group consisting of N-nitrosoureas; doxorubicin, 2-pyrrolpyrrolinoanthracycline, morpholinoanthracycline, diacetatoxyalkylanthracycline, daunorubicin, epirubicin, idarubicin, nemorubicin, PNU-159682, mitoxantrone; ametantrone; chlorambucil, bendamustine, melphalan, oxazaphosphorines; 5-fluorouracil, 5'-deoxy-5-fluorocytidine, 2'-deoxy-5-fluoridine, cytarabine, cladribine, fludarabine, pentostatine, gemcitabine, 4-amino-1-(((2S,3R,4S,5R)-3,4-dihydroxy-5-methyltetrahydrofuran-2-yl)methyl)-5-fluoropyrimidin-2 (1H)-one, thioguanine; methotrexate, raltitrexed, pemetrexed, plevitrexed; paclitaxel, docetaxel; topotecan, irinotecan, SN-38, 10-hydroxycamptothecin, GG211, lurtotecan, 9-aminocamptothecin, camptothecin, 7-formylcamptothecin, 7-acetylcamptothecin, 9-formylcamptothecin, 9-acetylcamptothecin, 9-formyl-10-hydroxycamptothecin, 10-formylcamptothecin, 10-acetylcamptothecin, 7-butyl-10-aminocamptothecin, 7-butyl-9-amino-10,11-methylenedioxocamptothecin; vinblastine, vincristine, vindesine, vinorelbine; calicheamicins; maytansine, maytansinol; auristatin (including but not limited to auristatin D, auristatin E, auristatin F, monomethyl auristatin D, monomethyl auristatin E, monomethyl auristatin F, monomethyl auristatin F methylester, auristatin PYE auristatin PHE, the related natural product dolastatin 10, and derivatives thereof); amatoxins (including but not limited to α-amanitin, β-amanitin, γ-amanitin, ε-amanitin, amanin, amaninamide, amanullin, and amanullinic acid and derivatives thereof); duocarmycin A, duocarmycin B1, duocarmycin B2, duocarmycin C, duocarmycin SA, CC1065, adozelesin, bizelesin, carzelesin; eribulin; trabectedin; pyrrolobenzodiazepine, anthramycin, tomaymycin, sibiromycin, DC-81, DSB-120; epothilones; bleomycin; dactinomycin; plicamycin, miromycin C, and cis-configured platinum(II) complexes; or a derivative of any of the foregoing.

In some embodiments, Agent is selected from the group consisting of N-nitrosoureas;

doxorubicin, 2-pyrrolpyrrolinoanthracycline, morpholinoanthracycline, diacetatoxyalkylanthracycline, daunorubicin, epirubicin, idarubicin, nemorubicin, PNU-159682, mitoxantrone; ametantrone; chlorambucil, bendamustine, melphalan, oxazaphosphorines; 5-fluorouracil, 2'-deoxy-5-fluoridine, cytarabine, cladribine, fludarabine, pentostatine, gemcitabine, 4-amino-1-(((2S,3R,4S,5R)-3,4-dihydroxy-5-methyltetrahydrofuran-2-yl)methyl)-5-fluoro-pyrimidin-2(1H)-one, thioguanine; methotrexate, raltitrexed, pemetrexed, plevitrexed; paclitaxel, docetaxel; topotecan, irinotecan, SN-38, 10-hydroxycamptothecin, GG211, lurtotecan, 9-aminocamptothecin, camptothecin, 7-formylcamptothecin, 9-formylcamptothecin, 9-formyl-10-hydroxycamptothecin, 7-butyl-10-aminocamptothecin, 7-butyl-9-amino-10,11-methylenedioxocamptothecin; vinblastine, vincristine, vindesine, vinorelbine; calicheamicins; maytansinoids; auristatins; epothilones; bleomycin, dactinomycin, plicamycin, miromycin C, and cis-configured platinum(II) complexes; or a derivative of any of the foregoing.

In some embodiments, $Z_1$, $Z_2$, $Z_3$ and $Z_4$ are each independently selected from the group consisting of —H, halogen, —C(O)OH, —C(O)O—$C_1$-$C_6$ alkyl, —$NO_2$, haloalkyl, —S(O)$_2$—$C_1$-$C_6$ alkyl, and —CN. In some embodiments, $Z_1$, $Z_2$, $Z_3$ and $Z_4$ are each independently selected from the group consisting of —H, —Cl, —Br, —I, —F, —C(O)OH, —$NO_2$, —$CF_3$, and —CN. In some embodiments, $Z_1$, $Z_2$, $Z_3$ and $Z_4$ are each independently selected from the group consisting of —H, —Cl, —F, —$NO_2$, and —$CF_3$. In some embodiments, $Z_1$, $Z_2$, $Z_3$ and $Z_4$ are each independently selected from the group consisting of —OP(O)(OH)$_2$, —P(O)(OH)OP(O)(OH)$_2$, —OP(O)(OH)OP(O)(OH)OP(O)(OH)$_2$, —OP(O)(OH)(NH$_2$), —P(O)(OH)$_2$, —SO$_3$H, and a pharmaceutically acceptable salt thereof. In some embodiments, at least one of $Z_1$, $Z_2$, $Z_3$ and $Z_4$ is not —H.

In some embodiments, $Z_1$, $Z_2$, $Z_3$ and $Z_4$ are each independently selected from the group consisting of —H, halogen, —C(O)OH, —C(O)O—$C_1$-$C_6$ alkyl, —$NO_2$, haloalkyl, —S(O)$_2$—$C_1$-$C_6$ alkyl, and —CN. In some embodiments, $Z_1$, $Z_2$, $Z_3$ and $Z_4$ are each independently selected from the group consisting of —H, —Cl, —Br, —I, —F, —C(O)OH, —$NO_2$, —$CF_3$, and —CN. In some embodiments, $Z_1$, $Z_2$, $Z_3$ and $Z_4$ are each independently selected from the group consisting of —H, —Cl, —F, —$NO_2$, and —$CF_3$. In some embodiments, at least one of $Z_1$, $Z_2$, $Z_3$ and $Z_4$ is not —H.

In some embodiments, $Z_1$ is selected from the group consisting of halogen, —C(O)OH, —C(O)O—$C_1$-$C_6$ alkyl, —$NO_2$, haloalkyl, —S(O)$_2$—$C_1$-$C_6$ alkyl, and —CN; and $Z_2$, $Z_3$ and $Z_4$ are each independently selected from the group consisting of —H, halogen, —C(O)OH, —C(O)O—$C_1$-$C_6$ alkyl, —$NO_2$, haloalkyl, —S(O)$_2$—$C_1$-$C_6$ alkyl, and —CN. In some embodiments, $Z_1$ is selected from the group consisting of —Cl, —Br, —I, —F, —C(O)OH, —$NO_2$, —$CF_3$, and —CN; and $Z_2$, $Z_3$ and $Z_4$ are each independently selected from the group consisting of —H, —Cl, —Br, —I, —F, —C(O)OH, —$NO_2$, —$CF_3$, and —CN. In some embodiments, $Z_1$ is selected from the group consisting of —Cl, —F, and —$NO_2$; and $Z_2$, $Z_3$ and $Z_4$ are each independently selected from the group consisting of —H, —Cl, —F, —$NO_2$, and —$CF_3$.

In some embodiments, the

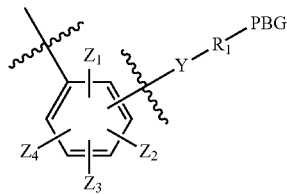

moiety of a compound of the invention is selected from the group consisting of:

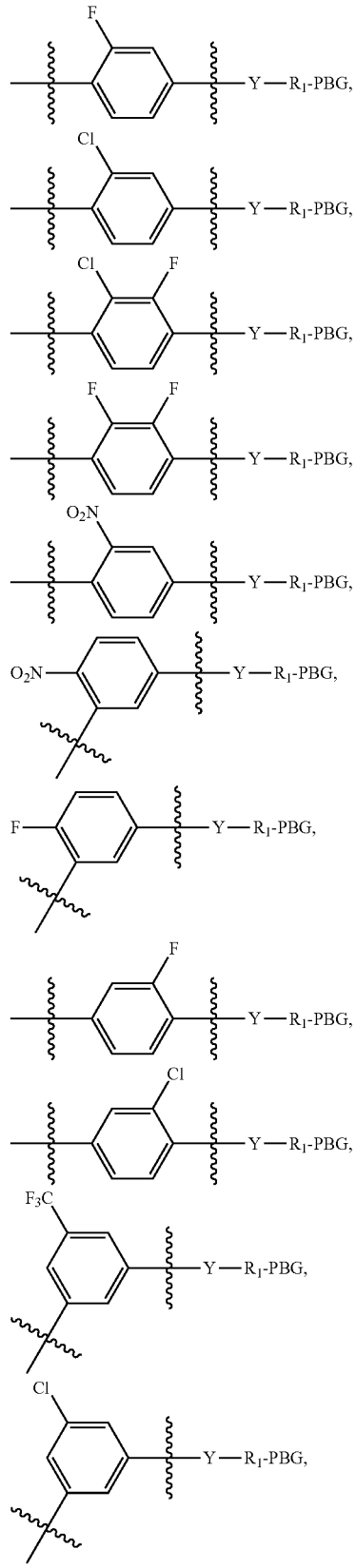

-continued

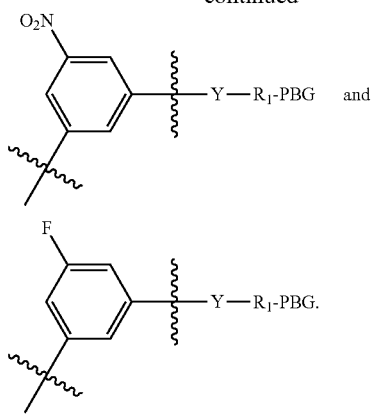

In some embodiments, the

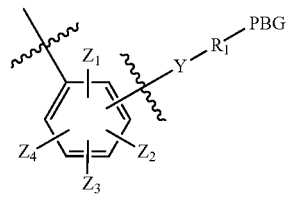

moiety of a compound of the invention is selected from the group consisting of:

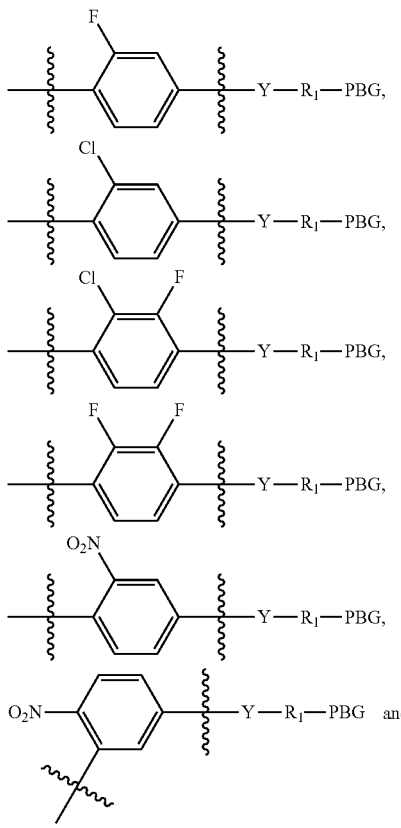

-continued

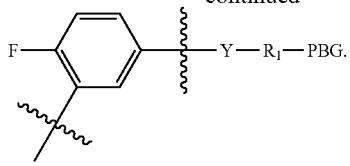

In some embodiments, Y is —C(O)—NH—. In some embodiments, Y is —C(O)—O—. In some embodiments, Y is absent.

In some embodiments, $R_1$ is selected from the group consisting of optionally substituted $C_1$-$C_{18}$ alkyl wherein optionally up to six carbon atoms in said $C_1$-$C_{18}$ alkyl are each independently replaced with —OCH$_2$CH$_2$—; optionally substituted $C_1$-$C_{18}$ alkyl-NH—C(O)—$R_5$— wherein optionally up to six carbon atoms in said $C_1$-$C_{18}$ alkyl are each independently replaced with —OCH$_2$CH$_2$—; and optionally substituted $C_1$-$C_{18}$ alkyl-C(O)—NH—$R_5$— wherein optionally up to six carbon atoms in said $C_1$-$C_{18}$ alkyl are each independently replaced with —OCH$_2$CH$_2$—.

In some embodiments, $R_1$ is selected from the group consisting of

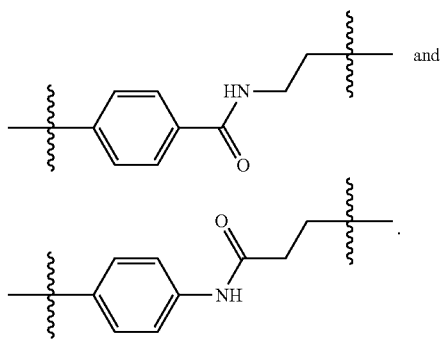

In some embodiments, $R_1$ is absent.

In some embodiments, PBG is an optionally substituted maleimide group. In some embodiments, PBG is

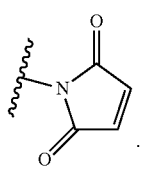 [SMILES: *N1C(=O)C=CC1=O]

In some embodiments, the

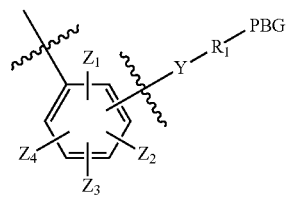

moiety of a compound of the invention is selected from the group consisting of:

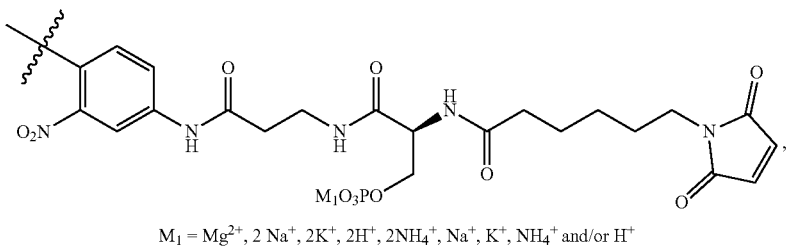
$M_1$ = $Mg^{2+}$, 2 $Na^+$, 2$K^+$, 2$H^+$, 2$NH_4^+$, $Na^+$, $K^+$, $NH_4^+$ and/or $H^+$
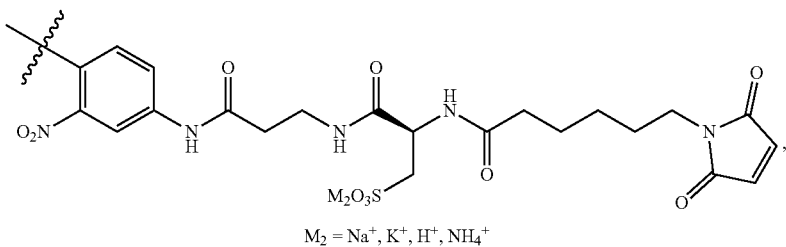
$M_2$ = $Na^+$, $K^+$, $H^+$, $NH_4^+$
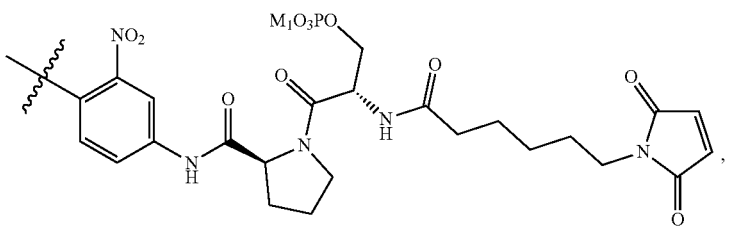
$M_1$ = $Mg^{2+}$, 2 $Na^+$, 2$K^+$, 2$H^+$, 2$NH_4^+$, $Na^+$, $K^+$, NH4$^+$ and/or $H^+$
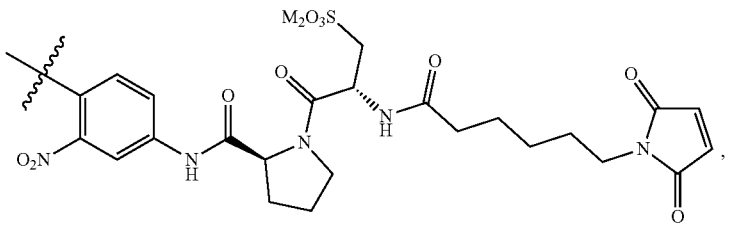
$M_2$ = $Na^+$, $K^+$, $H^+$, $NH_4^+$
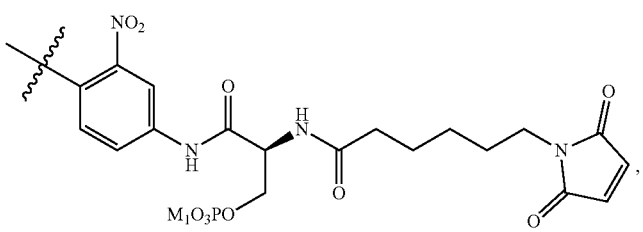
$M_1$ = $Mg^{2+}$, 2 $Na^+$, 2$K^+$, 2$H^+$, 2$NH_4^+$, $Na^+$, $K^+$, $NH_4^+$ and/or $H^+$
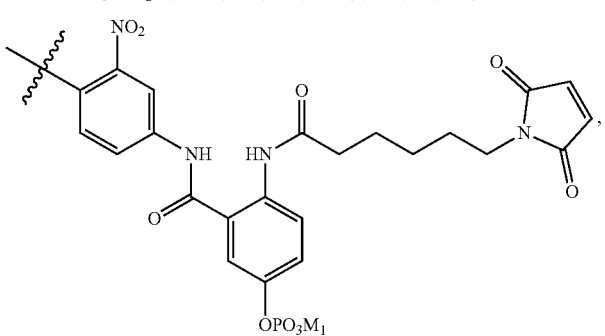
$M_1$ = $Mg^{2+}$, 2 $Na^+$, 2$K^+$, 2$H^+$, 2$NH_4^+$, $Na^+$, $K^+$, $NH_4^+$ and/or $H^+$

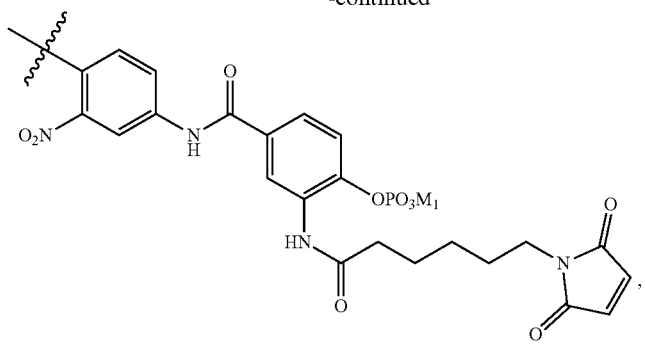
$M_1$ = $Mg^{2+}$, 2 $Na^+$, $2K^+$, $2H^+$, $2NH_4^+$, $Na^+$, $K^+$, $NH_4^+$ and/or $H^+$
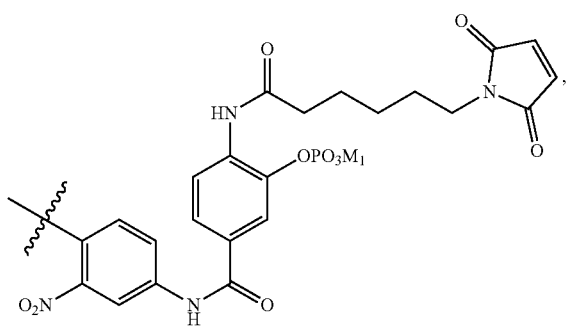
$M_1$ = $Mg^{2+}$, 2 $Na^+$, $2K^+$, $2H^+$, $2NH_4^+$, $Na^+$, $K^+$, $NH_4^+$ and/or $H^+$
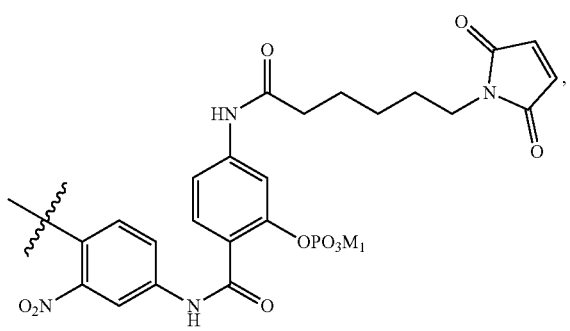
$M_1$ = $Mg^{2+}$, 2 $Na^+$, $2K^+$, $2H^+$, $2NH_4^+$, $Na^+$, $K^+$, $NH_4^+$ and/or $H^+$
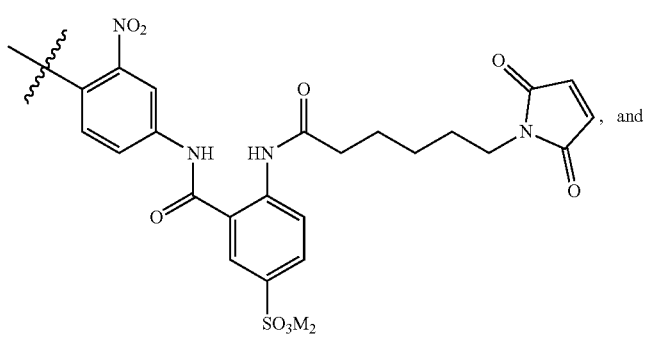
$M_2$ = $Na^+$, $K^+$, $H^+$, $NH_4^+$

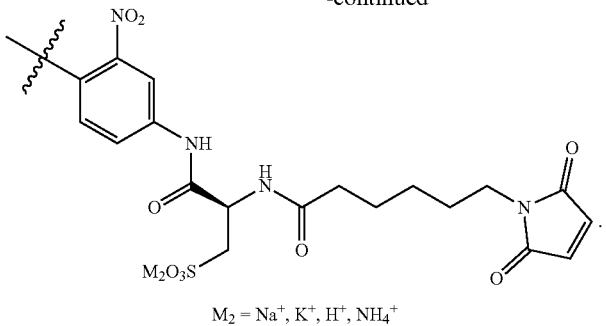

$M_2 = Na^+, K^+, H^+, NH_4^+$

In some embodiments, Spacer is

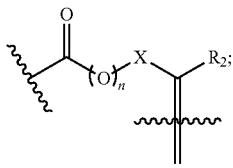

n is 0 or 1; and X is selected from the group consisting of optionally substituted $C_1$-$C_{18}$ alkyl wherein optionally up to six carbon atoms in said $C_1$-$C_{18}$ alkyl are each independently replaced with —OCH$_2$CH$_2$—; optionally substituted aryl; optionally substituted heteroaryl; and optionally substituted cycloalkyl; and $R_2$ is as defined for Formula I.

In some embodiments, Spacer is

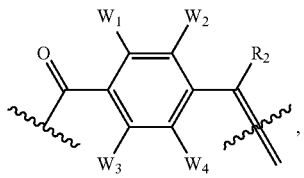

wherein $R_2$ is selected from the group consisting of: —H, optionally substituted $C_1$-$C_{12}$ alkyl, optionally substituted aryl, and optionally substituted heteroaryl; $W_1$, $W_2$, $W_3$ and $W_4$ are each independently selected from the group consisting of: —H, halogen, —C(O)OH, —C(O)O—$C_1$-$C_6$ alkyl, —NO$_2$, haloalkyl, —S(O)$_2$—$C_1$-$C_6$ alkyl, and —CN. In some embodiments, $W_1$, $W_2$, $W_3$ and $W_4$ are each independently selected from the group consisting of: —H, —Cl, —Br, —I, —F, —C(O)OH, —NO$_2$, —CF$_3$, and —CN. In some embodiments, $W_1$, $W_2$, $W_3$ and $W_4$ are each independently selected from the group consisting of: —H, —Cl, —F, —NO$_2$, and —CF$_3$. In some embodiments, $W_1$, $W_2$, $W_3$ and $W_4$ are each independently selected from the group consisting of: a phenoxy group, a primary, secondary or tertiary amine group, an ether group, a phenol group, an amide group, an ester group, an alkyl group, a substituted alkyl group, a phenyl group, and a vinyl group. In some embodiments, $W_1$, $W_2$, $W_3$ and $W_4$ are each independently selected from the group consisting of: —OP(O)(OH)$_2$, —P(O)(OH)OP(O)(OH)$_2$, —OP(O)(OH)OP(O)(OH)OP(O)(OH)$_2$, —OP(O)(OH)(NH$_2$), —P(O)(OH)$_2$, —SO$_3$H, and a pharmaceutically acceptable salt thereof. In some embodiments, at least one of $W_1$, $W_2$, $W_3$ and $W_4$ is not —H.

In some embodiments, $W_1$ is selected from the group consisting of: halogen, —C(O)OH, —C(O)O—$C_1$-$C_6$ alkyl, —NO$_2$, haloalkyl, —S(O)$_2$—$C_1$-$C_6$ alkyl, and —CN; and $W_2$, $W_3$ and $W_4$ are each independently selected from the group consisting of: —H, halogen, —C(O)OH, —C(O)O—$C_1$-$C_6$ alkyl, —NO$_2$, haloalkyl, —S(O)$_2$—$C_1$-$C_6$ alkyl, and —CN. In some embodiments, $W_1$ is selected from the group consisting of: —Cl, —Br, —I, —F, —C(O)OH, —NO$_2$, —CF$_3$, and —CN; and $W_2$, $W_3$ and $W_4$ are each independently selected from the group consisting of: —H, —Br, —I, —F, —C(O)OH, —NO$_2$, —CF$_3$, and —CN. In some embodiments, $W_1$ is selected from the group consisting of: —Cl, —F, and —NO$_2$; and $Z_2$, $Z_3$ and $Z_4$ are each independently selected from the group consisting of: —H, —Cl, —F, —NO$_2$, and —CF$_3$.

In some embodiments, Spacer is

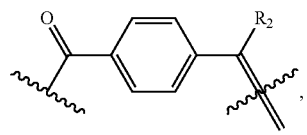

wherein $R_2$ is selected from the group consisting of —H, optionally substituted $C_1$-$C_{12}$ alkyl, optionally substituted aryl, and optionally substituted heteroaryl.

In some embodiments, Spacer is

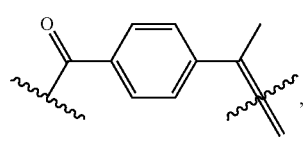 [SMILES: *C(=O)c1ccc(C(=*)C)cc1]

In some embodiments, Spacer is

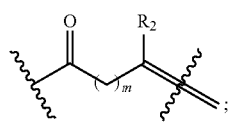

and m is 1, 2, 3, 4, 5, or 6.

In some embodiments, Spacer is

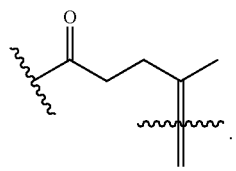 [SMILES: *C(=O)CCC(=*)C]

In some embodiments, the compound of the invention is selected from the group consisting of:
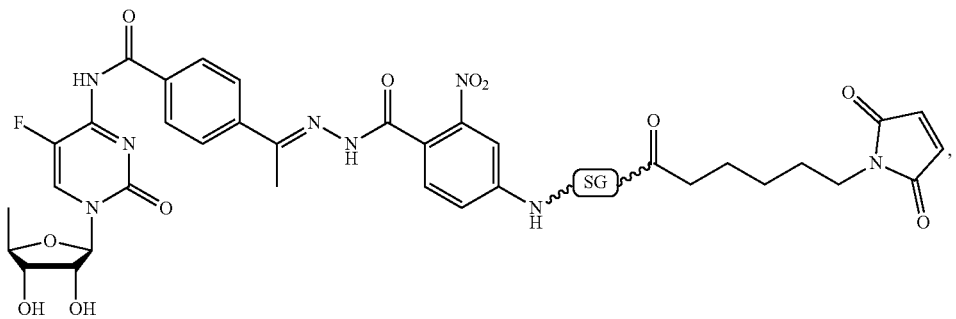
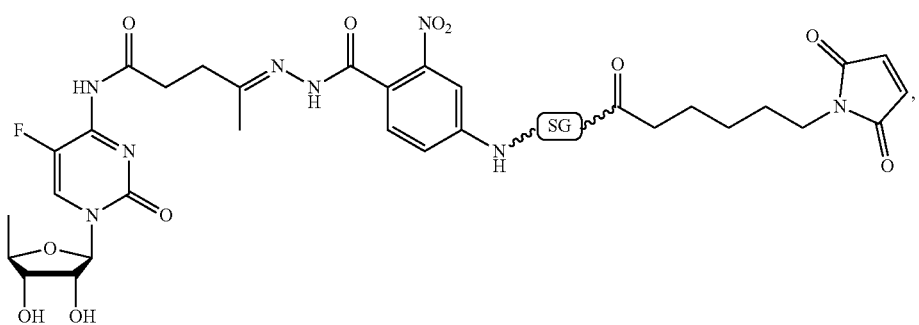
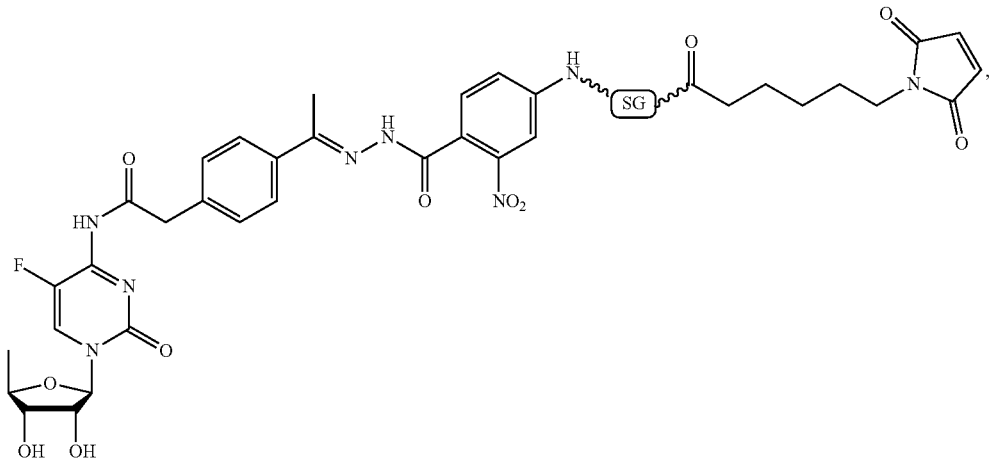
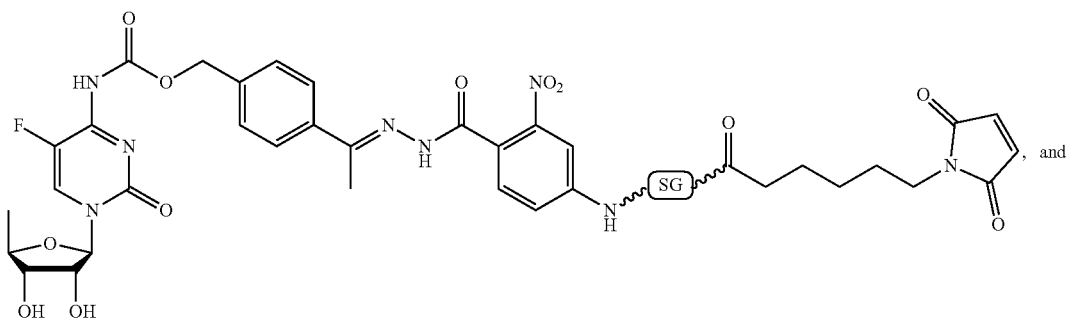

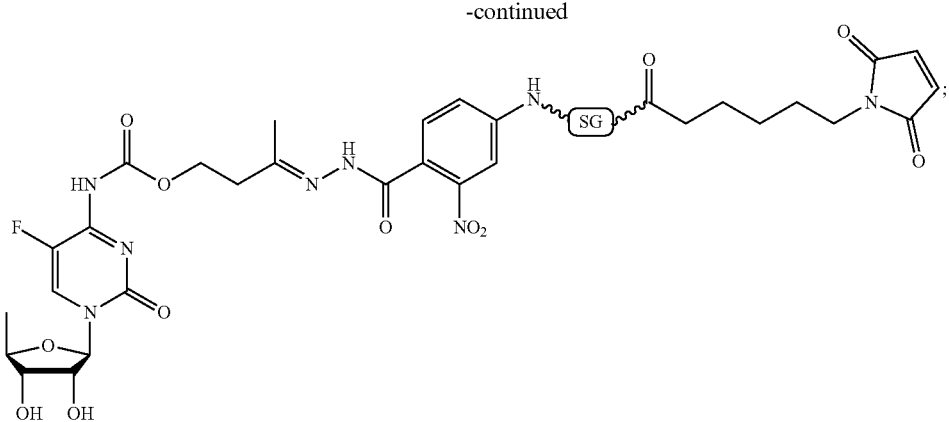

or a pharmaceutically acceptable salt, hydrate, solvate, or isomer thereof,
wherein:

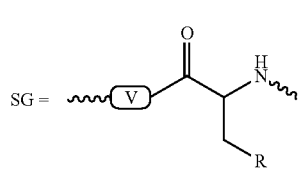

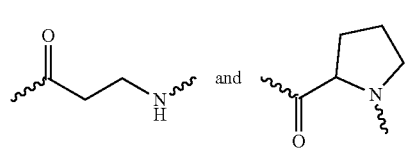 is absent, or is selected from the group consisting of:

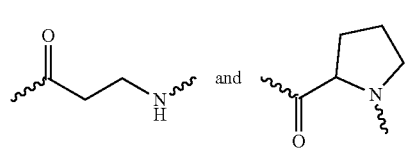

R is ⟿OPO$_3$M$_1$ wherein M$_1$=Mg$^{2+}$, 2 Na$^+$, 2K$^+$, 2H$^+$, 2NH$_4^+$, Na$^+$, K$^+$, NH$_4^+$, and/or H$^+$
or
⟿SO$_3$M$_2$ wherein M$_2$=Na$^+$, K$^+$, H$^+$, and/or NH$_4^+$.

In some embodiments, the compound of the invention is selected from the group consisting of:

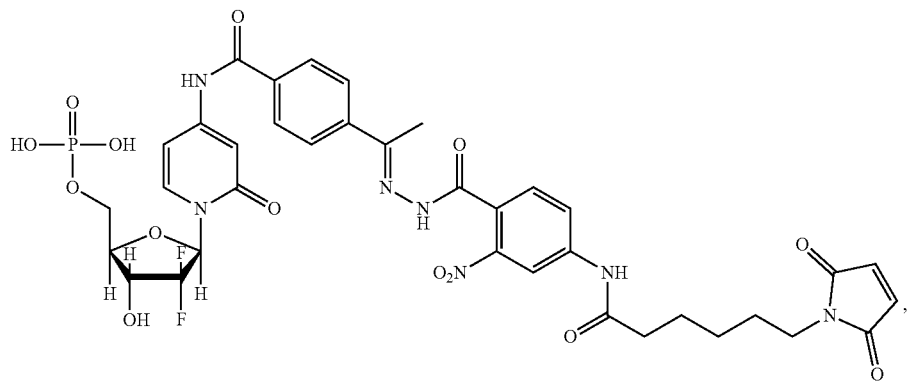

-continued
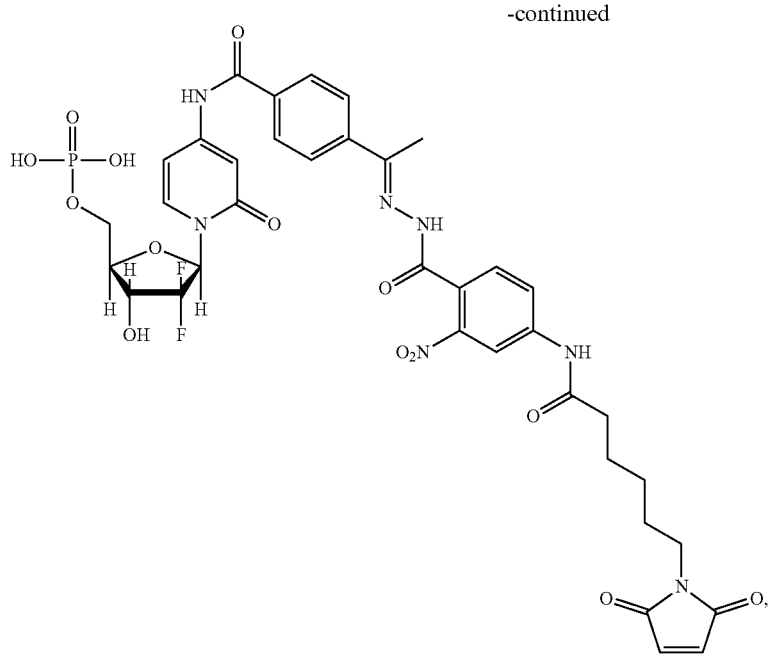
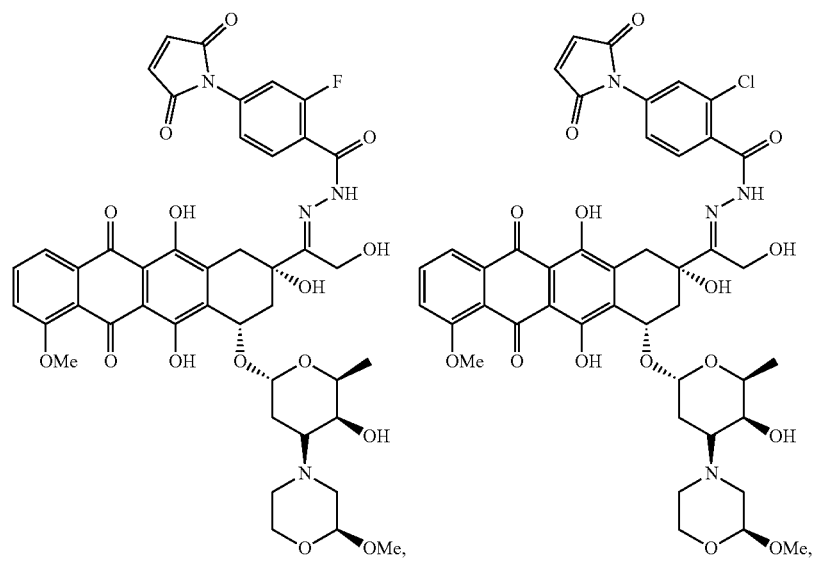

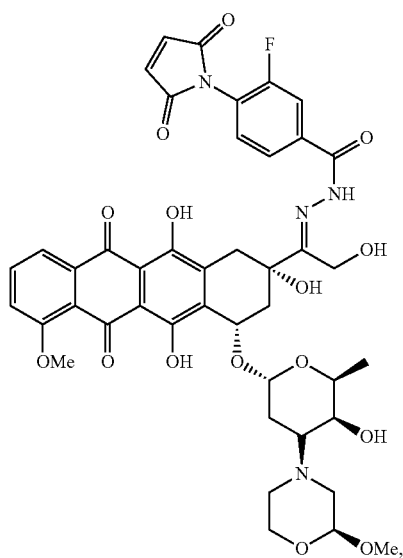
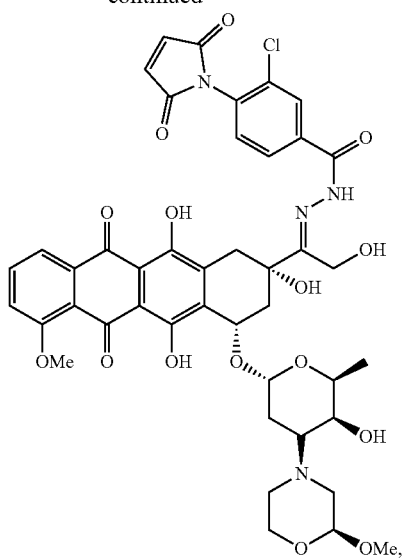
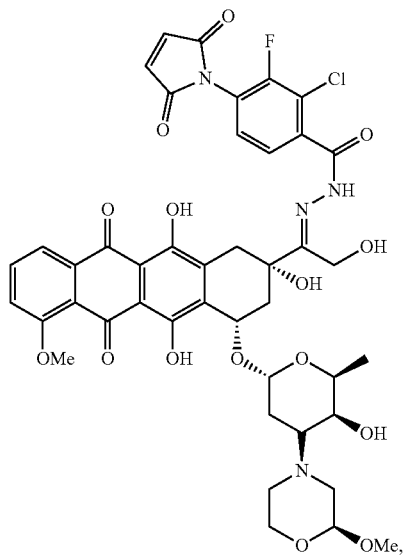
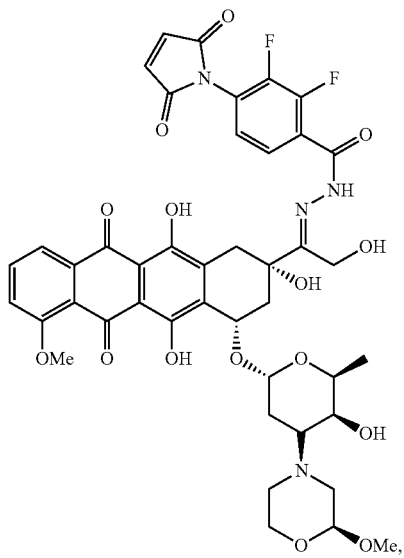
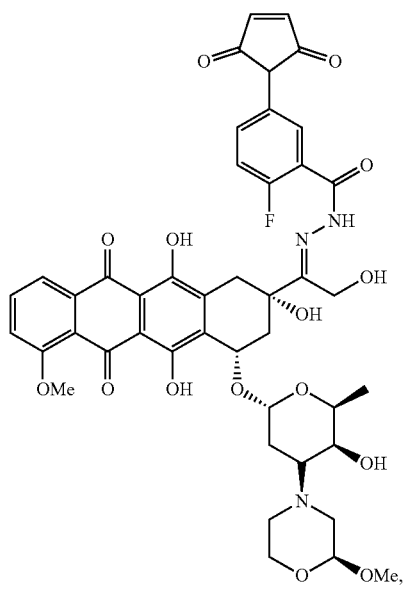
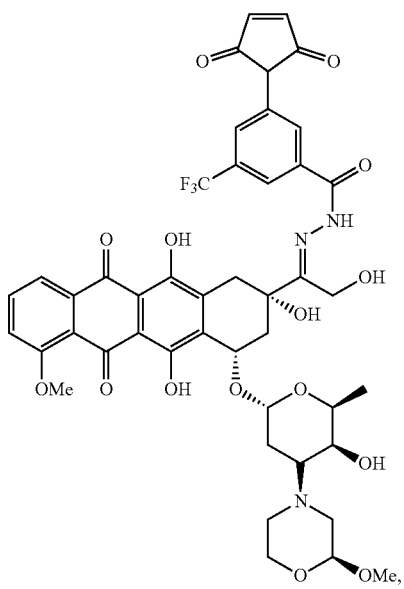

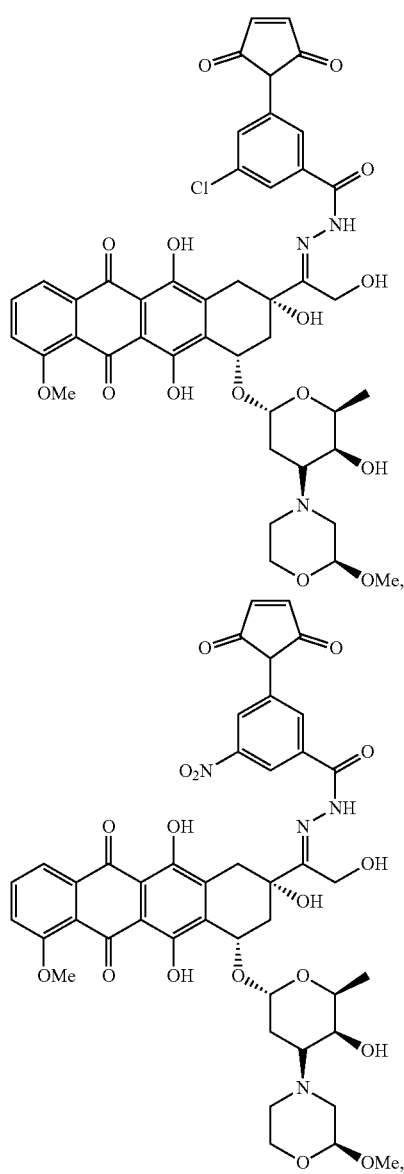
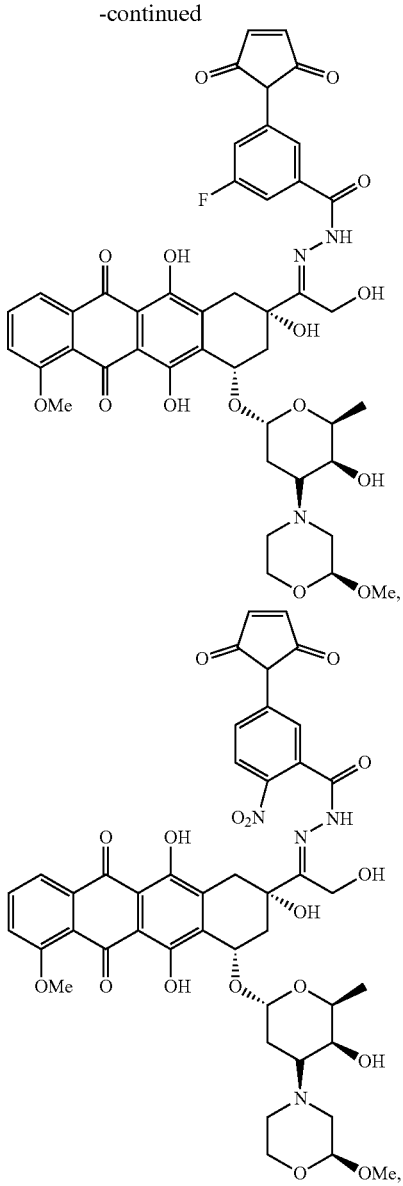
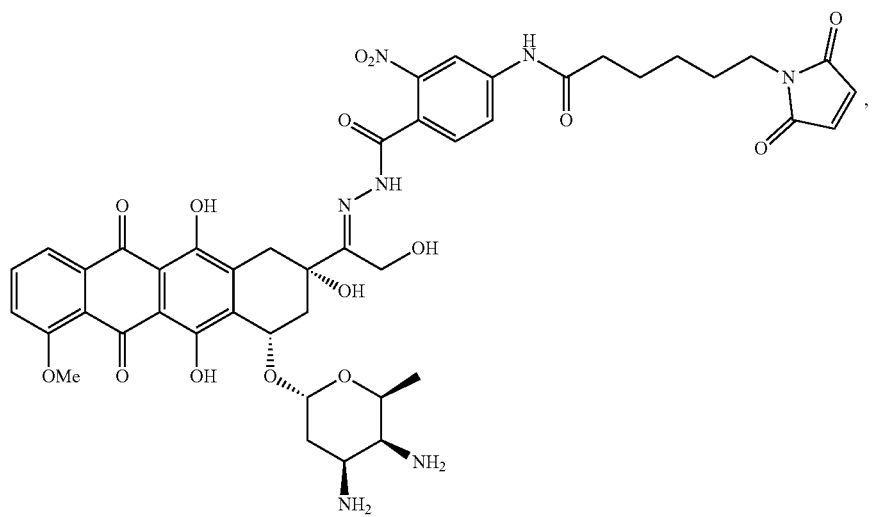

-continued
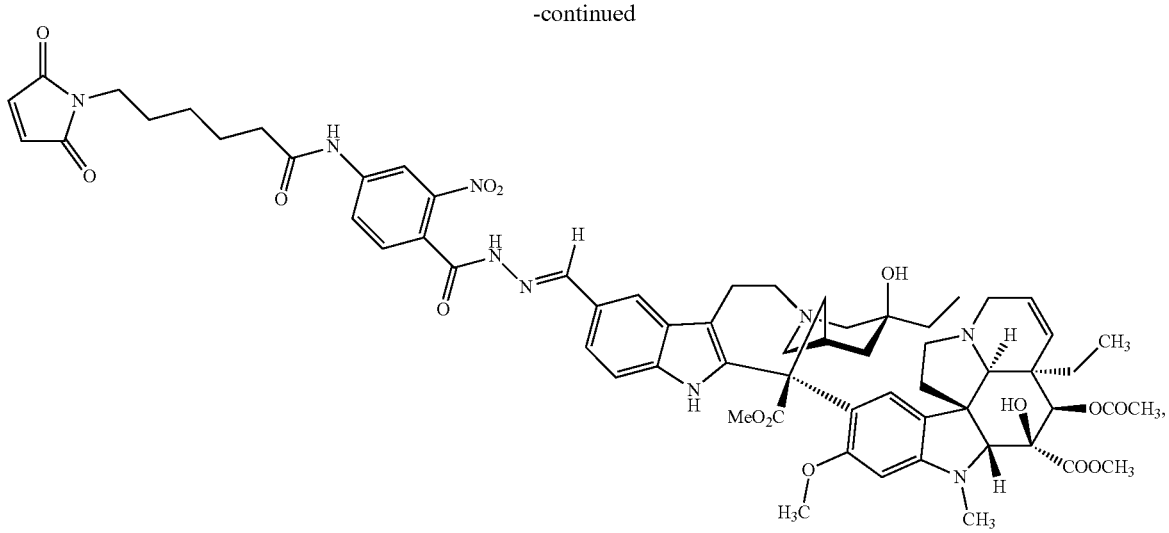
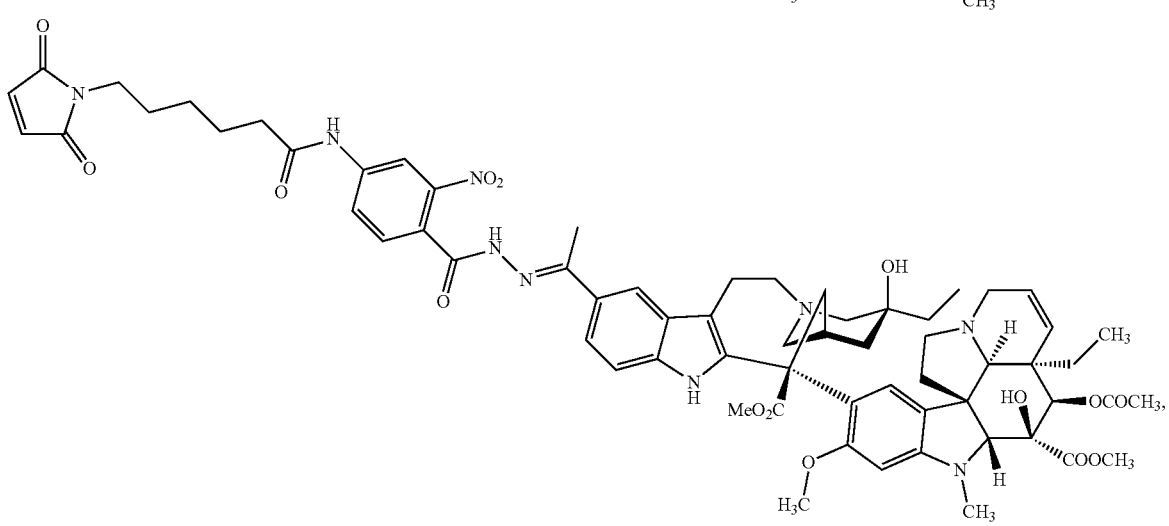
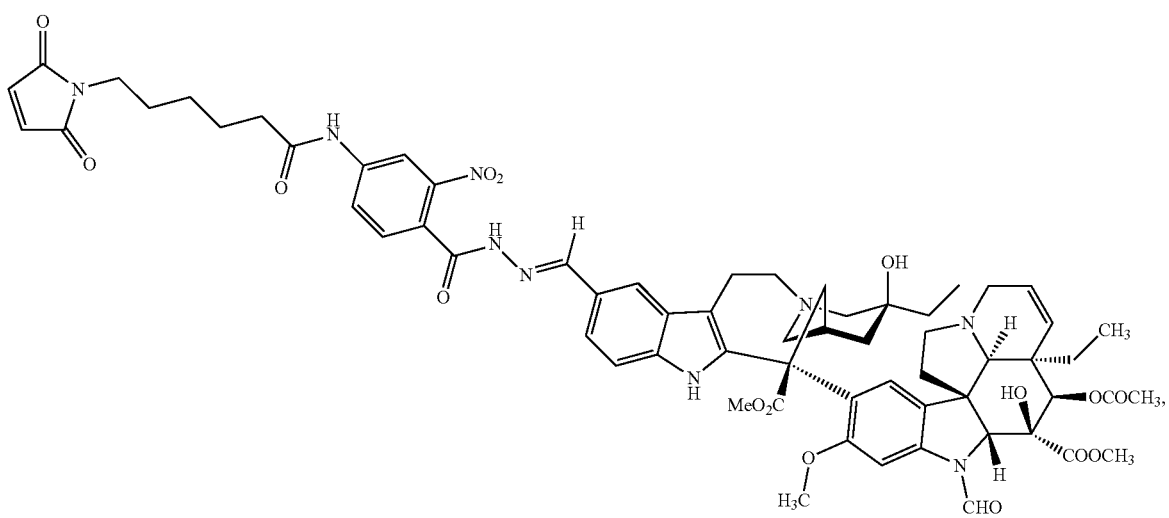

-continued
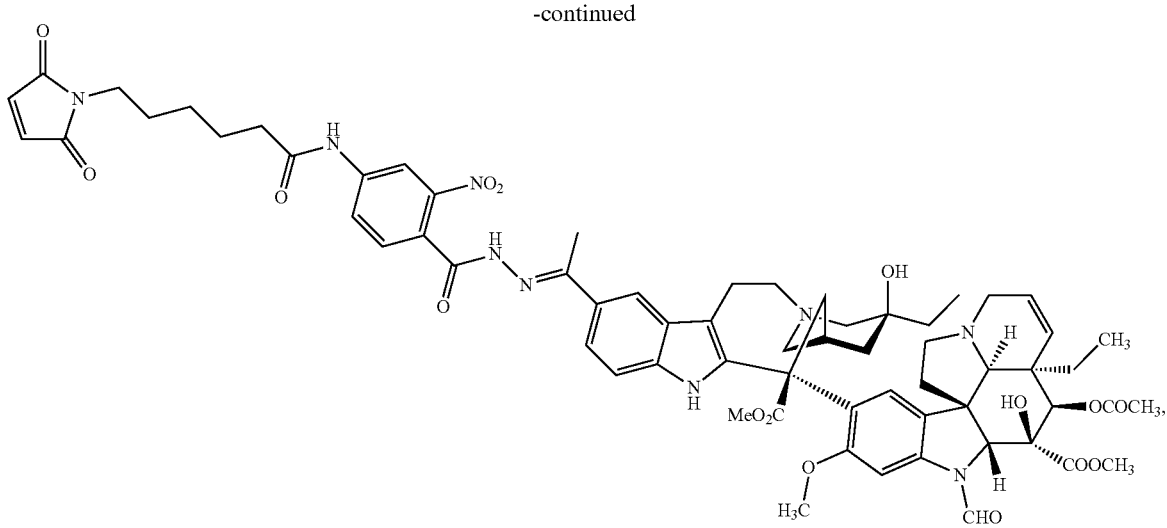
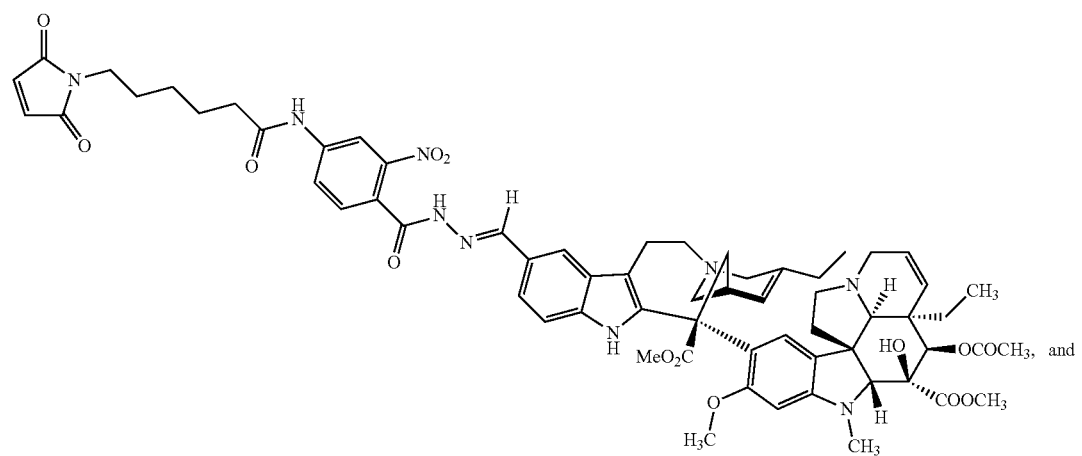
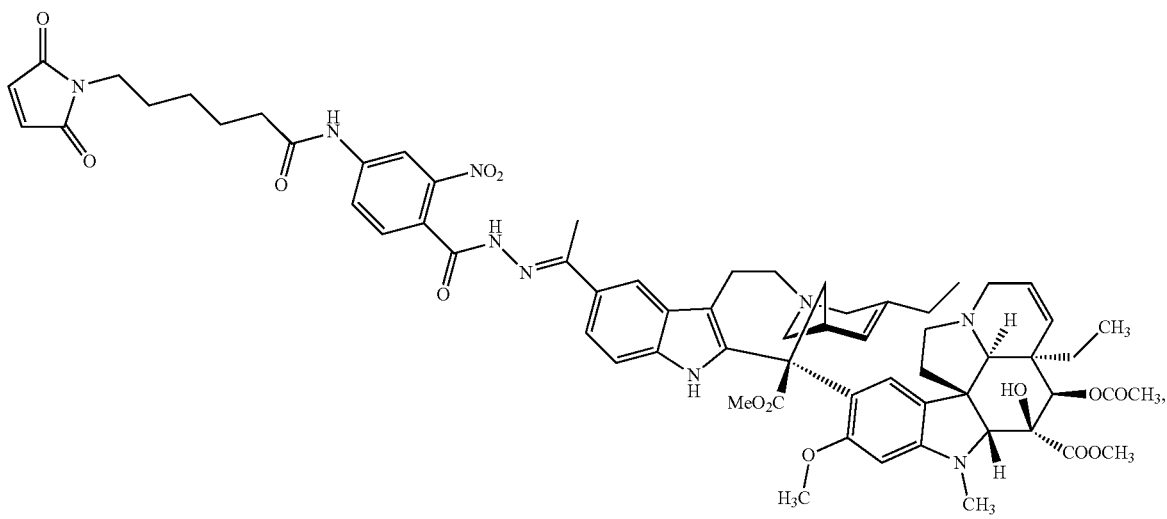
or a pharmaceutically acceptable salt, hydrate, solvate, or isomer thereof.

In some embodiments, Agent is α-amanitin, and the compound of the present invention is selected from the group consisting of:
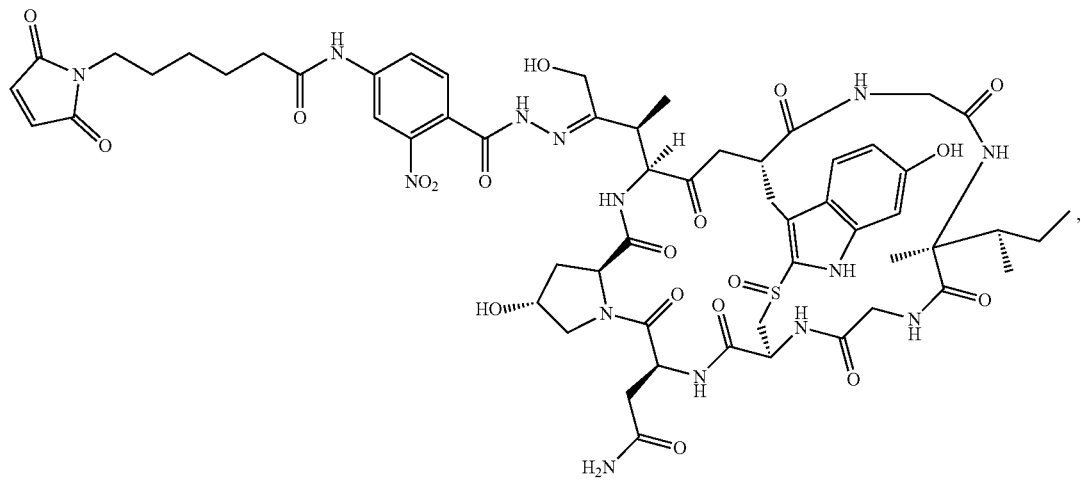
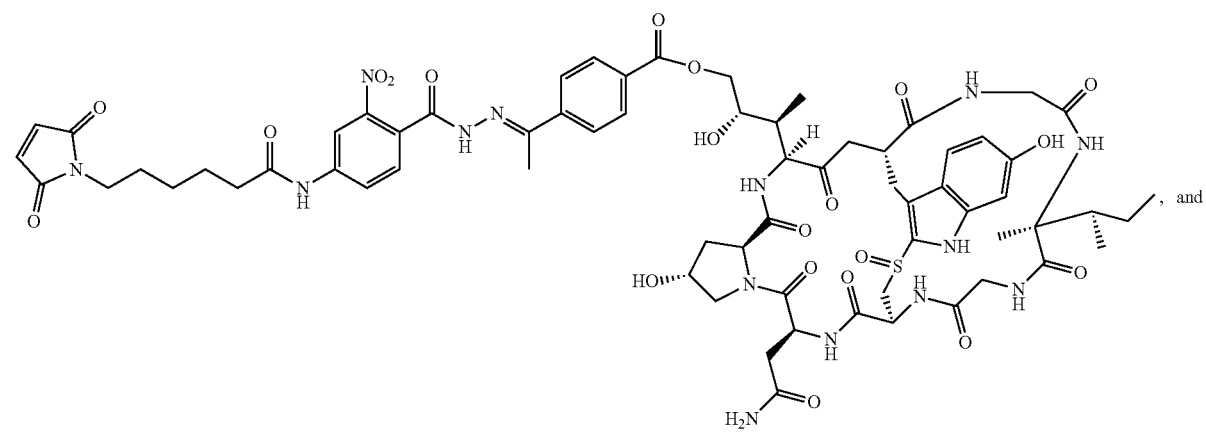
, and
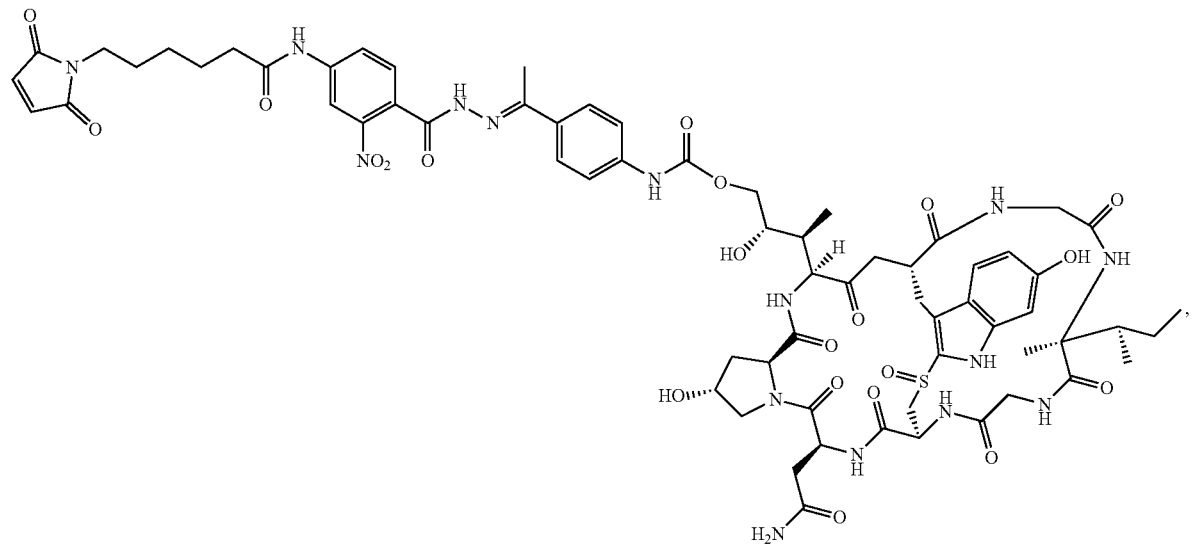
,
or a pharmaceutically acceptable salt, hydrate, solvate, or isomer thereof.

In some embodiments, Agent is an auristatin or derivative thereof and the compound of the present invention is selected from the group consisting of:

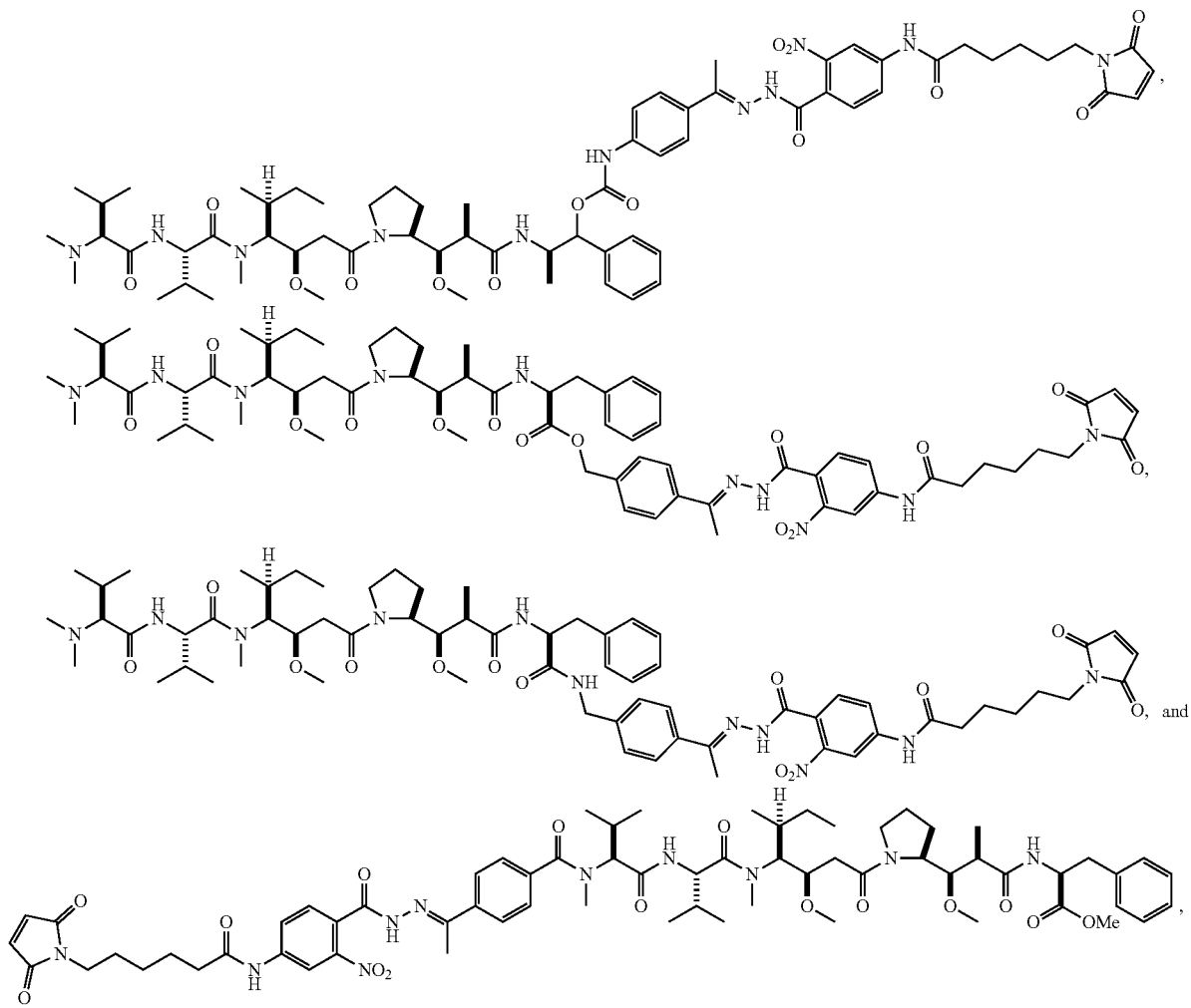

or a pharmaceutically acceptable salt, hydrate, solvate, or isomer thereof.

In certain embodiments, the invention provides a pharmaceutical composition comprising a compound as disclosed herein, and a pharmaceutically acceptable carrier.

In certain embodiments, the invention provides a method for treating a disease or condition selected from the group consisting of a cancer, a virus disease, autoimmune disease, acute or chronic inflammatory disease, and a disease caused by bacteria, fungi, or other micro-organisms, comprising administering to a patient in need thereof a therapeutically effective amount of a compound described herein or a pharmaceutical composition described herein.

In some embodiments, the invention provides compounds and compositions for use as a medicament. In some embodiments, the invention provides compounds and compositions for use in treating a disease or condition selected from the group consisting of a cancer, a virus disease, an autoimmune disease, an acute or chronic inflammatory disease, and a disease caused by bacteria, fungi, or other micro-organisms.

In some embodiments, the compound disclosed herein may be used in the manufacture or preparation of a medicament for the treatment of a disease or condition selected from the group consisting of a cancer, a virus disease, an autoimmune disease, an acute or chronic inflammatory disease, and a disease caused by bacteria, fungi, or other micro-organisms.

DETAILED DESCRIPTION OF THE INVENTION

Figure 1:
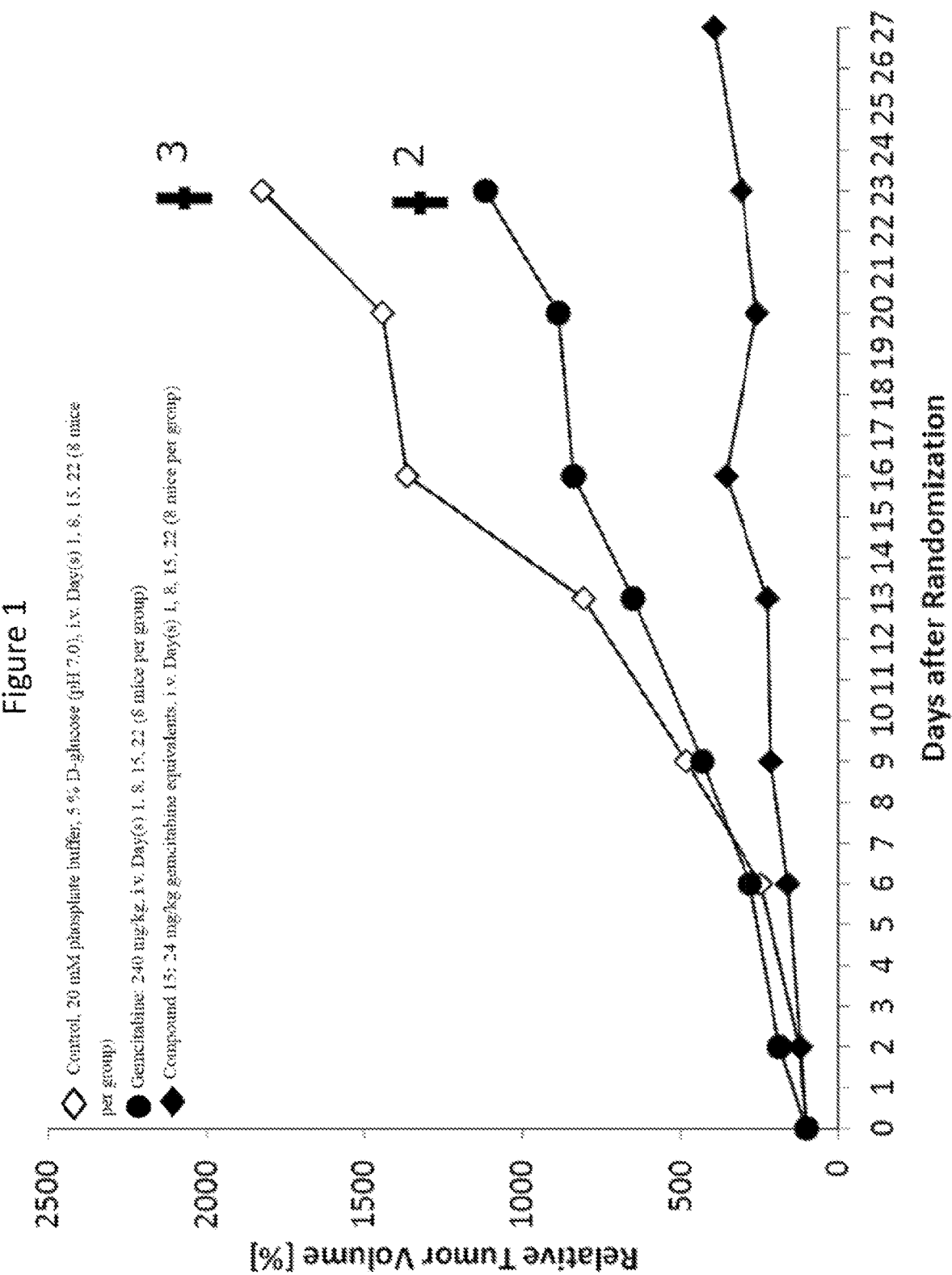
FIG. 1 shows the effect of compound 15 and gemcitabine on tumor growth in the NSLC xenograft model LXFE 397.

Unless otherwise defined herein, scientific and technical terms used in this application shall have the meanings that are commonly understood by those of ordinary skill in the art. Generally, nomenclature used in connection with, and techniques of, chemistry, molecular biology, cell and cancer biology, immunology, microbiology, pharmacology, and protein and nucleic acid chemistry, described herein, are those well known and commonly used in the art.

All publications, patents and published patent applications referred to in this application are specifically incorporated by reference herein. In case of conflict, the present specification, including its specific definitions, will control. Unless otherwise specified, it is to be understood that each embodiment of the invention may be used alone or in combination with any one or more other embodiments of the invention.

Throughout this specification, the word "comprise" or variations such as "comprises" or "comprising" will be understood to imply the inclusion of a stated integer (or components) or group of integers (or components), but not the exclusion of any other integer (or components) or group of integers (or components).

Throughout the application, where a compound or composition is described as having, including, or comprising, specific components, it is contemplated that such compound or composition also may consist essentially of, or consist of, the recited components. Similarly, where methods or processes are described as having, including, or comprising specific process steps, the processes also may consist essentially of, or consist of, the recited processing steps. Further, it should be understood that the order of steps or order for performing certain actions is immaterial so long as the compounds, compositions and methods described herein remains operable. Moreover, two or more steps or actions can be conducted simultaneously.

The singular forms "a," "an," and "the" include the plurals unless the context clearly dictates otherwise.

The term "including" is used to mean "including but not limited to." "Including" and "including but not limited to" are used interchangeably.

The term "or" as used herein should be understood to mean "and/or", unless the context clearly indicates otherwise.

The terms "drug," "agent," "therapeutic agent" or "therapeutically effective substance" are used to mean any compound which brings about a pharmacological effect either by itself or after its conversion in the organism in question, and thus also includes the derivatives from these conversions. The pharmacological effect of the drugs of the composition according to the present invention can be a single effect only, e.g. a cytostatic effect, or a broad pharmacological spectrum of actions, such as an immunosuppressive and antiphlogistic effect at the same time.

The term "anthracycline" refers to a class of antineoplastic antibiotics having an anthracenedione (also termed anthraquinone or dioxoanthracene) structural unit. For example, the term "anthracycline" is specifically intended to individually include doxorubicin, daunorubicin, epirubicin, idarubicin, nemorubicin, valrubicin, pirarubicin, zorubicin, aclarubicin, 2-pyrrolpyrrolinoanthracycline, morpholinoanthracycline, diacetatoxyalkylanthracycline, PNU-159682, caminomycin, mitoxantrone, and ametantrone.

The terms "patient," "subject," or "individual" are used interchangeably and refer to either a human or a non-human animal. These terms include mammals such as humans, primates, livestock animals (e.g., bovines, porcines), companion animals (e.g., canines, felines) and rodents (e.g., mice and rats). In certain embodiments, the patient or subject is a human patient or subject, such as a human patient having a condition in need of treatment.

The term "pharmaceutical composition" refers to a composition suitable for pharmaceutical use in a subject animal, including humans and mammals, e.g., combined with one or more pharmaceutically acceptable carriers, excipients or solvents. Such a composition may also contain diluents, fillers, salts, buffers, stabilizers, solubilizers, and other materials well known in the art. In certain embodiments, a pharmaceutical composition encompasses a composition comprising the active ingredient(s), and the inert ingredient(s) that make up the excipient, carrier or diluent, as well as any product that results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present disclosure encompass any composition made by admixing a compound of the disclosure and one or more pharmaceutically acceptable excipient(s), carrier(s) and/or diluent(s).

The term "pharmaceutically acceptable carrier" refers to a non-toxic carrier that may be administered to a patient, together with a therapeutically effective substance of this invention, and which does not destroy the pharmacological activity of the agent. The term "excipient" refers to an additive in a formulation or composition that is not a pharmaceutically active ingredient. In certain embodiments, a "pharmaceutically acceptable" substance is suitable for use in contact with cells, tissues or organs of animals or humans without excessive toxicity, irritation, allergic response, immunogenicity or other adverse reactions, in the amount used in the dosage form according to the dosing schedule, and commensurate with a reasonable benefit/risk ratio.

In certain embodiments, a "pharmaceutically acceptable" substance that is a component of a pharmaceutical composition is, in addition, compatible with the other ingredient(s) of the composition. In certain embodiments, the terms "pharmaceutically acceptable excipient", "pharmaceutically acceptable carrier" and "pharmaceutically acceptable diluent" encompass, without limitation, pharmaceutically acceptable inactive ingredients, materials, compositions and vehicles, such as liquid fillers, solid fillers, diluents, excipients, carriers, solvents and encapsulating materials. Carriers, diluents and excipients also include all pharmaceutically acceptable dispersion media, coatings, buffers, isotonic agents, stabilizers, absorption delaying agents, antimicrobial agents, antibacterial agents, antifungal agents, adjuvants, and so on. Except insofar as any conventional excipient, carrier or diluent is incompatible with the active ingredient, the present disclosure encompasses the use of conventional excipients, carriers and diluents in pharmaceutical compositions. See, e.g., Remington: The Science and Practice of Pharmacy, 21st Ed., Lippincott Williams & Wilkins (Philadelphia, Pa., 2005); Handbook of Pharmaceutical Excipients, 5th Ed., Rowe et al., Eds., The Pharmaceutical Press and the American Pharmaceutical Association (2005); Handbook of Pharmaceutical Additives, 3rd Ed., Ash and Ash, Eds., Gower Publishing Co. (2007); and Pharmaceutical Preformulation and Formulation, Gibson, Ed., CRC Press LLC (Boca Raton, Fla., 2004).

The terms "pharmaceutically effective amount," "therapeutically effective amount," or "therapeutically effective dose" refer to an amount effective to treat a disease in a patient, e.g., effecting a beneficial and/or desirable alteration in the general health of a patient suffering from a disease (e.g., cancer), treatment, healing, inhibition or amelioration of a physiological response or condition, etc. The full therapeutic effect does not necessarily occur by administration of one dose, and may occur only after administration of a series of doses. Thus, a therapeutically effective amount may be administered in one or more administrations. The precise effective amount needed for a subject will depend upon, for example, the subject's size, health and age, the nature and extent of disease, the therapeutics or combination of therapeutics selected for administration, and the mode of administration. The skilled worker can readily determine the effective amount for a given situation by routine experimentation. The skilled worker will recognize that treating cancer includes, but is not limited to, killing cancer cells, preventing the growth of new cancer cells, causing tumor regression (a decrease in tumor size), causing a decrease in metastasis, improving vital functions of a patient, improving the well-being of the patient, decreasing pain, improving appetite, improving the patient's weight, and any combination thereof. The terms "pharmaceutically effective amount," "therapeutically effective amount," or (therapeutically effective dose" also refer to the amount required to improve the clinical symptoms of a patient. The therapeutic methods or methods of treating cancer described herein are not to be interpreted or otherwise limited to "curing" cancer.

As used herein, the term "treating" or "treatment" includes reversing, reducing, or arresting the symptoms, clinical signs, and underlying pathology of a condition in manner to improve or stabilize a subject's condition. As used herein, and as well understood in the art, "treatment" is an approach for obtaining beneficial or desired results, including clinical results. Beneficial or desired clinical results can include, but are not limited to, alleviation, amelioration, or slowing the progression, of one or more symptoms or conditions associated with a condition, e.g., cancer, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Exemplary beneficial clinical results are described herein.

"Administering" or "administration of" a substance, a compound or an agent to a subject can be carried out using one of a variety of methods known to those skilled in the art. For example, a compound or an agent can be administered, intravenously, arterially, intradermally, intramuscularly, intraperitoneally, subcutaneously, ocularly, sublingually, orally (by ingestion), intranasally (by inhalation), intraspinally, intracerebrally, and transdermally (by absorption, e.g., through a skin duct). A compound or agent can also appropriately be introduced by rechargeable or biodegradable polymeric devices or other devices, e.g., patches and pumps, or formulations, which provide for the extended, slow or controlled release of the compound or agent. Administering can also be performed, for example, once, a plurality of times, and/or over one or more extended periods. In some aspects, the administration includes both direct administration, including self-administration, and indirect administration, including the act of prescribing a drug. For example, as used herein, a physician who instructs a patient to self-administer a drug, or to have the drug administered by another and/or who provides a patient with a prescription for a drug is administering the drug to the patient. When a method is part of a therapeutic regimen involving more than one agent or treatment modality, the disclosure contemplates that the agents may be administered at the same or differing times and via the same or differing routes of administration. Appropriate methods of administering a substance, a compound or an agent to a subject will also depend, for example, on the age of the subject, whether the subject is active or inactive at the time of administering, whether the subject is cognitively impaired at the time of administering, the extent of the impairment, and the chemical and biological properties of the compound or agent (e.g. solubility, digestibility, bioavailability, stability and toxicity).

The term "substituted" refers to moieties having substituents replacing a hydrogen on one or more carbons of the backbone of a chemical compound. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of the invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, an alkylthio, an acyloxy, a phosphoryl, a phosphate, a phosphonate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety.

"Optional" or "optionally" means that the subsequently described circumstance may or may not occur, so that the application includes instances where the circumstance occurs and instances where it does not. For example, the phrase "optionally substituted" means that a non-hydrogen substituent may or may not be present on a given atom, and, thus, the application includes structures wherein a non-hydrogen substituent is present and structures wherein a non-hydrogen substituent is not present.

Unless specifically stated as "unsubstituted," references to chemical moieties herein are understood to include substituted variants. For example, reference to an "alkyl" group or moiety implicitly includes both substituted and unsubstituted variants. Examples of substituents on chemical moieties includes but is not limited to, halogen, hydroxyl, carbonyl (such as carboxyl, alkoxycarbonyl, formyl, or acyl), thiocarbonyl (such as thioester, thioacetate, or thioformate), alkoxyl, alkylthio, acyloxy, phosphoryl, phosphate, phosphonate, amino, amido, amidine, imine, cyano, nitro, azido, sulfhydryl, alkylthio, sulfate, sulfonate, sulfamoyl, sulfonamido, sulfonyl, heterocyclyl, aralkyl, or aryl or heteroaryl moiety.

The term "acyl" is art-recognized and refers to a group represented by the general formula hydrocarbyl-C(O)—, preferably alkyl-C(O)—.

The term "alkyl" refers to the radical of saturated aliphatic groups, including straight-chain alkyl groups, and branched-chain alkyl groups. In preferred embodiments, a straight chain or branched chain alkyl has 30 or fewer carbon atoms in its backbone (e.g., $C_1$-$C_{30}$ for straight chains, $C_3$-$C_{30}$ for branched chains), and more preferably 20 or fewer. In certain embodiments, alkyl groups are lower alkyl groups, e.g., methyl, ethyl, n-propyl, i-propyl, n-butyl and n-pentyl. Moreover, the term "alkyl" as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. In certain embodiments, a straight chain or branched chain alkyl has 30 or fewer carbon atoms in its backbone (e.g., $C_1$-$C_{30}$ for straight chains, $C_3$-$C_{30}$ for branched chains). In preferred embodiments, the chain has ten or fewer carbon ($C_1$-$C_{10}$) atoms in its backbone. In other embodiments, the chain has six or fewer carbon ($C_1$-$C_6$) atoms in its backbone.

Such substituents can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, an alkylthio, an acyloxy, a phosphoryl, a phosphate, a phosphonate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aryl or heteroaryl moiety.

The term "amide", as used herein, refers to a group represented by

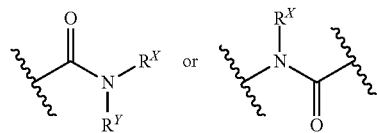

wherein $R^X$ and $R^Y$ each independently represent a hydrogen or hydrocarbyl group, or $R^X$ and $R^Y$ taken together with the N atom to which they are attached complete a heterocycle having from 4 to 8 atoms in the ring structure.

In some embodiments, the amide is —NH—C(O)— or —C(O)—NH—.

The terms "amine" and "amino" are art-recognized and refer to both unsubstituted and substituted amines and salts thereof, e.g., a moiety that can be represented by

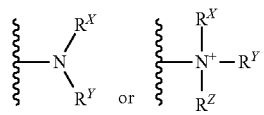

wherein $R^X$, $R^Y$, and $R^Z$ each independently represent a hydrogen or a hydrocarbyl group, or $R^X$ and $R^Y$ taken together with the N atom to which they are attached complete a heterocycle having from 4 to 8 atoms in the ring structure.

The term "aryl", as used herein, include substituted or unsubstituted single-ring aromatic groups in which each atom of the ring is carbon. Preferably the ring is a 5- to 7-membered ring, more preferably a 6-membered ring. Aryl groups include phenyl, phenol, aniline, and the like. The terms "aryl" also includes "polycyclyl", "polycycle", and "polycyclic" ring systems having two or more rings in which two or more atoms are common to two adjoining rings, e.g., the rings are "fused rings," wherein at least one of the rings is aromatic, e.g., the other cyclic rings can be cycloalkyls, cycloalkenyls, cycloalkynyls, aryls. In some preferred embodiments, polycycles have 2-3 rings. In certain preferred embodiments, polycyclic ring systems have two cyclic rings in which both of the rings are aromatic. Each of the rings of the polycycle can be substituted or unsubstituted. In certain embodiments, each ring of the polycycle contains from 3 to 10 atoms in the ring, preferably from 5 to 7. For example, aryl groups include, but are not limited to, phenyl, tolyl, anthracenyl, fluorenyl, indenyl, azulenyl, and naphthyl, as well as benzo-fused carbocyclic moieties such as 5,6,7,8-tetrahydronaphthyl, and the like.

In some embodiments, the aryl is a single-ring aromatic group. In some embodiments, the aryl is a two-ring aromatic group. In some embodiments, the aryl is a three-ring aromatic group.

The term "cycloalkyl", as used herein, refers to the radical of a saturated aliphatic ring. In preferred embodiments, cycloalkyls have from 3-10 carbon atoms in their ring structure, and more preferably from 5-7 carbon atoms in the ring structure. In some embodiments, the two cyclic rings can have two or more atoms in common, e.g., the rings are "fused rings." Suitable cycloalkyls include cycloheptyl, cyclohexyl, cyclopentyl, cyclobutyl and cyclopropyl.

In some embodiments, the cycloalkyl is a mono-cyclic group. In some embodiments, the cycloalkyl is a bi-cyclic group. In some embodiments, the cycloalkyl is a tri-cyclic group.

The term "haloalkyl", as used herein, means an alkyl group substituted with one or more halogens. When more than one halogen is present, the halogens may be the same or different. For examples, haloalkyl groups include, but are not limited to, fluoromethyl, difluoromethyl, trifluoromethyl, chlorodifluoromethyl, 2,2,2-trifluoroethyl, pentafluoroethyl, and the like.

The terms "halo" and "halogen", as used herein, mean halogen and includes chloro, fluoro, bromo, and iodo.

The term "heteroaryl" includes substituted or unsubstituted aromatic single ring structures, preferably 5- to 7-membered rings, more preferably 5- to 6-membered rings, whose ring structures include at least one heteroatom (e.g., O, N, or S), preferably one to four or one to 3 heteroatoms, more preferably one or two heteroatoms. When two or more heteroatoms are present in a heteroaryl ring, they may be the same or different. The term "heteroaryl" also includes "polycyclyl", "polycycle", and "polycyclic" ring systems having two or more cyclic rings in which two or more carbons are common to two adjoining rings, e.g., the rings are "fused rings," wherein at least one of the rings is heteroaromatic, e.g., the other cyclic rings can be cycloalkyls, cycloalkenyls, cycloalkynyls, aryls, heteroaryls, and/or heterocyclyls. In some preferred embodiments, preferred polycycles have 2-3 rings. In certain embodiments, preferred polycyclic ring systems have two cyclic rings in which both of the rings are aromatic. In certain embodiments, each ring of the polycycle contains from 3 to 10 atoms in the ring, preferably from 5 to 7. For examples, heteroaryl groups include, but are not limited to, pyrrole, furan, thiophene, imidazole, oxazole, thiazole, pyrazole, pyridine, pyrazine, pyridazine, quinoline, pyrimidine, indolizine, indole, indazole, benzimidazole, benzothiazole, benzofuran, benzothiophene, cinnoline, phthalazine, quinazoline, carbazole, phenoxazine, quinoline, purine and the like.

In some embodiments, the heteroaryl is a single-ring aromatic group. In some embodiments, the heteroaryl is a two-ring aromatic group. In some embodiments, the heteroaryl is a three-ring aromatic group.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. In certain embodiments, the ring structure can have two cyclic rings. In some embodiments, the two cyclic rings can have two or more atoms in common, e.g., the rings are "fused rings." Heterocyclyl groups include, for example, piperidine, piperazine, pyrrolidine, morpholine, lactones, lactams, and the like.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to aryl, heteroaryl, carbocycle, heterocycle, alkyl, alkenyl, alkynyl, and combinations thereof.

The terms "hydrazone moiety" or "hydrazone" refer to

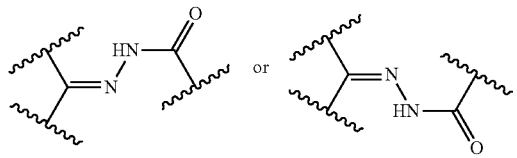

The stereochemistry of the hydrazone moiety can be E or Z. The term hydrazone as used herein includes both E and Z isomers.

At various places in the present specification substituents of compounds of the disclosure are disclosed in groups or in ranges. It is specifically intended that the disclosure include each and every individual subcombination of the members of such groups and ranges. For example, the term "$C_1$-$C_6$ alkyl" is specifically intended to individually disclose methyl, ethyl, propyl, isopropyl, n-butyl, sec-butyl, isobutyl, etc.

A "pharmaceutically acceptable salt" is a salt of a compound that is suitable for pharmaceutical use, including but not limited to metal salts (e.g., sodium, potassium, magnesium, calcium, etc.), acid addition salts (e.g., mineral acids, carboxylic acids, etc.), and base addition salts (e.g., ammonia, organic amines, etc.). The acid addition salt form of a compound that occurs in its free form as a base can be obtained by treating said free base form with an appropriate acid such as an inorganic acid, for example, a hydrohalic such as hydrochloric or hydrobromic, sulfuric, nitric, phosphoric and the like; or an organic acid, such as, for example, acetic, hydroxyacetic, propanoic, lactic, pyruvic, malonic, succinic, maleic, fumaric, malic, tartaric, citric, methanesulfonic, ethanesulfonic, benzenesulfonic, p-toluenesulfonic, cyclic, salicylic, p-aminosalicylic, pamoic and the like. See, e.g., WO 01/062726. Some pharmaceutically acceptable salts listed by Berge et al., *Journal of Pharmaceutical Sciences*, 66: 1-19 (1977), incorporated herein by reference in its entirety. Compounds containing acidic protons may be converted into their therapeutically active, non-toxic base addition salt form, e.g. metal or amine salts, by treatment with appropriate organic and inorganic bases. Appropriate base salt forms include, for example, ammonium salts, alkali and earth alkaline metal salts or ions, e.g., lithium, sodium, potassium, magnesium, calcium salts and the like, salts with organic bases, e.g. N-methyl-D-glucamine, hydrabamine salts, and salts with amino acids such as, for example, arginine, lysine and the like. Conversely, said salt forms can be converted into the free forms by treatment with an appropriate base or acid. Compounds and their salts can be in the form of a solvate, which is included within the scope of the present disclosure. Such solvates include for example hydrates, alcoholates and the like. See, e.g., WO 01/062726.

The disclosure further provides pharmaceutical compositions comprising one or more compounds of the disclosure together with a pharmaceutically acceptable carrier or excipient. Compounds or pharmaceutical compositions of the disclosure may be used in vitro or in vivo.

The term "isomer" as used herein includes, but is not limited to, tautomers, cis- and trans-isomers (E (entgegen), Z (zusammen)), R- and S-enantiomers (said R and S notation is used in correspondence with the rules described in Pure Appl. Chem. (1976), 45, 11-30), diastereomers, (D)-isomers, (L)-isomers, stereoisomers, the racemic mixtures thereof, and other mixtures thereof. All such isomers, as well as mixtures thereof, are intended to be included in this invention. Tautomers, while not explicitly indicated in the formulae described herein, are intended to be included within the scope of the present invention.

Compounds of the Invention

The present invention provides a compound having the structure represented by Formula (I):

Formula (I)

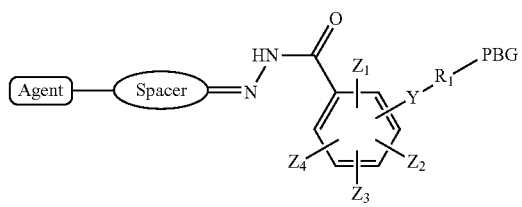

or a pharmaceutically acceptable salt, hydrate, solvate, or isomer thereof;

wherein:

Agent is selected from the group consisting of: a cytostatic agent, a cytotoxic agent, a cytokine, an immunosuppressive agent, an antirheumatic, an antiphlogistic, an antibiotic, an analgesic, a virostatic agent, an anti-inflammatory agent, an antimicotic agent, a transcription factor inhibitor, a cell cycle modulator, an MDR modulator, a proteasome or protease inhibitor, an apoptosis modulator, an enzyme inhibitor, a signal transduction inhibitor, a protease inhibitor, an angiogenesis inhibitor, a hormone or hormone derivative, an antibody or a fragment thereof, a therapeutically or diagnostically active peptide, a radioactive substance, a light emitting substance, a light absorbing substance, and a derivative of any of the foregoing;

Spacer is absent, or is selected from the group consisting of

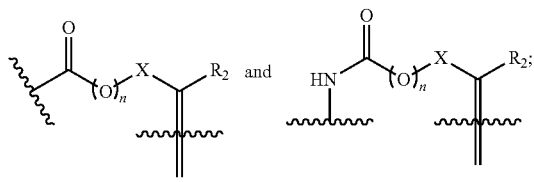

n is 0 or 1;

X is selected from the group consisting of optionally substituted $C_1$-$C_{18}$ alkyl wherein optionally up to six carbon atoms in said $C_1$-$C_{18}$ alkyl are each independently replaced with —$OCH_2CH_2$—; optionally substituted $C_1$-$C_{18}$ alkyl-NH—C(O)—$R_5$— wherein optionally up to six carbon atoms in said $C_1$-$C_{18}$ alkyl are each independently replaced with —$OCH_2CH_2$—, optionally substituted $C_1$-$C_{18}$ alkyl-C(O)—NH—$R_5$— wherein optionally up to six carbon atoms in said $C_1$-$C_{18}$ alkyl are each independently replaced with —$OCH_2CH_2$—; optionally substituted aryl; optionally substituted heteroaryl; and optionally substituted cycloalkyl;

$R_5$ is selected from the group consisting of an optionally substituted aryl, optionally substituted heteroaryl, and optionally substituted cycloalkyl;

Y is absent or selected from the group consisting of optionally substituted $C_1$-$C_6$ alkyl, —NH—C(O)—, —C(O)—NH—, —C(O)—O—, and —O—C(O)—;

$R_1$ is absent or selected from the group consisting of optionally substituted $C_1$-$C_{18}$ alkyl wherein optionally up to six carbon atoms in said $C_1$-$C_{18}$ alkyl are each independently replaced with —$OCH_2CH_2$—; optionally substituted $C_1$-$C_{18}$ alkyl-NH—C(O)$R_5$— wherein optionally up to six carbon atoms in said $C_1$-$C_{18}$ alkyl are each independently replaced with —$OCH_2CH_2$—, and optionally substituted $C_1$-$C_{18}$ alkyl-C(O)—NH—$R_5$— wherein optionally up to six carbon atoms in said $C_1$-$C_{18}$ alkyl are each independently replaced with —$OCH_2CH_2$—, or $R_1$ is a naturally or non-naturally occurring amino acid, or $R_1$ has the following formula:

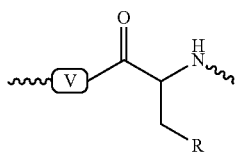

wherein:

<span style="border:1px solid">V</span> is absent, or is selected from the group consisting of:

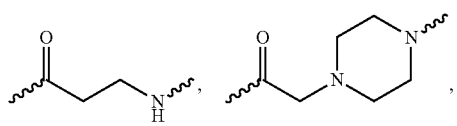

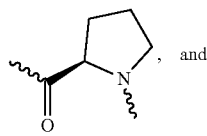

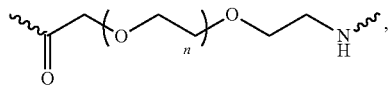

R is: ⤳ $OPO_3M_1$ wherein $M_1$=$Mg^{2+}$, 2 $Na^+$, 2$K^+$, 2$H^+$, 2$NH_4^+$ or ⤳ $SO_3M_2$ wherein $M_2$=$Na^+$, $K^+$, $H^+$, $NH_4^+$;

$R_2$ is selected from the group consisting of optionally substituted $C_1$-$C_{12}$ alkyl, optionally substituted aryl, and optionally substituted heteroaryl;

$Z_1$, $Z_2$, $Z_3$ and $Z_4$ are each independently selected from —H, an electron-withdrawing group, and/or a water-soluble group;

PBG is a protein-binding group selected the group consisting of from an optionally substituted maleimide group, an optionally substituted haloacetamide group, an optionally substituted haloacetate group, an optionally substituted pyridylthio group, an optionally substituted isothiocyanate group, an optionally substituted vinylcarbonyl group, an optionally substituted aziridine group, an optionally substituted disulfide group, an optionally substituted acetylene group, an optionally substituted N-hydroxysuccinimide ester group, an antibody or fragment thereof, and a derivatized antibody of derivatized fragment thereof;

wherein when Spacer is absent, Agent is linked to the nitrogen adjacent to Spacer by a double bond; and wherein at least one of $Z_1$, $Z_2$, $Z_3$ and $Z_4$ is an electron-withdrawing group.

In some embodiments of the compounds described herein, PBG is a protein-binding group selected from the group consisting of an optionally substituted maleimide group, an optionally substituted haloacetamide group, an optionally substituted haloacetate group, an optionally substituted pyridylthio group, an optionally substituted isothiocyanate group, an optionally substituted vinylcarbonyl group, an optionally substituted aziridine group, an optionally substituted disulfide group, an optionally substituted acetylene group, and an optionally substituted N-hydroxysuccinimide ester group.

In some embodiments, the PBG is associated with an antibody or fragment thereof. In some embodiments, the PBG is covalently bound to an antibody or fragment thereof. In some embodiments, the PBG is associated with albumin. In other embodiments, the PBG is covalently bound to endogenous or exogenous albumin. In other embodiments, the PGB is covalently bound to the cysteine-34 of endogenous or exogenous albumin.

In certain embodiments, the present invention provides a compound having the structure represented by Formula (I):

Formula (I)

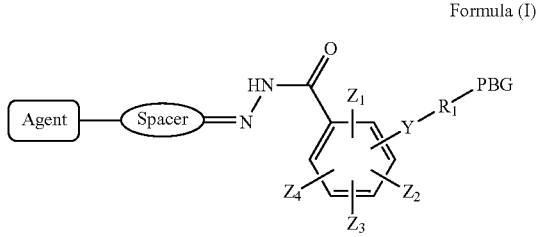

or a pharmaceutically acceptable salt, hydrate, solvate, or isomer thereof; wherein Agent is selected from the group consisting of a cytostatic agent, a cytotoxic agent, a cytokine, an immunosuppressive agent, an antirheumatic, an antiphlogistic, an antibiotic, an analgesic, a virostatic agent, an anti-inflammatory agent, an antimicotic agent, a transcription factor inhibitor, a cell cycle modulator, an MDR modulator, a proteasome or protease inhibitor, an apoptosis modulator, an enzyme inhibitor, a signal transduction inhibitor, a protease inhibitor, an angiogenesis inhibitor, a hormone or hormone derivative, an antibody or a fragment thereof, a therapeutically or diagnostically active peptide, a radioactive substance, a light emitting substance, a light absorbing substance, and a derivative of any of the foregoing;

Spacer is absent,

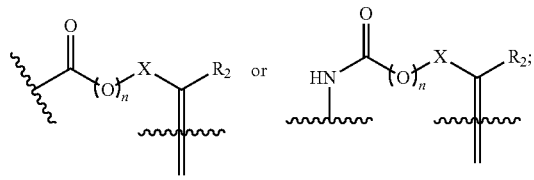

n is 0 or 1;

X is selected from the group consisting of optionally substituted $C_1$-$C_{18}$ alkyl wherein optionally up to six carbon atoms in said $C_1$-$C_{18}$ alkyl are each independently replaced with —$OCH_2CH_2$—; optionally substituted $C_1$-$C_{18}$ alkyl-NH—C(O)—$R_5$— wherein optionally up to six carbon atoms in said $C_1$-$C_{18}$ alkyl are each independently replaced with —$OCH_2CH_2$—, optionally substituted $C_1$-$C_{18}$ alkyl-C(O)—NH—$R_5$— wherein optionally up to six carbon atoms in said $C_1$-$C_{18}$ alkyl are each independently replaced with —$OCH_2CH_2$—; optionally substituted aryl; optionally substituted heteroaryl; and optionally substituted cycloalkyl;

$R_5$ is selected from the group consisting of an optionally substituted aryl, optionally substituted heteroaryl, and optionally substituted cycloalkyl;

Y is absent or selected from the group consisting of optionally substituted $C_1$-$C_6$ alkyl, —NH—C(O)—, —C(O)—NH—, —C(O)—O—, and —O—C(O)—;

$R_1$ is absent or selected from the group consisting of optionally substituted $C_1$-$C_{18}$ alkyl wherein optionally up to six carbon atoms in said $C_1$-$C_{18}$ alkyl are each independently replaced with —$OCH_2CH_2$—; optionally substituted $C_1$-$C_{18}$ alkyl-NH—C(O)$R_5$— wherein optionally up to six carbon atoms in said $C_1$-$C_{18}$ alkyl are each independently replaced with —$OCH_2CH_2$—, and optionally substituted $C_1$-$C_{18}$ alkyl-C(O)—NH—$R_5$— wherein optionally up to six carbon atoms in said $C_1$-$C_{18}$ alkyl are each independently replaced with —$OCH_2CH_2$—;

$R_2$ is selected from the group consisting of —H, optionally substituted $C_1$-$C_{12}$ alkyl, optionally substituted aryl, oand optionally substituted heteroaryl;

$Z_1$, $Z_2$, $Z_3$ and $Z_4$ are each independently selected from the group consisting of —H and an electron-withdrawing group;

PBG is a protein-binding group selected from the group consisting of an optionally substituted maleimide group, an optionally substituted haloacetamide group, an optionally substituted haloacetate group, an optionally substituted pyridylthio group, an optionally substituted isothiocyanate group, an optionally substituted vinylcarbonyl group, an optionally substituted aziridine group, an optionally substituted disulfide group, an optionally substituted acetylene group, an optionally substituted N-hydroxysuccinimide ester group and an antibody or fragment thereof;

wherein when Spacer is absent, Agent is linked to the nitrogen adjacent to Spacer by a double bond; and at least one of $Z_1$, $Z_2$, $Z_3$ and $Z_4$ is an electron-withdrawing group.

In some embodiments of the compounds described herein, PBG is a protein-binding group selected from the group consisting of an optionally substituted maleimide group, an optionally substituted haloacetamide group, an optionally substituted haloacetate group, an optionally substituted pyridylthio group, an optionally substituted isothiocyanate group, an optionally substituted vinylcarbonyl group, an optionally substituted aziridine group, an optionally substituted disulfide group, an optionally substituted acetylene group, and an optionally substituted N-hydroxysuccinimide ester group.

In some embodiments, the PBG is associated with an antibody or fragment thereof. In some embodiments, the PBG is covalently bound to an antibody or fragment thereof. In some embodiments, the PBG is associated with albumin. In other embodiments, the PBG is covalently bound to endogenous or exogenous albumin. In other embodiments, the PGB is covalently bound to the cysteine-34 of endogenous or exogenous albumin.

In certain embodiments, the invention provides a compound having the structure represented by Formula (II):

Formula (II)

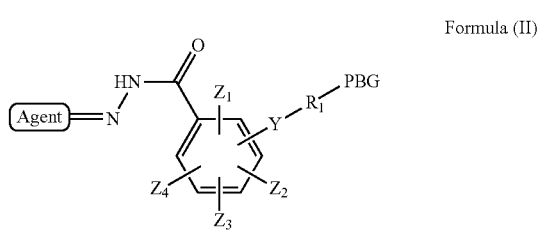

or a pharmaceutically acceptable salt, hydrate, solvate, or isomer thereof;

wherein Agent, PBG, Y, $R_1$, $Z_1$, $Z_2$, $Z_3$ and $Z_4$ are as defined for a compound of Formula (I).

In certain embodiments, the invention provides a compound having the structure represented by Formula (III):

Formula (III)

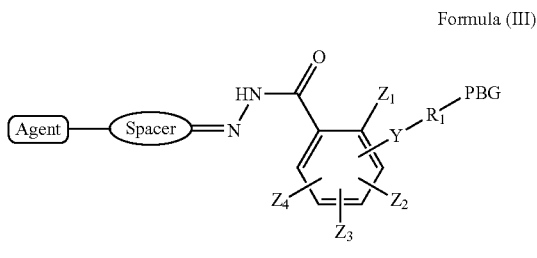

or a pharmaceutically acceptable salt, hydrate, solvate, or isomer thereof;

wherein Agent, Spacer, PBG, Y, $R_1$, $Z_2$, $Z_3$ and $Z_4$ are as defined for a compound of Formula (I); and wherein $Z_1$ is an electron withdrawing group.

In certain embodiments, the invention provides a compound having the structure represented by Formula (IV):

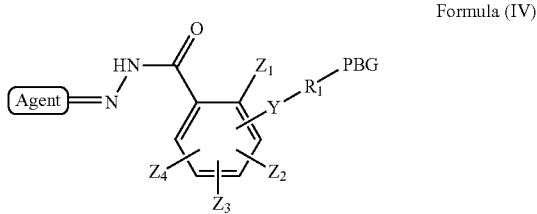

Formula (IV)

or a pharmaceutically acceptable salt, hydrate, solvate, or isomer thereof;

wherein Agent, PBG, Y, $R_1$, $Z_2$, $Z_3$ and $Z_4$ are as defined for a compound of Formula (I); and wherein $Z_1$ is an electron withdrawing group.

In certain embodiments, the invention provides a compound having the structure represented by Formula (V):

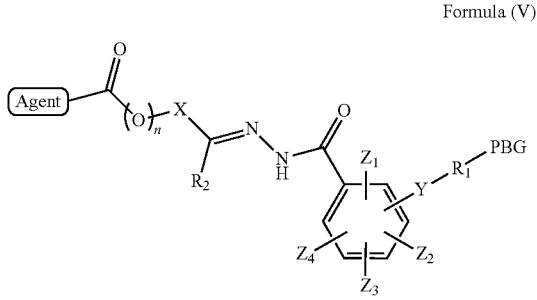

Formula (V)

or a pharmaceutically acceptable salt, hydrate, solvate, or isomer thereof;

wherein Agent, PBG, n, Y, $R_1$, $R_2$, $Z_1$, $Z_2$, $Z_3$ and $Z_4$ are as defined for a compound of Formula (I).

In certain embodiments, the invention provides a compound having the structure represented by Formula (VI):

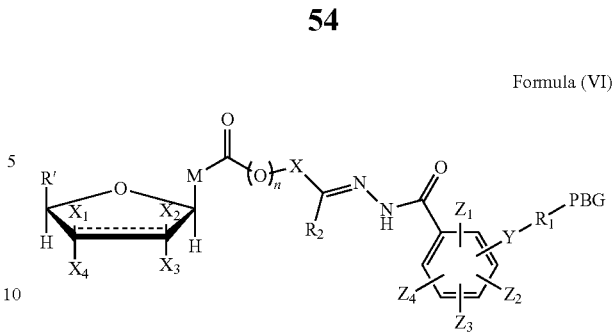

Formula (VI)

or a pharmaceutically acceptable salt, hydrate, solvate, or isomer thereof;

wherein:

M is a pyrimidine or purine group that contains at least one primary or secondary amino group and optionally contains one or more substituents selected from halogen;

$X_1$ and $X_2$ are each independently selected from the group consisting of —H, —OH, $C_1$-$C_6$ alkyl, halogen, and —$N_3$;

$X_3$ and $X_4$ are each independently, as valence permits, absent or selected from the group consisting of —H, —OH, $C_1$-$C_6$ alkyl, halogen, and —$N_3$;

R' is —$R_3$ or —$CH_2R_3$;

wherein each occurrence of $R_3$ is independently selected from the group consisting of —OH, —$CH_3$, —OP(O)(OH)$_2$, —P(O)(OH)OP(O)(OH)$_2$, —OP(O)(OH)OP(O)(OH)OP(O)(OH)$_2$, —OP(O)(OH)(NH$_2$), an amino acid, an acyl group, and a pharmaceutically acceptable salt thereof, wherein the salt contains an alkali metal ion, an alkaline metal ion, an ammonium or an alkyl substituted ammonium ion; and wherein X, n, $Z_1$, $Z_2$, $Z_3$, $Z_4$, Y, $R_1$, $R_2$ and PBG are as defined for a compound of Formula (V).

In certain embodiments, the invention provides a compound having the structure represented by Formula (VI):

Formula (VI)

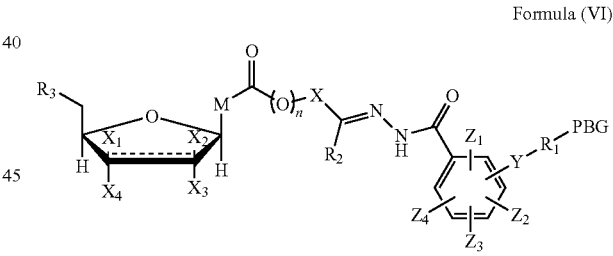

or a pharmaceutically acceptable salt, hydrate, solvate, or isomer thereof; wherein M is a pyrimidine or purine group that contains at least one primary or secondary amino group.

$X_1$ and $X_2$ are each independently selected from the group consisting of —H, —OH, $C_1$-$C_6$ alkyl, halogen, and —$N_3$.

$X_3$ and $X_4$ are each independently, as valence permits, absent or selected from the group consisting of —H, —OH, $C_1$-$C_6$ alkyl, halogen, and —$N_3$.

$R_3$ is selected from the group consisting of —OH, —OP(O)(OH)$_2$, —P(O)(OH)OP(O)(OH)$_2$, —OP(O)(OH)OP(O)(OH)OP(O)(OH)$_2$, —OP(O)(OH)(NH$_2$), an amino acid, an acyl group, and a pharmaceutically acceptable salt thereof, wherein the salt contains an alkali metal ion, an alkaline metal ion, an ammonium or an alkyl substituted ammonium ion; and wherein X, n, $Z_1$, $Z_2$, $Z_3$, $Z_4$, Y, $R_1$, $R_2$ and PBG are as defined for a compound of Formula (V).

In certain embodiments, the invention provides a compound having the structure represented by Formula (VII):

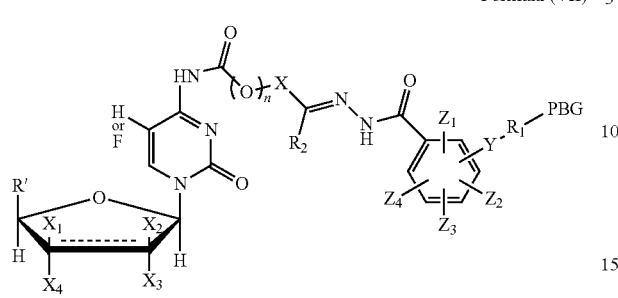

Formula (VII)

or a pharmaceutically acceptable salt, hydrate, solvate, or isomer thereof;

wherein R' is —$R_3$ or —$CH_2R_3$; and X, $X_1$, $X_2$, $X_3$, $X_4$, n, Y, $R_1$, $R_2$, $R_3$, $Z_1$, $Z_2$, $Z_3$, $Z_4$ and PBG are as defined for a compound of Formula (VI).

In certain embodiments, the invention provides a compound having a structure represented by Formula (VII):

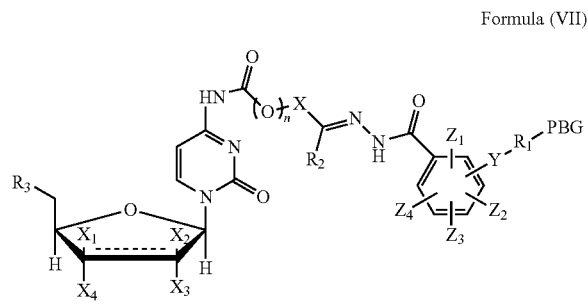

Formula (VII)

or a pharmaceutically acceptable salt, hydrate, solvate, or isomer thereof;

wherein X, $X_1$, $X_2$, $X_3$, $X_4$, n, Y, $R_1$, $R_2$, $R_3$, $Z_1$, $Z_2$, $Z_3$, $Z_4$ and PBG are as defined for a compound of Formula (V).

In certain embodiments, the present invention provides a compound having the structure represented by Formula (VIII):

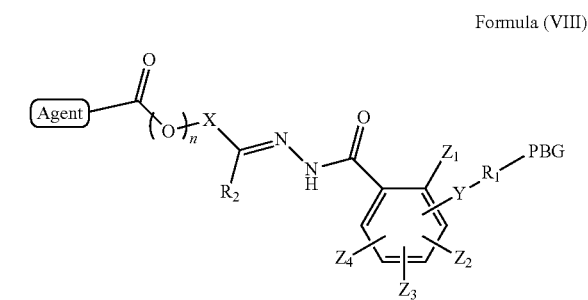

Formula (VIII)

or pharmaceutically acceptable salt, hydrate, solvate, or isomer thereof; wherein $Z_1$ is an electron withdrawing group; and wherein Agent, X, n, $R_2$, PBG, Y, $R_1$, $Z_2$, $Z_3$ and $Z_4$ are as defined for a compound of Formula (V).

In certain embodiments, the invention provides a compound having the structure represented by Formula (IX):

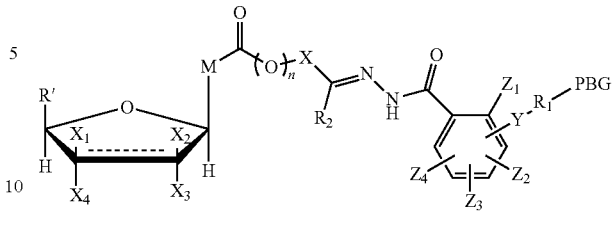

Formula (IX)

or a pharmaceutically acceptable salt, hydrate, solvate, or isomer thereof;

wherein:

M is a pyrimidine or purine group that contains at least one primary or secondary amino group and optionally contains one or more substituents selected from halogen;

$X_1$ and $X_2$ are each independently selected from the group consisting of —H, —OH, $C_1$-$C_6$ alkyl, halogen, and —$N_3$;

$X_3$ and $X_4$ are each independently, as valence permits, absent or selected from the group consisting of —H, —OH, $C_1$-$C_6$ alkyl, halogen, and —$N_3$;

R' is —$R_3$ or —$CH_2R_3$;

wherein each occurence of $R_3$ is independently selected from the group consisting of —OH, —$CH_3$, —OP(O)(OH)$_2$, —P(O)(OH)OP(O)(OH)$_2$, —OP(O)(OH)OP(O)(OH)OP(O)(OH)$_2$, —OP(O)(OH)(NH$_2$), an amino acid, an acyl group, and a pharmaceutically acceptable salt thereof, wherein the salt contains an alkali metal ion, an alkaline metal ion, an ammonium or an alkyl substituted ammonium ion; and wherein X, n, Y, $Z_1$, $Z_2$, $Z_3$, $Z_4$, $R_1$, $R_2$ and PBG are as defined for a compound of Formula (VIII).

In certain embodiments, the present invention provides a compound having the structure represented by Formula (IX):

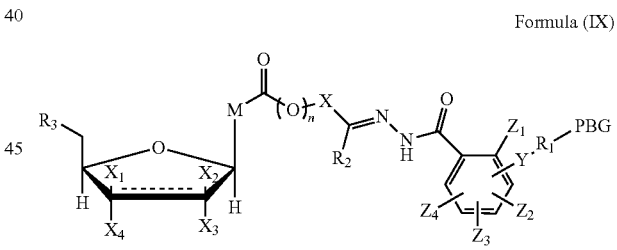

Formula (IX)

or a pharmaceutically acceptable salt, hydrate, solvate, or isomer thereof, wherein M is a pyrimidine or purine group that contains at least one primary or secondary amino group;

$X_1$ and $X_2$ are each independently selected from the group consisting of —H, —OH, $C_1$-$C_6$ alkyl, halogen, and —$N_3$;

$X_3$ and $X_4$ are each independently, as valence permits, absent or selected from the group consisting of —H, —OH, $C_1$-$C_6$ alkyl, halogen, adn —$N_3$;

$R_3$ is selected from —OH, —OP(O)(OH)$_2$, —P(O)(OH)OP(O)(OH)$_2$, —OP(O)(OH)OP(O)(OH)OP(O)(OH)$_2$, —OP(O)(OH)(NH$_2$), an amino acid, an acyl group, and a pharmaceutically acceptable salt thereof, wherein the salt contains an alkali metal ion, an alkaline metal ion, an ammonium or an alkyl substituted ammonium ion; and wherein X, n, Y, $Z_1$, $Z_2$, $Z_3$, $Z_4$, $R_1$, $R_2$ and PBG are as defined for a compound of Formula (VIII).

In certain embodiments, $X_1$, $X_2$, $X_3$, and $X_4$ are each independently selected from the group consisting of —H, —OH, —CH$_3$, —F, —Cl, —Br, —I, and —N$_3$.

In certain embodiments, the invention provides a compound having the structure represented by Formula (X):

Formula (X)

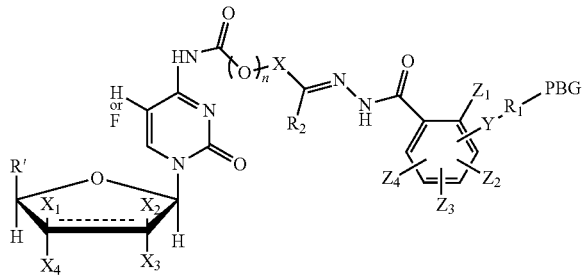

or a pharmaceutically acceptable salt, hydrate, solvate, or isomer thereof;

wherein R' is —R$_3$ or —CH$_2$R$_3$; and $X_1$, $X_2$, $X_3$, $X_4$, $R_3$, X, n, Y, $Z_1$, $Z_2$, $Z_3$, $Z_4$, $R_1$ and $R_2$ are as defined for a compound of Formula (IX).

In certain embodiments, the present invention provides a compound having the structure represented by Formula (X):

Formula (X)

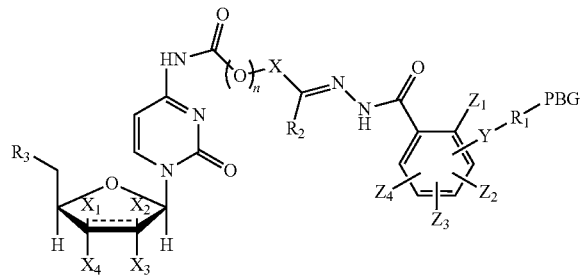

or a pharmaceutically acceptable salt, hydrate, solvate, or isomer thereof; wherein $X_1$, $X_2$, $X_3$, $X_4$, $R_3$, X, n, Y, $Z_1$, $Z_2$, $Z_3$, $Z_4$, $R_1$ and $R_2$ are as defined for a compound of Formula (IX).

In some embodiments, Agent is selected from the group consisting of N-nitrosoureas; doxorubicin, 2-pyrrolpyrrolinoanthracycline, morpholinoanthracycline, diacetatoxyalkylanthracycline, daunorubicin, epirubicin, idarubicin, nemorubicin, PNU-159682, mitoxantrone; ametantrone; chlorambucil, bendamustine, melphalan, oxazaphosphorines; 5-fluorouracil, 5'-deoxy-5-fluorocytidine, 2'-deoxy-5-fluoridine, cytarabine, cladribine, fludarabine, pentostatine, gemcitabine, 4-amino-1-(((2S,3R,4S,5R)-3,4-dihydroxy-5-methyltetrahydrofuran-2-yl)methyl)-5-fluoropyrimidin-2 (1H)-one, thioguanine; methotrexate, raltitrexed, pemetrexed, plevitrexed; paclitaxel, docetaxel; topotecan, irinotecan, SN-38, 10-hydroxycamptothecin, GG211, lurtotecan, 9-aminocamptothecin, camptothecin, 7-formylcamptothecin, 7-acetylcamptothecin, 9-formylcamptothecin, 9-acetylcamptothecin, 9-formyl-10-hydroxycamptothecin, 10-formylcamptothecin, 10-acetylcamptothecin, 7-butyl-10-aminocamptothecin, 7-butyl-9-amino-10,11-methylenedioxocamptothecin; vinblastine, vincristine, vindesine, vinorelbine; calicheamicins; maytansine, maytansinol; auristatin (including but not limited to auristatin D, auristatin E, auristatin F, monomethyl auristatin D, monomethyl auristatin E, monomethyl auristatin F, monomethyl auristatin F methylester, auristatin PYE auristatin PHE, the related natural product dolastatin 10, and derivatives thereof); amatoxins (including but not limited to α-amanitin, β-amanitin, γ-amanitin, ε-amanitin, amanin, amaninamide, amanullin, and amanullinic acid and derivatives thereof); duocarmycin A, duocarmycin B1, duocarmycin B2, duocarmycin C, duocarmycin SA, CC1065, adozelesin, bizelesin, carzelesin; eribulin; trabectedin; pyrrolobenzodiazepine, anthramycin, tomaymycin, sibiromycin, DC-81, DSB-120; epothilones; bleomycin; dactinomycin; plicamycin, miromycin C and cis-configured platinum(II) complexes; or a derivative of any of the foregoing.

In some embodiments, Agent is selected from the group consisting of N-nitrosoureas; doxorubicin, 2-pyrrollinoanthracycline, morpholinoanthracycline, diacetatoxyalkylanthracycline, daunorubicin, epirubicin, idarubicin, nemorubicin, mitoxantrone; ametantrone; chlorambucil, bendamustine, melphalan, oxazaphosphorines; 5-fluorouracil, 2'-deoxy-5-fluoridine, cytarabine, cladribine, fludarabine, pentostatine, gemcitabine, thioguanine; methotrexate, raltitrexed, pemetrexed, plevitrexed; paclitaxel, docetaxel; topotecan, irinotecan, SN-38, 1 0-hydroxycamptothecin, GG211, lurtotecan, 9-aminocamptothecin, camptothecin; vinblastine, vincristine, vindesine, vinorelbine; calicheamicins; maytansinoids; auristatins; epothilones; bleomycin, dactinomycin, plicamycin, miromycin C and cis-configured platinum(II) complexes; or a derivative of any of the foregoing.

In some embodiments, $Z_1$, $Z_2$, $Z_3$ and $Z_4$ are each independently selected from the group consisting of: —H, halogen, —C(O)OH, —C(O)O—C$_1$-C$_6$ alkyl, —NO$_2$, haloalkyl, —S(O)$_2$—C$_1$-C$_6$ alkyl, and —CN. In some embodiments, $Z_1$, $Z_2$, $Z_3$ and $Z_4$ are each independently selected from the group consisting of: —H, —Cl, —Br, —I, —F, —C(O)OH, —NO$_2$, —CF$_3$, and —CN. In some embodiments, $Z_1$, $Z_2$, $Z_3$ and $Z_4$ are each independently selected from the group consisting of: —H, —F, —NO$_2$, and —CF$_3$. In some embodiments, $Z_1$, $Z_2$, $Z_3$ and $Z_4$ are each independently selected from the group consisting of: —OP(O)(OH)$_2$, —P(O)(OH)OP(O)(OH)$_2$, —OP(O)(OH)OP(O)(OH)OP(O)(OH)$_2$, —OP(O)(OH)(NH$_2$), —P(O)(OH)$_2$, —SO$_3$H, and a pharmaceutically acceptable salt thereof. In some embodiments, at least one of $Z_1$, $Z_2$, $Z_3$ and $Z_4$ is not —H.

In some embodiments, $Z_1$, $Z_2$, $Z_3$ and $Z_4$ are each independently selected from the group consisting of —H, halogen, —C(O)OH, —C(O)O—C$_1$-C$_6$ alkyl, —NO$_2$, haloalkyl, —S(O)$_2$—C$_1$-C$_6$ alkyl, and —CN. In some embodiments, $Z_1$, $Z_2$, $Z_3$ and $Z_4$ are each independently selected from the group consisting of —H, —Cl, —Br, —I, —F, —C(O)OH, —NO$_2$, —CF$_3$, and —CN. In some embodiments, $Z_1$, $Z_2$, $Z_3$ and $Z_4$ are each independently selected from the group consisting of —H, —Cl, —F, —NO$_2$, and —CF$_3$. In some embodiments, at least one of $Z_1$, $Z_2$, $Z_3$ and $Z_4$ is not —H.

In some embodiments, $Z_1$ is selected from halogen, —C(O)OH, —C(O)O—C$_1$-C$_6$ alkyl, —NO$_2$, haloalkyl, —S(O)$_2$—C$_1$-C$_6$ alkyl, and —CN; and $Z_2$, $Z_3$ and $Z_4$ are each independently selected from the group consisting of —H, halogen, —C(O)OH, —C(O)O—C$_1$-C$_6$ alkyl, —NO$_2$, haloalkyl, —S(O)$_2$—C$_1$-C$_6$ alkyl, and —CN. In some embodiments, $Z_1$ is selected from the group consisting of —Cl, —Br, —I, —F, —C(O)OH, —NO$_2$, —CF$_3$, and —CN; and $Z_2$, $Z_3$ and $Z_4$ are each independently selected from the group consisting of —H, —Cl, —Br, —I, —F, —C(O)OH, —NO$_2$, —CF$_3$, and —CN. In some embodiments, $Z_1$ is selected from the group consisting of —Cl, —F, and —NO$_2$; and $Z_2$, $Z_3$ and $Z_4$ are each independently selected from the group consisting of —H, —Cl, —F, —NO$_2$, and —CF$_3$.

In some embodiments, $R_2$ is methyl.

In some embodiments, $X_1$ is —H, $X_2$ is —F, $X_3$ is —F and $X_4$ is —OH.

The Hydrazone Moiety

The drug delivery system contains an acid-labile, cleavable hydrazone moiety. The cleavage of the hydrazone moiety and the half-life of the drug release vary according to the electron-withdrawing substituents and their position on the phenyl ring to which the hydrazone is attached. The phenyl ring may be substituted as follows

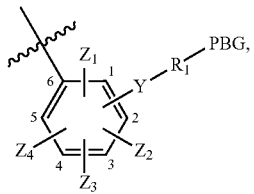

wherein PBG, $R_1$, Y, $Z_1$, $Z_2$, $Z_3$ and $Z_4$ are as defined herein.

In some embodiments, the phenyl ring comprises at least one electron-withdrawing group. In some preferred embodiments, the phenyl ring comprises one electron-withdrawing group attached to position 1. In some embodiments, the phenyl ring comprises one electron-withdrawing group attached to position 2. In some embodiments, the phenyl ring comprises one electron-withdrawing group attached to position 3. In some preferred embodiments, the phenyl ring comprises two electron-withdrawing group attached to positions 1 and 2. In some embodiments, the phenyl ring comprises two electron-withdrawing group attached to positions 1 and 3. In some embodiments, the phenyl ring comprises two electron-withdrawing group attached to positions 1 and 4. In some embodiments, the phenyl ring comprises two electron-withdrawing group attached to positions 1 and 5. In some embodiments, the phenyl ring comprises two electron-withdrawing group attached to positions 2 and 3. In some embodiments, the phenyl ring comprises two electron-withdrawing group attached to positions 2 and 4. In some embodiments, the phenyl ring comprises two electron-withdrawing group attached to positions 2 and 5. In some embodiments, the phenyl ring comprises two electron-withdrawing group attached to positions 3 and 4. In some embodiments, the phenyl ring comprises two electron-withdrawing group attached to positions 3 and 5. In some embodiments, the phenyl ring comprises three electron-withdrawing group attached to positions 1, 3 and 5.

In some embodiments, $Z_1$, $Z_2$, $Z_3$ and $Z_4$ are each independently selected from the group consisting of: —H, halogen, —C(O)OH, —C(O)O—C$_1$-C$_6$ alkyl, —NO$_2$, haloalkyl, —S(O)$_2$—C$_1$-C$_6$ alkyl, and —CN. In some embodiments, $Z_1$, $Z_2$, $Z_3$ and $Z_4$ are each independently selected from the group consisting of: —H, —Cl, —Br, —I, —F, —C(O)OH, —NO$_2$, —CF$_3$, and —CN. In some embodiments, $Z_1$, $Z_2$, $Z_3$ and $Z_4$ are each independently selected from the group consisting of: —H, —F, —NO$_2$, and —CF$_3$. In some embodiments, $Z_1$, $Z_2$, $Z_3$ and $Z_4$ are each independently selected from the group consisting of: —OP(O)(OH)$_2$, —P(O)(OH)OP(O)(OH)$_2$, —OP(O)(OH)OP(O)(OH)OP(O)(OH)$_2$, —OP(O)(OH)(NH$_2$), —P(O)(OH)$_2$, —SO$_3$H, and a pharmaceutically acceptable salt thereof. In some embodiments, at least one of $Z_1$, $Z_2$, $Z_3$ and $Z_4$ is not —H.

In some embodiments, $Z_1$, $Z_2$, $Z_3$ and $Z_4$ are each independently selected from the group consisting of —H, —Cl, —Br, —I, —F, —C(O)OH, —NO$_2$, —CF$_3$, and —CN, wherein at least one of $Z_1$, $Z_2$, $Z_3$ and $Z_4$ is not —H. In some embodiments, $Z_1$, $Z_2$, $Z_3$ and $Z_4$ are each independently selected from the group consisting of —H, —F, —NO$_2$, and —CF$_3$ wherein at least one of $Z_1$, $Z_2$, $Z_3$ and $Z_4$ is not —H. In some embodiments, $Z_1$, $Z_2$, $Z_3$ and $Z_4$ are each independently selected from the group consisting of —H, —F, —NO$_2$, and —CF$_3$ wherein at least one of $Z_1$, $Z_2$, $Z_3$ and $Z_4$ is not —H.

In some embodiments, half-life of drug release is about 1.5 hours, about 2.0 hours, about 2.5 hours, about 3.0 hours, about 3.5 hours, about 4.0 hours, about 4.5 hours, about 5.0 hours, about 5.5 hours, about 6.0 hours, about 6.5 hours, about 7.0 hours, about 7.5 hours, about 8.0 hours, about 8.5 hours, about 9.0 hours, about 9.5 hours, about 10.0 hours, about 10.5 hours, about 11.0 hours, about 11.5 hours, about 12.0 hours, about 12.5 hours, about 13.0 hours, about 13.5 hours, about 14.0 hours, about 14.5 hours, about 15.0 hours, about 15.5 hours, about 16.0 hours, about 16.5 hours, about 17.0 hours, about 17.5 hours, about 18.0 hours, about 18.5 hours, about 19.0 hours, about 19.5 hours, or about 20.0 hours.

Without being bound by theory, a phenyl ring comprising one electron-withdrawing group attached to position 1 stabilizes the hydrazone moiety, resulting in a slow and prolonged release of Agent in acidic conditions. In some embodiments, the position of the electron-withdrawing group on the phenyl ring with respect to the position of the hydrazone moiety on the phenyl ring provides a method for controlling the release of the drug.

In some embodiments, the invention provides a method of making a compound to control the release of a drug by modifying the drug to add a

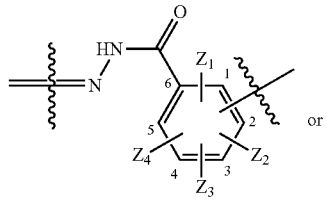

or

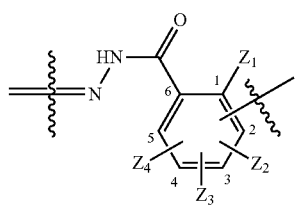

moiety as described herein for Formulae I, II, III, IV, V, VI, VII, VIII, IX and X.

Some embodiments of the invention include conjugates with the substitution patterns and the corresponding half-lives of drug release shown in Table A (HSA stands for human serum albumin). The structure of nemorubicin is

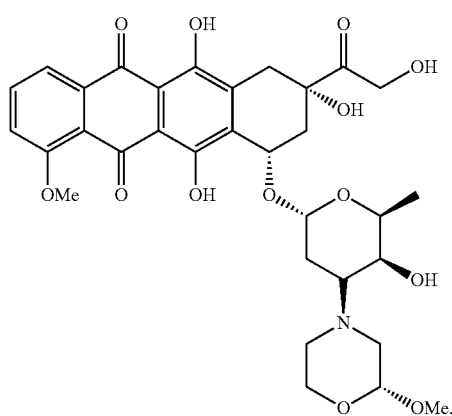

The nemorubicin conjugates represented in Table A have the following structure:

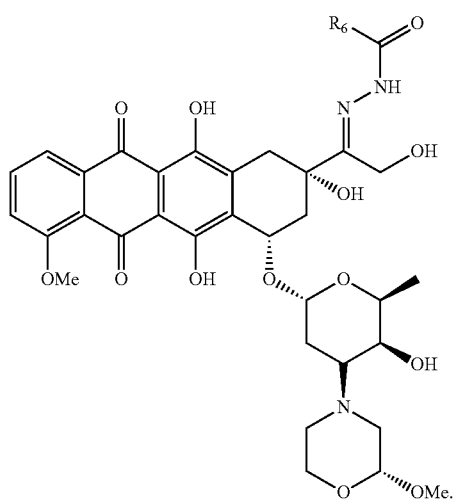

TABLE A

| Compound | R₆ | Half-life at pH 5.0 (h) |
|---|---|---|
| 1 | HSA-succinimide-phenyl | 1.35 |
| 2 | HSA-succinimide-(3-F)phenyl | 3.05 |
| 3 | HSA-succinimide-(2-F)phenyl | 1.45 |
| 4 | HSA-succinimide-(3-Cl)phenyl | 3.45 |
| 5 | HSA-succinimide-(2-Cl)phenyl | 1.45 |
| 6 | HSA-succinimide-(2-F,3-Cl)phenyl | 4.40 |
| 7 | HSA-succinimide-(2,3-diF)phenyl | 3.00 |
| 8 | HSA-succinimide-(meta)phenyl | 1.35 |
| 9 | HSA-succinimide-(4-F,meta)phenyl | 3.20 |
| 10 | HSA-succinimide-(3-CF₃,5-)phenyl | 2.00 |

TABLE A-continued
| Compound | R6 | Half-life at pH 5.0 (h) |
|---|---|---|
| 11 | *(3-chloro-phenyl succinimide, HSA)* | 2.20 |
| 12 | *(3-fluoro-phenyl succinimide, HSA)* | 2.05 |
| 13 | *(3-nitro-phenyl succinimide, HSA)* | 2.30 |
| 14 | *(4-nitro-phenyl succinimide, HSA)* | 10.40 |
In some embodiments, the compound of the invention is selected from:
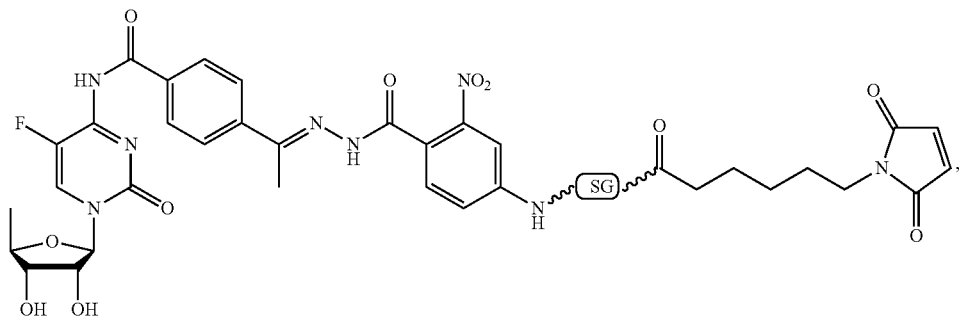
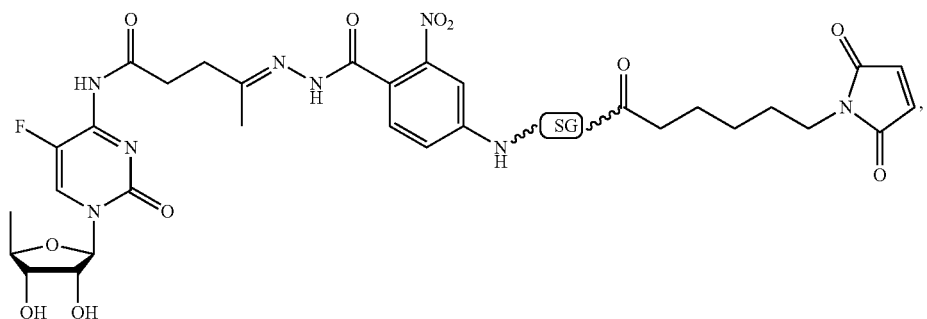

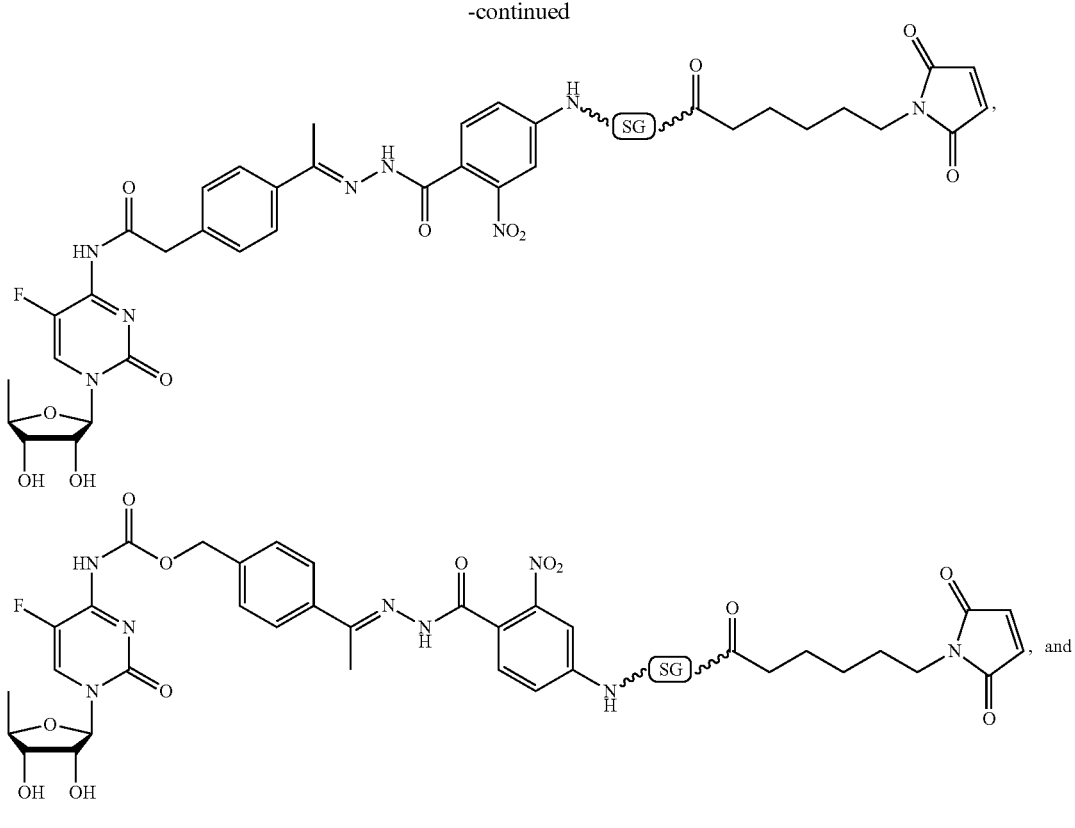
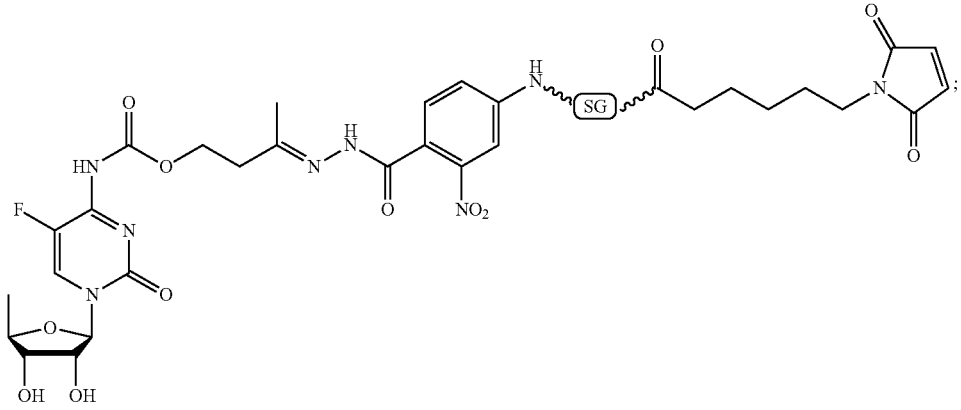
or a pharmaceutically acceptable salt, hydrate, solvate, or isomer thereof,
wherein:
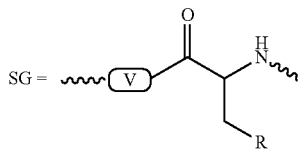
☐v☐ is absent, or is selected from the group consisting of:
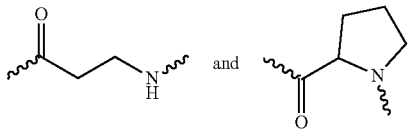
R is ⟿OPO$_3$M$_1$ wherein M$_1$=Mg$^{2+}$, 2 Na$^+$, 2K$^+$, 2H$^+$, 2NH$_4^+$, Na$^+$, K$^+$, NH$_4^+$, and/or H+
or
⟿SO$_3$M$_2$ wherein M$_2$=Na$^+$, K$^+$, H$^+$, and/or NH$_4^+$.

In some embodiments, the compound is selected from the group consisting of:
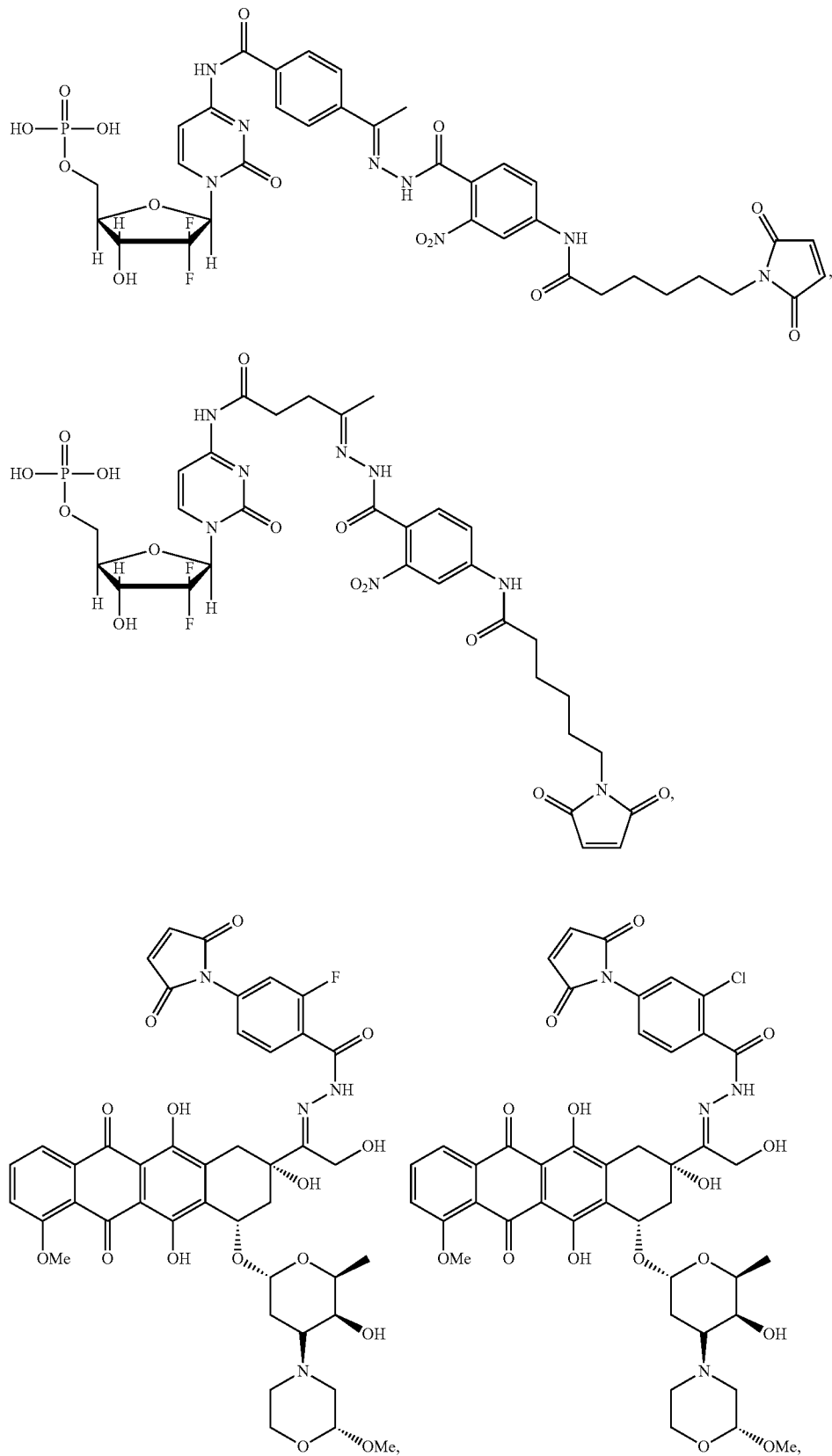

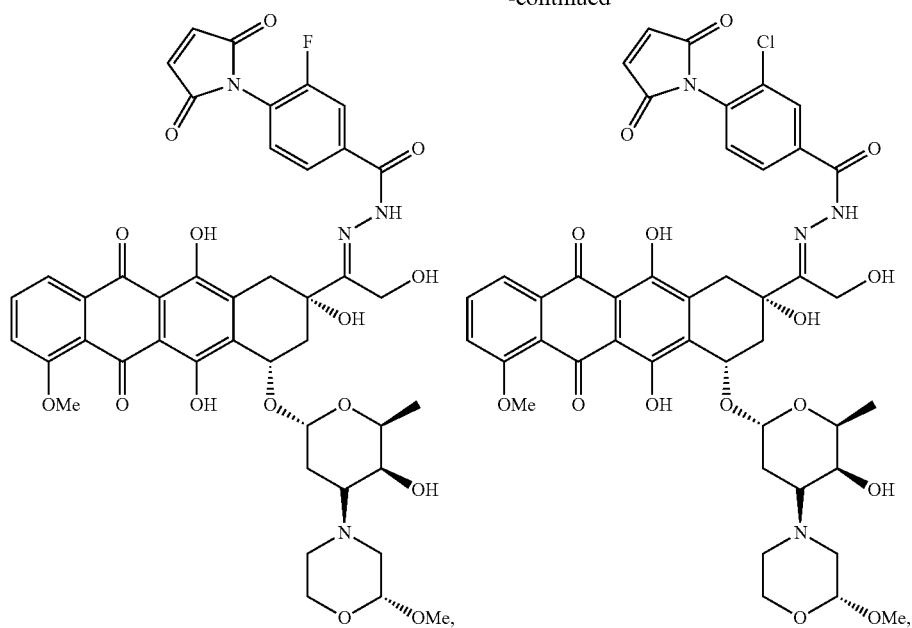
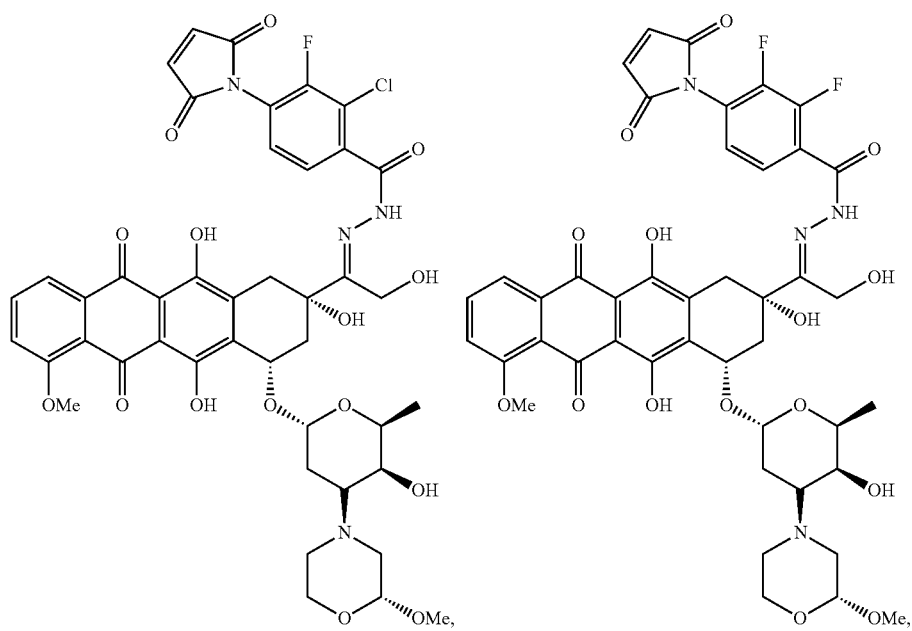

71   72
-continued
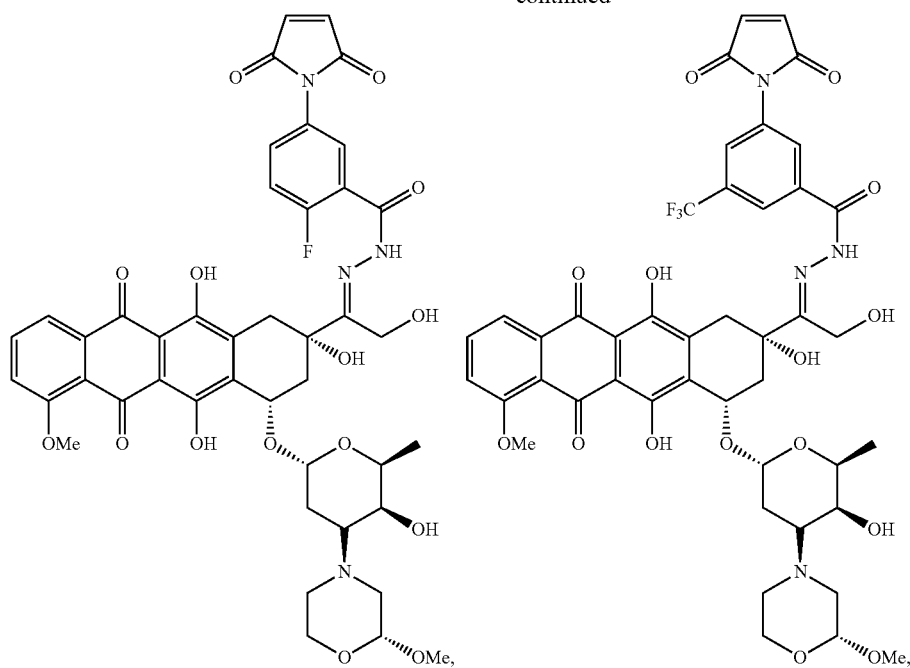
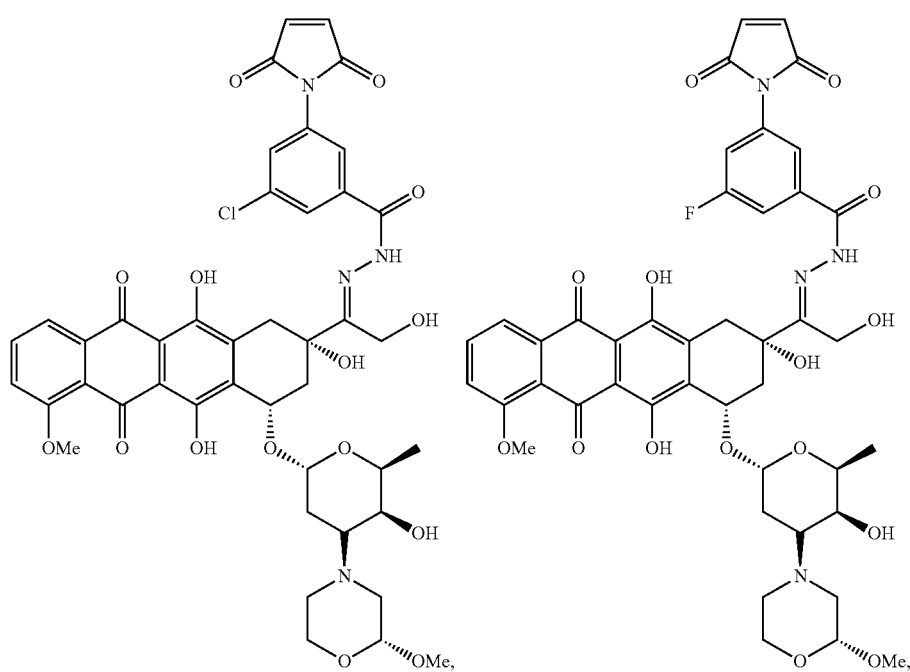

73 74
-continued
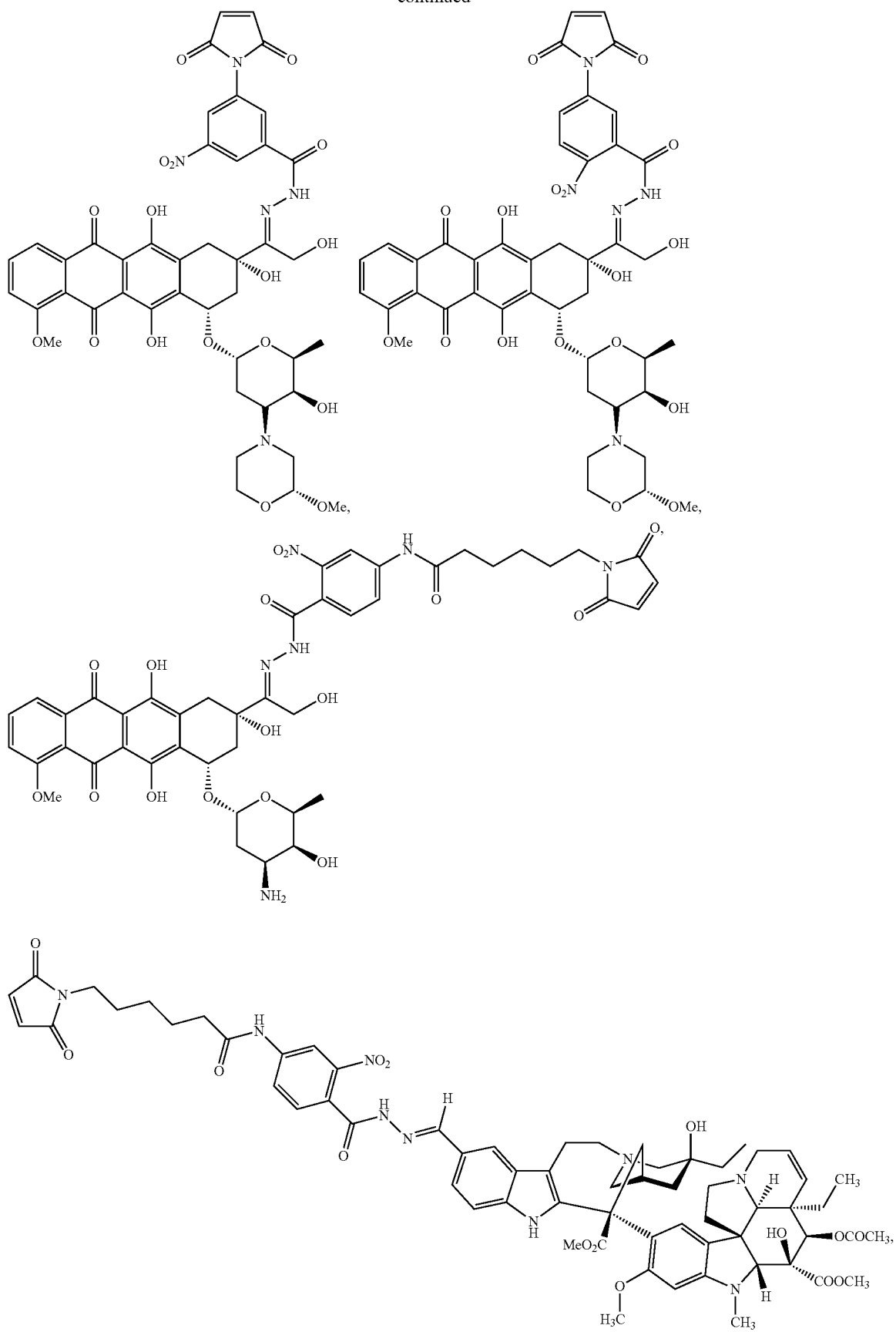

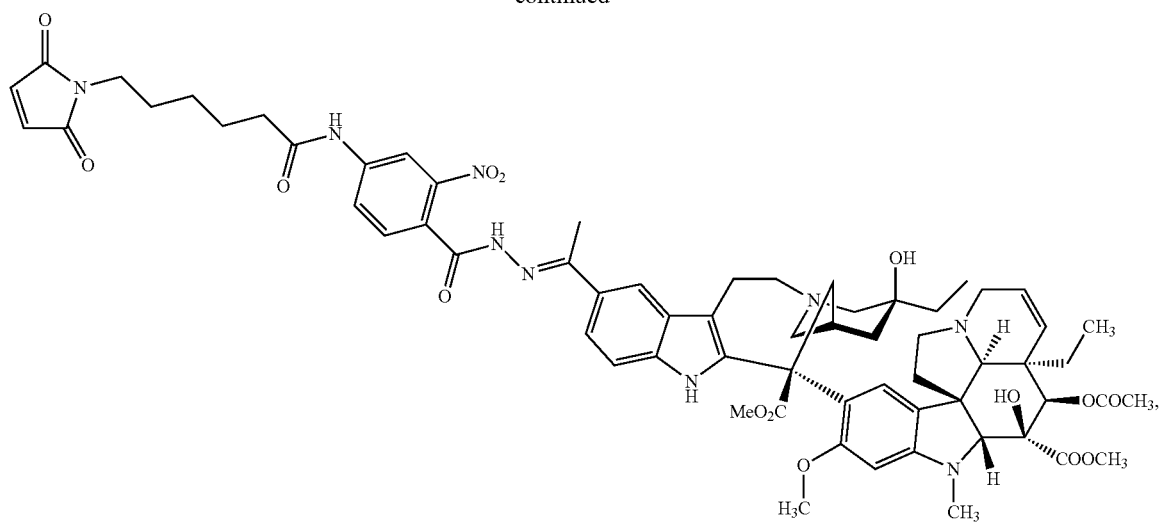
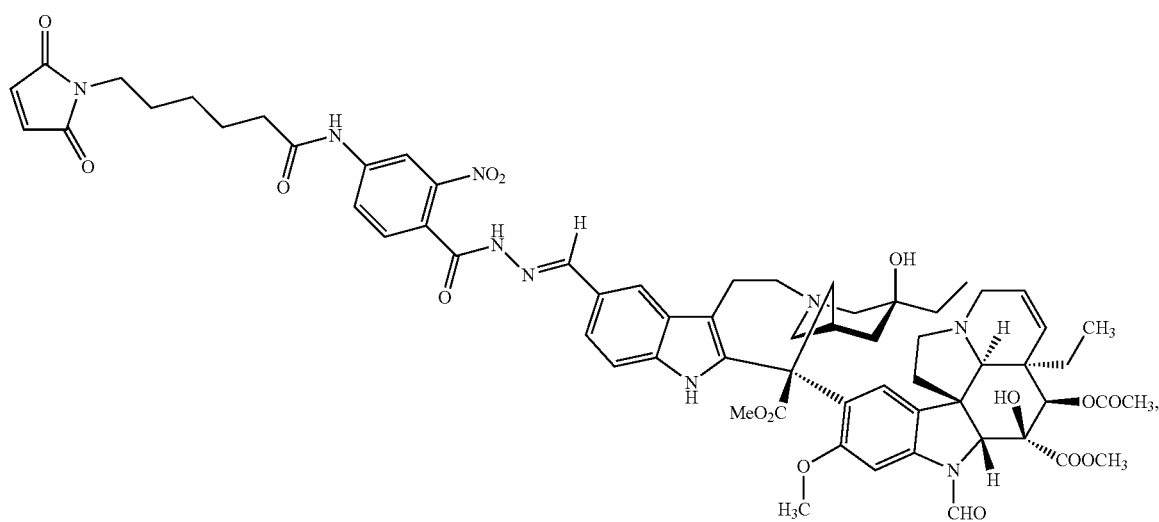
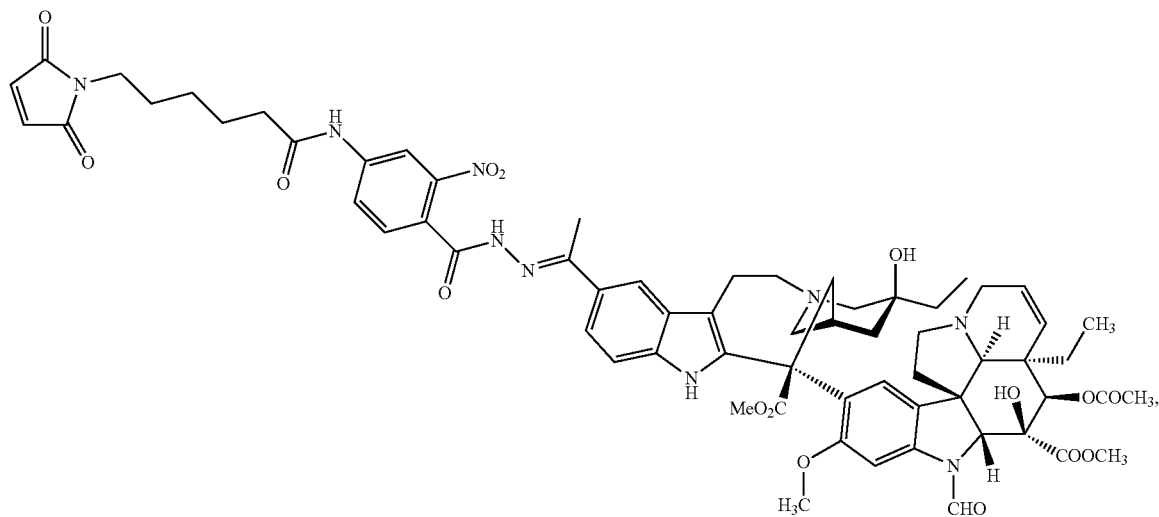

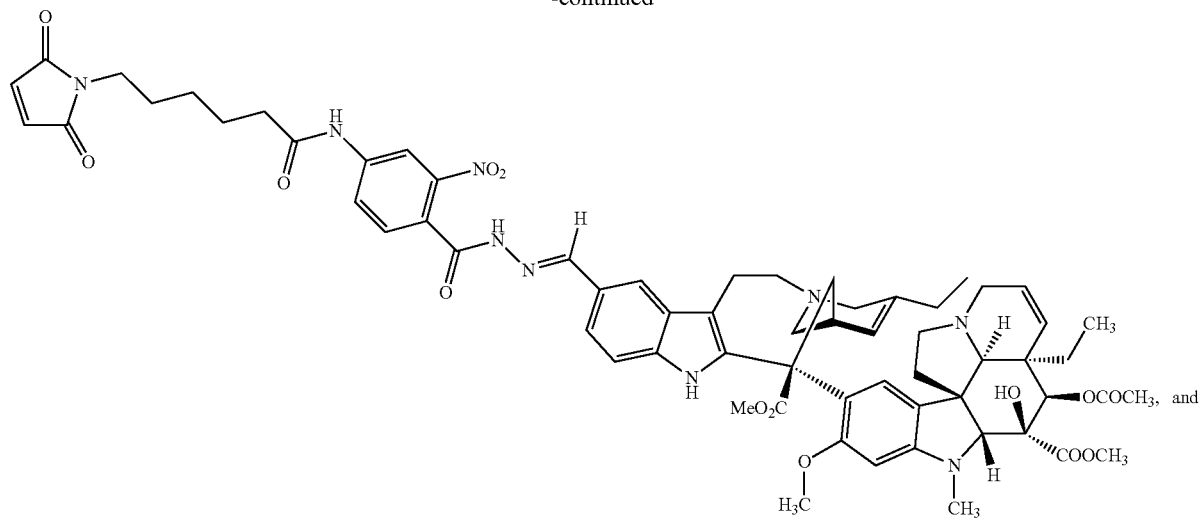
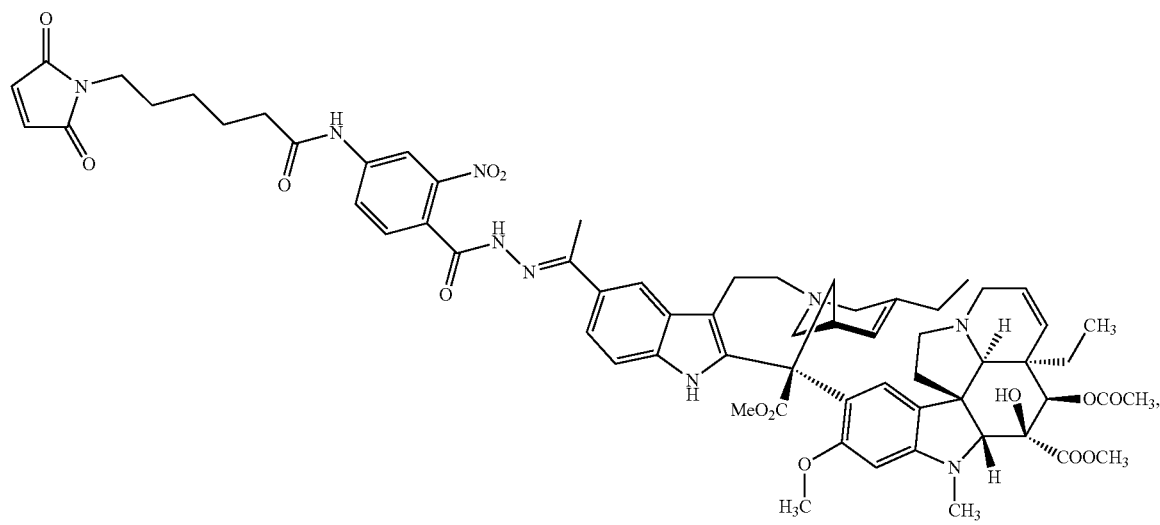
or a pharmaceutically acceptable salt, hydrate, solvate, or isomer thereof.
In some embodiments, the compound of the present invention is selected from the group consisting of:
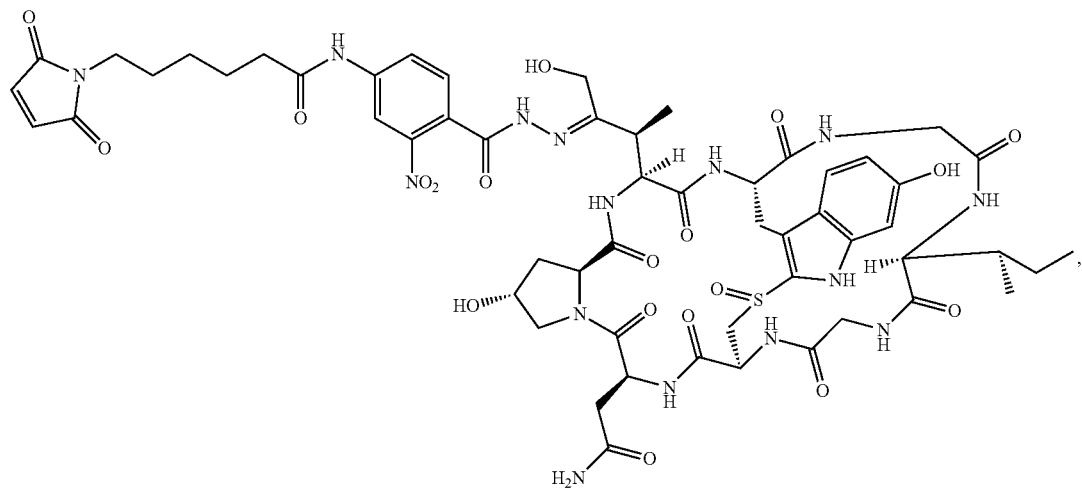

-continued
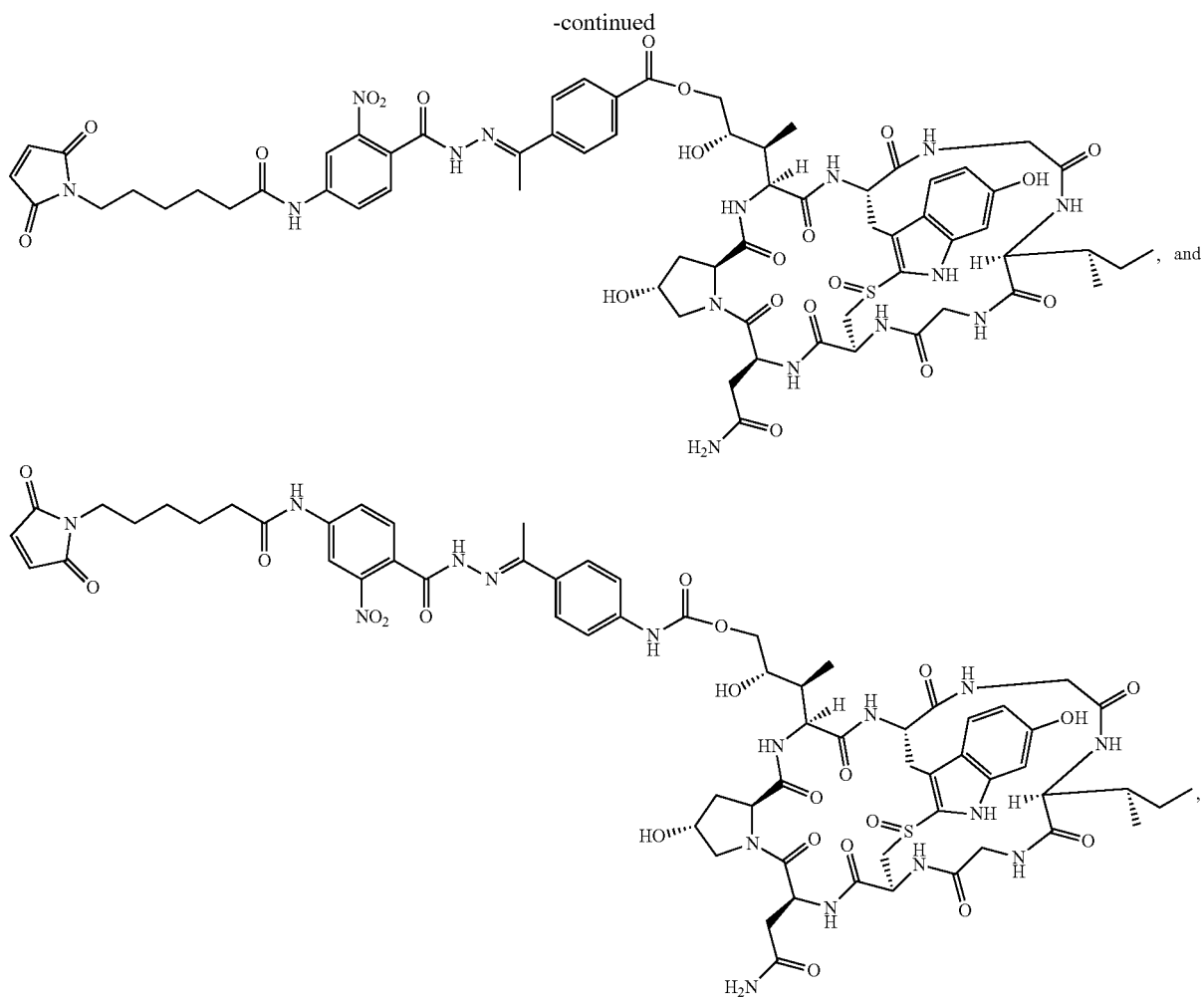
or a pharmaceutically acceptable salt, hydrate, solvate, or isomer thereof.
In some embodiments, the compound of the present invention is selected from the group consisting of:
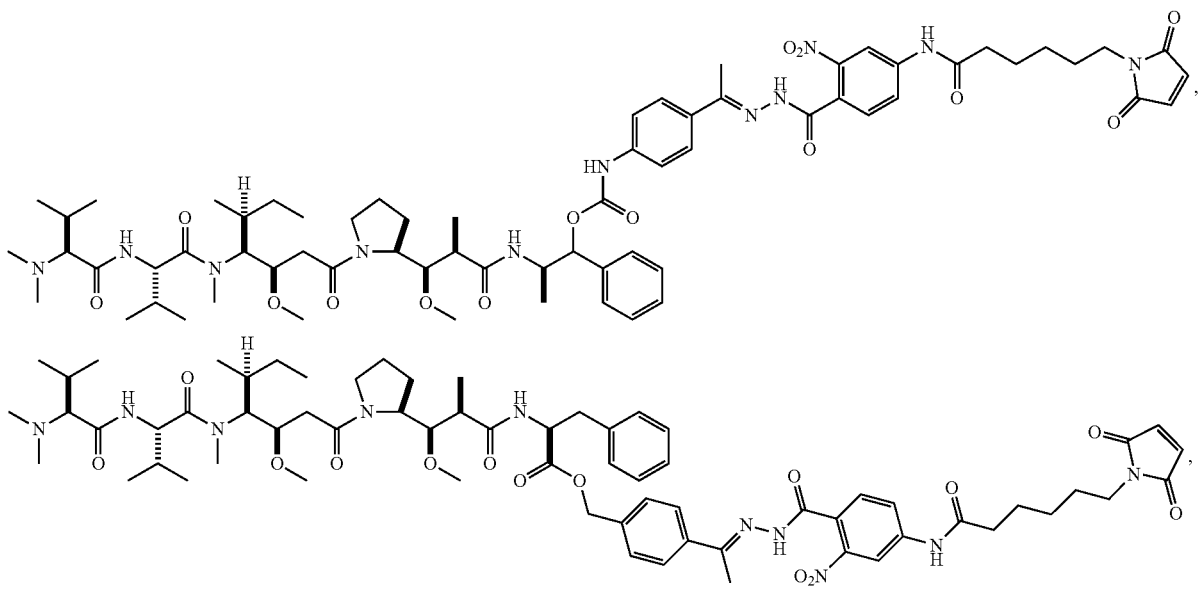

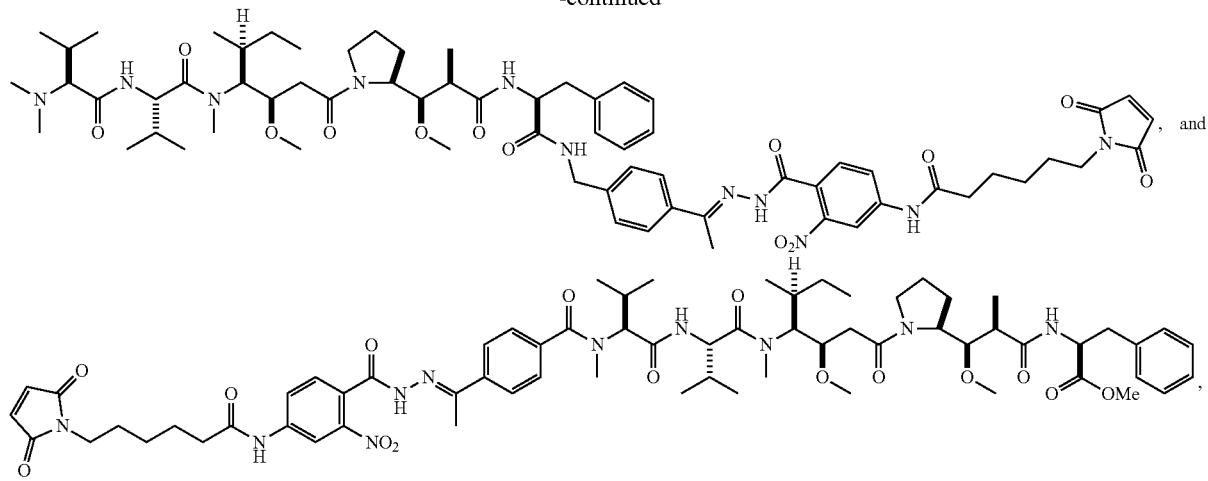

or a pharmaceutically acceptable salt, hydrate, solvate, or isomer thereof.

In some embodiments, the compound is compound 15, having the structure:

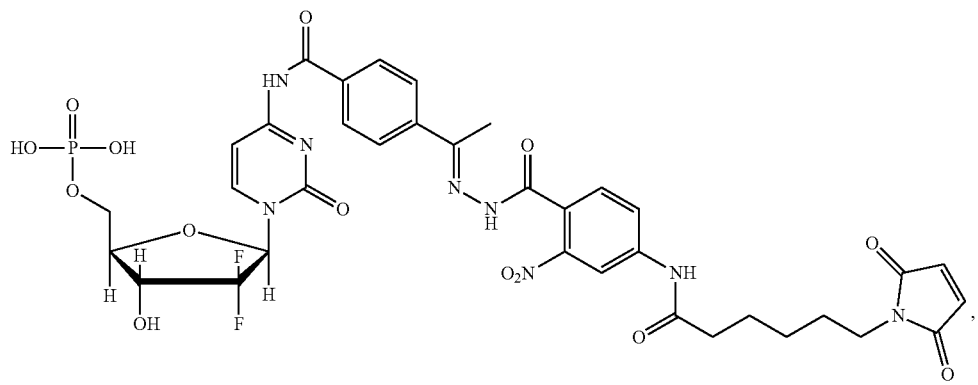

In some embodiments, compound 15 prevents deactivation of gemcitabine, resulting in sustained tumor exposure.

The Agent

In some embodiments, the Agent is selected from the group consisting of a cytostatic agent, a cytotoxic agent, a cytokine, an immunosuppressant, an antirheumatic, an antiphlogistic, an antibiotic, an analgesic, an anti-inflammatory agent, a virostatic, an antimicotic agent, a transcription factor inhibitor, a cell cycle modulator, an MDR modulator, a proteasome or protease inhibitor, an apoptosis modulator, an enzyme inhibitor, an angiogenesis inhibitor, a hormone or hormone derivative, an antibody or a fragment thereof, a therapeutically or diagnostically active peptide, a radioactive substance, a light emitting substance, a light absorbing substance, a derivative of any of the foregoing, a pharmaceutically acceptable salt, hydrate, solvate, or isomer of any of the foregoing.

In some embodiments, Agent is selected from the group consisting of N-nitrosoureas; doxorubicin, 2-pyrrolpyrrolinoanthracycline, morpholinoanthracycline, diacetatoxyalkylanthracycline, daunorubicin, epirubicin, idarubicin, nemorubicin, PNU-159682, mitoxantrone; ametantrone; chlorambucil, bendamustine, melphalan, oxazaphosphorines; 5-fluorouracil, 5'-deoxy-5-fluorocytidine, 2'-deoxy-5-fluoridine, cytarabine, cladribine, fludarabine, pentostatine, gemcitabine, 4-amino-1-(((2S,3R,4S,5R)-3,4-dihydroxy-5-methyltetrahydrofuran-2-yl)methyl)-5-fluoropyrimidin-2(1H)-one, thioguanine; methotrexate, raltitrexed, pemetrexed, plevitrexed; paclitaxel, docetaxel; topotecan, irinotecan, SN-38, 10-hydroxycamptothecin, GG211, lurtotecan, 9-aminocamptothecin, camptothecin, 7-formylcamptothecin, 7-acetylcamptothecin, 9-formylcamptothecin, 9-acetylcamptothecin, 9-formyl-10-hydroxycamptothecin, 10-formylcamptothecin, 10-acetylcamptothecin, 7-butyl-10-aminocamptothecin, 7-butyl-9-amino-10,11-methylenedioxocamptothecin; vinblastine, vincristine, vindesine, vinorelbine; calicheamicins; maytansine, maytansinol; auristatin (including but not limited to auristatin D, auristatin E, auristatin F, monomethyl auristatin D, monomethyl auristatin E, monomethyl auristatin F, monomethyl auristatin F methylester, auristatin PYE auristatin PHE, the related natural product dolastatin 10, and derivatives thereof); amatoxins (including but not limited to α-amanitin, γ-amanitin, ε-amanitin, amanin, amaninamide, amanullin, and amanullinic acid and derivatives thereof); duocarmycin A, duocarmycin B1, duocarmycin B2, duocarmycin C, duocarmycin SA, CC1065, adozelesin, bizelesin, carzelesin; eribulin; trabectedin; pyrrolobenzodiazepine, anthramycin, tomaymycin, sibiromycin, DC-81, DSB-120; epothilones; bleomycin; dactinomycin; plicamycin; miromycin C and cis-configured platinum(II) complexes; or a derivative of any of the foregoing.

In some embodiments, Agent is selected from the group consisting of N-nitrosoureas; doxorubicin, 2-pyrrolpyrrolinoanthracycline, morpholinoanthracycline, diacetatoxyalkylanthracycline, daunorubicin, epirubicin, idarubicin, nemorubicin, PNU-159682, mitoxantrone; ametantrone; chlorambucil, bendamustine, melphalan, oxazaphosphorines; 5-fluorouracil, 2'-deoxy-5-fluoridine, cytarabine, cladribine, fludarabine, pentostatine, gemcitabine, 4-amino-1-(((2S,3R,4S,5R)-3,4-dihydroxy-5-methyltetrahydrofuran-2-yl)methyl)-5-fluoropyrimidin-2(1H)-one, thioguanine; methotrexate, raltitrexed, pemetrexed, plevitrexed; paclitaxel, docetaxel; topotecan, irinotecan, SN-38, 10-hydroxycamptothecin, GG211, lurtotecan, 9-aminocamptothecin, camptothecin, 7-formylcamptothecin, 9-formylcamptothecin, 9-formyl-10-hydroxycamptothecin, 7-butyl-10-aminocamptothecin, 7-butyl-9-amino-10,11-methylenedioxocamptothecin; vinblastine, vincristine, vindesine, vinorelbine; calicheamicins; maytansinoids; auristatins; epothilones; bleomycin, dactinomycin, plicamycin, miromycin C and cis-configured platinum(II) complexes; or a derivative of any of the foregoing.

In some embodiments, the Agent is a N-nitrosourea.

In some embodiments, the Agent is an anthracycline, such as but not limited to, doxorubicin, 2-pyrrolpyrrolinoanthracycline, morpholinoanthracycline, diacetatoxyalkylanthracycline, daunorubicin, epirubicin, idarubicin, nemorubicin, PNU-159682, mitoxantrone or ametantrone.

In some embodiments, the Agent is an alkylating agent, such as but not limited to, chlorambucil, bendamustine, melphalan or oxazaphosphorines.

In some embodiments, the Agent is an antimetabolite, such as but not limited to, 5-fluorouracil, 2'-deoxy-5-fluoridine, cytarabine, cladribine, fludarabine, pentostatine, gemcitabine, 4-amino-1-(((2S,3R,4S,5R)-3,4-dihydroxy-5-methyltetrahydrofuran-2-yl)methyl)-5-fluoropyrimidin-2 (1H)-one or thioguanine. In some embodiments, the antimetabolite is a pyrimidine, or purine analogue containing at least one primary or secondary amino group.

In some embodiments, the Agent is an the folic acid antagonist, such as but not limited to, methotrexate, raltitrexed, pemetrexed, or plevitrexed.

In some embodiments, the Agent is a taxane, such as but not limited to, paclitaxel or docetaxel.

In some embodiments, the Agent is a camptothecin, such as but not limited to, topotecan, irinotecan, SN-38, 10-hydroxycamptothecin, GG211, lurtotecan, 9-amino camptothecin, camptothecin, -formylcamptothecin, 9-formylcamptothecin, 9-formyl-10-hydroxycamptothecin, 7-butyl-10-aminocamptothecin or 7-butyl-9-amino-10,11-methylenedioxocamptothecin.

In some embodiments, the Agent is a *Vinca* alkaloid, such as but not limited to, vinblastine, vincristine, vindesine, vinorelbine or calicheamicins.

In some embodiments, the Agent is a maytansinoid, an auristatin, an epothilones, a bleomycin, dactinomycin, plicamycin, miromycin C, a cis-configured platinum(II) complex, or a derivative of any of the foregoing.

The Spacer
The Amide Bond
In some embodiments, Spacer is

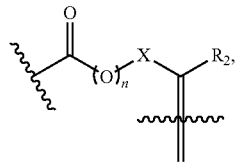

wherein n, X and $R_2$ are as defined herein.
In some embodiments, Spacer is

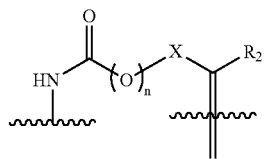

wherein n, X and $R_2$ are as defined herein.

In some embodiments, n is 0 or 1.

In some embodiments, X is selected from the group consisting of optionally substituted $C_1$-$C_{18}$ alkyl wherein optionally up to six carbon atoms in said $C_1$-$C_{18}$ alkyl are each independently replaced with —$OCH_2CH_2$—; optionally substituted $C_1$-$C_{18}$ alkyl-NH—C(O)—$R_5$— wherein optionally up to six carbon atoms in said $C_1$-$C_{18}$ alkyl are each independently replaced with —$OCH_2CH_2$—, optionally substituted $C_1$-$C_{18}$ alkyl-C(O)—NH—$R_5$— wherein optionally up to six carbon atoms in said $C_1$-$C_{18}$ alkyl are each independently replaced with —$OCH_2CH_2$—; optionally substituted aryl; optionally substituted heteroaryl; and optionally substituted cycloalkyl.

In some embodiments, X is optionally substituted $C_1$-$C_{18}$ alkyl. In some embodiments, X is optionally substituted $C_1$-$C_{18}$ alkyl wherein one carbon atom in said $C_1$-$C_{18}$ alkyl is replaced with —$OCH_2CH_2$—. In some embodiments, $X_1$ is optionally substituted $C_1$-$C_{18}$ alkyl wherein two carbon atoms in said $C_1$-$C_{18}$ alkyl are replaced with —$OCH_2CH_2$—. In some embodiments, X is optionally substituted $C_1$-$C_{18}$ alkyl wherein three carbon atoms in said $C_1$-$C_{18}$ alkyl are replaced with —$OCH_2CH_2$—. In some embodiments, X is optionally substituted $C_1$-$C_{18}$ alkyl wherein four carbon atoms in said $C_1$-$C_{18}$ alkyl are replaced with —$OCH_2CH_2$—. In some embodiments, X is optionally substituted $C_1$-$C_{18}$ alkyl wherein five carbon atoms in said $C_1$-$C_{18}$ alkyl are replaced with —$OCH_2CH_2$—. In some embodiments, X is optionally substituted $C_1$-$C_{18}$ alkyl wherein six carbon atoms in said $C_1$-$C_{18}$ alkyl are replaced with —$OCH_2CH_2$—.

In some embodiments, X is optionally substituted $C_1$-$C_{18}$ alkyl-NH—C(O)$R_5$—. In some embodiments, X is optionally substituted $C_1$-$C_{18}$ alkyl-NH—C(O)$R_5$— wherein one carbon atom in said $C_1$-$C_{18}$ alkyl is replaced with —$OCH_2CH_2$—. In some embodiments, X is optionally substituted $C_1$-$C_{18}$ alkyl-NH—C(O)$R_5$— wherein two carbon atoms in said $C_1$-$C_{18}$ alkyl are replaced with —$OCH_2CH_2$—. In some embodiments, X is optionally substituted $C_1$-$C_{18}$ alkyl-NH—C(O)$R_5$— wherein three carbon atoms in said $C_1$-$C_{18}$ alkyl are replaced with —$OCH_2CH_2$—. In some embodiments, X is optionally substituted $C_1$-$C_{18}$ alkyl-NH—C(O)$R_5$— wherein four carbon atoms in said C$_1$-C$_{18}$ alkyl are replaced with —OCH$_2$CH$_2$—. In some embodiments, X is optionally substituted C$_1$-C$_{18}$ alkyl-NH—C(O)R$_5$— wherein five carbon atoms in said C$_1$-C$_{18}$ alkyl are replaced with —OCH$_2$CH$_2$—. In some embodiments, X is optionally substituted C$_1$-C$_{18}$ alkyl-NH—C(O)R$_5$— wherein six carbon atoms in said C$_1$-C$_{18}$ alkyl are replaced with —OCH$_2$CH$_2$—.

In some embodiments, X is optionally substituted C$_1$-C$_{18}$ alkyl-C(O)—NH—R$_5$—. In some embodiments, X is optionally substituted C$_1$-C$_{18}$ alkyl-C(O)—NH—R$_5$— wherein one carbon atom in said C$_1$-C$_{18}$ alkyl is replaced with —OCH$_2$CH$_2$—. In some embodiments, X is optionally substituted C$_1$-C$_{18}$ alkyl-C(O)—NH—R$_5$— wherein two carbon atoms in said C$_1$-C$_{18}$ alkyl are replaced with —OCH$_2$CH$_2$—. In some embodiments, X is optionally substituted C$_1$-C$_{18}$ alkyl-C(O)—NH—R$_5$— wherein three carbon atoms in said C$_1$-C$_{18}$ alkyl are replaced with —OCH$_2$CH$_2$—. In some embodiments, X is optionally substituted C$_1$-C$_{18}$ alkyl-C(O)—NH—R$_5$— wherein four carbon atoms in said C$_1$-C$_{18}$ alkyl are replaced with —OCH$_2$CH$_2$—. In some embodiments, X is optionally substituted C$_1$-C$_{18}$ alkyl-C(O)—NH—R$_5$— wherein five carbon atoms in said C$_1$-C$_{18}$ alkyl are replaced with —OCH$_2$CH$_2$—. In some embodiments, X is optionally substituted C$_1$-C$_{18}$ alkyl-C(O)—NH—R$_5$— wherein six carbon atoms in said C$_1$-C$_{18}$ alkyl are replaced with —OCH$_2$CH$_2$—.

In some embodiments, X is optionally substituted aryl. In some embodiments, X is

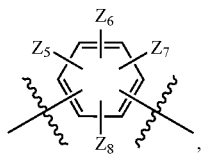

wherein Z$_5$, Z$_6$, Z$_7$ and Z$_8$ are each independently selected from the group consisting of —H, halogen, —OH, —NO$_2$, —CN, —OC$_1$-C$_6$ alkyl, optionally substituted C$_1$-C$_6$ alkyl, optionally substituted C$_1$-C$_6$ haloalkyl, and optionally substituted C$_1$-C$_6$ haloalkoxy.

In some embodiments, X is

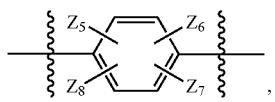

wherein Z$_5$, Z$_6$, Z$_7$ and Z$_8$ are each independently selected from the group consisting of —H, halogen, —OH, —NO$_2$, —CN, optionally substituted —OC$_1$-C$_6$ alkyl, optionally substituted C$_1$-C$_6$ alkyl, optionally substituted C$_1$-C$_6$ haloalkyl, and optionally substituted C$_1$-C$_6$ haloalkoxy. In some embodiments, Z$_5$, Z$_6$, Z$_7$ and Z$_8$ are each —H.

In some embodiments, X is optionally substituted heteroaryl.

In some embodiments, X is optionally substituted cycloalkyl.

In some embodiments, R$_5$ is selected from the group consisting of an optionally substituted aryl, optionally substituted heteroaryl, and optionally substituted cycloalkyl. In some embodiments, R$_5$ is an optionally substituted aryl.

In some embodiments, R$_2$ is selected from the group consisting of —H, optionally substituted C$_1$-C$_{12}$ alkyl, optionally substituted aryl, and optionally substituted heteroaryl.

In some embodiments, Spacer is absent.

In some embodiments, Spacer comprises a moiety or a bond that is enzyme-cleavable. In some embodiments, the bond being cleaved is a peptide bond, an imide bond, or an amide bond. In some embodiments, the amide bond may be designed to be specifically cleavable by an esterase and/or amidases. In some embodiments, Spacer comprises an amide bond that is selectively cleaved by carboxylesterases. In preferred embodiments, Spacer comprises an amide bond that is selectively cleaved by carboxylesterase 2. In preferred embodiments, Spacer comprises an amide bond that is attached to an aryl ring as follows:

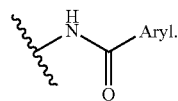

In some embodiments, Spacer comprises an amide bond that is attached to an aryl ring as follows:

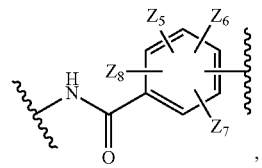

wherein Z$_5$, Z$_6$, Z$_7$ and Z$_8$ are each independently selected from the group consisting of —H, halogen, —OH, —NO$_2$, —CN, —OC$_1$-C$_6$ alkyl, optionally substituted C$_1$-C$_6$ alkyl, optionally substituted C$_1$-C$_6$ haloalkyl, and optionally substituted C$_1$-C$_6$ haloalkoxy. In some embodiments, Spacer comprises an amide bond that is attached to an aryl ring as follows:

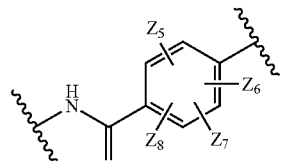

wherein Z$_5$, Z$_6$, Z$_7$ and Z$_8$ are each independently selected from the group consisting of —H, halogen, —OH, —NO$_2$, —CN, —OC$_1$-C$_6$ alkyl, optionally substituted C$_1$-C$_6$ alkyl, optionally substituted C$_1$-C$_6$ haloalkyl, and optionally substituted C$_1$-C$_6$ haloalkoxy. In some embodiments, Z$_5$, Z$_6$, Z$_7$ and Z$_8$ are each —H.

In some embodiments, Spacer is

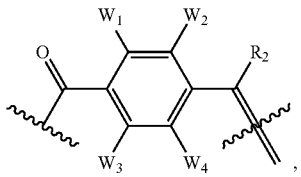

wherein $R_2$ is selected from the group consisting of: —H, optionally substituted $C_1$-$C_{12}$ alkyl, optionally substituted aryl, and optionally substituted heteroaryl; and $W_1$, $W_2$, $W_3$ and $W_4$ are each independently selected from the group consisting of: —H, halogen, —C(O)OH, —C(O)O—$C_1$-$C_6$ alkyl, —NO$_2$, haloalkyl, —S(O)$_2$—$C_1$-$C_6$ alkyl, and —CN. In some embodiments, $W_1$, $W_2$, $W_3$ and $W_4$ are each independently selected from the group consisting of: —H, —Cl, —Br, —I, —F, —C(O)OH, —NO$_2$, —CF$_3$, and —CN. In some embodiments, $W_1$, $W_2$, $W_3$ and $W_4$ are each independently selected from the group consisting of: —H, —Cl, —F, —NO$_2$, and —CF$_3$. In some embodiments, $W_1$, $W_2$, $W_3$ and $W_4$ are each independently selected from the group consisting of: a phenoxy group, a primary, secondary or tertiary amine group, an ether group, a phenol group, an amide group, an ester group, an alkyl group, a substituted alkyl group, a phenyl group, and a vinyl group. In some embodiments, $W_1$, $W_2$, $W_3$ and $W_4$ are each independently selected from the group consisting of: —OP(O)(OH)$_2$, —P(O)(OH)OP(O)(OH)$_2$, —OP(O)(OH)OP(O)(OH)OP(O)(OH)$_2$, —OP(O)(OH)(NH$_2$), —P(O)(OH)$_2$, —SO$_3$H, and a pharmaceutically acceptable salt thereof. In some embodiments, at least one of $W_1$, $W_2$, $W_3$ and $W_4$ is not —H.

In some of the above embodiments, $W_1$ is selected from the group consisting of: halogen, —C(O)OH, —C(O)O—$C_1$-$C_6$ alkyl, —NO$_2$, haloalkyl, —S(O)$_2$—$C_1$-$C_6$ alkyl, and —CN; and $W_2$, $W_3$ and $W_4$ are each independently selected from the group consisting of: —H, halogen, —C(O)OH, —C(O)O—$C_1$-$C_6$ alkyl, —NO$_2$, haloalkyl, —S(O)$_2$—$C_1$-$C_6$ alkyl, and —CN. In some embodiments, $W_1$ is selected from the group consisting of: —Cl, —Br, —I, —F, —C(O)OH, —NO$_2$, —CF$_3$, and —CN; and $W_2$, $W_3$ and $W_4$ are each independently selected from the group consisting of: —H, —Cl, —Br, —I, —F, —C(O)OH, —NO$_2$, —CF$_3$, and —CN. In some embodiments, $W_1$ is selected from the group consisting of: —Cl, —F, and —NO$_2$; and $Z_2$, $Z_3$ and $Z_4$ are each independently selected from the group consisting of: —H, —Cl, —F, —NO$_2$, and —CF$_3$.

In some embodiments, Spacer is,

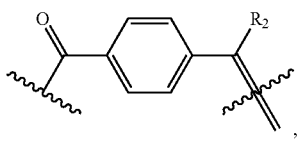

wherein $R_2$ is as defined herein. In some embodiments, Spacer is

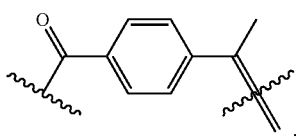 [SMILES: *C(=O)c1ccc(C(=*)C)cc1]

In some embodiments, Spacer is

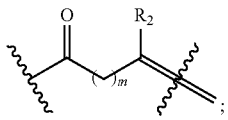

and m is 1, 2, 3, 4, 5, or 6.

In some embodiments, Spacer is

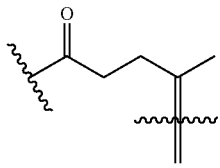

In some embodiments, $R_2$ is selected from the group consisting of —H, optionally substituted $C_1$-$C_{12}$ alkyl, optionally substituted aryl, and optionally substituted heteroaryl.

In one aspect, the spacer may operate as a protecting group, preventing metabolic degradation of Agent, thereby allowing for a targeted use of a higher doses of Agent. In some embodiments, Agent is gemcitabine.

The Linker

In some embodiments, the linker comprises Y and $R_1$. In some embodiments, Y is absent. In some embodiments, $R_1$ is absent. In some embodiments, both Y and $R_1$ are absent.

In some embodiments, Y is selected from the group consisting of methyl, ethyl, —NH—C(O)—, —C(O)—NH—, —C(O)—O—, and —O—C(O)—.

In some embodiments, $R_1$ is optionally substituted $C_1$-$C_{18}$ alkyl. In some embodiments, $R_1$ is optionally substituted $C_1$-$C_{18}$ alkyl wherein one carbon atom in said $C_1$-$C_{18}$ alkyl is replaced with —OCH$_2$CH$_2$—. In some embodiments, $R_1$ is optionally substituted $C_1$-$C_{18}$ alkyl wherein two carbon atoms in said $C_1$-$C_{18}$ alkyl are replaced with —OCH$_2$CH$_2$—. In some embodiments, $R_1$ is optionally substituted $C_1$-$C_{18}$ alkyl wherein three carbon atoms in said $C_1$-$C_{18}$ alkyl are replaced with —OCH$_2$CH$_2$—. In some embodiments, $R_1$ is optionally substituted $C_1$-$C_{18}$ alkyl wherein four carbon atoms in said $C_1$-$C_{18}$ alkyl are replaced with —OCH$_2$CH$_2$—. In some embodiments, $R_1$ is optionally substituted $C_1$-$C_{18}$ alkyl wherein five carbon atoms in said $C_1$-$C_{18}$ alkyl are replaced with —OCH$_2$CH$_2$—. In some embodiments, $R_1$ is optionally substituted $C_1$-$C_{18}$ alkyl wherein six carbon atoms in said $C_1$-$C_{18}$ alkyl are replaced with —OCH$_2$CH$_2$—.

In some embodiments, $R_1$ is optionally substituted $C_1$-$C_{18}$ alkyl-NH—C(O)R$_5$—. In some embodiments, $R_1$ is optionally substituted $C_1$-$C_{18}$ alkyl-NH—C(O)R$_5$— wherein one carbon atom in said $C_1$-$C_{18}$ alkyl is replaced with —OCH$_2$CH$_2$—. In some embodiments, $R_1$ is optionally substituted $C_1$-$C_{18}$ alkyl-NH—C(O)R$_5$— wherein two carbon atoms in said $C_1$-$C_{18}$ alkyl are replaced with —OCH$_2$CH$_2$—. In some embodiments, $R_1$ is optionally substituted $C_1$-$C_{18}$ alkyl-NH—C(O)R$_5$— wherein three carbon atoms in said $C_1$-$C_{18}$ alkyl are replaced with —OCH$_2$CH$_2$—. In some embodiments, $R_1$ is optionally substituted $C_1$-$C_{18}$ alkyl-NH—C(O)R$_5$— wherein four carbon atoms in said $C_1$-$C_{18}$ alkyl are replaced with —OCH$_2$CH$_2$—. In some embodiments, $R_1$ is optionally substituted $C_1$-$C_{18}$ alkyl-NH—C(O)R$_5$— wherein five carbon atoms in said $C_1$-$C_{18}$ alkyl are replaced with —OCH₂CH₂—. In some embodiments, R₁ is optionally substituted $C_1$-$C_{18}$ alkyl-NH—C(O)R₅— wherein six carbon atoms in said $C_1$-$C_{18}$ alkyl are replaced with —OCH₂CH₂—.

In some embodiments, R₁ is optionally substituted $C_1$-$C_{18}$ alkyl-C(O)—NH—R₅—. In some embodiments, R₁ is optionally substituted $C_1$-$C_{18}$ alkyl-C(O)—NH—R₅— wherein one carbon atom in said $C_1$-$C_{18}$ alkyl is replaced with —OCH₂CH₂—. In some embodiments, R₁ is optionally substituted $C_1$-$C_{18}$ alkyl-C(O)—NH—R₅— wherein two carbon atoms in said $C_1$-$C_{18}$ alkyl are replaced with —OCH₂CH₂—. In some embodiments, R₁ is optionally substituted $C_1$-$C_{18}$ alkyl-C(O)—NH—R₅— wherein three carbon atoms in said $C_1$-$C_{18}$ alkyl are replaced with —OCH₂CH₂—. In some embodiments, R₁ is optionally substituted $C_1$-$C_{18}$ alkyl-C(O)—NH—R₅— wherein four carbon atoms in said $C_1$-$C_{18}$ alkyl are replaced with —OCH₂CH₂—. In some embodiments, R₁ is optionally substituted $C_1$-$C_{18}$ alkyl-C(O)—NH—R₅— wherein five carbon atoms in said $C_1$-$C_{18}$ alkyl are replaced with —OCH₂CH₂—. In some embodiments, R₁ is optionally substituted $C_1$-$C_{18}$ alkyl-C(O)—NH—R₅— wherein six carbon atoms in said $C_1$-$C_{18}$ alkyl are replaced with —OCH₂CH₂—.

In some embodiments, R₅ is selected from the group consisting of an optionally substituted aryl, optionally substituted heteroaryl, and optionally substituted cycloalkyl.

In some embodiments, the

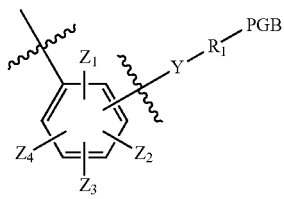

moiety of a compound of the invention is selected from the group consisting of:

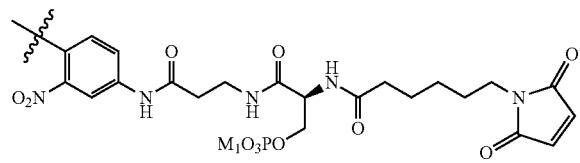

$M_1$ = $Mg^{2+}$, $2Na^+$, $2K^+$, $2H^+$, $2NH_4^+$, $Na^+$, $K^+$, $NH_4^+$ and/or $H^+$

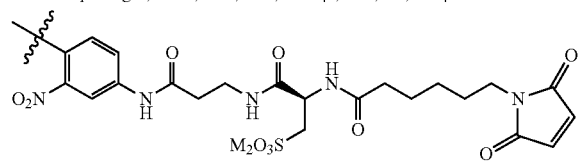

$M_2$ = $Na^+$, $K^+$, $H^+$, $NH_4^+$

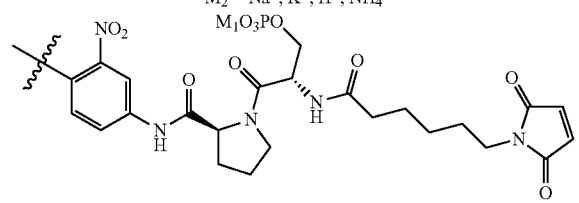

$M_1$ = $Mg^{2+}$, $2Na^+$, $2K^+$, $2H^+$, $2NH_4^+$, $Na^+$, $K^+$, $NH_4^+$ and/or $H^+$

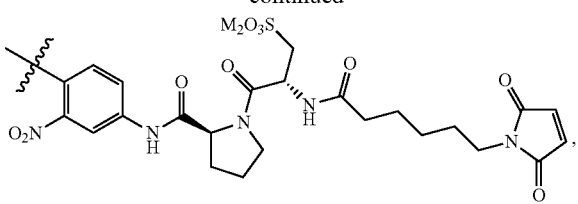

$M_2$ = $Na^+$, $K^+$, $H^+$, $NH_4^+$

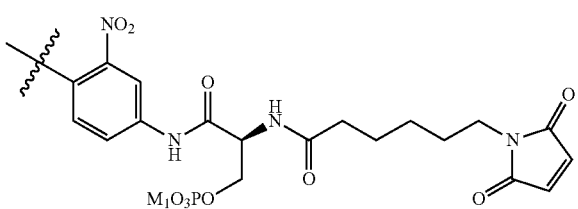

$M_1$ = $Mg^{2+}$, $2Na^+$, $2K^+$, $2H^+$, $2NH_4^+$, $Na^+$, $K^+$, $NH_4^+$ and/or $H^+$

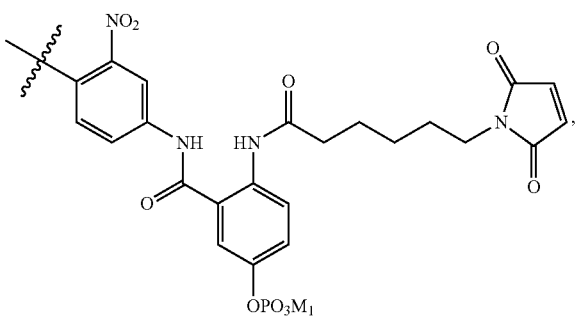

$M_1$ = $Mg^{2+}$, $2Na^+$, $2K^+$, $2H^+$, $2NH_4^+$, $Na^+$, $K^+$, $NH_4^+$ and/or $H^+$

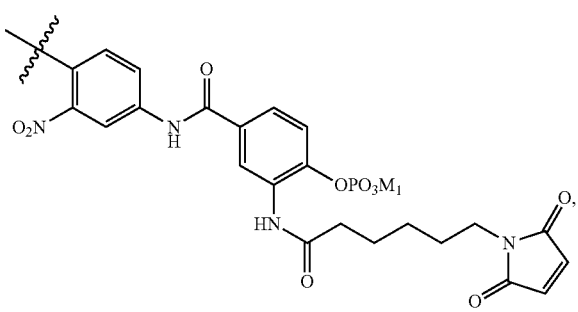

$M_1$ = $Mg^{2+}$, $2Na^+$, $2K^+$, $2H^+$, $2NH_4^+$, $Na^+$, $K^+$, $NH_4^+$ and/or $H^+$

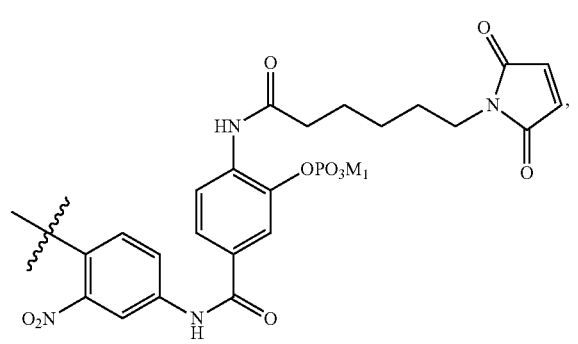

$M_1$ = $Mg^{2+}$, $2Na^+$, $2K^+$, $2H^+$, $2NH_4^+$, $Na^+$, $K^+$, $NH_4^+$ and/or $H^+$

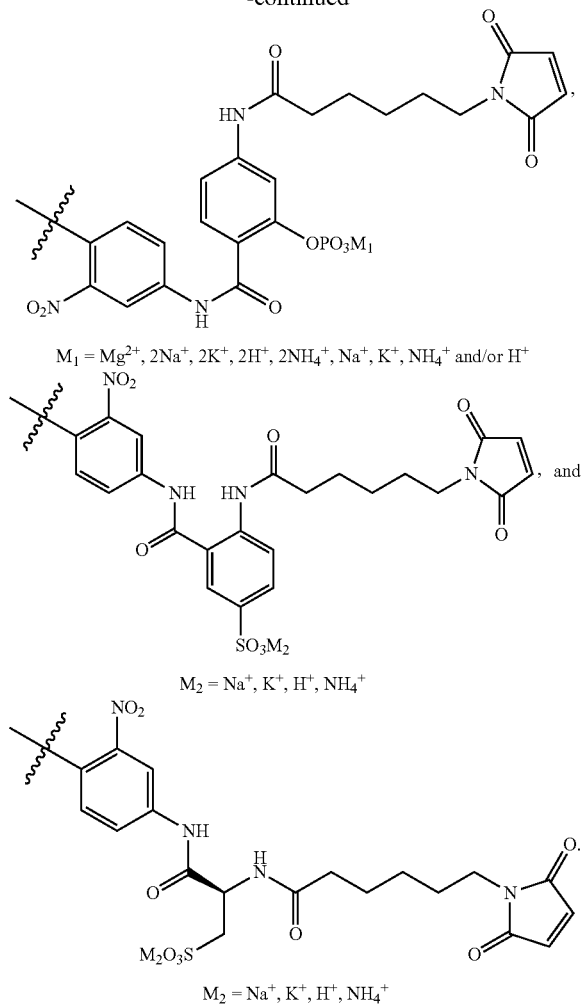

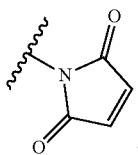

In some embodiments, PBG is substituted with $C_1$-$C_6$ alkyl or halogen. In some embodiments, PBG is substituted with methyl, —Cl or —Br. In some embodiments, PBG includes an antibody or a fragment thereof. In some embodiments, PBG includes a ligand with specificity for the receptor, e.g., a low- or high-molecular weight compound such as folic acid, vitamins, peptides, sugars, native or modified proteins.

A disulfide group may be activated by a thionitrobenzoic acid (e.g. 5'-thio-2-nitrobenzoic acid) as the exchangeable group. A maleimide, pyridyldithio, or N-hydroxysuccinimide ester group can, where appropriate, be substituted by an alkyl group or by the above water-soluble groups. In general, a protein-binding group possesses protein-binding properties, i.e., it binds covalently ("a covalent protein-binding group") or noncovalently ("a noncovalent protein-binding group"), in a physiological environment, to particular amino acids on the surface of the protein. The maleimide group, the haloacetamide group, the haloacetate group, the pyridyldithio group, the disulfide group, the vinylcarbonyl group, the aziridine group, and/or the acetylene group preferably reacts with thiol (—SH) groups of cysteines, while the N-hydroxysuccinimide ester group and/or the isothiocyanate group preferably react with the amino group (—NH) of lysines, on the surface of a protein. For example, the protein-binding group, such as a maleimide group, may bind to the cysteine-34 of albumin. In some embodiments, the albumin is not modified (e.g., it is not modified to be charged, either positively or negatively). In some embodiments, a PBG as described herein may bind to an antibody or fragment thereof, such as those described herein.

The compound used in the invention includes any and all combinations of one or more Agents, spacers, linkers, protein-binding groups, cleavable moieties, i.e., hydrazone, amide bond. Compounds may comprise an anthracycline, and an acid-cleavable moiety that can be cleaved in such a way as to control the release of the anthracycline. In certain embodiments, the therapeutically effective substance comprises an anthracycline, a hydrazone as the acid-cleavable moiety whose cleavage and the half-life of the drug release vary according to the electron-withdrawing substituents and their position on the phenyl ring to which the hydrazone is attached, and a maleimide group as the covalent protein-binding group. In some other embodiments, compounds may comprise gemcitabine, and an acid-cleavable moiety that can be cleaved in such a way as to control the release of gemcitabine. In some other embodiments, compounds may comprise a *Vinca* alkaloid, and an acid-cleavable moiety that can be cleaved in such a way as to control the release of *Vinca* alkaloid.

The Protein Binding Group

Protein-binding groups ("PBG") include, but are not limited to, a substituted or unsubstituted maleimide group, a substituted or unsubstituted haloacetamide group, a substituted or unsubstituted haloacetate group, a substituted or unsubstituted pyridylthio group, a substituted or unsubstituted isothiocyanate group, a substituted or unsubstituted vinylcarbonyl group, a substituted or unsubstituted aziridine group, a substituted or unsubstituted disulfide group, a substituted or unsubstituted acetylene group, a substituted or unsubstituted N-hydroxysuccinimide ester group, an antibody or fragment thereof. In some embodiments, protein-binding groups ("PBG") include, but are not limited to, a substituted or unsubstituted maleimide group, a substituted or unsubstituted haloacetamide group, a substituted or unsubstituted haloacetate group, a substituted or unsubstituted pyridylthio group, a substituted or unsubstituted isothiocyanate group, a substituted or unsubstituted vinylcarbonyl group, a substituted or unsubstituted aziridine group, a substituted or unsubstituted disulfide group, a substituted or unsubstituted acetylene group, or a substituted or unsubstituted N-hydroxysuccinimide ester group. In some embodiments, the protein-binding group is a substituted or unsubstituted maleimide group. In some embodiments, the protein-binding group is Antibodies as Carriers Cancer cells possess specific markers, known as antigens, which play a role in tumor growth and progression. Antigens are proteins, often located on the surface of the tumor. An important feature of antibodies is their ability to bind target antigens with high specificity.

However, despite the specific binding to antigens, antibodies often lack therapeutic activity (Panowski et al., mAbs, 6, 34-45 (2014); Chari et al., Angewandte Chem. Int.

Ed., 53, 3796-3827 (2014)). Because of their high specificity for antigens, antibodies can be used as carriers for drug delivery. They can be conjugated to a therapeutically effective substance—forming an antibody-drug conjugate (ADC)—to deliver the therapeutically effective substance to a targeted site such as a tumor. Upon binding of the ACD to the antigen, the antigen-ADC complex is internalized through endocytosis. Once inside the tumor, the ADC releases the therapeutically effective substance. For an ADC to be successful, the choice of the therapeutically effective substance, the linker and the antibody is important. The selection of antigen, and consequently a corresponding antibody, is important as the efficiency of the internalization of the antigen-antibody complex influences how much therapeutically effective substance is delivered. Moreover for an ADC to be effective, the number of molecules of drug required to kill a cell has to be below the amount the drug that can delivered. Thus, a potent drug, with potency in the picomolar range, is preferred. Finally, once the ADC is internalized, the linker should be cleaved to release the therapeutically effective substance. Preferred linkers provide efficient and controlled release of the therapeutically effective substance the acidic environment of the tumor, while preventing the release of the therapeutically effective substance in the plasma which could lead to off-target toxicity and a narrower therapeutic window for the use of the therapeutically effective substance. The linkers disclosed herein can be conjugated with antibodies that are directed towards any antigens or receptors expressed on a malignant cell. The antibody may be chimeric, humanized, human or a genetically engineered or chemically modified antibody such as a thio antibody (THIOMAB), and allow linker attachment without reducing significantly the target binding capacity of the antibody.

In some embodiments the protein binding groups (PBG) of the compounds described herein are associated with an antibody or fragment thereof as described herein thereby forming an ADC. In some embodiments, the PBG is covalently bound to an antibody or fragment thereof. In other embodiments, the PBG is non-covalently bound to an antibody or fragment thereof.

In certain aspects, the PBG of the present application may bind to a carrier. In some embodiments, the carrier is a polypeptide binding agent. The disclosure encompasses polypeptide binding agents, such as antibodies, antigen binding portions of antibodies, and non-immunoglobulin antigen binding scaffolds in part, which can effectively target antigens.

Monoclonal antibodies binding to antigens present on the surface of the tumor may be used in the disclosed methods and compositions.

In some embodiments, antibodies can be modified antibodies, or antigen-binding fragments thereof that bind to the extracellular domain of antigen.

In some embodiments, the deimmunized antibody or antigen binding fragment thereof that binds the extracellular domain of antigen, including a heavy chain variable region and a light chain variable region, wherein each variable region has between 2 to 20 amino acid substitutions in the framework region in comparison to a nonhuman or parent antibody that binds the extracellular domain of antigen.

In some embodiments, the deimmunized antibody or antigen binding fragment thereof has one or more complementarity determining regions (CDRs) from a nonhuman or parent antibody that binds the extracellular domain of antigen. In one embodiment, between 1-5 substitutions are present in the complementarity determining regions (CDRs).

In some embodiments, single chain antibodies, and chimeric, humanized or primatized (CDR-grafted) antibodies, as well as chimeric or CDR-grafted single chain antibodies, comprising portions derived from different species, may be used as antigen binding portions of an antibody. The various portions of these antibodies can be joined together chemically by conventional techniques, or can be prepared as a contiguous protein using genetic engineering techniques. For example, nucleic acids encoding a chimeric or humanized chain can be expressed to produce a contiguous protein. See, e.g., Cabilly et al., U.S. Pat. No. 4,816,567; Cabilly et al., European Patent No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; and Winter, European Patent No. 0,239,400 B1. See also, Newman, R. et al., BioTechnology, 10: 1455-1460 (1992), regarding primatized antibody. See, e.g., Ladner et al., U.S. Pat. No. 4,946,778; and Bird, R. E. et al., Science, 242: 423-426 (1988)), regarding single chain antibodies.

In addition, functional fragments of antibodies, including fragments of chimeric, humanized, primatized or single chain antibodies, can also be used. Functional fragments of the subject antibodies retain at least one binding function and/or modulation function of the full-length antibody from which they are derived. In certain embodiments, functional fragments retain an antigen binding function of a corresponding full-length antibody (e.g., specificity for a tumor).

For example, antibody fragments capable of binding to an antigen receptor or portion thereof, including, but not limited to, Fv, Fab, Fab' and F(ab')$_2$ fragments are encompassed by the invention. Such fragments can be produced by enzymatic cleavage or by recombinant techniques. For instance, papain or pepsin cleavage can generate Fab or F(ab')$_2$ fragments, respectively. Antibodies produced in a variety of truncated forms using antibody genes in which one or more stop codons has been introduced upstream of the natural stop site are encompassed by the invention. For example, a chimeric gene encoding a F(ab')$_2$ heavy chain portion can be designed to include DNA sequences encoding the $CH_1$ domain and hinge region of the heavy chain.

The term "humanized immunoglobulin" as used herein refers to an immunoglobulin comprising portions of immunoglobulins of different origin, wherein at least one portion is of human origin. Accordingly, the present invention encompasses a humanized immunoglobulin having binding specificity for an antigen (e.g., human antigen), said immunoglobulin comprising an antigen binding region of nonhuman origin (e.g., rodent) and at least a portion of an immunoglobulin of human origin (e.g., a human framework region, a human constant region or portion thereof). For example, the humanized antibody can comprise portions derived from an immunoglobulin of nonhuman origin with the requisite specificity, such as a mouse, and from immunoglobulin sequences of human origin (e.g., a chimeric immunoglobulin), joined together chemically by conventional techniques (e.g., synthetic) or prepared as a contiguous polypeptide using genetic engineering techniques (e.g., DNA encoding the protein portions of the chimeric antibody can be expressed to produce a contiguous polypeptide chain).

Another example of a humanized immunoglobulin is an immunoglobulin containing one or more immunoglobulin chains comprising a CDR of nonhuman origin (e.g., one or more CDRs derived from an antibody of nonhuman origin)

and a framework region derived from a light and/or heavy chain of human origin (e.g., CDR-grafted antibodies with or without framework changes).

In some embodiments, the antibody is an antagonist antibody. As described herein, the term "antagonist antibody" refers to an antibody that can inhibit one or more functions of the target, such as a binding activity (e.g., ligand binding) and a signaling activity (e.g., amino acid transport). For example, an antagonist antibody can inhibit (reduce or prevent) the transport of glutamine by antigen.

In some embodiments, anti-idiotypic antibodies are also useful. Anti-idiotypic antibodies recognize antigenic determinants associated with the antigen-binding site of another antibody. Anti-idiotypic antibodies can be prepared against a second antibody by immunizing an animal of the same species, and may be of the same strain, as the animal used to produce the second antibody. See e.g., U.S. Pat. No. 4,699,880. In one embodiment, antibodies are raised against receptor or a portion thereof, and these antibodies are used in turn to produce an anti-idiotypic antibody. Such an anti-idiotypic antibody can also be an inhibitor of an antigen transporter function, although it does not bind antigen itself. Such an anti-idiotypic antibody can also be called an antagonist antibody.

In some embodiments, suitable antibodies can be fragmented using conventional techniques and the fragments screened for utility in the same manner as described above for whole antibodies. For example, F(ab)2 fragments can be generated by treating antibody with pepsin. The resulting F(ab)2 fragment can be treated to reduce disulfide bridges to produce Fab fragments.

In some embodiments, suitable antibodies are further intended to include bispecific, single-chain, and chimeric and humanized molecules having affinity for an antigen polypeptide conferred by at least one CDR region of the antibody. Techniques for the production of single chain antibodies (U.S. Pat. No. 4,946,778) can also be adapted to produce single chain antibodies. Also, transgenic mice or other organisms including other mammals, may be used to express humanized antibodies. Methods of generating these antibodies are known in the art. See, e.g., Cabilly et al., U.S. Pat. No. 4,816,567; Cabilly et al., European Patent No. 0,125,023 B1; Queen et al., European Patent No. 0,451,216 B1; Boss et al., U.S. Pat. No. 4,816,397; Boss et al., European Patent No. 0,120,694 E1; Neuberger, M. S. et al., WO 86/01533; Neuberger, M. S. et al., European Patent No. 0,194,276 B1; Winter, U.S. Pat. No. 5,225,539; winter, European Patent No. 0,239,400 B1; Padlan, E. A. et al., European Patent Application No. 0,519,596 A1. See also, Ladner et al., U.S. Pat. No. 4,946,778; Huston, U.S. Pat. No. 5,476,786; and Bird, R. E. et al., Science, 242: 423-426 (1988)).

Such humanized immunoglobulins can be produced using synthetic and/or recombinant nucleic acids to prepare genes (e.g., cDNA) encoding the desired humanized chain. For example, nucleic acid (e.g., DNA) sequences coding for humanized variable regions can be constructed using PCR mutagenesis methods to alter DNA sequences encoding a human or humanized chain, such as a DNA template from a previously humanized variable region (see e.g., Kamman, M., et al., Nucl. Acids Res., 17: 5404 (1989)); Sato, K., et al., Cancer Research, 53: 851-856 (1993); Daugherty, B. L. et al., Nucleic Acids Res., 19(9): 2471-2476 (1991); and Lewis, A. P. and J. S. Crowe, Gene, 101: 297-302 (1991)). Using these or other suitable methods, variants can also be readily produced. In one embodiment, cloned variable regions can be mutagenized, and sequences encoding variants with the desired specificity can be selected (e.g., from a phage library; see e.g., Krebber et al., U.S. Pat. No. 5,514,548; Hoogenboom et al., WO 93/06213, published Apr. 1, 1993)).

In some embodiments, an antibody is a monoclonal antibody. For example, a method for generating a monoclonal antibody that binds specifically to an antigen polypeptide may comprise administering to a mouse an amount of an immunogenic composition comprising the antigen polypeptide effective to stimulate a detectable immune response, obtaining antibody-producing cells (e.g., cells from the spleen) from the mouse and fusing the antibody—producing cells with myeloma cells to obtain antibody-producing hybridomas, and testing the antibody-producing hybridomas to identify a hybridoma that produces a monoclonal antibody that binds specifically to the antigen polypeptide. Once obtained, a hybridoma can be propagated in a cell culture, optionally in culture conditions where the hybridoma-derived cells produce the monoclonal antibody that binds specifically to an antigen polypeptide. The monoclonal antibody may be purified from the cell culture.

In addition, the techniques used to screen antibodies in order to identify a desirable antibody may influence the properties of the antibody obtained. For example, an antibody to be used for certain therapeutic purposes may be able to target a particular cell type. Accordingly, to obtain antibodies of this type, it may be desirable to screen for antibodies that bind to cells that express the antigen of interest (e.g., by fluorescence activated cell sorting). Likewise, if an antibody is to be used for binding an antigen in solution, it may be desirable to test solution binding. A variety of different techniques are available for testing antibody: antigen interactions to identify particularly desirable antibodies. Such techniques include ELISAs, surface plasmon resonance binding assays (e.g., the Biacore binding assay, Biacore AB, Uppsala, Sweden), sandwich assays (e.g., the paramagnetic bead system of IGEN International, Inc., Gaithersburg, Md.), Western blots, immunoprecipitation assays and immunohistochemistry.

Pharmaceutical Compositions

In some embodiments, the invention provides a pharmaceutical composition comprising a compound described herein.

The total amount of a compound in a composition to be administered to a patient is one that is suitable for that patient. One of skill in the art would appreciate that different individuals may require different total amounts of the therapeutically effective substance. In some embodiments, the amount of the compound is a pharmaceutically effective amount. The skilled worker would be able to determine the amount of the compound in a composition needed to treat a patient based on factors such as, for example, the age, weight, and physical condition of the patient. The concentration of the compound depends on its solubility in the intravenous administration solution and the volume of fluid that can be administered. For example, the concentration of the compound may be from about 0.1 mg/ml to about 50 mg/ml in the injectable composition. In some embodiments, the concentration of the compound may be from about 0.1 mg/ml to about 25 mg/ml, from about 7 mg/ml to about 17 mg/ml, from about 0.1 mg/ml to about 5 mg/ml, or from about 0.25 mg/ml to about 4.5 mg/ml. In particular embodiments, the concentration of the compound may be about 0.1 mg/ml, about 0.2 mg/ml, about 0.3 mg/ml, about 0.4 mg/ml, about 0.5 mg/ml, about 0.6 mg/ml, about 0.7 mg/ml, about 0.8 mg/ml, about 0.9 mg/ml, about 1.0 mg/ml, about 1.1 mg/ml, about 1.2 mg/ml, about 1.3 mg/ml, about 1.4 mg/ml, about 1.5 mg/ml, about 1.6 mg/ml, about 1.7 mg/ml, about 1.8 mg/ml, about 1.9 mg/ml, about 2.0 mg/ml, about 2.1 mg/ml, about 2.2 mg/ml, about 2.3 mg/ml, about 2.4 mg/ml, about 2.5 mg/ml, about 2.6 mg/ml, about 2.7 mg/ml, about 2.8 mg/ml, about 2.9 mg/ml, about 3.0 mg/ml, about 3.1 mg/ml, about 3.2 mg/ml, about 3.3 mg/ml, about 3.4 mg/ml, about 3.5 mg/ml, about 3.6 mg/ml, about 3.7 mg/ml, about 3.8 mg/ml, about 3.9 mg/ml, about 4.0 mg/ml, about 4.1 mg/ml, about 4.2 mg/ml, about 4.3 mg/ml, about 4.4 mg/ml, about 4.5 mg/ml, about 4.6 mg/ml, about 4.7 mg/ml, about 4.8 mg/ml, about 4.9 mg/ml, about 5.0 mg/ml, about 5.1 mg/ml, about 5.2 mg/ml, about 5.3 mg/ml, about 5.4 mg/ml, about 5.5 mg/ml, about 5.6 mg/ml, about 5.7 mg/ml, about 5.8 mg/ml, about 5.9 mg/ml, or about 6.0 mg/ml. In some embodiments, the concentration of the compound may be about 7 mg/ml, about 8 mg/ml, about 9 mg/ml, about 10 mg/ml, about 11 mg/ml, about 12 mg/ml, about 13 mg/ml, about 14 mg/ml, about 15 mg/ml, about 16 mg/ml, about 17 mg/ml, about 18 mg/ml, about 19 mg/ml, about 20 mg/ml, about 21 mg/ml, about 22 mg/ml, about 23 mg/ml, about 24 mg/ml, about 25 mg/ml, about 26 mg/ml, about 27 mg/ml, about 28 mg/ml, about 29 mg/ml, or about 30 mg/ml.

The pharmaceutical compositions and kits of the present invention may also contain diluents, fillers, salts, buffers, stabilizers, solubilizers, and other materials well known in the art. The term "pharmaceutically acceptable" means a non-toxic material that does not interfere with the effectiveness of the biological activity of the active ingredient(s). The characteristics of the carrier will depend on the route of administration.

The compositions may be administered in a variety of conventional ways. Exemplary routes of administration that can be used include oral, parenteral, intravenous, intra-arterial, cutaneous, subcutaneous, intramuscular, topical, intracranial, intraorbital, ophthalmic, intravitreal, intraventricular, intracapsular, intraspinal, intracisternal, intraperitoneal, intranasal, aerosol, central nervous system (CNS) administration, or administration by suppository. In some embodiments, the compositions are suitable for parenteral administration. These compositions may be administered, for example, intraperitoneally, intravenously, or intrathecally. In some embodiments, the compositions are injected intravenously. In some embodiments, a reconstituted formulation can be prepared by reconstituting a lyophilized anthracycline compound composition in a reconstitution liquid comprising ethanol and water. Such reconstitution may comprise adding the reconstitution liquid and mixing, for example, by swirling or vortexing the mixture. The reconstituted formulation then can be made suitable for injection by mixing e.g., Lactated Ringer's solution with the formulation to create an injectable composition. One of skill in the art would appreciate that a method of administering a therapeutically effective substance formulation or composition would depend on factors such as the age, weight, and physical condition of the patient being treated, and the disease or condition being treated. The skilled worker would, thus, be able to select a method of administration optimal for a patient on a case-by-case basis.

In some embodiments, the invention provides compounds and compositions for use as a medicament. In some embodiments, the invention provides compounds and compositions for use in treating a cancer, a virus disease, autoimmune disease, acute or chronic inflammatory disease, and a disease caused by bacteria, fungi, or other micro-organisms.

In some embodiments, the compound disclosed herein may be used in the manufacture or preparation of a medicament for treating a disease or condition selected from a group consisting of a cancer, a virus disease, autoimmune disease, acute or chronic inflammatory disease, and a disease caused by bacteria, fungi, and other micro-organisms.

In some embodiments, the cancer is a blood cancer or a solid tumor cancer. In some embodiments, the cancer is selected from carcinoma, sarcoma, leukemia, lymphoma, multiple myeloma, or melanoma.

In some embodiments, the cancer is adenocarcinoma, uveal melanoma, acute leukaemia, acoustic neuroma, ampullary carcinoma, anal carcinoma, astrocytomas, basalioma, pancreatic cancer, connective tissue tumor, bladder cancer, bronchial carcinoma, non-small cell bronchial carcinoma, breast cancer, Burkitt's lymphoma, corpus carcinoma, CUP syndrome, colon cancer, cancer of the small intestine, ovarian cancer, endometrial carcinoma, gallbladder cancer, gallbladder carcinomas, uterine cancer, cervical cancer, neck, nose and ear tumors, haematological neoplasias, hairy cell leukaemia, urethral cancer, skin cancer, gliomas, testicular cancer, Kaposi's sarcoma, laryngeal cancer, bone cancer, colorectal carcinoma, head/neck tumors, colon carcinoma, craniopharyngeoma, liver cancer, eukaemia, lung cancer, non-small cell lung cancer, Hodgkin's lymphoma, non-Hodgkin's lymphoma, stomach cancer, colon cancer, medulloblastoma, melanoma, meningioma, kidney cancer, renal cell carcinomas, oligodendroglioma, oesophageal carcinoma, osteolytic carcinomas and osteoplastic carcinomas, osteosarcoma, ovarian carcinoma, pancreatic carcinoma, penile cancer, prostate cancer, tongue cancer, ovary carcinoma or lymph gland cancer.

In some embodiments, the present invention provides a kit comprising a compound as described herein and, a pharmaceutically acceptable excipient, a carrier, and/or a diluent.

In some embodiments, one or more excipients may be included in the composition. One of skill in the art would appreciate that the choice of any one excipient may influence the choice of any other excipient. For example, the choice of a particular excipient may preclude the use of one or more additional excipients because the combination of excipients would produce undesirable effects. One of skill in the art would be able to empirically determine which excipients, if any, to include in the compositions. Excipients may include, but are not limited to, co-solvents, solubilizing agents, buffers, pH adjusting agents, bulking agents, surfactants, encapsulating agents, tonicity-adjusting agents, stabilizing agents, protectants, and viscosity modifiers. In some embodiments, it may be beneficial to include a pharmaceutically acceptable carrier in the compositions.

In some embodiments, a solubilizing agent may be included compositions. Solubilizing agents may be useful for increasing the solubility of any of the components of the composition, including a compound or an excipient. The solubilizing agents described herein are not intended to constitute an exhaustive list, but are provided merely as exemplary solubilizing agents that may be used in the compositions. In certain embodiments, solubilizing agents include, but are not limited to, ethyl alcohol, tert-butyl alcohol, polyethylene glycol, glycerol, methylparaben, propylparaben, polyethylene glycol, polyvinyl pyrrolidone, and any pharmaceutically acceptable salts and/or combinations thereof.

The pH of the compositions may be any pH that provides desirable properties for the formulation or composition. Desirable properties may include, for example, compound stability, increased compound retention as compared to compositions at other pHs, and improved filtration efficiency. In some embodiments, the pH of the compositions may be from about 3.0 to about 9.0, e.g., from about 5.0 to about 7.0. In particular embodiments, the pH of the compositions may be 5.5±0.1, 5.6±0.1, 5.7±0.1, 5.8±0.1, 5.9±0.1, 6.0±0.1, 6.1±0.1, 6.2±0.1, 6.3±0.1, 6.4±0.1, or 6.5±0.1.

In some embodiments, it may be beneficial to buffer the pH by including one or more buffers in the compositions. In certain embodiments, a buffer may have a pKa of, for example, about 5.5, about 6.0, or about 6.5. One of skill in the art would appreciate that an appropriate buffer may be chosen for inclusion in compositions based on its pKa and other properties. Buffers are well known in the art. Accordingly, the buffers described herein are not intended to constitute an exhaustive list, but are provided merely as exemplary buffers that may be used in the formulations or compositions of the invention. In certain embodiments, a buffer includes, but is not limited to Tris, Tris HCl, potassium phosphate, sodium phosphate, sodium citrate, sodium ascorbate, combinations of sodium and potassium phosphate, Tris/Tris HCl, sodium bicarbonate, arginine phosphate, arginine hydrochloride, histidine hydrochloride, cacodylate, succinate, 2-(N-morpholino)ethanesulfonic acid (MES), maleate, bis-tris, phosphate, carbonate, and any pharmaceutically acceptable salts and/or combinations thereof.

In some embodiments, a pH-adjusting agent may be included in the compositions. Modifying the pH of a composition may have beneficial effects on, for example, the stability or solubility of a compound, or may be useful in making a composition suitable for parenteral administration. pH-adjusting agents are well known in the art. Accordingly, the pH-adjusting agents described herein are not intended to constitute an exhaustive list, but are provided merely as exemplary pH-adjusting agents that may be used in the compositions. pH-adjusting agents may include, for example, acids and bases. In some embodiments, a pH-adjusting agent includes, but is not limited to, acetic acid, hydrochloric acid, phosphoric acid, sodium hydroxide, sodium carbonate, and combinations thereof.

In some embodiments, a bulking agent may be included in the compositions. Bulking agents are commonly used in lyophilized compositions to provide added volume to the composition and to aid visualization of the composition, especially in instances where the lyophilized pellet would otherwise be difficult to see. Bulking agents also may help prevent a blowout of the active component(s) of a pharmaceutical composition and/or to aid cryoprotection of the composition. Bulking agents are well known in the art. Accordingly, the bulking agents described herein are not intended to constitute an exhaustive list, but are provided merely as exemplary bulking agents that may be used in the compositions.

Exemplary bulking agents may include carbohydrates, monosaccharides, disaccharides, polysaccharides, sugar alcohols, amino acids, and sugar acids, and combinations thereof. Carbohydrate bulking agents include, but are not limited to, mono-, di-, or poly-carbohydrates, starches, aldoses, ketoses, amino sugars, glyceraldehyde, arabinose, lyxose, pentose, ribose, xylose, galactose, glucose, hexose, idose, mannose, talose, heptose, glucose, fructose, methyl α-D-glucopyranoside, maltose, lactone, sorbose, erythrose, threose, arabinose, allose, altrose, gulose, idose, talose, erythrulose, ribulose, xylulose, psicose, tagatose, glucosamine, galactosamine, arabinans, fructans, fucans, galactans, galacturonans, glucans, mannans, xylans, inulin, levan, fucoidan, carrageenan, galactocarolose, pectins, amylose, pullulan, glycogen, amylopectin, cellulose, pustulan, chitin, agarose, keratin, chondroitin, dermatan, hyaluronic acid, xanthin gum, sucrose, trehalose, dextran, and lactose. Sugar alcohol bulking agents include, but are not limited to, alditols, inositols, sorbitol, and mannitol. Amino acid bulking agents include, but are not limited to, glycine, histidine, and proline. Sugar acid bulking agents include, but are not limited to, aldonic acids, uronic acids, aldaric acids, gluconic acid, isoascorbic acid, ascorbic acid, glucaric acid, glucuronic acid, gluconic acid, glucaric acid, galacturonic acid, mannuronic acid, neuraminic acid, pectic acids, and alginic acid.

In some embodiments, a surfactant may be included in the compositions. Surfactants, in general, reduce the surface tension of a liquid composition. This may provide beneficial properties such as improved ease of filtration. Surfactants also may act as emulsifying agents and/or solubilizing agents. Surfactants are well known in the art. Accordingly, the surfactants described herein are not intended to constitute an exhaustive list, but are provided merely as exemplary surfactants that may be used in the formulations or compositions of the invention. Surfactants that may be included include, but are not limited to, sorbitan esters such as polysorbates (e.g., polysorbate 20 and polysorbate 80), lipopolysaccharides, polyethylene glycols (e.g., PEG 400 and PEG 3000), poloxamers (i.e., pluronics), ethylene oxides and polyethylene oxides (e.g., Triton X-100), saponins, phospholipids (e.g., lecithin), and combinations thereof.

In some embodiments, an encapsulating agent may be included in the compositions. Encapsulating agents can sequester molecules and help stabilize or solubilize them. Encapsulating agents are well known in the art. Accordingly, the encapsulating agents described herein are not intended to constitute an exhaustive list, but are provided merely as exemplary encapsulating agents that may be used in the compositions. Encapsulating agents that may be included in compositions include, but are not limited to, dimethyl-β-cyclodextrin, hydroxyethyl-β-cyclodextrin, hydroxypropyl-β-cyclodextrin, and trimethyl-β-cyclodextrin, and combinations thereof.

In some embodiments, a tonicity-adjusting agent may be included in the compositions. The tonicity of a liquid composition is an important consideration when administering the composition to a patient, for example, by parenteral administration. Tonicity-adjusting agents, thus, may be used to help make a composition suitable for administration. Tonicity-adjusting agents are well known in the art. Accordingly, the tonicity-adjusting agents described herein are not intended to constitute an exhaustive list, but are provided merely as exemplary tonicity-adjusting agents that may be used in the compositions. Tonicity-adjusting agents may be ionic or non-ionic and include, but are not limited to, inorganic salts, amino acids, carbohydrates, sugars, sugar alcohols, and carbohydrates. Exemplary inorganic salts may include sodium chloride, potassium chloride, sodium sulfate, and potassium sulfate. An exemplary amino acid is glycine. Exemplary sugars may include sugar alcohols such as glycerol, propylene glycol, glucose, sucrose, lactose, and mannitol.

In some embodiments, a stabilizing agent may be included in the compositions. Stabilizing agents help increase the stability of a compound in the compositions. This may occur by, for example, reducing degradation or preventing aggregation of a compound. Without wishing to be bound by theory, mechanisms for enhancing stability may include sequestration of the compound from a solvent or inhibiting free radical oxidation of the therapeutically effective substance. Stabilizing agents are well known in the art. Accordingly, the stabilizing agents described herein are not intended to constitute an exhaustive list, but are provided merely as exemplary stabilizing agents that may be used in the compositions. Stabilizing agents may include, but are not limited to, emulsifiers and surfactants.

In some embodiments, a protectant may be included in the compositions. Protectants are agents that protect a pharmaceutically active ingredient (e.g., a therapeutically effective substance or compound) from an undesirable condition (e.g., instability caused by freezing or lyophilization, or oxidation). Protectants can include, for example, cryoprotectants, lyoprotectants, and antioxidants. Cryoprotectants are useful in preventing loss of potency of an active pharmaceutical ingredient (e.g., an anthracycline compound) when a composition is exposed to a temperature below its freezing point. For example, a cryoprotectant could be included in a reconstituted lyophilized formulation so that the formulation could be frozen before dilution for intravenous (IV) administration. Cryoprotectants are well known in the art. Accordingly, the cryoprotectants described herein are not intended to constitute an exhaustive list, but are provided merely as exemplary cryoprotectants that may be used in the compositions. Cryoprotectants include, but are not limited to, solvents, surfactants, encapsulating agents, stabilizing agents, viscosity modifiers, and combinations thereof. Cryoprotectants may include, for example, disaccharides (e.g., sucrose, lactose, maltose, and trehalose), polyols (e.g., glycerol, mannitol, sorbitol, and dulcitol), glycols (e.g., ethylene glycol, polyethylene glycol and propylene glycol).

Lyoprotectants are useful in stabilizing the components of a composition. For example, a therapeutically effective substance could be lyophilized with a lyoprotectant prior to reconstitution. Lyoprotectants are well known in the art. Accordingly, the lyoprotectants described herein are not intended to constitute an exhaustive list, but are provided merely as exemplary lyoprotectants that may be used in the compositions. Lyoprotectants include, but are not limited to, solvents, surfactants, encapsulating agents, stabilizing agents, viscosity modifiers, and combinations thereof. Exemplary lyoprotectants may be, for example, sugars and polyols. Trehalose, sucrose, dextran, and hydroxypropyl-beta-cyclodextrin are non-limiting examples of lyoprotectants.

Antioxidants are useful in preventing oxidation of the components of a composition. Oxidation may result in aggregation of a drug product or other detrimental effects to the purity of the drug product or its potency. Antioxidants are well known in the art. Accordingly, the antioxidants described herein are not intended to constitute an exhaustive list, but are provided merely as exemplary antioxidants that may be used in the compositions. Antioxidants may be, for example, sodium ascorbate, citrate, thiols, metabisulfite, and combinations thereof.

In some embodiments, a viscosity modifying agent may be included in the composition. Viscosity modifiers change the viscosity of liquid compositions. This may be beneficial because viscosity plays an important role in the ease with which a liquid composition is filtered. A composition may be filtered prior to lyophilization and reconstitution, or after reconstitution. Viscosity modifiers are well known in the art. Accordingly, the viscosity modifiers described herein are not intended to constitute an exhaustive list, but are provided merely as exemplary viscosity modifiers that may be used in the compositions. Viscosity modifiers include solvents, solubilizing agents, surfactants, and encapsulating agents. Exemplary viscosity modifiers that may be included in compositions include, but are not limited to, N-acetyl-DL-tryptophan and N-acetyl-cysteine.

Methods of Treatment

The compounds and compositions described herein are useful for a variety of clinical applications.

The compounds and compositions of this invention are capable of inducing prolonged or long-term inhibition of tumor growth. In certain embodiments, the prolonged or long term inhibition of tumor growth is without any loss in body weight or bone marrow toxicity.

The disclosure also provides a method of treating a condition or disease in a patient, said condition or disease selected from a cancer, a virus disease, autoimmune disease, acute or chronic inflammatory disease, and a disease caused by bacteria, fungi, or other micro-organisms, comprising administering to the patient a compound or a pharmaceutical composition as described herein.

In some embodiments, the cancer is a blood cancer or a solid tumor cancer. In some embodiments, the cancer is selected from carcinoma, sarcoma, leukemia, lymphoma, multiple myeloma, or melanoma.

In some embodiments, the cancer is adenocarcinoma, uveal melanoma, acute leukaemia, acoustic neuroma, ampullary carcinoma, anal carcinoma, astrocytomas, basalioma, pancreatic cancer, connective tissue tumor, bladder cancer, bronchial carcinoma, non-small cell bronchial carcinoma, breast cancer, Burkitt's lymphoma, corpus carcinoma, CUP syndrome, colon cancer, cancer of the small intestine, ovarian cancer, endometrial carcinoma, gallbladder cancer, gallbladder carcinomas, uterine cancer, cervical cancer, neck, nose and ear tumors, haematological neoplasias, hairy cell leukaemia, urethral cancer, skin cancer, gliomas, testicular cancer, Kaposi's sarcoma, laryngeal cancer, bone cancer, colorectal carcinoma, head/neck tumors, colon carcinoma, craniopharyngeoma, liver cancer, eukaemia, lung cancer, non-small cell lung cancer, Hodgkin's lymphoma, non-Hodgkin's lymphoma, stomach cancer, colon cancer, medulloblastoma, melanoma, meningioma, kidney cancer, renal cell carcinomas, oligodendroglioma, oesophageal carcinoma, osteolytic carcinomas and osteoplastic carcinomas, osteosarcoma, ovarian carcinoma, pancreatic carcinoma, penile cancer, prostate cancer, tongue cancer, ovary carcinoma or lymph gland cancer.

Variations and Modifications

Variations, modifications, and other implementations of what is described herein will occur to those of ordinary skill without departing from the spirit and the scope of the invention.

Accordingly, the invention is not to be limited to the preceding description or the following examples.

Exemplification

With aspects of the invention now being generally described, these will be more readily understood by reference to the following examples, which are included merely for purposes of illustration of certain features and embodiments of the invention and are not intended to be limiting.

Equivalents

Those skilled in the art will recognize, or be able to ascertain using no more than routine experimentation, numerous equivalents to the compounds, compositions, and methods of use thereof described herein. Such equivalents are considered to be within the scope of the invention.

EXAMPLES

Example 1

Evaluation of Gemcitabine and the Albumin-Binding Gemcitabine Phosphate Compound 15 in a Human Xenograft Non Small Cell Lung Cancer Model LXFE 397.

Female NMRI nude mice received unilateral tumor implants subcutaneously in the left flank while under isoflurane anesthesia with human LXFE 397 (squamous cell carcinoma, differentiation: poor) until tumors were palpable and had reached a volume of 50-150 mm$^3$. Animals were kept in cages, the temperature inside the cages maintained at 25±1° C. with a relative humidity of 45-65% and an air change rate in the cage of 60-fold per hour. The animals were fed with autoclaved Teklad Global 19% Protein Extruded Diet (T.2019S.12) from Harlan Laboratories and had access to sterile filtered and acidified (pH 2.5) tap water which was changed twice weekly. Feed and water are provided ad libitum. Prior to therapy, the animals are randomized (8 mice per group) considering a comparable median and mean of group tumor volume. Animals are routinely monitored twice daily on working days and daily on Saturdays and Sundays. Starting on day 0, animals are weighed twice a week. Relative body weights (RBW) of individual animals are calculated by dividing the individual absolute body weight on day X (BWx) by the individual body weight on the day of randomization. The tumor volume is determined by a two-dimensional measurement with calipers on the day of randomization (Day 0) and then twice weekly. Tumor volumes are calculated according to the following equation: Tumor Vol [mm$^3$]=a [mm]×b$^2$ [mm$^2$]×0.5, where "a" is the largest diameter and "b" is the perpendicular diameter of the tumor representing an idealized ellipsoid. The relative volume of an individual tumor on day X (RTVx) is calculated by dividing the absolute volume [mm$^3$] of the respective tumor on day X (Tx) by the absolute volume of the same tumor on the day of randomization. Schedules are applied to the extent that animal welfare policies allow. Termination of individual mice at tumor volume >2000 mm$^3$. Stock solutions of compound 15 were prepared as follows for the two treatment groups:

1) 8 mice, 40 g average weight: 24 mg/kg Gemcitabine equivalents≡78.48 mg/kg≡3.14 mg/mouse. Sample preparation: 154 mg weighed in a 20 mL vial dissolved in 14.7 mL 20 mM sodium phosphate buffer pH 7; 4 aliquots with 3.6 mL each in 10 mL vials. Frozen in liquid nitrogen, lyophilized (>48 h) and stoppered.

2) 8 mice, 40 g average weight: 36 mg/kg Gemcitabine equivalents≡117.7 mg/kg≡4.71 mg/mouse. Sample preparation: 231 mg weighed in a 20 mL vial dissolved in 14.7 mL 20 mM sodium phosphate buffer pH 7; 4 aliquots with 3.6 mL each in 10 mL vials. Frozen in liquid nitrogen, lyophilized (>48 h) and stoppered.

On the day of treatment the lyophilized samples were dissolved in 20 mM sodium phosphate buffer pH 7, containing 5% Glucose and injected intravenously. Intravenous administration with vehicle (20 mM sodium phosphate buffer, 5% D-glucose—pH 7.0), gemcitabine (dissolved in 5% D-glucose; dose 240 mg/kg) and compound 15 (dissolved in 20 mM sodium phosphate buffer, 5% D-glucose—pH 7.0; 24 mg/kg gemcitabine equivalents) was carried on days 1, 8, 15, and 22. On day 23, 3 mice from the control group and 2 mice of the gemcitabine treated group had to be sacrificed due to the tumor volume exceeding 2000 mm$^3$. Body weight change (BWC) versus control: Gemcitabine (day 23) approximately −6%; compound 15 (day 27) ~0.5%. Tumor growth development in the NSLC xenograft model LXFE 397 shows superior antitumor efficacy of compound 15 versus gemcitabine at one tenth of the dose of gemcitabine ($p<0.05$) at equitoxic toxicity as indicated by comparable and low body weight loss. See FIG. 1.

FIG. 1 shows the effect of compound 15 and gemcitabine on tumor growth in the NSLC xenograft model LXFE 397.

Example 2

Evaluation of Gemcitabine and the Albumin-Binding Gemcitabine Phosphate Compound 15 in a Human Non-Small Cell Carcinoma Xenograft Model LXFE 937.

Female NMRI nude mice received unilateral tumor implants subcutaneously in the left flank while under isoflurane anesthesia with human LXFE 937 tumor pieces until tumors were palpable and had reached a volume of ~100 mm$^3$. Animals were kept in cages, the temperature inside the cages maintained at 25±1° C. with a relative humidity of 45-65% and an air change rate in the cage of 60-fold per hour. The animals were fed with autoclaved Teklad Global 19% Protein Extruded Diet (T.2019S.12) from Harlan Laboratories and had access to sterile filtered and acidified (pH 2.5) tap water which was changed twice weekly. Feed and water were provided ad libitum. Prior to therapy, the animals were randomized (8 mice per group) considering a comparable median and mean of group tumor volume. Animals were routinely monitored twice daily on working days and daily on Saturdays and Sundays. Starting on day 0, animals were weighed twice a week. Relative body weights (RBW) of individual animals are calculated by dividing the individual absolute body weight on day X (BWx) by the individual body weight on the day of randomization. The tumor volume is determined by a two-dimensional measurement with calipers on the day of randomization (Day 0) and then twice weekly. Tumor volumes are calculated according to the following equation: Tumor Vol [mm$^3$]=a [mm]×b$^2$ [mm$^2$]×0.5, where "a" is the largest diameter and "b" is the perpendicular diameter of the tumor representing an idealized ellipsoid. The relative volume of an individual tumor on day X (RTVx) is calculated by dividing the absolute volume [mm$^3$] of the respective tumor on day X (Tx) by the absolute volume of the same tumor on the day of randomization. Schedules are applied to the extent that animal welfare policies allow. Termination of individual mice at tumor volume >2000 mm$^3$. Stock solutions of compound 15 were prepared as follows for the two treatment groups:

1) 8 mice, 40 g average weight: 2×18 mg/kg gemcitabine equivalents (bi-weekly dosing; d 0, 3, 7, 10 etc. for 4 weeks)≡58.4 mg/kg≡2.35 mg/mouse. Sample preparation: 115.5 mg weighed in a 10 mL vial dissolved in 7.35 mL 20 mM sodium phosphate buffer pH 7; 4 aliquots with 1.86 mL each in 10 mL vials. Frozen in liquid nitrogen, lyophilized (>48 h) and stoppered. On the day of treatment the lyophilized samples were dissolved in 20 mM sodium phosphate buffer pH 7, containing 5% Glucose and injected intravenously. Intravenous administration with vehicle (20 mM sodium phosphate buffer, 5% D-glucose—pH 7.0), gemcitabine (dissolved in 5% D-glucose; dose 240 mg/kg) and carried out on 1, 8, 15, and 22 and compound 15 (dissolved in 20 mM sodium phosphate buffer, 5% D-glucose—pH 7.0; 18 mg/kg gemcitabine equivalents) was carried on days 0, 3, 7, 10, 14, 17, 21, and 24.

Body weight change (BWC) versus control was comparable, approximately +10% for the gemcitabine treated group and approximately +2% in the group treated with compound 15. Tumors in the gemcitabine treated groups started regrowth ~20 days after therapy reaching an average tumor volume ~700 mm$^3$~50 days after therapy with 2 mice of the gemcitabine treated group having to be sacrificed between day 78 to 85 due to the tumor volume exceeding 2000 mm$^3$. In contrast, complete tumor remissions were observed ~60 days after the end of therapy in the group treated with 15. Thus, tumor growth development in the human non-small cell carcinoma xenograft model LXFE 937 shows superior antitumor efficacy of compound 15 versus gemcitabine at approximately one seventh of the dose of gemcitabine (p<0.05) at equitoxic toxicity as indicated by comparable and body weight gain. See FIGS. 2 and 3.

Figure 2:
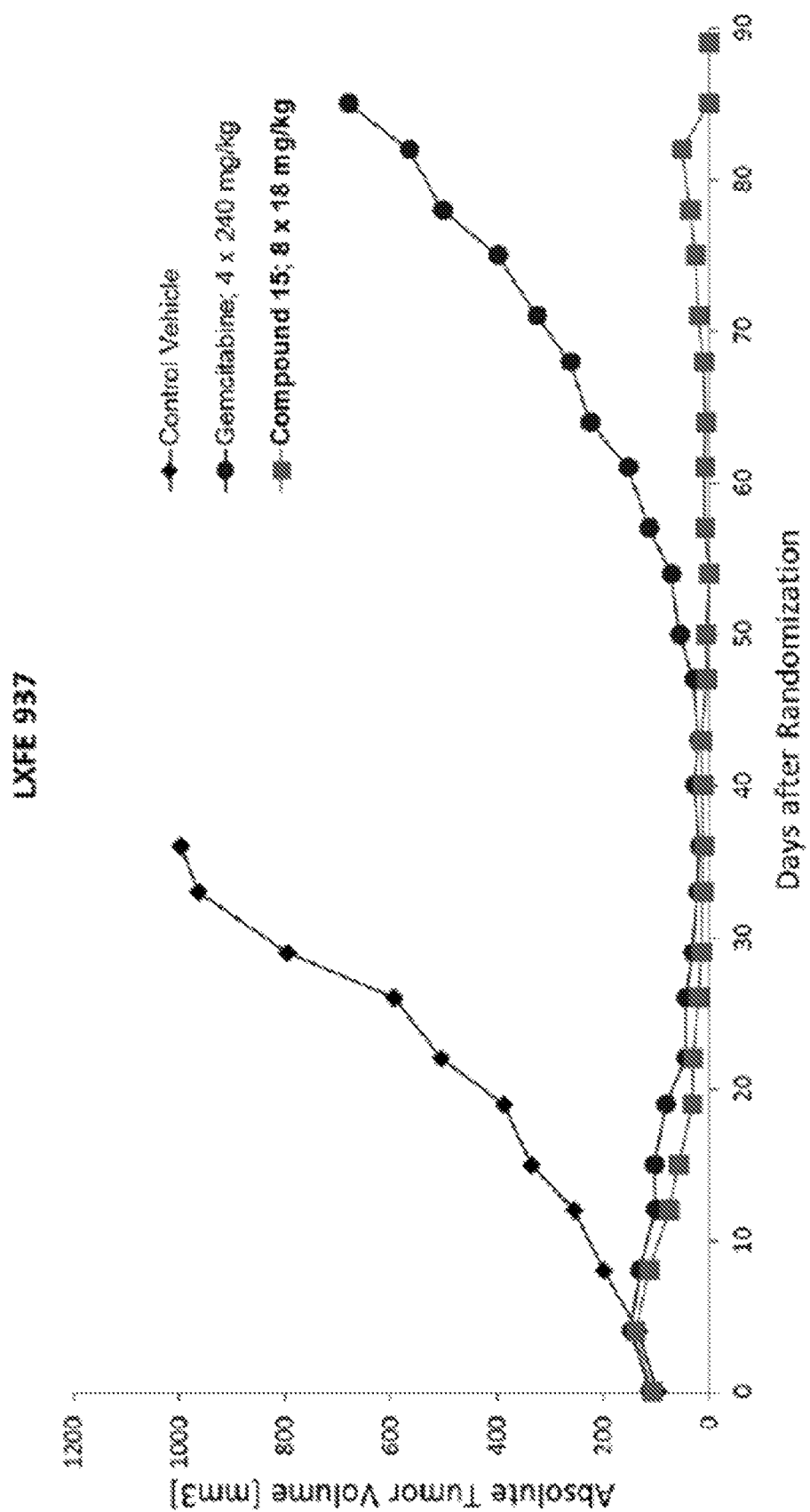
FIG. 2 shows the effect of compound 15 and gemcitabine on tumor growth in a NSLC xenograft model LXFE 397.

FIG. 2 shows tumor growth curves of the control group, the gemcitabine treated group, and the group treated with compound 15 in the human non-small cell carcinoma xenograft model LXFE 937.

Figure 3:
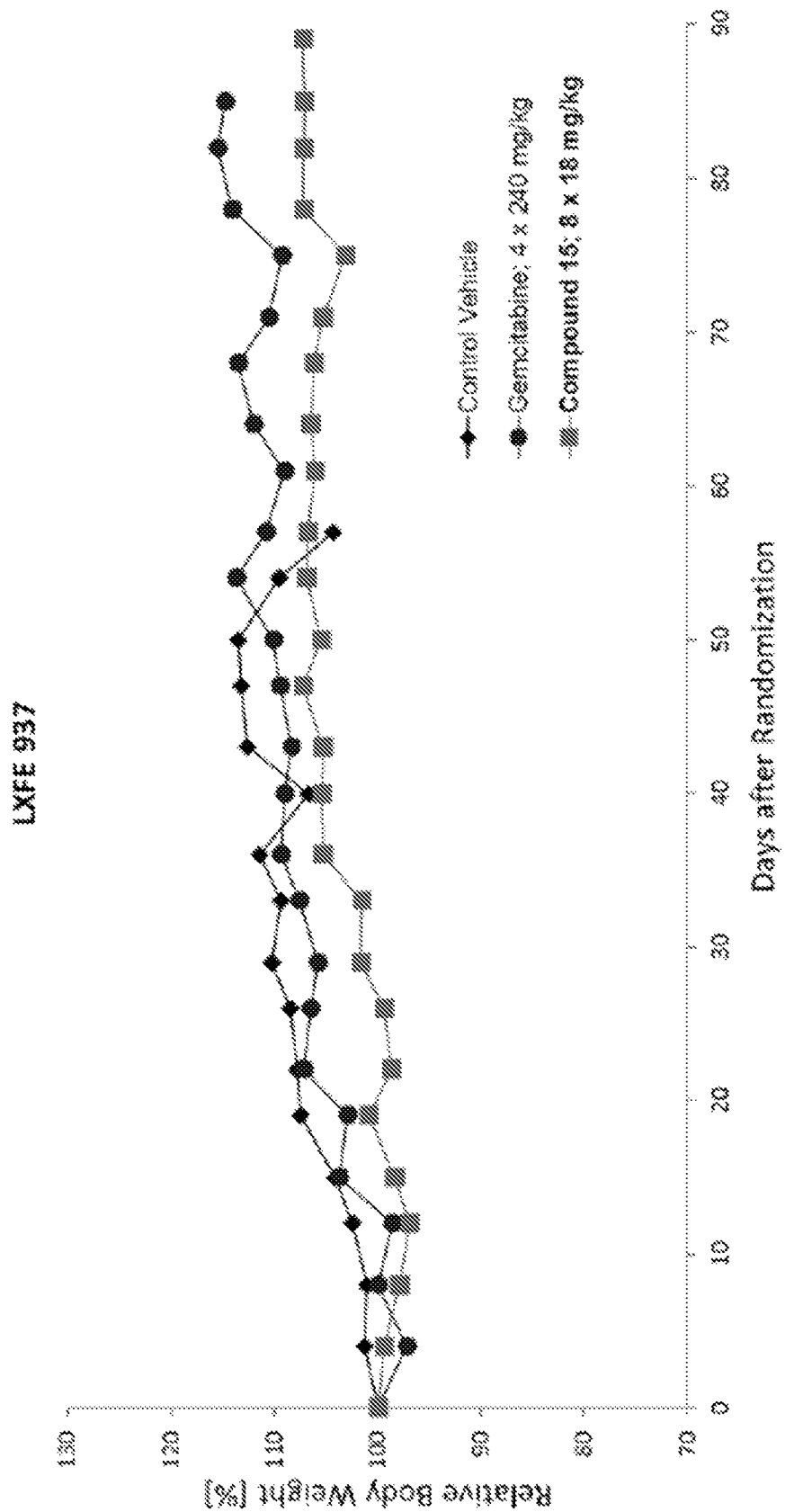
FIG. 3 shows the effect of compound 15 and gemcitabine on body weight change in a human non-small cell carcinoma xenograft model LXFE 937.

FIG. 3 shows curves of body weight change in the control group, the gemcitabine treated group, and the group treated with compound 15 in the human non-small cell carcinoma xenograft model LXFE 937.

Example 3

Evaluation of Gemcitabine and the Albumin-Binding Gemcitabine Phosphate Compound 15 in a Human Ovarian Carcinoma Xenograft Model OVXF 899.

Female NMRI nude mice received unilateral tumor implants subcutaneously in the left flank while under isoflurane anesthesia with human OVXF 899 tumor pieces until tumors were palpable and had reached a volume of ~200 mm$^3$. Animals were kept in cages, the temperature inside the cages maintained at 25±1° C. with a relative humidity of 45-65% and an air change rate in the cage of 60-fold per hour. The animals were fed with autoclaved Teklad Global 19% Protein Extruded Diet (T.20195.12) from Harlan Laboratories and had access to sterile filtered and acidified (pH 2.5) tap water which was changed twice weekly. Feed and water were provided ad libitum. Prior to therapy, the animals were randomized (8 mice per group) considering a comparable median and mean of group tumor volume. Animals were routinely monitored twice daily on working days and daily on Saturdays and Sundays. Starting on day 0, animals were weighed twice a week. Relative body weights (RBW) of individual animals are calculated by dividing the individual absolute body weight on day X (BWx) by the individual body weight on the day of randomization. The tumor volume is determined by a two-dimensional measurement with calipers on the day of randomization (Day 0) and then twice weekly. Tumor volumes are calculated according to the following equation: Tumor Vol [mm$^3$]=a [mm]×b$^2$ [mm$^2$]× 0.5, where "a" is the largest diameter and "b" is the perpendicular diameter of the tumor representing an idealized ellipsoid. The relative volume of an individual tumor on day X (RTVx) is calculated by dividing the absolute volume [mm$^3$] of the respective tumor on day X (Tx) by the absolute volume of the same tumor on the day of randomization. Schedules are applied to the extent that animal welfare policies allow. Termination of individual mice at tumor volume >2000 mm$^3$. Stock solutions of compound 15 were prepared as follows for the two treatment groups:

8 mice, 40 g average weight: 2×18 mg/kg gemcitabine equivalents (bi-weekly dosing; d 1, 4, 8, etc. for 4 weeks) ≡58.4 mg/kg≡2.35 mg/mouse. Sample preparation: 115.5 mg weighed in a 10 mL vial dissolved in 7.35 mL 20 mM sodium phosphate buffer pH 7; 4 aliquots with 1.86 mL each in 10 mL vials. Frozen in liquid nitrogen, lyophilized (>48 h) and stoppered. On the day of treatment the lyophilized samples were dissolved in 20 mM sodium phosphate buffer pH 7, containing 5% Glucose and injected intravenously. Intravenous administration with vehicle (20 mM sodium phosphate buffer, 5% D-glucose—pH 7.0) gemcitabine (dissolved in 5% D-glucose; dose 240 mg/kg) and carried out on 1, 8, 15, and 22 and compound 15 (dissolved in 20 mM sodium phosphate buffer, 5% D-glucose—pH 7.0; 18 mg/kg gemcitabine equivalents) was carried on days 1, 4, 8, 11, 15, 18, 22, and 25.

Body weight change (BWC) versus control was comparable, approximately +5% for the gemcitabine treated group and approximately +10% in the group treated with compound 15. Tumors in the gemcitabine treated group started regrowth ~10 days after therapy reaching an average tumor volume ~2000 mm$^3$ 50 days after therapy with 3 mice of the gemcitabine treated group having to be sacrificed on day 74 due to the tumor volume exceeding 2000 mm$^3$. In contrast, complete tumor remissions were observed 50 days after the end of therapy in the group treated with 15. Thus, tumor growth development in the ovarian carcinoma xenograft model OVXF 899 shows superior antitumor efficacy of compound 15 versus gemcitabine at approximately one seventh of the dose of gemcitabine (p<0.05) at equitoxic toxicity as indicated by comparable and body weight gain. See FIGS. 4, 5 and 6.

Figure 4:
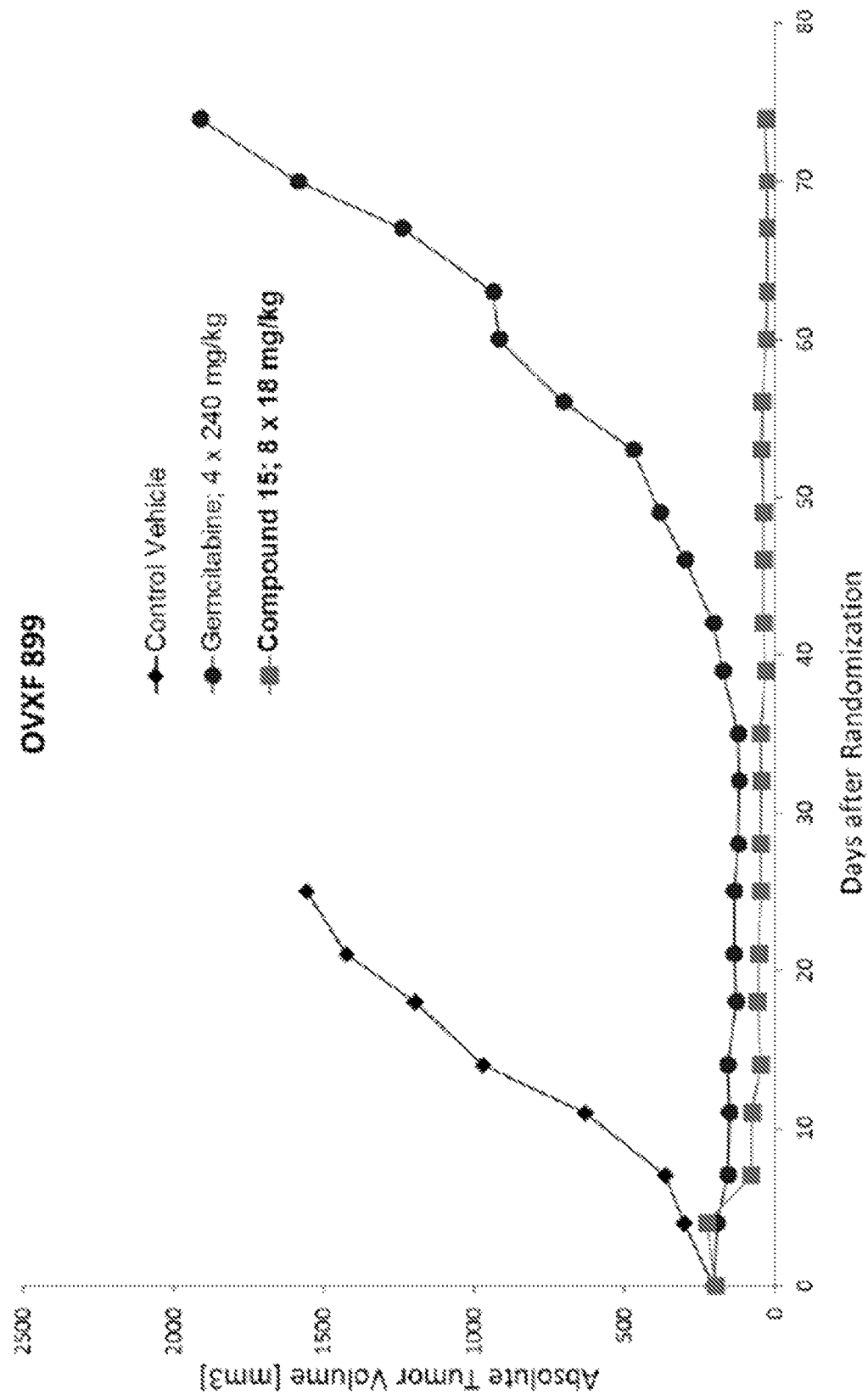
FIG. 4 shows the effect of compound 15 and gemcitabine on tumor growth in an ovarian cancer OVXF 899 xenograft model.

FIG. 4 shows tumor growth curves of the control group, the gemcitabine treated group, and the group treated with compound 15 in the human ovarian OVXF carcinoma xenograft model.

Figure 5:
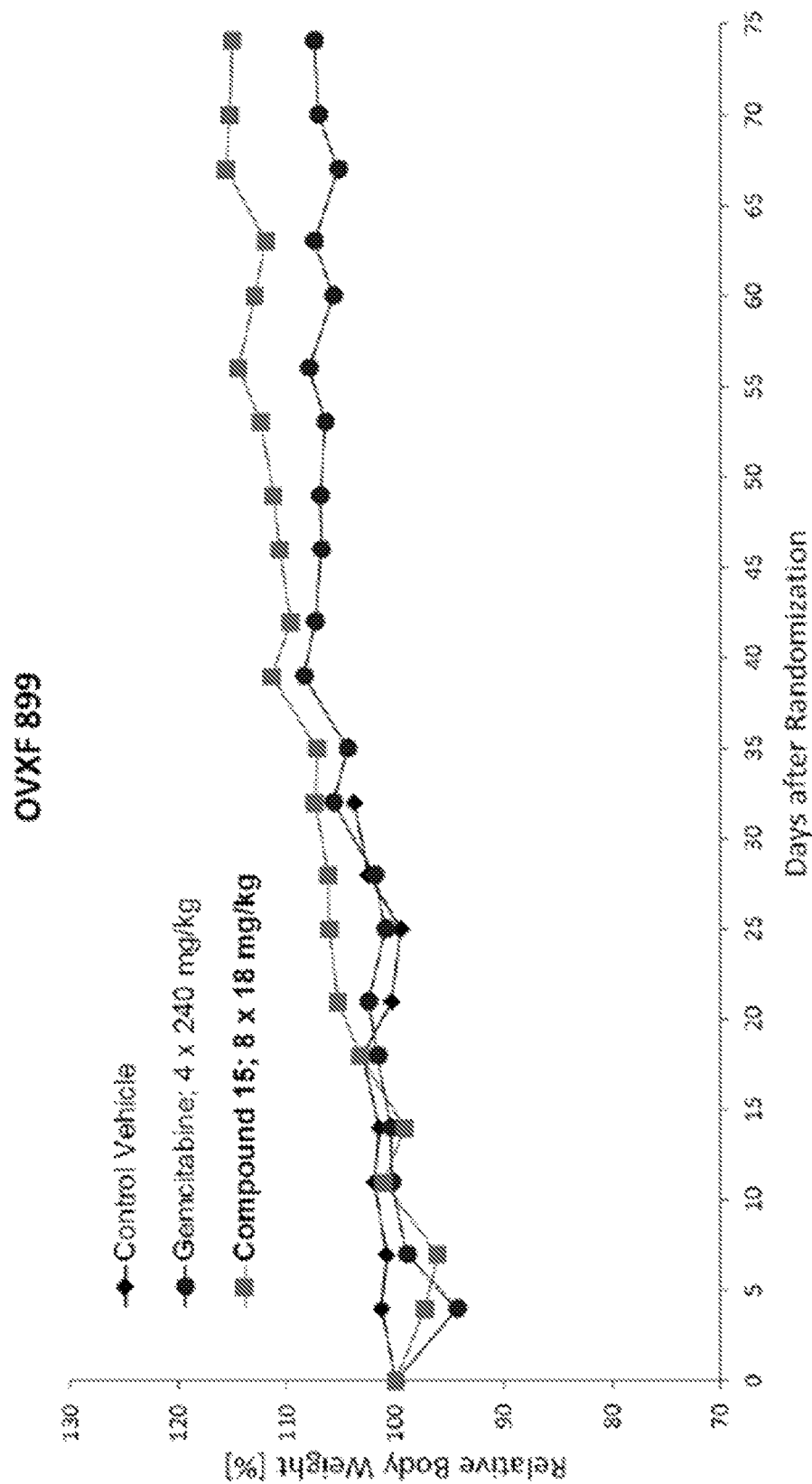
FIG. 5 shows the effect of compound 15 and gemcitabine on body weight change in a human ovarian cancer OVXF 899 xenograft model.

FIG. 5 shows curves of body weight change in the control group, the gemcitabine treated group, and the group treated with compound 15 in the human ovarian OVXF carcinoma xenograft model.

Figure 6:
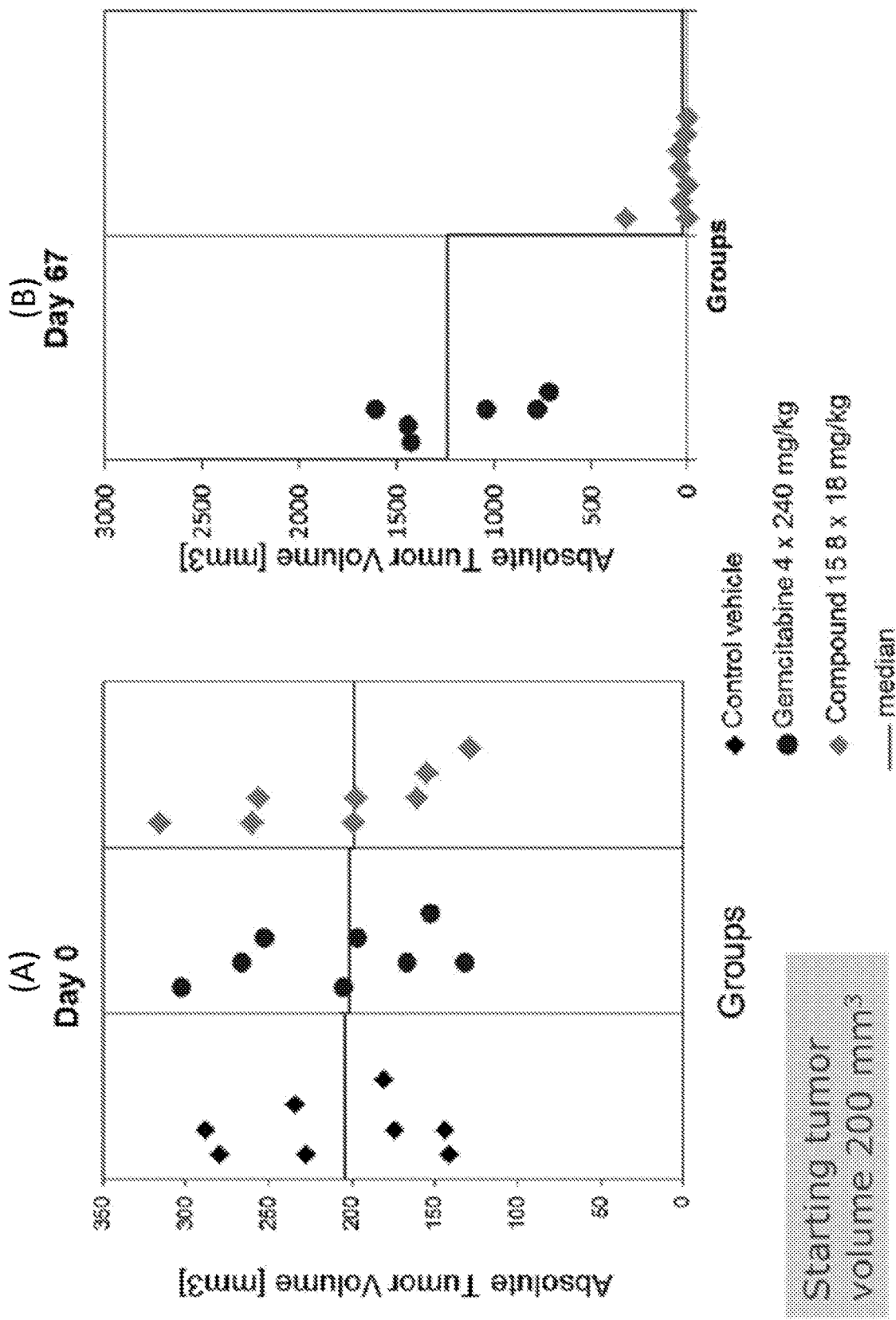
FIG. 6 shows scatter plots for the individual tumor volumes after treatment with compound 15 or gemcitabine in an ovarian cancer OVXF 899 xenograft model. Panel (A) shows the absolute tumor volume on day 0; Panel (B) shows the absolute tumor volume on day 67.

FIG. 6 shows scatter plots for the individual tumor volumes after treatment with compound 15 or gemcitabine in the ovarian cancer OVXF 899 xenograft model.

Example 4

Evaluation of Gemcitabine and the Albumin-Binding Gemcitabine Phosphate Compound 15 in a Human Pancreatic Carcinoma Xenograft Model Panc11159

Female NMRI nude mice (nu/nu) received unilateral Panc11159 tumor pieces subcutaneously implanted until tumors were palpable and had reached a volume of ~200 mm$^3$. Animals were kept in cages (Macrolon Type-II wire-mesh), the temperature inside the cages maintained at 22±1° C. with a relative humidity of 50±10%. Light period: artificial; 12-hours dark/12 hours light rhythm (light 06.00 to 18.00 hours). The health of the mice was examined at the start of the experiment and twice per day during the experiment; identification: Ear mark and cage labels. The animals were fed with Ssniff NM, Soest, Germany and had access to autoclaved and acidified (pH 4.0) drinking. Feed and water were provided ad libitum. Prior to therapy, the animals are randomized (10 mice per group) considering a comparable median and mean of group tumor volume.

Body weight change was performed two or three times per week. Tumor diameters (median and medium) were measured two or three times a week with a caliper. Tumor volumes were calculated according to V=(length×(width)2)/ 2. For calculation of the relative tumor volume (RTV) the tumor volumes at each measurement day were related to the day of first treatment. Stock solutions of compound 15 were prepared as follows for the two treatment groups: 10 mice, 30-40 g average weight: 2×18 mg/kg gemcitabine equivalents (bi-weekly dosing for 4 weeks)≡58.4 mg/kg≡2.35 mg/mouse. Sample preparation: 115.5 mg weighed in a 10 mL vial dissolved in 7.35 mL 20 mM sodium phosphate buffer pH 7; 4 aliquots with 1.86 mL each in 10 mL vials. Frozen in liquid nitrogen, lyophilized (>48 h) and stoppered. On the day of treatment the lyophilized samples were dissolved in 20 mM sodium phosphate buffer pH 7, containing 5% Glucose and injected intravenously. Intravenous administration with vehicle (20 mM sodium phosphate buffer, 5% D-glucose—pH 7.0) gemcitabine (dissolved in 5% D-glucose; dose 240 mg/kg) and carried out on d 36, 43, 50, 57 compound 15 (dissolved in 20 mM sodium phosphate buffer, 5% D-glucose—pH 7.0; 18 mg/kg gemcitabine equivalents) was carried on days d 36, 40, 43, 47, 50, 54, 57, and 60.

Body weight change (BWC) versus control was comparable, approximately +3% for both the gemcitabine treated group and the group treated with compound 15.

Tumor volumes in the gemcitabine treated group had doubled at day 85 while tumor volumes in the group treated with 15 demonstrated slight regression or stable disease. Thus, tumor growth development in the human pancreatic carcinoma xenograft model Panc11159 showed superior antitumor efficacy of compound 15 versus gemcitabine at approximately one seventh of the dose of gemcitabine (p<0.05) at equitoxic toxicity as indicated by comparable and body weight gain. See FIGS. 7 and 8.

Figure 7:
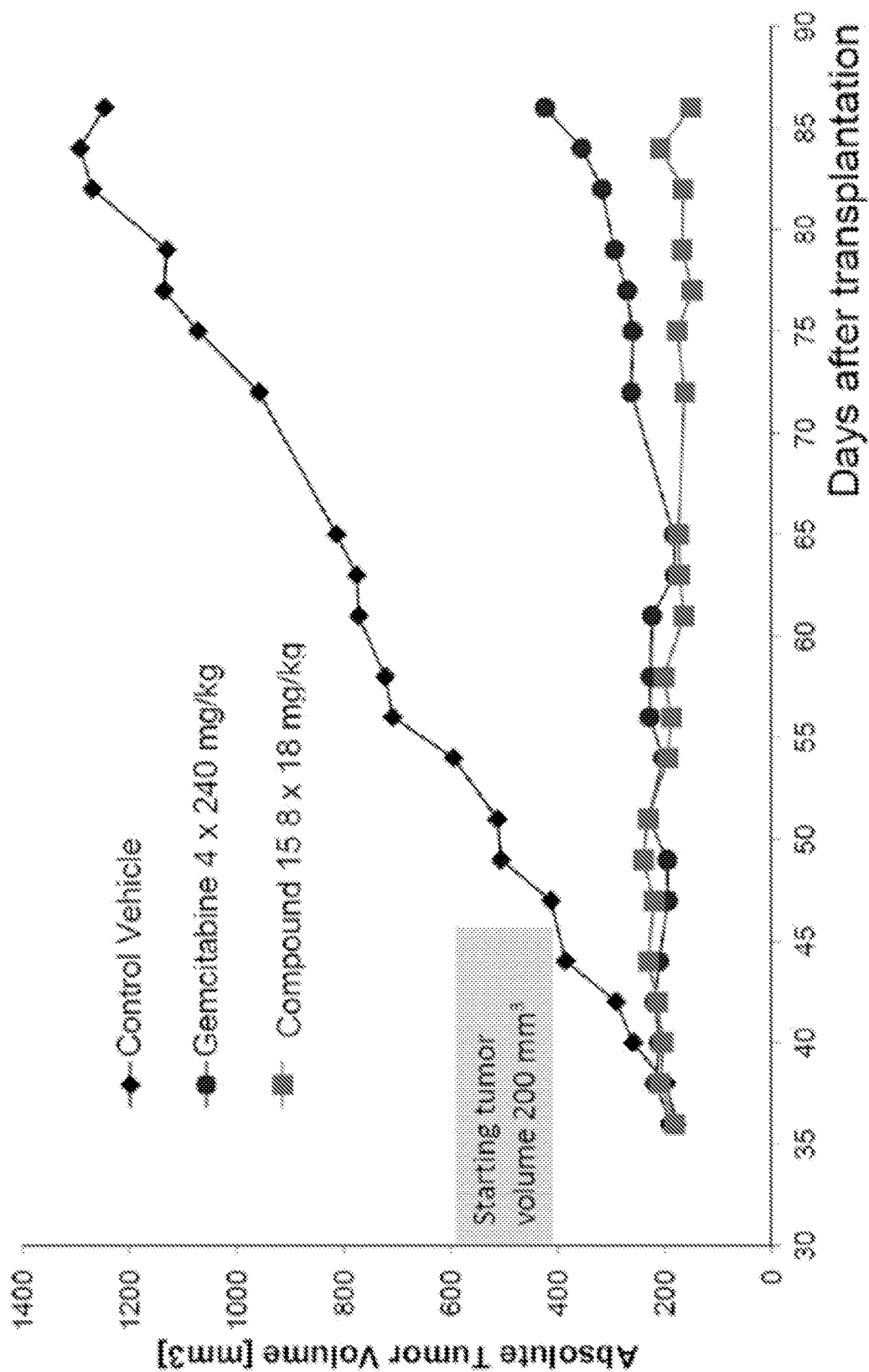
FIG. 7 shows the effect of compound 15 and gemcitabine on tumor growth in a pancreatic cancer Panc11159 xenograft model.

FIG. 7 shows tumor growth curves of the control group, the gemcitabine treated group, and the group treated with compound 15 in the pancreatic cancer Panc11159 xenograft model.

Figure 8:
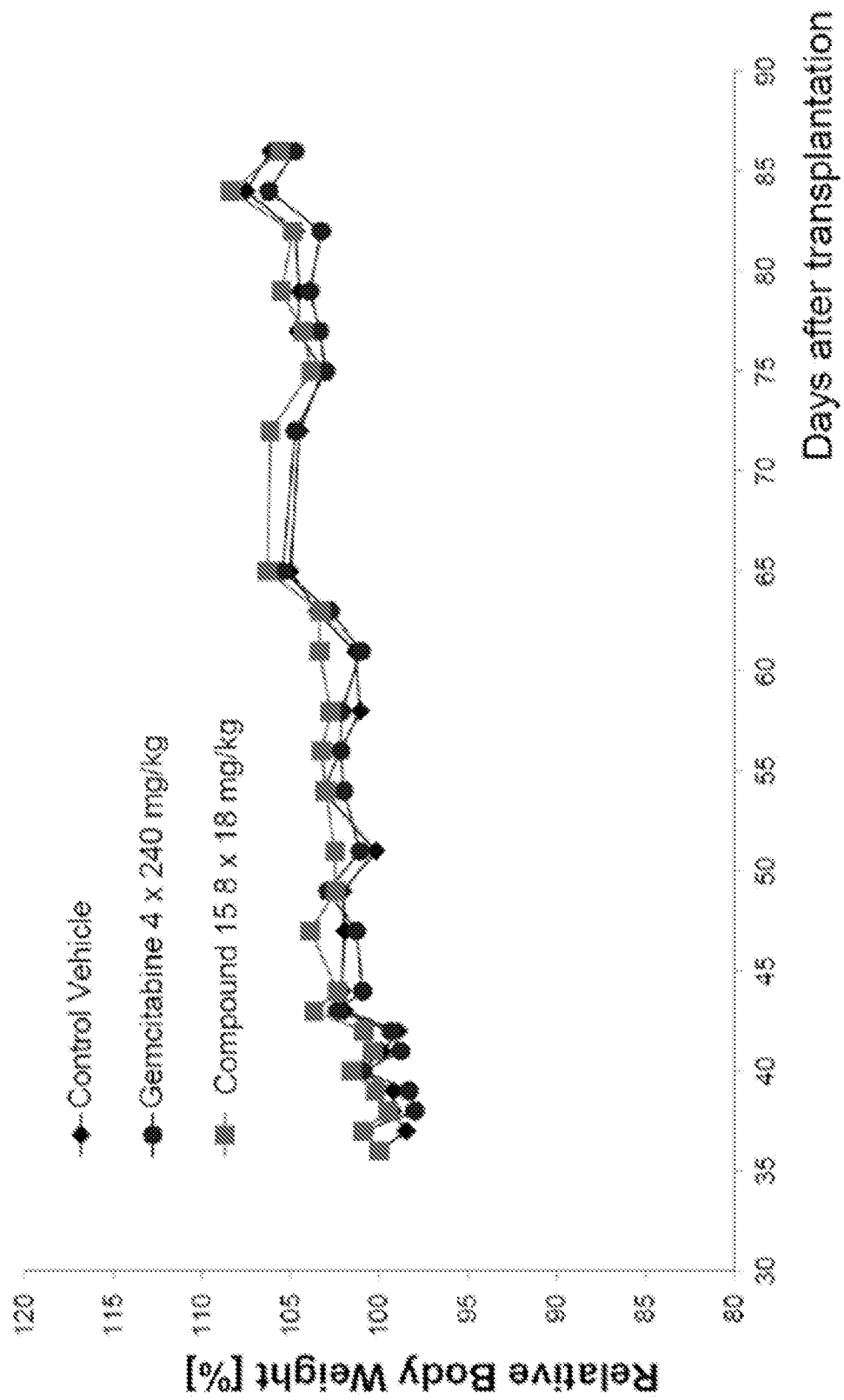
FIG. 8 shows the effect of compound 15 and gemcitabine on body weight change in a pancreatic cancer Panc11159 xenograft model.

FIG. 8 shows curves of body weight change in the control group, the gemcitabine treated group, and the group treated with compound 15 in the pancreatic cancer Panc11159 xenograft model.

Example 5

General Procedure for the Synthesis of Substituted Maleimidobenzoyl Hydrazone Derivatives of Nemorubicin Typically, to a mixture of nemorubicin (1 equivalent), and the substituted maleimidobenzoic acid hydrazide trifluoroacetate (2 equivalent) was added anhydrous methanol at room temperature (RT) and the reaction mixture was stirred at RT. After the reaction was completed, as shown by TLC, the substituted maleimidobenzoyl hydrazone derivatives of nemorubicin were isolated as a red solid by precipitation or crystallization with a mixture of isopropanol and diisopropylether, and the obtained product dried under high vacuum.

General Procedure for the Release Studies of the Albumin-Bound Substituted Maleimidobenzoyl Hydrazone Derivatives of Nemorubicin Typically, the substituted maleimidobenzoyl hydrazone derivatives of nemorubicin were dissolved in 20:80 EtOH/5%-Glucose and added to human serum albumin (HSA)—fully reduced at the cysteine-34 position—in 4 mM phosphate buffer pH 7.4 and incubated at 37° C. for 2 hours. The albumin drug conjugate was isolated using Sephadex G-25 and eluted with 4 mM phosphate buffer pH 7.4 containing 150 mM NaCl. The purity of the nemorubicin albumin conjugate was measured analyzed by RP-HPLC and the content of anthracycline in the sample was determined spectrophotometrically. For drug release studies at pH 5.0, a 200 µM solution of the respective nemorubicin human serum albumin (HSA) conjugate, adjusted to pH 5.0 with 50 mM sodium acetate buffer, was monitored with the aid of RP-HPLC and the release of nemorubicin determined at 495 nm. Results are presented in Table A.

Example 6

Method A: Preparation of Compound 15

Compound 15 may be prepared as described below and shown in Scheme 1.

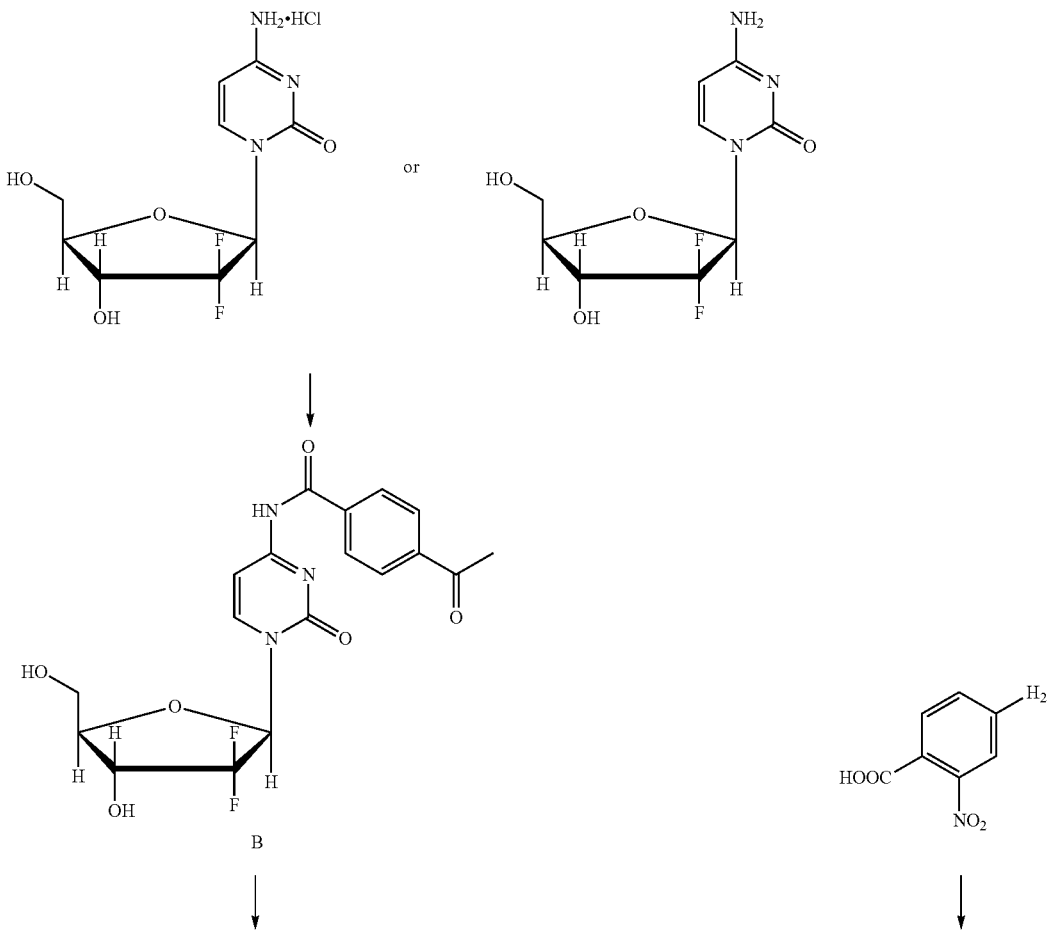

SCHEME 1

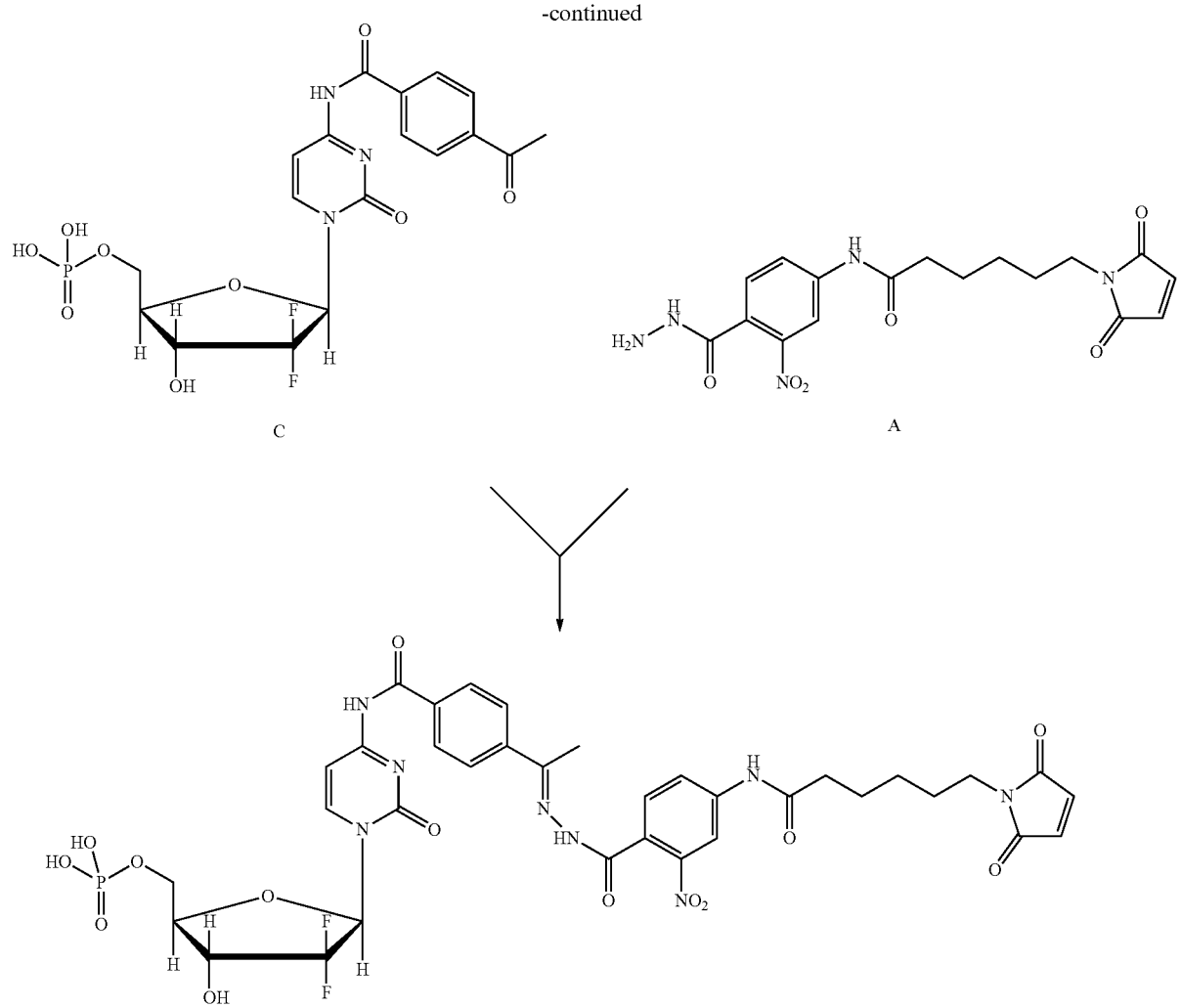

Synthesis of 4-acetyl-N-(1-((2R,4R,5R)-3,3-difluoro-4-hydroxy-5-(hydroxymethyl)-tetrahydrofuran-2-yl)-2-oxo-1,2-dihydropyrimidin-4-yl)benzamide (B)

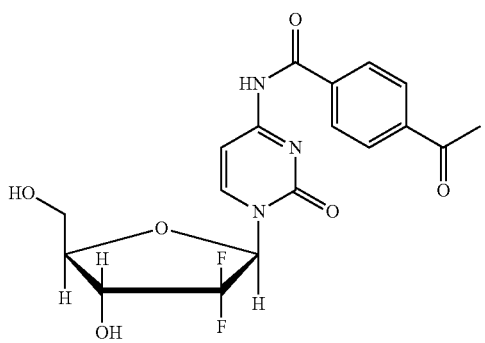

To a stirred solution of 4-acetylbenzoic acid (8.25 g, 50.30 mmol) in $CH_2Cl_2$ (165 mL) were added oxalyl chloride (8.31 mL, 95.57 mmol) and DMF (catalytic amount) at 0° C. The resulting mixture was stirred at room temperature for 2 h. The reaction mixture was concentrated to dryness under high vacuum to give the 4-acetylbenzoyl chloride as a pale yellow solid. The crude material was used as such in the next step without any further purification. Yield: 9.15 g, 99.67%.

To a stirred solution of Gemcitabine hydrochloride (15 g, 50 mmol) in pyridine (150 mL), was added chlorotrimethylsilane (31.6 mL, 250 mmol) dropwise [~1.0 mL/min] over 30 min at 0° C. The resulting mixture was stirred at room temperature for 2 h. 4-acetylbenzoyl chloride (9.12 g, 50 mmol) was added to the reaction mixture portionwise (3 portions, ~3.04 g/5.0 min) over 15 min. The resulting mixture was stirred at 45° C. for 16 h. Then ethanol (150 mL) was added to the above reaction mixture and stirred for 30 min. Subsequently desalted water (75 mL) was added and stirred for additional 5 h. Then the reaction mixture was concentrated to dryness and the residue was quenched with ice water (300 mL). The resulting solid was filtered through Whatman filter paper (11 μm) and dried under high vacuum for 5 h. The crude product was purified by silica gel flash chromatography. The crude mass was dissolved in $CH_2Cl_2$ and adsorbed on silica gel (60-120 mesh, 60 g) and purified over 60×12.5 cm flash column using 240 g of 60-120 mesh silica gel and ~20 L of 60% ethyl acetate in petrol ether as an eluent. The resulting solid was washed with methanol (100 mL), filtered and dried under high vacuum for 5 h to give the 4-acetyl-N-(1-((2R,4R,5R)-3,3-difluoro-4-hydroxy-5-(hydroxymethyl)-tetrahydrofuran-2-yl)-2-oxo-1,2-dihydropyrimidin-4-yl)benzamide (B) as a white solid. Yield: 5.2 g, 12.71 mmol, 25.42%.

Synthesis of Intermediate (C)

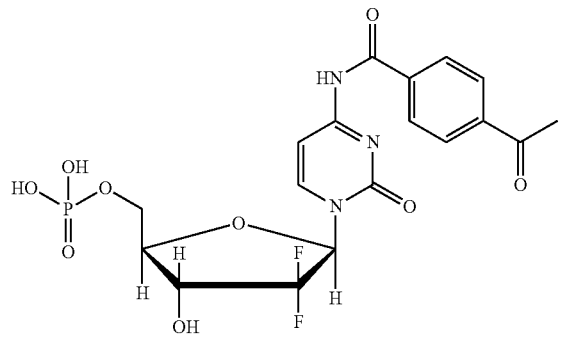

In a 50 ml flask, 1.816 mL (19.54 mmol) phosphoryl chloride were added to 12.2 mL of trimethyl phosphate. The clear, colorless solution was cooled in an ice-bath, followed by the addition of 2 g (4.89 mmol) of (B). The suspension cleared after ~15 min and the resulting light yellow solution was stirred in an ice-bath. After 2 h, 5 µL of the reaction mixture were added carefully to 1 ml of a 1:1 mixture of diethyl ether and saturated aqueous sodium bicarbonate. The milky suspension in the organic phase dissipated upon thorough mixing. 50 µL of the aqueous phase were removed, diluted with 150 µL Millipore water and analysed by LC-MS. After ~2.5 h, the reaction mixture was added dropwise with intermittent shaking to a mixture of 140 mL Millipore water, 140 mL saturated NaHCO₃ and 600 mL diethyl ether in a 1000 mL Erlenmeyer flask cooled in an ice-bath. The mixture was transferred to a 1000 mL separating funnel and shaken well. The aqueous phase was washed with another 400 mL diethyl ether. The aqueous phase (pH 7-8) was isolated, filtered through a fritted funnel (pore size 3) into a 500 mL flask and acidified to pH 4 with conc. HCl. The mixture was transferred into eight 50 mL Falcon tubes (~40 mL each), then stored at 4° C. in the fridge overnight. The suspension was centrifuged (3220 rpm/30 min), the supernatant removed by pipette and the residue lyophilized. Yield: (4.195 g/175%, theoretical: 2.393 g). The solid was dissolved in 275 mL methanol, then 75 mL tetrahydrofuran were added and the mixture stored at 5° C. for 3 days. The solvent was removed in vacuo to ~150 mL, then 60 mL tetrahydrofuran were added forming a white precipitate which was filtered and washed with 20 ml tetrahydrofuran/methanol (1:1). (C) was isolated as a white solid from the filtrate. Yield: 3 g.

Synthesis of Linker (A)

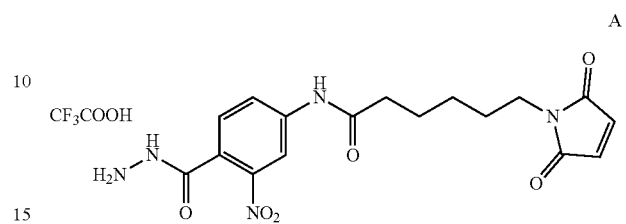

4-amino-2-nitrobenzoic acid (4.62 g, 25.36 mmol) was stirred with tert-butyl carbazate (5.04 g, 38.14 mmol), HOBt hydrate (5.297 g, 34.6 mmol) and EDC (4.84 g, 25.25 mmol) in 120 mL of a 1:2-mixture dimethylformamide/dichloromethane in an ice-bath for 15 min then at room temperature overnight. TLC (CHCl₃/methanol, 9:1) shows completion of the reaction after 26 h. The crude product was purified by column chromatography on silica yielding the pure compound as a yellow foam (6.2 g, 82%). In a 250 mL flask, 4-amino-2-nitro carbazate (2.827 g, 9.54 mmol) was dissolved in 80 mL tetrahydrofuran. To the stirring solution, 6-maleimidocaproic acid chloride (2.41 g, 10.5 mmol), dissolved in 30 mL tetrahydrofuran, was added. Triethylamine (1.455 mL, 10.5 mmol), mixed with 40 mL THF, was added dropwise to the mixture over 1 h using a dropping funnel. The resulting light brown suspension was stirred at room temperature for 15 h. TLC (CHCl₃/methanol, 9:1) showed completion of the reaction. The crude product was purified by silica gel flash chromatography (CHCl₃/methanol, 9:1), yielding the pure product as a yellow solid (3 g, 64%). The product (3 g, 6.13 mmol) was suspended in 10 mL dichloromethane and cooled in an ice-bath. 10 mL trifluoroacetic acid were added dropwise over 30 min using a dropping funnel to the cooled, stirring mixture. TLC (CHCl₃/methanol, 9:1) of the yellow solution after 3 h shows complete cleavage of the BOC group. All solvents were removed by under reduced pressure and the residue dried under high vacuum overnight. The residue was dissolved in a minimum amount of tetrahydrofuran and precipitated in a 1:1-mixture of diisopropyl ether and n-hexane, then stored at 5° C. overnight. The cream-colored precipitate was isolated by centrifugation, washed with diethyl ether and dried under high vacuum to yield 2.5 g (81%) of linker A as a beige solid.

Synthesis of Compound 15

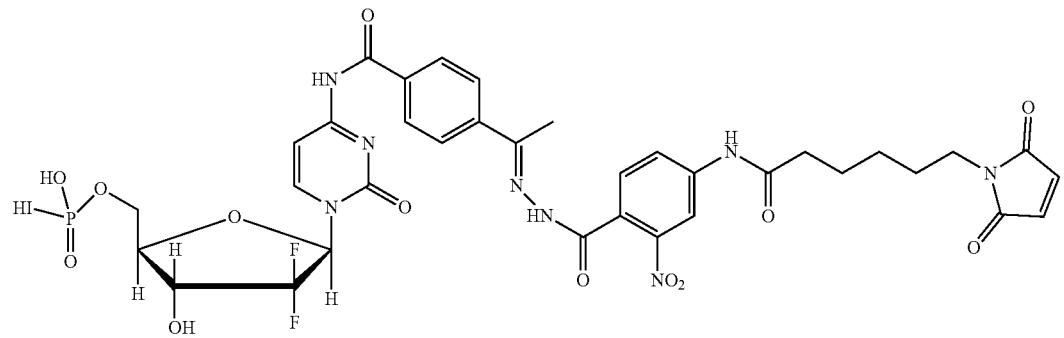

(C) was dissolved (2×375 mg (1.226 mmol) in 30 mL anhydrous methanol each in two 50 mL Falcon tubes), centrifuged (3220 rpm, 10 min), the supernatants added to linker (A) (1.235 g, 2.452 mmol), suspended in 20 mL anhydrous methanol in a 250 mL flask. Another 40 mL methanol and 2 mL acetonitrile were added and the light-yellow, cloudy solution was stirred at room temperature. TLC (RP-18, acetonitrile/NaH$_2$PO$_4$, 30:70) of the reaction mixture after 15 h shows complete consumption of (C). The mixture was evaporated to ~30 mL, transferred to a 50 mL Falcon tube and stored at 5° C. (1 h). The precipitate was collected by centrifugation (3220 rpm, 10 min), the supernatant (3×10 mL) was added to a cold 3:1-mixture of diisopropyl ether/isopropanol (3×30 mL) in three 50 mL Falcon tubes and stored at 5° C. overnight. The precipitate was collected by centrifugation (3220 rpm, 15 min), washed with 5 ml diethyl ether, dried in air and under high vacuum to yield 903 mg (85.6% of theoretical 1.055 g) of compound 15 as a yellow solid. The crude product was combined in one 50 mL Falcon tube, washed with tetrahydrofuran (6×10-15 mL) and centrifuged after each washing step (3220 rpm, 10 min). Finally, the product was washed 3 times with 5-10 mL diethyl ether and dried in air and under high vacuum to yield 694.4 mg (66%) of compound 15 as a yellowish solid.

pH Dependent Stability of the HSA Compound 15 at pH 7.0 and 5.0

Stability at pH 7.0 (phosphate buffer 4 mM, NaCl 150 mM): compound 15 was added to a solution of fully reduced HSA (human serum albumin) and complete binding to the cysteine-34 position verified by HPLC. A 200 µM solution of the obtained HSA conjugate of compound 15 was incubated at 37° C. and analysed by HPLC every hour. Approximately 0.18% of (C) was released per hour. Stability at pH 5.0 (phosphate buffer 4 mM, NaCl 150 mM, adjusted with 1 M HCl): The HSA conjugate of compound 15 was prepared at pH 7.0 (see above) and adjusted to pH 5.0 by addition of 1 M HCl. A 200 µM solution of the obtained HSA conjugate of compound 15 was incubated at 37° C. and analysed by HPLC every hour. The half-life ($t_{1/2}$) for the release of (C) is approximately 13 h.

Method B: Preparation of Compound 15.

Compound 15 may be prepared by the following alternative method.

Synthesis of 4-acetyl-N-(1-((2R,4R,5R)-3,3-difluoro-4-hydroxy-5-(hydroxymethyl)-tetrahydrofuran-2-yl)-2-oxo-1,2-dihydropyrimidin-4-yl)benzamide (B)

Synthesis of 2,5-dioxopyrrolidin-1-yl 4-acetylbenzoate

Under a nitrogen atmosphere a 4-liter three-neck round-bottom flask was charged with 4-acetylbenzoic acid (1.0 equiv., 487.8 mmol, 80.00 g), N-hydroxysuccinimide (NHS) (1.1 equiv., 536.6 mmol, 61.75 g), and anhydrous THF (1.80 L). An IKA Eurostar digital overhead stirrer (power control at 190 rpm) was used to stir the contents of the reaction solution at constant speed. The solution was cooled using an ice bath (60 min). A solution of N,N'-dicyclohexylcarbodiimide (DCC) (1.1 equiv, 536.6 mmol, 110.71 g) in anhydrous THF (720 mL) was then added dropwise (over the course of 90 min), under nitrogen while stirring (the addition funnel was washed with anhydrous THF, 2×5 mL). After about 30 minutes of adding DCC the reaction mixture became turbid due to formation of N,N'-dicyclohexylurea (DCU) as a white precipitate. The reaction mixture was stirred at 0° C. for additional 2 hours whilst ice was continuously added to the ice-bath. The reaction mixture was then allowed to warm up slowly to room temperature without removing the ice bath to react until HPLC analysis indicated complete consumption of the carboxylic acid after 25 h 30 min. The solid material was removed by suction filtration. The solid was washed with dry THF (4×100 mL), and the combined fractions were evaporated to dryness in vacuo at 40° C. The residue was dissolved in dry dichloromethane (400 mL), and the solution was stored at 4° C. for 15 h and then filtered again. The solid was rinsed with precooled dry dichloromethane (2×20 mL). The solvent was removed in vacuo at 30° C., the residue was re-dissolved in dry DCM (750 mL), and the organic layer was washed with cold 5% NaOH aq. solution (2×400 mL). The organic layer was washed with distilled H$_2$O (400 mL), then dried over sodium sulfate (~20 g), suction filtered, and concentrated in vacuo at 30° C. to afford the title compound. The compound was dried in high vacuum for 24 h to yield (100.2 g, 79%) as an off-white solid (HPLC$_{250nm}$>95.9%).

Synthesis of (B):

Gemcitabine (1.0 equiv., 76.02 mmol, 20.00 g) was added to THF (532 mL) and distilled water (45.6 mL) was added in one portion to form a fine suspension which became a clear solution after refluxing (67° C.) for 5 min. Then, a solution of 2,5-dioxopyrrolidin-1-yl 4-acetylbenzoate (1.05 equiv., 79.82 mmol, 20.84 g) in THF (229 mL) was added dropwise via cannula over the period of 6 min. After the addition was completed, the reaction mixture was stirred while refluxing (67° C.) for 16 h. After 16 h, HPLC (PDA 266 nm) and LC-MS analyses showed approximately 20% of unreacted starting material gemcitabine. According to HPLC analysis (PDA 266 nm), the reaction solution contained 53.8% of the product, 33.6% total polar impurities, and 12.6% total non-polar impurities. The purification of the product of this batch employed successive and selective washing steps of the crude product to remove any undesired polar and non-polar impurities. The process comprised slurry washing steps with different solvents, which selectively dissolved the polar and non-polar impurities, in which the product is ideally insoluble or only slightly soluble. Therefore, after 16 h the pale yellow reaction solution was allowed to reach room temperature, and the solvents were evaporated under vacuum at 40° C. to yield a sticky residue. The first step of purification was applied to remove the polar impurities by washing with water followed by filtration and further washing with water. Thus, water (300 mL) was added to the above crude product, and the contents of the flask were triturated at room temperature (30 min) until a fine white suspension was obtained. The resulting suspension was then stirred at 50° C. for 15 min, filtered off through a filter funnel (Por. 4), and washed with water (2×25 mL) to yield an amorphous solid (solid 1) which was dried under vacuum for 15 h affording 26.34 g. HPLC analysis (266 nm) of this solid (solid 1) showed a purity of 91.9%, with a total of 3.7% of polar impurities and 4.4% of non-polar impurities.

The second step of purification was applied to remove the non-polar and the remaining polar impurities from solid 1 by slurry washing with a mixture of water and chloroform (2:1, v/v). Thus, water (200 mL) was poured into the flask containing solid 1 and the obtained suspension was stirred at 50° C. for 5 min, allowed to cool down to room temperature (0.5 h), slurried with chloroform (100 mL) at room temperature and stirred for 10 minutes until it was homogeneous. The mixture was then allowed to settle (approximately 5 minutes) and the heterogeneous mixture was filtered off through a filter funnel (Por. 4), and washed with cold water (2×15 mL) to yield an amorphous solid (solid 2) which was then dried under high vacuum for 24 h to afford the title compound (23.60 g, 76%) as a white solid (HPLC (266 nm) >94.21%). HPLC analysis (266 nm) of the filtered solid 2 showed a purity of 94.2%, with a total of 1.7% of polar impurities and 4.1% of non-polar impurities.

Chemical Formula: $C_{18}H_{17}F_2N_3O_6$, Calculated $[M+H]^+$ 410.12, found $[M+H]^+$ 410.15.

Synthesis of Intermediate (C)

Phosphorus oxychloride (4.2 equiv., 102.6 mmol, 9.59 mL) was added to cold (0° C., ice-water bath) trimethyl phosphate (60 mL) and the clear solution was kept at 0° C. for 20 min. Then, solid (B) (1.0 equiv., 24.42 mmol, 10.00 g) was added in three portions (3 g, 3 g, and 4 g). After about 20 minutes, the reaction mixture became homogeneous and turned light-yellow, and was kept at 0° C. for 3.5 h. HPLC and LC-MS analyses after 3 h showed approx. 99% conversion. Once the phosphorylation was completed (3.5 h), the mixture was filtered through a fritted funnel, and then poured dropwise for 30 min with into a cold (0° C.) vigorously stirred freshly prepared mixture of saturated aqueous sodium hydrogen carbonate ($NaHCO_3$) and diethyl ether (450 mL, 300 mL). Stirring was continued for 10 min at 0° C. and for 60 min at room temperature until a clear aqueous phase was obtained (internal temperature 15° C.).

The organic layer was removed and the aqueous layer was washed with diethyl ether (1×300 mL). The aqueous phase stayed partially emulsified and subsequently more saturated $NaHCO_3$ was added to reach demulsifying conditions. The addition of 330 mL saturated $NaHCO_3$ helped to break the emulsified droplets and phases were separated. The combined aqueous extracts (780 mL) were stirred at room temperature and adjusted to pH 4.0 with concentrated HCl (approximately 19 mL) and the solution was evenly split into 50 mL capacity Falcon tubes (16 in total) and stored at 4° C. for 2.5 days. After this period, a white solid precipitate was formed and the following steps were carried out prior to analysis:

- The samples were centrifuged for 20 minutes at 10° C. and 4,000 rpm.
- The supernatants (aqueous phase) were removed by decantation, combined and dried in vacuo at 50° C. and the obtained solid was dried under high vacuum for 17 h.
- The amorphous precipitates were re-dissolved in methanol (400 ml). The solution was transferred to a 1 liter round-bottom flask and the solvents were evaporated under vacuum at 40° C. to yield a white solid (solid 1, 10.96 g) which was further dried under high vacuum for 20 h.

HPLC analysis of solid 95.4% (220 nm).

Chemical Formula: $C_{18}H_{18}F_2N_3O_9P$, Calculated $[M-H]^+$ 488.07, found $[M-H]^+$ 488.55.

Synthesis of Linker (A)

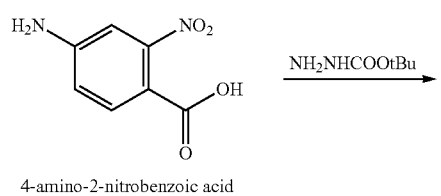

4-amino-2-nitrobenzoic acid

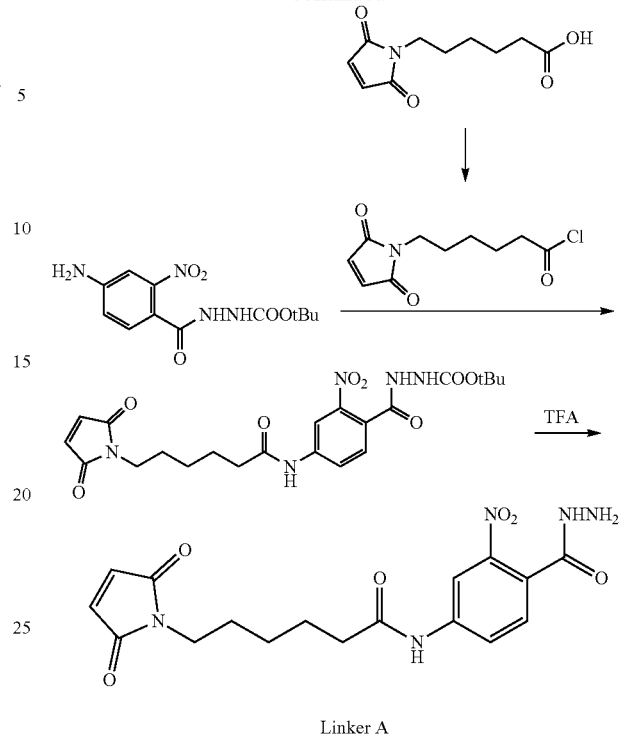

Linker A

Synthesis of tert-Butyl 2-(4-amino-2-nitrobenzoyl)hydrazine-1-carboxylate

4-Amino-2-nitro benzoic acid (1.0 eq, 164.7 mmol, 30.00 g) was dissolved in a mixture of acetonitrile and tetrahydrofuran (1:1; 720 mL) and cooled to 6° C. with a salt-ice bath, then tert-butyl carbazate (1.5 eq, 247.1 mmol, 32.65 g), HOBt (1.1 eq, 181.2 mmol, 27.93 g) and EDC-HCl (1.0 eq, 164.7 mmol, 31.64 g) were added, and the reaction mixture was stirred for 90 min on ice, after which the ice bath was removed and the solution was stirred at room temperature for 16 h. The initially remaining solid in the reaction mixture dissolved upon stirring within the first two hours. After stirring the reaction solution for 16 h, the solvents were removed under reduced pressure (water bath: 40° C.). The crude (a viscous dark brown oil) was dissolved in 2% n-butanol in dichloromethane (600 mL), washed with saturated $NH_4Cl$ (2×600 mL), saturated $NaHCO_3$ (1×600 mL), and distilled water (1×600 mL). The organic layer was then dried over sodium sulfate, $Na_2SO_4$, (200 g). The solvents were removed under reduced pressure (water bath: 40° C.) yielding the title compound as a brown foam (purity: 98.4%, according to HPLC (220 nm); yield: 30.42 g (62%). Chemical Formula: $C_{12}H_{16}N_4O_5$, calculated $[M+Na]^+$: 319.10, found $[M+Na]^+$: 319.08.

Synthesis of 6-maleimidocaproic Acid Chloride

Dry dichloromethane (250 mL) was added at room temperature under stirring in one portion to a one-liter one-neck round-bottom flask containing 6-maleimidocaproic acid (1.0 equiv., 236.6 mmol, 49.97 g) resulting in a yellow solution. A small amount of insoluble impurities were removed by filtration through a filter paper (MN 617¼, ⌀185 mm) followed by rinsing with dry DCM (25 mL). To the solution at room temperature was added oxalic acid chloride (1.1 equiv., 259.6 mmol, 22.50 mL) dropwise via a dropping funnel (over the course of 2 h) while stirring the reaction solution. Caution: Gas evolution was observed during the addition process. The reaction mixture was stirred at room temperature and allowed to react until HPLC analysis indicated complete consumption of 6-maleimidocaproic acid after 7 h 30 min. The color of the reaction solution changed to dark yellow during the reaction time. 5 h 30 min after the complete addition of oxalic acid chloride the solvent was removed in vacuo at 30° C. The resulting dark yellow oil was then dried in high vacuum for 20 hours. The obtained light brownish solid was crushed with a spatula and dried for further 20 h under high vacuum to yield (53.35 g, 98%) as an light brownish solid (HPLC (220 nm) >97.6% as the methyl ester).

Synthesis of Boc-protected Linker A:

A solution of 6-maleimidocaproic acid chloride (1.1 eq, 216.6 mmol, 49.70 g) in dry THF, (382 mL) was added in one portion at room temperature to a solution of tert-butyl 2-(4-amino-2-nitrobenzoyl)hydrazine-1-carboxylate (1.0 eq, 196.9 mmol, 58.34 g) in dry THF (580 mL). The clear reaction mixture was stirred at room temperature for 10 min. A solution of DIPEA (1.1 eq, 216.6 mmol, 37.7 mL) in dry THF (120 mL) was then added dropwise via a dropping funnel (over the course of one hour) while stirring moderately at room temperature. After completion of the reaction as indicated by HPLC, the reaction mixture was stored at 4° C. for 14 h. The solvent was then removed under reduced pressure to yield a dark brown viscous oil, which was then dissolved in DCM (450 mL) while shaking using a KL 2 shaker (approx. 150 rpm; Edmund Baler GmbH, Hechingen, Germany) for 10 min at room temperature. This solution was transferred to a 2 L separatory funnel, and the round bottom flask was rinsed with additional DCM (450 mL) which was then added to the separatory funnel. The organic phase was successively washed with 5% HCl (900 mL), aq. sat. $NaHCO_3$ (900 mL) and 1M $NaH_2PO_4$ (900 mL). After the aqueous work up, the organic phase was dried over $Na_2SO_4$. The solvent was removed under reduced pressure, and the residue was dried for 16 h under high vacuum to yield the title compound (79.25 g) as a light brown foam. The crude product was further purified by flash chromatography to give 31.21 g with HPLC purity 99.6% (220 nm). Chemical Formula: $C_{22}H_{27}N_5O_8$, calculated $[M+Na]^+$: 512.18, found $[M+Na]^+$: 512.04.

Synthesis of Linker A:

The protected linker (1.0 equiv., 30.60 mmol, 15.06 g) was placed into a 250 mL, one neck round-bottom flask and precooled in an ice bath for 10 minutes. Precooled TFA (26 equiv., 784 mmol, 60 mL) was added in one portion under stirring with a magnetic stirring bar (250 rpm). The mixture was further stirred under ice bath cooling for 45 minutes until HPLC analysis indicated complete consumption of the protected linker. Because it was found that the removal of TFA at room temperature or higher temperatures leads to the dimerization of the linker A, TFA was removed at low temperature (ice bath) under high vacuum. To facilitate the removal of TFA, toluene was chosen as an entrainer. Toluene (30 mL) was added to the reaction solution at 0° C., and the TFA-toluene mixture was then removed at 0° C. (caution: 1) careful control of the high vacuum, 2) without stirring of the solution to avoid its fast transfer to the trap) under high vacuum. An empty two-neck round-bottom flask (500 mL) cooled with liquid nitrogen was used as an additional cooling trap for the condensed TFA and toluene. During the removal of TFA, the mixture bubbled from time to time and part of the solution was spilled inside the connecting tube. After 30 minutes most of the TFA-toluene mixture was removed, and an oily residue was obtained. For further removal of TFA, another 30 mL of toluene were added to the flask and TFA was removed as described above. After 80 minutes, this process was repeated after adding further 20 mL of toluene. After 110 minutes the additional cooling trap was removed and the wax-like substance was directly connected to the high vacuum system. After 3 h 30 minutes the ice bath was removed and the oily residue was dried for another 30 minutes at room temperature to yield a foam. The foam-like residue was dissolved in N,N-dimethylformamide, DMF (30 mL) and the product was precipitated by dropwise addition of the DMF solution at room temperature into a mixture of diisopropylether/methanol (45:5, 1.5 L) under vigorous stirring. Another 2 mL of DMF were used to rinse the reaction flask. The precipitate was filtered through a fritted filter (Por. 4) by suction, and the product (filter cake) was washed with diisopropylether (3×200 mL) without letting the cake become dry. After a final washing step with 200 mL n-pentane the cake was sucked dry. The yellowish solid was collected in a flask and dried under high vacuum for 18 h. The product was stored at −20° C. Yield: 10.94 g (91.8%). Purity (average of three measurements): 99.0% (220 nm), 98.7% (247 nm). Calculated $[M+H]^+$ 390.14, found $[M+H]^+$ 390.12.

Synthesis of Compound 15

Gemcitabine derivative (C) (1.0 equiv., 9.29 mmol, 4.55 g) was suspended in anhydrous methanol (68.9 mL) followed by the addition of anhydrous DMSO (45.9 mL) and the clear transparent solution was stirred at room temperature for 5 minutes. After this period, linker (A) (1.0 equiv., 9.29 mmol, 3.62 g) was added in three portions followed by 1.0 equiv. of TFA. The reaction mixture turned light-yellow and was stirred at room temperature. Once the reaction was completed (4 h) as confirmed by HPLC (220 nm) and LC-MS analyses, the mixture was added dropwise for 2-3 minutes into a cold (0° C.) freshly prepared 1:3 mixture of tert-butyl methyl ether and isopropanol (600 mL) under vigorous stirring. The stirring was continued for 10 min at 0° C. (internal temperature: 5° C.). The precipitate was filtered, washed four times with cold THF, transferred to a new fritted funnel and slurried with cold tert-butyl methyl ether (1×100 mL, 4° C.). This final amorphous precipitate was transferred to a 250 mL round-bottom flask and dried under high vacuum for 20 h to yield the title compound 15 as a pale solid (4.52 g). HPLC analysis 96.2% (220 nm), Chemical Formula: $C_{35}H_{35}F_2N_8O_{14}P$, calculated $[M-H]^+$ 859.19, found $[M-H]^+$ 859.40.

Example 7

Preparation of Compound 16

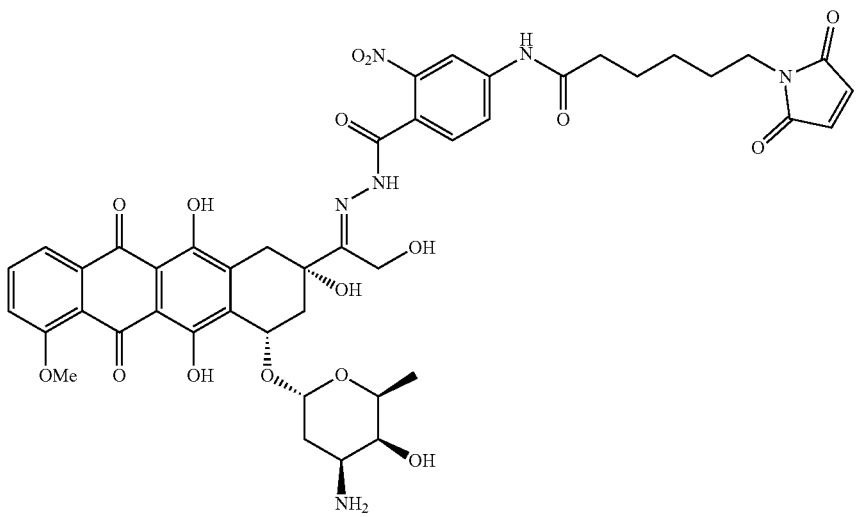 [SMILES: COc1cccc2c1C(=O)c1c(O)c3c(c(O)c1C2=O)C[C@@](O)(/C(CO)=N/NC(=O)c1ccc(NC(=O)CCCCCN2C(=O)C=CC2=O)cc1[N+](=O)[O-])C[C@@H]3O[C@H]1C[C@H](N)[C@H](O)[C@H](C)O1]

80 mg of Doxorubicin.HCl (138 µmol) and 139 mg of Linker A (276 µmol; 2 eq) were dissolved in 20 mL anhydrous methanol under vigorous stirring at room temperature. Reaction was stirred for 4 h. Precipitation was carried out with 105 mL of a 2:1 mixture of isopropanol and diisopropylether and the reaction stored at −20° C. overnight. The red precipitate was centrifuged (3200×g, 10 min) and discarded, and the supernatant transferred into a fresh vessel. The supernatant was precipitated again with 150 mL of diisopropylether and stored overnight at −20° C. The red precipitate was centrifuged and washed twice with 8 mL acetonitrile and once with 40 mL of a 1:3 mixture of isopropanol/diisopropylether. The obtained product was then dried under high vacuum to yield Compound 16 as a red solid. Yield: 53.9 mg (40%).

Stability of the HSA Conjugate of Compound 16 at pH 7.0 and 5.0

Stability at pH 7 (Phosphate buffer 4 mM NaCl 150 mM): Compound 16 was added to a solution of fully reduced HSA (human serum albumin) and complete binding to cysteine-34 position verified by HPLC. A 200 µM solution of the obtained HSA conjugate of compound 16 was incubated at 37° C. and analyzed with HPLC every hour.

Merely 0.36% of free doxorubicin was released per hour.

Stability at pH 5 (Phosphate buffer 4 mM, sodium chloride 150 mM and sodium acetate buffer 50 mM): the HSA conjugate of compound 16 was prepared at pH 7 (see above) and a sodium acetate buffer (50 mM) was added to adjust the pH value to 5.0. A 200 µM solution of the obtained HSA conjugate of compound 16 at pH 5.0 was incubated at 37° C. and analyzed with HPLC every hour. The half-life for the release of doxorubicin was approximately 9 h.

Example 8

Synthesis of a Vinblastine Prodrug Based on Linker A

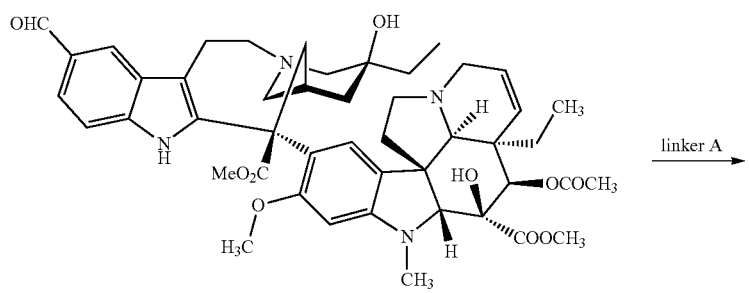

-continued

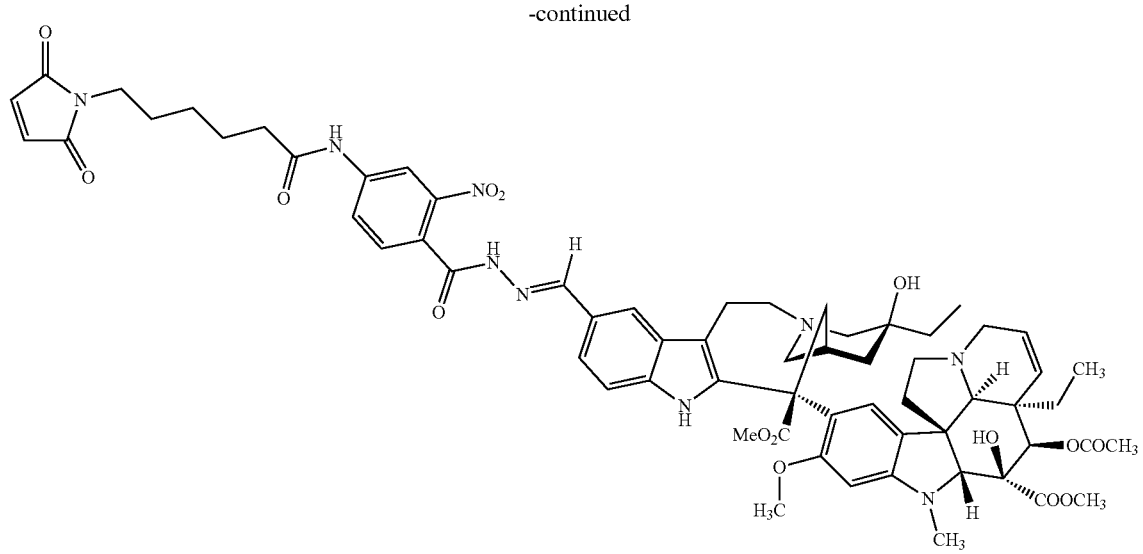

12'-Formylvinblastine was prepared from vinblastine and hexamethylenetetramine according to the procedure published in WO 2005/055939 A2. 12'-Formylvinblastine (320 mg, 336 µmol) and linker A (172.3 mg, 442.5 µmol; 1.31 eq.) were dissolved in dry MeOH (32 mL) under vigorous stirring in a 50 mL reaction tube. After 2 h, the reaction was brought to end by adding diisopropylether (34 mL), and the solution was stored at −20° C. for 2 h. A small amount of impurities was precipitated, which was centrifuged off and discarded. To the supernatant was added a mixture of n-hexan/diisopropylether (20 mL, 50:50) and stored at −20° C. for 16 h. The precipitate was centrifuged, dissolved in 1 mL CHCl$_3$/MeOH (90:10) and reprecipitated from 20 mL n-hexan/diisopropylether (50:50), centrifuged and washed with 8 mL AcN/diethylether (1:3) and further centrifuged. The product was dissolved in 5 mL CHCl$_3$/MeOH (99:1), reprecipitated from 20 mL n-hexan/diisopropylether (50:50) and centrifuged. This washing step was repeated twice. Afterwards the product was dried under high vacuum to give a white solid.

Yield: 253 mg (57%), Purity HPLC: 90.1% (220 nm) 93.0% (310 nm)

Chemical Formula: $C_{64}H_{75}N_9O_{15}$, calculated [M+H]$^+$.: 1210.55, Found [M+H]$^+$: 1210.42.

Example 9

Synthesis of Vinblastine Prodrug Based on Linker B

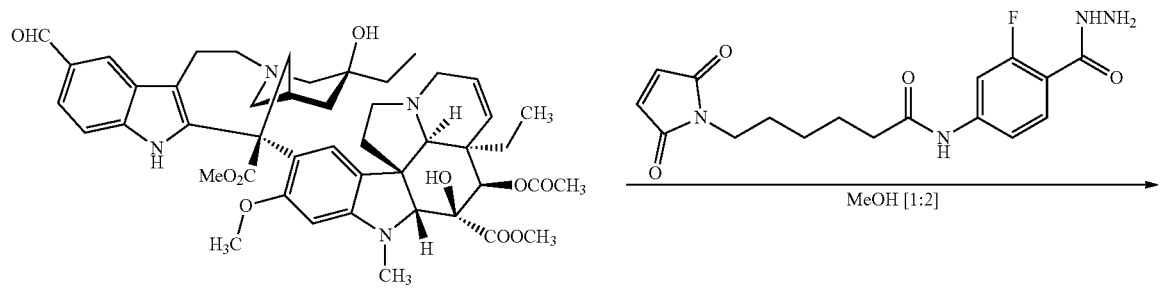

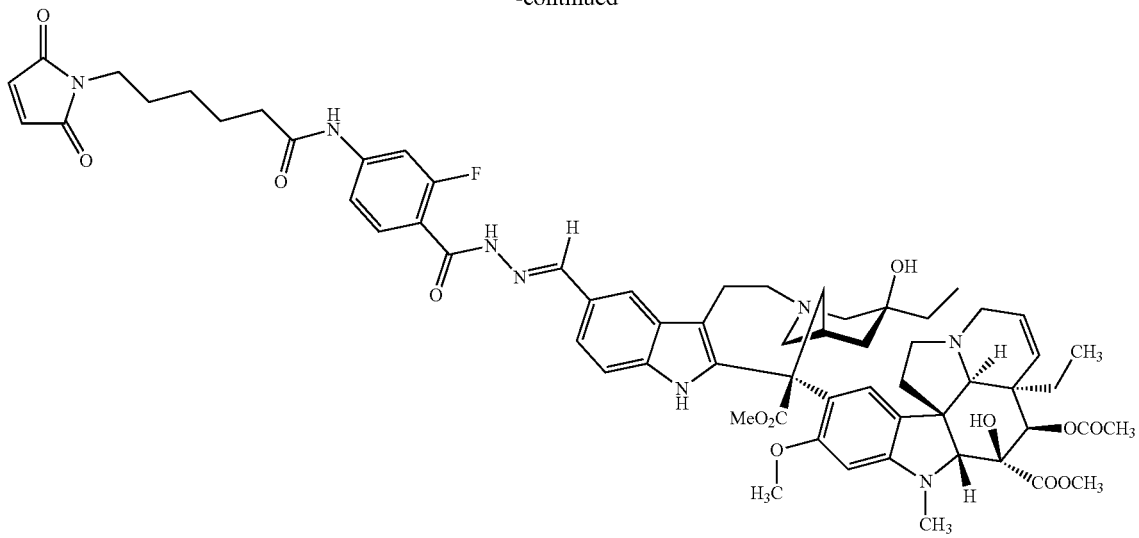

12'-Formylvinblastine was prepared from vinblastine and hexamethylenetetramine according to the procedure published in WO 2005/055939 A2.

12'-Formylvinblastine (300 mg, 315 µmol) and linker B (153 mg, 321 µmol; 1.02 eq.) were dissolved in dry MeOH (25 mL) and stirred at RT. After 1 h, the reaction was brought to end by adding n-hexan/diisopropylether (23 mL, 50:50), and the solution was stored at –20° C. for 4 h. A small amount of impurities was precipitated, which was centrifuged off and discarded. To the supernatant was then added diisopropylether (20 mL) and stored at –20° C. for 2 h.

The precipitate was centrifuged, dissolved in 1 mL $CHCl_3$/MeOH (99:1) and reprecipitated from 20 mL, n-hexan/diisopropylether (50:50), centrifuged and washed with 10 mL AcN/diethylether (1:3) and further centrifuged.

The product was dissolved in 5 mL $CHCl_3$/MeOH (90:1), reprecipitated from 20 mL diisopropylether, centrifuged and dried under high vacuum to give a white powder.

Yield: 251 mg (63%), Purity HPLC: 90.1% (220 nm) 94.0% (310 nm)

Chemical Formula: $C_{64}H_{75}FN_8O_{12}$, calculated $[M+H]^+$.: 1183.55, Found $[M+H]^+$: 1183.45

Preparation of Linker B

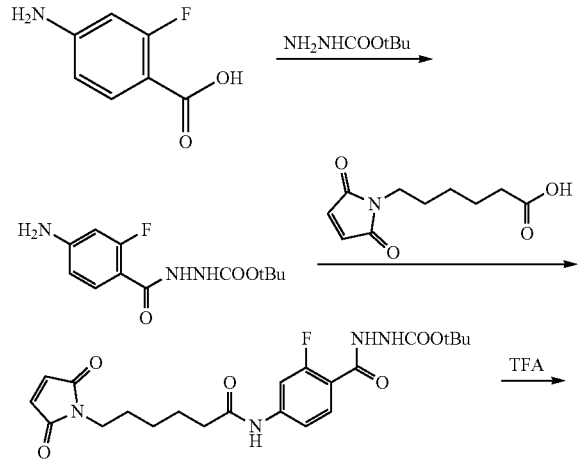

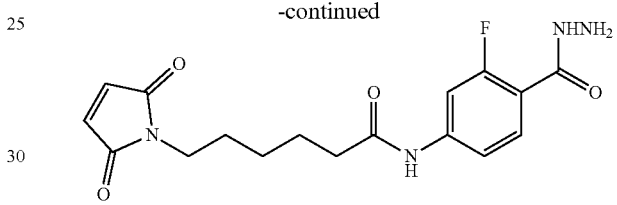

To a solution of 4-amino-2-fluorobenzoic acid (8.1 g, 52.22 mmol), tert-butyl carbazate (8.28 g, 62.66 mmol) and N-methylmorpholine (14.35 ml, 130.54 mmol) in tetrahydrofuran (25 ml) and EtOAc 7(5 ml), 1.67 M T3P (50% in ethyl acetate, 40.65 ml) was dropwise added via a funnel. The mixture was stirred at RT for 16 h. Water was added and the organic layer was washed with saturated $KHCO_3$ and water, dried over $MgSO_4$, filtered and concentrated in vacuo. The crude product was triturated in MTBE, filtered and dried in vacuo to give 9.7 g (69%) of tert-butyl 2-(4-amino-2-fluorobenzoyl)hydrazinecarboxylate as a white solid. Chemical Formula: $C_{12}H_{16}FN_3O_3$, calculated $[M-H]^+$: 268.11, found $[M-H]^+$: 268.00.

To a solution of tert-butyl 2-(4-amino-2-fluorobenzoyl)hydrazinecarboxylate (9.68 g, 35.94 mmol), 6-maleimidohexanoic acid (6.6 g, 31.25 mmol) and N-methylmorpholine (8.59 ml, 0.08 mol) in tetrahydrofuran (40 ml) and EtOAc (120 ml), 1.67M T3P (50% in ethyl acetate, 24.32 ml) was added and the mixture was stirred at 60° C. for 48 h. Water and EtOAc were added, and the organic layer was washed with saturated $KHCO_3$, water and brine, dried over $MgSO_4$, filtered and concentrated in vacuo. The crude was purified by chromatography column using n-hexane:EtOAc 1:1 to 1:2 as an eluent. The obtained solid was triturated in MTBE to provide 7.5 g (51.9%, purity >98%) of N-Boc-O-fluorolinker as a white solid. Chemical Formula: $C_{22}H_{27}FN_4O_6$, calculated $[M-H]^+$: 461.18, found $[M-H]^+$: 461.00.

To a suspension of N-Boc-O-fluorolinker (7 g, 15.14 mmol) in dichloromethane (40 ml) at 0° C., TFA (40.54 ml, 0.53 mol) was added. The mixture was stirred at 0° C. for 15 min and at RT for 15 min. The solvent was removed in vacuo at 0° C. The crude product was triturated in MTBE/DCM 7:1. The solid was filtered and dried in vacuo to give 6.5 g (90.1%) of O-Fluor maleimide linker as a white solid. Purity HPLC 96.8% (220 nm). Chemical Formula: $C_{17}H_{18}FN_4O_4$, calculated $[M-H]^+$: 361.13, found $[M-H]^+$: 361.10.

Example 10

Preparation of Linker C.
The linkers of this invention can be made by the methods depicted in the reaction scheme shown below.

added (9H-fluoren-9-yl)methyl (S)-2-(chlorocarbonyl)pyrrolidine-1-carboxylate (250 mg, 0.70 mmol) as a solution in THF (2 mL) followed by the dropwise addition of triethyl amine (49 µL, 0.35 mmol) as a solution in THF (200 µL). After stirring for 12 h, TLC (CHCl$_3$/acetone, 7:3) showed complete conversion of the starting material. The reaction mixture was filtered and dried in vacuo via rotoevaporation.

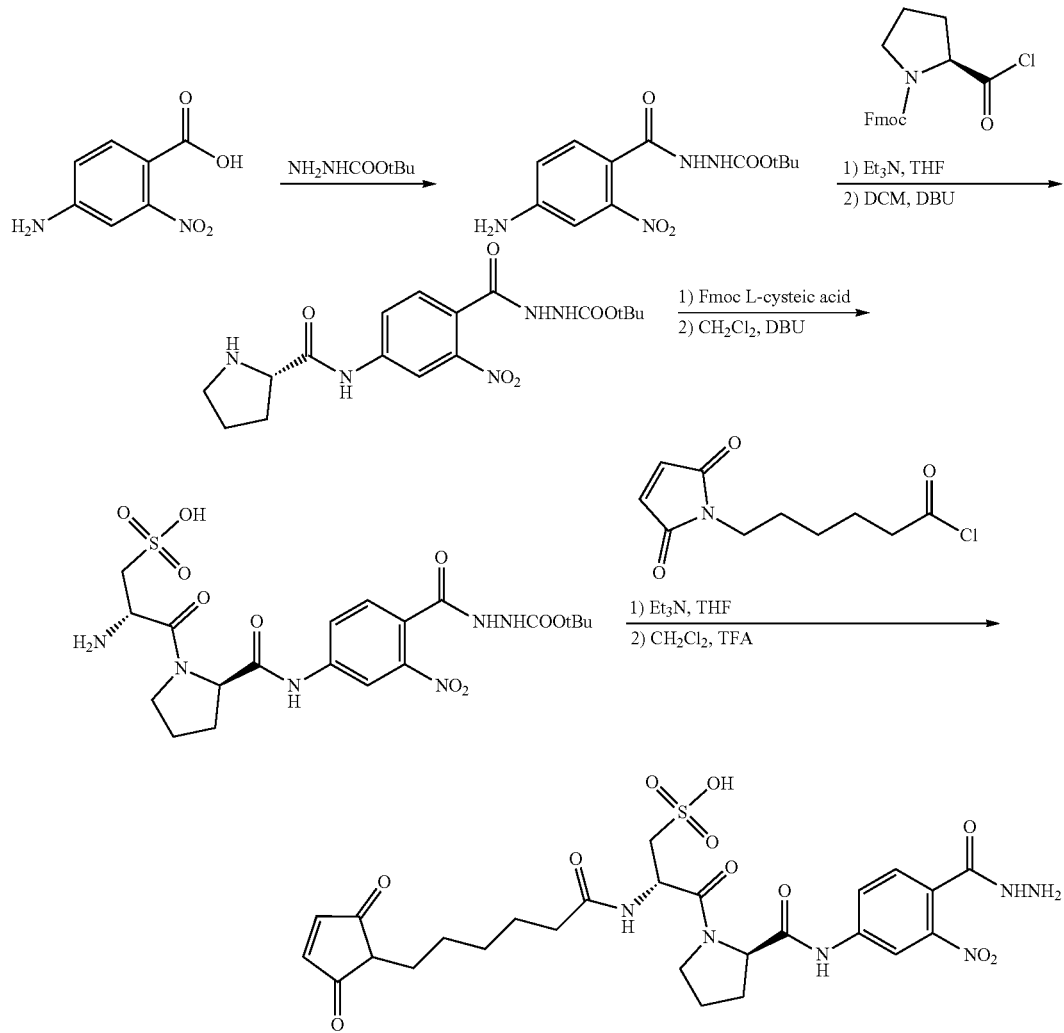

Linker C

Synthesis of Fmoc-L-Proline Acid Chloride:
Fmoc-L-proline (250 mg, 0.74 mmol) was dissolved in CH$_2$Cl$_2$ (4 mL). Thionyl chloride (800 µL, 10.36 mmol) was added and the solution was stirred at reflux for 3 h with monitoring by quenching with methanol as a diluent and following the formation of the methanol adduct by TLC (CH$_2$Cl$_2$:MeOH; 9:1). Subsequently the reaction was dried in vacuo to give 250 mg of crude, which was then used in the subsequent reaction without any further purification.

Synthesis of tert-butyl 2-(2-nitro-4-(pyrrolidine-2-carboxamido)benzoyl)hydrazine-1-carboxylate To a solution of tert-butyl 2-(4-amino-2-nitrobenzoyl)hydrazine-1-carboxylate (104 mg, 0.35 mmol) in THF (2 mL) was The resultant oil was then purified via Biotage FCC with a methanol and chloroform gradient to yield 279 mg of a pale solid.
To a solution of the previous solid in anhydrous CH$_2$Cl$_2$ (2 mL) was added DBU (10%, 200 µL) and the mixture was stirred at RT for 30 min. The reaction was monitored by LC/MS until starting material was consumed. The reaction mixture was dried in vacuo via rotoevaporation. The resultant oil was then purified via Biotage FCC with a methanol and chloroform gradient to yield the title compound as a brown solid (63 mg, 46% yield, 2 steps). Chemical Formula: $C_{17}H_{23}N_5O_6$, calculated $[M+H]^+$: 394.17, found $[M+NH]^+$: 394.14.

Synthesis of (((9H-fluoren-9-yl)methoxy)carbonyl)(sulfo)-D-alanine

L-Cysteic acid (500 mg, 2.95 mmol) was suspended in a mixture of 10% aqueous $Na_2CO_3$ (17.5 mL) and 1,4-dioxane (7.5 mL) and cooled in an ice bath. N-fluorenylmethoxycarbonyl succinimide (1.19 g, 3.54 mmol) was dissolved in 1,4-dioxane (12.5 mL) by gentle heating and the solution was added over 30 min via a dropping funnel with efficient stirring. The reaction mixture was stirred overnight and the organic solvent was removed in vacuo. The suspension was diluted with $H_2O$ (10 mL), washed with tert-butyl methyl ether (2×10 mL) and the aqueous phase was acidified with conc. HCl to pH 3.0. The solution was lyophilized to give 1.02 g of fmoc-cysteic-acid as white hygroscopic solid. This solid was used without further purification. Chemical Formula: $C_{18}H_{17}NO_7S$, calculated $[M-H]^+$:390.06, found $[M-H]^+$=390.07.

Synthesis of (R)-2-((((9H-fluoren-9-yl)methoxy)carbonyl)amino)-3-((S)-2-((4-(2-(tert butoxycarbonyl)hydrazine-1-carbonyl)-3-nitrophenyl)carbamoyl)pyrrolidin-1-yl)-3-oxopropane-1-sulfonic Acid In a flame-dried flask, fmoc-L-cysteic acid (96 mg, 0.30 mmol) was dissolved in a mixture of anhydrous DMSO:$CH_2Cl_2$:DMF (1:1:1, 3 mL). HATU (114 mg, 0.30 mmol) was added, followed by HOAt (41 mg, 0.30 mmol). After 5 min, a solution of tert-butyl (S)-2-(2-nitro-4-(pyrrolidine-2-carboxamido)benzoyl)hydrazine-1-carboxylate (100 mg, 0.25 mmol) in anhydrous DMF (2 mL) was added followed by the dropwise addition of NMM (55 µL, 0.50 mmol) and the resulting solution was stirred at room temperature for 17 h. Normal-phase flash chromatography ($CHCl_3$:methanol gradient) yielded the title compound (152 mg, 78%). Chemical Formula: $C_{35}H_{38}N_6O_{12}S$, calculated $[M-CO_2^tBu+H]^+$: 667.18 found $[M-CO_2^tBu+H]^+$, 667.11.

Synthesis of (R)-2-amino-3-((S)-2-((4-(2-(tert-butoxycarbonyl)hydrazine-1-carbonyl)-3-nitrophenyl)carbamoyl)pyrrolidin-1-yl)-3-oxopropane-1-sulfonic Acid To a solution of (S)-2-((((9H-fluoren-9-yl)methoxy)carbonyl)amino)-3-((S)-2-((4-(2-(tert-butoxycarbonyl)hydrazine-1-carbonyl)-3-nitrophenyl)carbamoyl)pyrrolidin-1-yl)-3-oxopropane-1-sulfonic acid (152 mg, 0.198 mmol) in anhydrous $CH_2Cl_2$ (2 mL) was added DBU (10%, 200 µL) at 0° C. and the mixture was stirred at rt for 30 min. LC-MS (sample in MeCN) chromatogram showed complete conversion of the starting material. The organic solvent was evaporated under vacuum yielding an oily residue. Purification of this residue by flash ($CHCl_3$/methanol gradient; 2 to 95%) yielded the title compound as a brown solid (80.4 mg, 75% yield). Chemical Formula: $C_{20}H_{28}N_6O_{10}S$, calculated $[M+Na]^+$567.15 found $[M+Na]^+$567.19.

Synthesis of (R)-3-((S)-2-((4-(2-(tert-butoxycarbonyl)hydrazine-1-carbonyl)-3-nitrophenyl)carbamoyl)pyrrolidin-1-yl)-2-(6-(2,5-dioxo-2,5-dihydro-1H-pyrrol-1-yl)hexanamido)-3-oxopropane-1-sulfonic Acid To a solution of (R)-2-amino-3-((S)-2-((4-(2-(tert-butoxycarbonyl)hydrazine-1-carbonyl)-3-nitrophenyl)carbamoyl)pyrrolidin-1-yl)-3-oxopropane-1-sulfonic acid (80.4 mg, 0.14 mmol) in THF (2 mL) was added 6-maleimidocaproic acid chloride (41.0 mg, 0.14 mmol) in one portion as a solution in THF (1 mL). After stirring for 5 min at rt, a solution of triethylamine (24 µL, 0.14 mmol) in THF (200 µL) was added dropwise over 10 min. The brown solution was stirred at rt for further 3 h. The reaction mixture was filtered and dried under vacuum yielding a brown oily residue. Purification of this residue by flash chromatography ($CHCl_3$/MeOH gradient, 100:0 to 2:98) yielded the title compound (71 mg, 65%). Chemical Formula: $C_{30}H_{39}N_7O_{13}S$, calculated $[M-CO_2^tBu+H]^+$: 638.18, found $[M-CO_2^tBu+H]^+$: 638.02.

(R)-2-(6-(2,5-dioxo-2,5-dihydro-1H-pyrrol-1-yl)hexanamido)-3-((S)-2-((4-(hydrazinecarbonyl)-3-nitrophenyl)carbamoyl)pyrrolidin-1-yl)-3-oxopropane-1-sulfonic Acid To an ice-cold stirred solution of (R)-3-((S)-2-((4-(2-(tert-butoxycarbonyl)hydrazine-1-carbonyl)-3-nitrophenyl)carbamoyl)pyrrolidin-1-yl)-2-(6-(2,5-dioxo-2,5-dihydro-1H-pyrrol-1-yl)hexanamido)-3-oxopropane-1-sulfonic acid (71 mg, 0.09 mmol) in $CH_2Cl_2$ (1 mL) was added TFA (293 µL, 3.83 mmol). The reaction mixture was stirred for 2 h until LC-MS showed the consumption of the starting material. The desired product was obtained from the reaction mixture by evaporation of the solvent and used without further purification. Brown solid (91 mg, traces of TFA). LRMS (ESI) for $C_{25}H_{31}N_7O_{11}S$, calculated $[M+H]^+$: 637.18, found $[M+H]^+$: 638.07 (M+H). Purity: 96% (HPLC, 220 nm).

Example 11

Synthesis of Gemcitabine Hydrazine: (R)-3-((R)-2-((4-(2-((Z)-1-(4-((1-((2R,4R,5R)-3,3-difluoro-4-hydroxy-5-(hydroxymethyl)tetrahydrofuran-2-yl)-2-oxo-1,2-dihydropyrimidin-4-yl)carbamoyl)phenyl)ethylidene)hydrazine-1-carbonyl)-3-nitrophenyl)carbamoyl)pyrrolidin-1-yl)-2-(6-(2,5-dioxo-2,5-dihydro-1H-pyrrol-1-yl)hexanamido)-3-oxopropane-1-sulfonic Acid

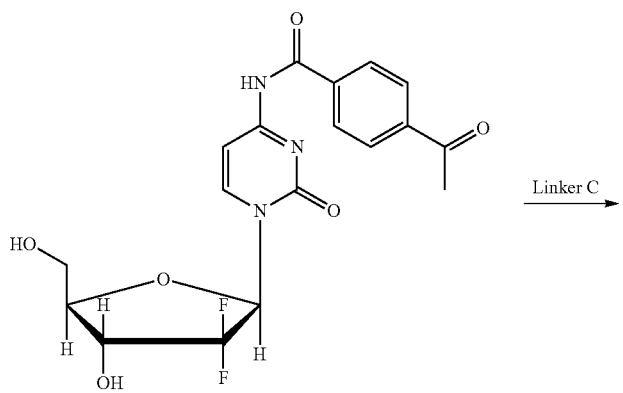

-continued

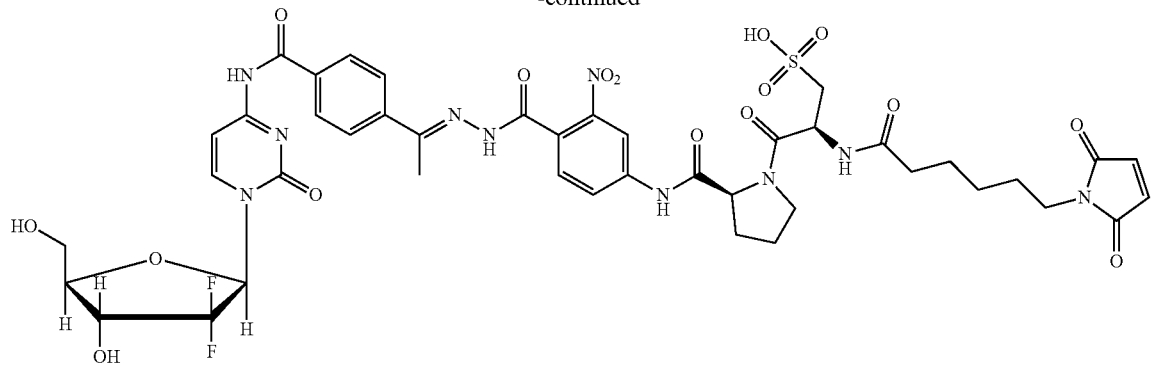

To a stirred suspension of 4-acetyl-N-(1-((2R,4R,5R)-3,3-difluoro-4-hydroxy-5-(hydroxymethyl)tetrahydrofuran-2-yl)-2-oxo-1,2-dihydropyrimidin-4-yl)benzamide (3 mg, 0.071 mmol) and R)-2-(6-(2,5-dioxo-2,5-dihydro-1H-pyrrol-1-yl)hexanamido)-3-4S)-2-((4-(hydrazinecarbonyl)-3-nitrophenyl)carbamoyl)pyrrolidin-1-yl)-3-oxopropane-1-sulfonic acid (5 mg, 0.078 mmol) in methanol (250 μL) was added TFA (9 μL, 0.117 mmol). The reaction mixture was stirred for 3 days monitoring by LC-MS. After this time, the pale solution was concentrated in vacuo. Normal-phase flash chromatography (CHC13:methanol gradient) yielded the title compound (5.6 mg, 74%). Chemical formula: $C_{43}H_{46}F_2N_{10}O_{16}S$, calculated $[M+H]^+$: 1028.27, found $[M+H]^+$: 1029.05.

Example 12

Synthesis of Nemorubicin Hydrazone

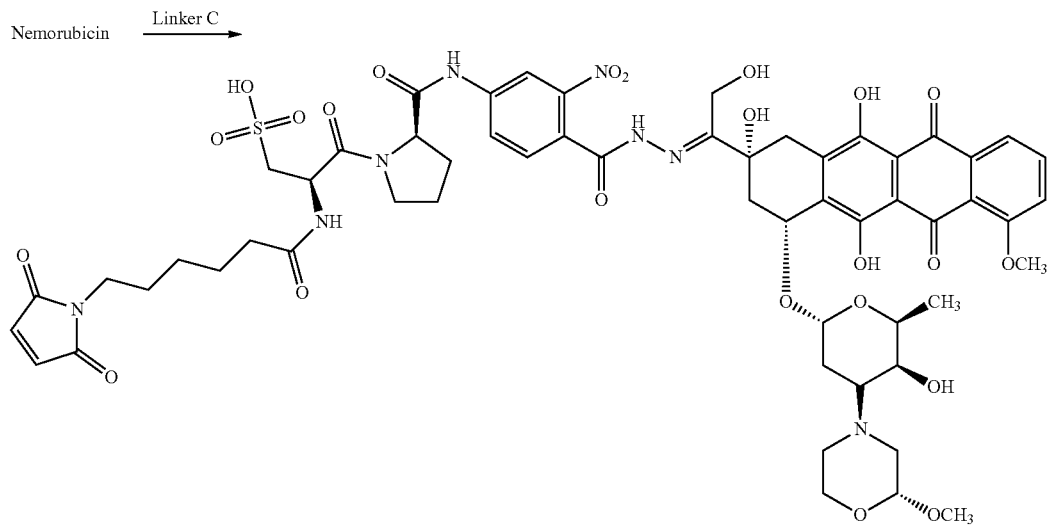

Nemorubicin (3 mg, 4.7 μmol, 1 eq) was dissolved in dry MeOH (750 μL) and added to Linker C (10.5 mg, 14.0 μmol, 3 eq) in a 2 mL reaction tube. TFA (1.1 μL, 2 eq) was added and the reaction mixture was stirred overnight. During the reaction a precipitate could be observed. After 16 h, MeOH (800 μL) was added and reaction mixture was centrifuged (20000× g, 2 min). The supernatant was split into 2 new 2-mL reaction tubes and further precipitated with 1 mL diisopropylether each. Second precipitate was centrifuged off, dried and analyzed.

Purity: 89% (220 nm) 80% (495 nm)

Chemical Formula: $C_{57}H_{66}N_8O_{23}S$, calculated $[M-H]^+$: 1261.39, Found $[M-H]^+$: 1261.60.

Example 13

Synthesis of N-(4-Acetylbenzoyl)-MMAE (Compound 17)

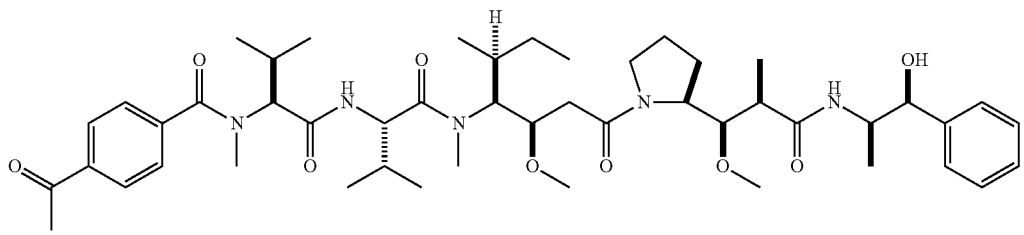

compound 17

54.9 mg of 4-acetylbenzoic acid (334 µmol, 2 eq), 127 mg of HATU (334 µmol, 2 eq) and 45.6 mg HOAt (334 µmol, 2 eq) were dissolved in 5 mL of anhydrous DMF and 36.7 µL of NMM (2 eq) were added. The reaction mixture was stirred for 15 minutes at room temperature. Subsequently, a solution of 120 mg of MMAE (167 µmol, 1 eq) and 36.7 µL NMM (334 µmol, 2 eq) in 5 mL anhydrous DMF was added and stirring was continued for 72 h at room temperature. The reaction mixture was diluted with 40 mL of chloroform and washed twice with 10 mL of a 5% HCl solution and thrice with 10 mL of saturated sodium bicarbonate solution. The organic layer was dried over sodium sulfate, filtered and the solvent was removed under vacuum. The residue was dissolved in 2 mL CHCl$_3$ and purified using flash chromatography (solvent A: CHCl$_3$, solvent B: MeOH, 36 mL/min, column volume (CV)=19 mL, gradient: 2 CV (0% B), 4 CV (0 to 3% B), 2.4 CV (3% B), 2 CV (3 to 5% B), 3 CV (5% B), 1.5 CV (5 to 9% B), ZIP® Sphere 10 g, Biotage® Isolera™ One). After drying in vacuo compound 17 (115 mg, 80%) was obtained as a colorless foam. HPLC Purity: 97.5% (220 nm).

Synthesis of the Hydrazone of N-(4-Acetylbenzoyl)-MMAE with Maleimide Linker A (Compound 18)

To a solution of 20.6 mg of compound 17 (23.3 µmol, 1 eq) in 3 mL of methanol were added 23.5 mg of maleimide linker A (46.6 µmol, 2 eq) in a 50 mL reaction tube. Subsequently, 3.7 µL of TFA (46.6 µmol, 2 eq) were added to the slightly turbid reaction mixture upon which the solution cleared off immediately. After 4 h stirring at room temperature, 4 mL n-hexane/diisopropyl ether (1:1) followed by 16 mL n-hexane were added. The formed precipitate was centrifuged (3,220×g, 10 min), dissolved in 1 mL of chloroform/methanol (1:1) and purified using repeated flash chromatography (1. chromatography: solvent A: CHCl$_3$, solvent B: MeOH, 32 mL/min, column volume (CV)=19 mL, gradient: 1 CV (1 to 5% B), 2 CV (5% B), 3 CV (5 to 8% B), 4 CV (8% B), 1 CV (8 to 9% B), 6 CV (9% B), ZIP® Sphere 10 g, Biotage® Isolera™ One, 2. chromatography: solvent A: water, solvent B: acetonitrile, 12 mL/min, column volume (CV)=21 mL gradient: 1 CV (10% B), 4 CV (10 to 50% B), 3 CV (50% B), 6 CV (50 to 80% B) SNAP® Ultra C18 12 g, Biotage® Isolera™ One). After drying in vacuo compound 18 (17.0 mg, 58%) was obtained as a colorless powder. HPLC Purity: 99.1% (220 nm).

Synthesis of a Conjugate of Compound 18 with Trastuzumab (Compound 19)

Commercial trastuzumab (Herceptin®, Roche) was reconstituted with WFI and the pH was adjusted with 0.5 M Tris buffer, 25 mM EDTA (4% of batch volume) to pH 8. The mAb solution was diluted to 10 mg/ml with 10 mM PBS pH 7.4. Then, 2.25 eq of TCEP (tris-(2-carboxyethyl)phosphine) was added and the mixture was incubated for 90 min at 20° C. Subsequently, the NMA (N,N-dimethylacetamide) content of the mixture was adjusted to 5%, and 5.5 equivalents of compound 18 were added. The mixture was incubated for 60 min at 20° C. Then the reaction was quenched by adding 11 equivalents of NAC (N-acetyl cysteine). Removal of unbound drug and exchange of buffer into 10 mM PBS pH 7.4 was achieved by Tangential Flow Filtration (10 dia-volumes). The solution was concentrated and the protein concentration was determined. Then the solution was diluted to 7.2 mg/mL with 10 mM PBS pH 7.4. The resulting trastuzumab conjugate (compound 19) had a DAR of 4.0 as determined by HIC (TOSOH Bioscience, Butyl-NPR 4.6 mm ID×3.5 cm, 2.5 µm; mobile phase A: 3 M ammonium sulfate, 25 mM sodium phosphate monobasic monohydrate in purified water, pH 6.95; mobile phase B: 25% isopropanol and 75% 25 mM sodium phosphate monobasic monohydrate in purified water, pH pH 6.95; flow: 0.8 mL min$^{-1}$ at 25° C. for 18 min using a systematic gradient) and 0.41% of unbound compound 18 as determined by HPLC (Waters Xterra MS, C18, 3.5 µM, 2.1×100 mm, mobile phase A: 20 mM ammonium acetate, pH 7.0±0.1, mobile phase B: acetonitrile, gradient: 0 min: 70% A, 20 min: 30% A, 25 min: 10% A, 25.1 min: 70% A, 35 min: 70% A).

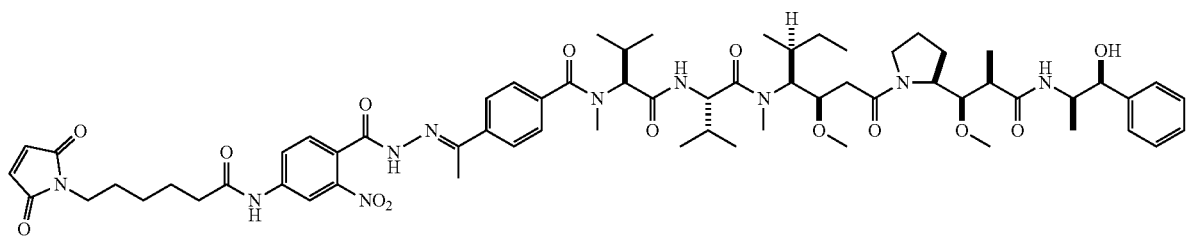

compound 18

Stability and Release Kinetics of Compound 19 in Buffer Solutions at pH 4.0 and pH 7.4

For studying stability and release kinetics, the conjugate compound 19 was incubated in buffer solutions at 37° C. Thus, a 3-mL aliquot of a solution of compound 19 in phosphate buffer (7.2 mg/mL in 10 mM PBS) was acidified to pH 4.0 using 0.5 M acetic acid and placed together with an untreated 3-mL aliquot (pH 7.4) in a heating block at 37° C. After appropriate intervals, samples (50 µL aliquots) at both pH were drawn and stored at −20° C. until analysis. Prior to analysis, the samples were removed from the freezer and 7 µL of 5 M NaCl as well as 93 µL of chilled methanol were added. Then the samples were stored for 30 min at −20° C., centrifuged at 4° C. and 200 rpm for 60 min. Subsequently, 75 µL of the supernatant was diluted with 75 µL of purified water and the mixture vortexed and analyzed using HPLC (Waters Xterra MS, C18, 3.5 µM, 2.1×100 mm, gradient: mobile phase A: 20 mM ammonium acetate, pH 7.0±0.1, mobile phase B: acetonitrile, gradient: 0 min: 70% A, 20 min: 30% A, 25 min: 10% A, 25.1 min: 70% A, 35 min: 70% A). A standard curve of compound 17 was prepared at 2.00, 1.00, 0.50, 0.30, 0.20, 0.10, 0.05 and 0.01 µM. A range of 2.00 to 0.05 µM was used for UV quantitation at 214 nm. Compound 17 was found to be the sole release product. After 24 h, 2.7% of compound 17 has been released from the ADC at pH 7.4 while at pH 4.0 39.6% of free compound 17 was observed.

The invention claimed is:

1. A compound having the structure of Formula (I):

Formula (I)

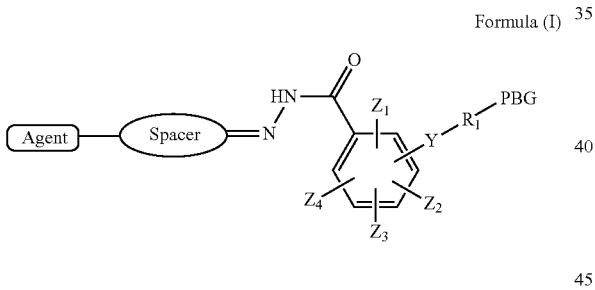

or a pharmaceutically acceptable salt, hydrate, solvate, or isomer thereo;

wherein:

Agent is selected from the group consisting of a cytostatic agent, a cytotoxic agent, a cytokine, an immunosuppressive agent, an antirheumatic, an antiphlogistic, an antibiotic, an analgesic, a virostatic agent, an anti-inflammatory agent, an antimicotic agent, a transcription factor inhibitor, a cell cycle modulator, an MDR modulator, a proteasome or protease inhibitor, an apoptosis modulator, an enzyme inhibitor, a signal transduction inhibitor, a protease inhibitor, an angiogenesis inhibitor, a hormone or hormone derivative, an antibody or a fragment thereof, a therapeutically or diagnostically active peptide, a radioactive substance, a light emitting substance, a light absorbing substance, and a derivative of any of the foregoing;

Spacer is absent, or is selected from the group consisting of

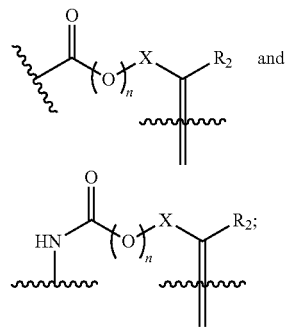

$n$ is 0 or 1;

X is selected from the group consisting of optionally substituted $C_1$-$C_{18}$ alkyl wherein optionally up to six carbon atoms in said $C_1$-$C_{18}$ alkyl are each independently replaced with —$OCH_2CH_2$—; optionally substituted $C_1$-$C_{18}$ alkyl-NH—C(O)—$R_5$— wherein optionally up to six carbon atoms in said $C_1$-$C_{18}$ alkyl are each independently replaced with —$OCH_2CH_2$—; optionally substituted $C_1$-$C_{18}$ alkyl-C(O)—NH—$R_5$— wherein optionally up to six carbon atoms in said $C_1$-$C_{18}$ alkyl are each independently replaced with —$OCH_2CH_2$—; optionally substituted aryl; optionally substituted heteroaryl; and optionally substituted cycloalkyl;

$R_5$ is selected from the group consisting of an optionally substituted aryl, optionally substituted heteroaryl, and optionally substituted cycloalkyl;

Y is absent or selected from the group consisting of optionally substituted $C_1$-$C_6$ alkyl, —NH—C(O)—, —C(O)—NH—, —C(O)—O—, and —O—C(O)—;

$R_1$ is absent or selected from the group consisting of optionally substituted $C_1$-$C_{18}$ alkyl wherein optionally up to six carbon atoms in said $C_1$-$C_{18}$ alkyl are each independently replaced with —$OCH_2CH_2$—; optionally substituted $C_1$-$C_{18}$ alkyl-NH—C(O)$R_5$— wherein optionally up to six carbon atoms in said $C_1$-$C_{18}$ alkyl are each independently replaced with —$OCH_2CH_2$—; and optionally substituted $C_1$-$C_{18}$ alkyl-C(O)—NH—$R_5$— wherein optionally up to six carbon atoms in said $C_1$-$C_{18}$ alkyl are each independently replaced with —$OCH_2CH_2$—, or $R_1$ is a naturally or non-naturally occurring amino acid, or $R_1$ has the following formula:

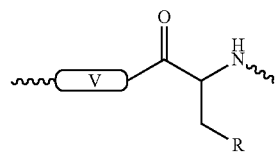

wherein:

V is absent, or is selected from the group consisting of:

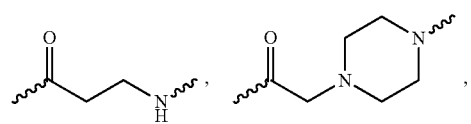

-continued

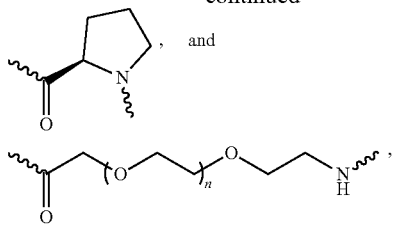

R is: ~~OPO$_3$M$_1$ wherein M$_1$=Mg$^{2+}$, 2Na$^+$, 2K$^+$ and/or 2NH$_4^+$, or
~~OSO$_3$M$_2$ wherein M$_2$=Na$^+$, K$^+$, H$^+$, and/or NH$_4^+$;

R$_2$ is selected from the group consisting of —H, optionally substituted C$_1$-C$_{12}$ alkyl, optionally substituted aryl, and optionally substituted heteroaryl;

Z$_1$, Z$_2$, Z$_3$ and Z$_4$ are each independently —H, an electron-withdrawing group, and/or a water-soluble group; wherein at least one of Z$_1$, Z$_2$, Z$_3$ and Z$_4$ is an electron-withdrawing group;

PBG is

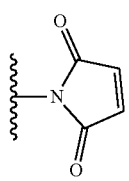 [SMILES: *N1C(=O)C=CC1=O]

which may be optionally substituted; and
wherein when Spacer is absent, Agent is linked to the nitrogen adjacent to Spacer by a double bond.

2. The compound according to claim 1, wherein said compound has a structure of Formula (II):

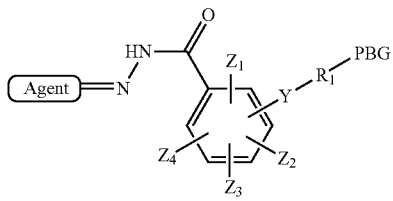

Formula (II)

or a pharmaceutically acceptable salt, hydrate, solvate, or isomer thereof;
wherein Agent, PBG, Y, R$_1$, Z$_1$, Z$_2$, Z$_3$ and Z$_4$ are as defined in claim 1.

3. The compound according to claim 1, said compound having the structure of Formula (III):

Formula (III)

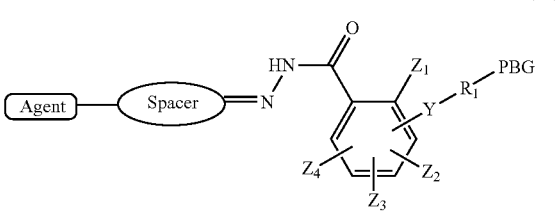

or a pharmaceutically acceptable salt, hydrate, solvate, or isomer thereof;
wherein Agent, Spacer, Z$_1$, Z$_2$, Z$_3$, Z$_4$, Y, R$_1$ and PBG are as defined in claim 1; and
wherein Z$_1$ is an electron withdrawing group.

4. The compound according to claim 1, said compound having the structure of Formula (IV):

Formula (IV)

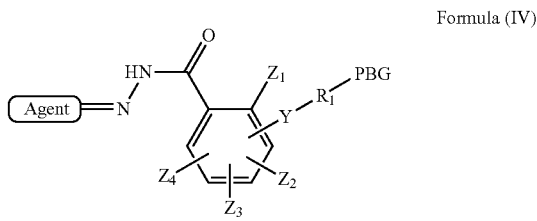

or pharmaceutically acceptable salt, hydrate, solvate, or isomer thereof;
wherein Agent, PBG, Y, R$_1$, Z$_1$, Z$_2$, Z$_3$ and Z$_4$ are as defined in claim 1; and
wherein Z$_1$ is an electron withdrawing group.

5. The compound according to claim 1, said compound having the structure of Formula (V):

Formula (V)

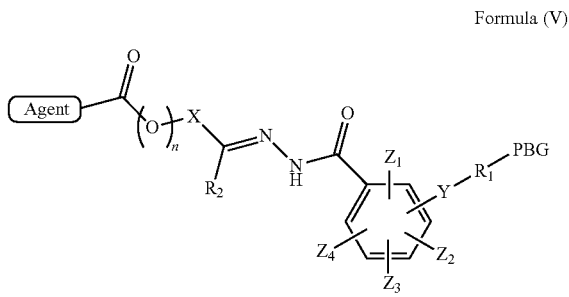

or a pharmaceutically acceptable salt, hydrate, solvate, or isomer thereof;
wherein Agent, n, X, R$_1$, R$_2$, Z$_1$, Z$_2$, Z$_3$, Z$_4$, Y, R$_1$, and PBG are as defined in claim 1.

6. The compound according to claim 5, said compound having the structure of Formula (VI):

Formula (VI)

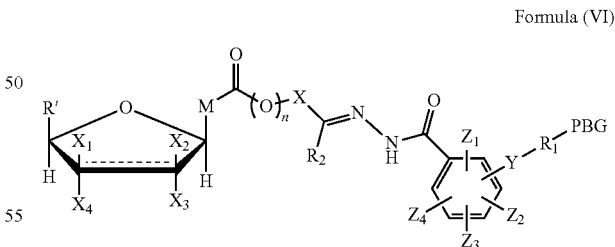

or a pharmaceutically acceptable salt, hydrate, solvate, or isomer thereof;
wherein:
M is a pyrimidine or purine group that contains at least one primary or secondary amino group and optionally contains one or more substituents selected from halogen;
X$_1$ and X$_2$ are each independently selected from the group consisting of —H, —OH, C$_1$-C$_6$ alkyl, halogen, and —N$_3$;

$X_3$ and $X_4$ are each independently, as valence permits, absent or selected from the group consisting of —H, —OH, $C_1$-$C_6$ alkyl, halogen, and —$N_3$;

R' is —$R_3$ or —$CH_2R_3$;

wherein each occurrence of $R_3$ is independently selected from the group consisting of —OH, —$CH_3$, —OP(O)(OH)$_2$, —P(O)(OH)OP(O)(OH)$_2$, —OP(O)(OH)OP(O)(OH)OP(O)(OH)$_2$, —OP(O)(OH)(NH$_2$), an amino acid, an acyl group, and a pharmaceutically acceptable salt thereof, wherein the salt contains an alkali metal ion, an alkaline metal ion, an ammonium or an alkyl substituted ammonium ion; and wherein X, n, $Z_1$, $Z_2$, $Z_3$, $Z_4$, Y, $R_1$, $R_2$ and PBG are as defined in claim 5.

7. The compound according to claim 5, said compound having the structure of Formula (VI):

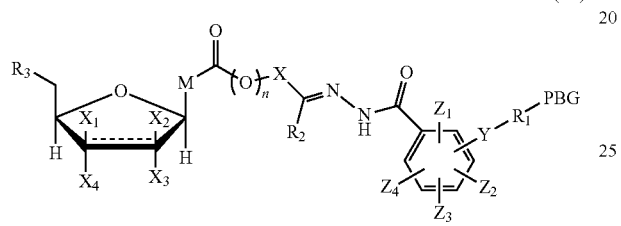

Formula (VI)

or a pharmaceutically acceptable salt, hydrate, solvate, or isomer thereof;

wherein

M is a pyrimidine or purine group that contains at least one primary or secondary amino group;

$X_1$ and $X_2$ are each independently selected from the group consisting of —H, —OH, $C_1$-$C_6$ alkyl, halogen, and —$N_3$;

$X_3$ and $X_4$ are each independently, as valence permits, absent or selected from the group consisting of —H, —OH, $C_1$-$C_6$ alkyl, halogen, and —$N_3$;

$R_3$ is selected from the group consisting of —H, —OH, —OP(O)(OH)$_2$, —OP(O)(OH)OP(O)(OH)$_2$, —OP(O)(OH)OP(O)(OH)OP(O)(OH)$_2$, —OP(O)(OH)(NH$_2$), an amino acid, an acyl group, and a pharmaceutically acceptable salt thereof, wherein the salt contains an alkali metal ion, an alkaline metal ion, an ammonium or an alkyl substituted ammonium ion; and wherein X, n, $Z_1$, $Z_2$, $Z_3$, $Z_4$, Y, $R_1$, $R_2$ and PBG are as defined in claim 5.

8. The compound according to claim 6, said compound having the structure of Formula (VII):

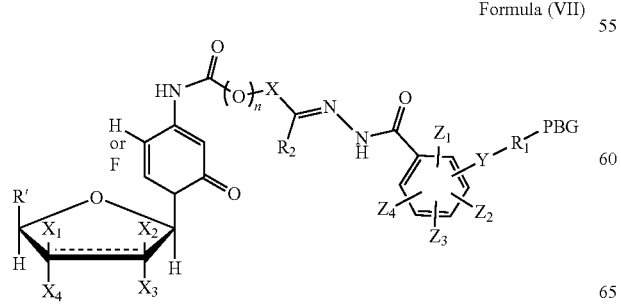

Formula (VII)

or a pharmaceutically acceptable salt, hydrate, solvate, or isomer thereof;

wherein R' is —$R_3$ or —$CH_2R_3$; and X, $X_1$, $X_2$, $X_3$, $X_4$, n, Y, $R_1$, $R_2$, $R_3$, $Z_1$, $Z_2$, $Z_3$, $Z_4$ and PBG are as defined in claim 6.

9. The compound according to claim 7, said compound having the structure of Formula (VII):

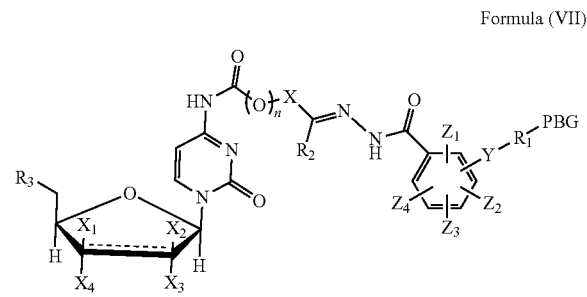

Formula (VII)

or a pharmaceutically acceptable salt, hydrate, solvate, or isomer thereof;

wherein X, $X_1$, $X_2$, $X_3$, $X_4$, n, Y, $R_1$, $R_2$, $R_3$, $Z_1$, $Z_2$, $Z_3$, $Z_4$ and PBG are as defined in claim 7.

10. The compound of claim 5, said compound having the structure of formula (VIII):

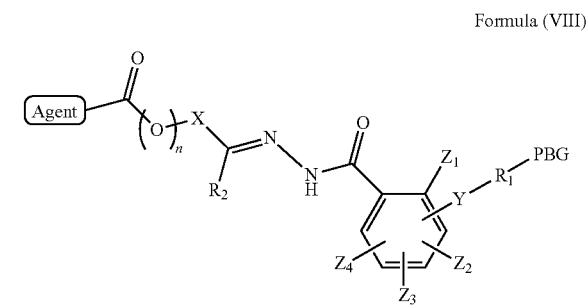

Formula (VIII)

or pharmaceutically acceptable salt, hydrate, solvate, or isomer thereof;

wherein Agent, X, n, $R_2$, PBG, Y, $R_1$, $Z_1$, $Z_2$, $Z_3$ and $Z_4$ are as defined in claim 5, and wherein $Z_1$ is an electron withdrawing group.

11. The compound according to claim 10, said compound having the structure of Formula (IX):

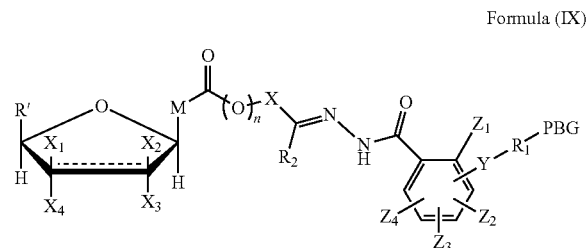

Formula (IX)

or a pharmaceutically acceptable salt, hydrate, solvate, or isomer thereof;

wherein:
M is a pyrimidine or purine group that contains at least one primary or secondary amino group and optionally contains one or more substituents selected from halogen;

$X_1$ and $X_2$ are each independently selected from the group consisting of —H, —OH, $C_1$-$C_6$ alkyl, halogen, and —$N_3$;

$X_3$ and $X_4$ are each independently, as valence permits, absent or selected from the group consisting of —H, —OH, $C_1$-$C_6$ alkyl, halogen, and —$N_3$;

R' is —$R_3$ or —$CH_2R_3$;

wherein each occurrence of $R_3$ is independently selected from the group consisting of —OH, —$CH_3$, —OP(O)(OH)$_2$, —P(O)(OH)OP(O)(OH)$_2$, —OP(O)(OH)OP(O)(OH)OP(O)(OH)$_2$, —OP(O)(OH)(NH$_2$), an amino acid, an acyl group, and a pharmaceutically acceptable salt thereof; wherein the salt contains an alkali metal ion, an alkaline metal ion, an ammonium or an alkyl substituted ammonium ion; and wherein X, n, Y, $Z_1$, $Z_2$, $Z_3$, $Z_4$, $R_1$, $R_2$ and PBG are as defined in claim 10.

12. The compound according to claim 10, said compound having the structure of Formula (IX):

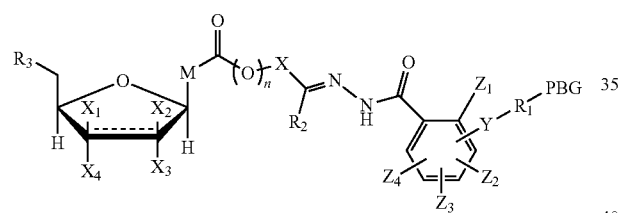

Formula (IX)

or a pharmaceutically acceptable salt, hydrate, solvate, or isomer thereof;

wherein

M is a pyrimidine or purine group that contains at least one primary or secondary amino group;

$X_1$ and $X_2$ are each independently selected from the group consisting of —H, —OH, $C_1$-$C_6$ alkyl, halogen, and —$N_3$;

$X_3$ and $X_4$ are each independently, as valence permits, absent or selected from the group consisting of —H, —OH, $C_1$-$C_6$ alkyl, halogen, and —$N_3$;

$R_3$ is selected from the group consisting of —H, —OH, —OP(O)(OH)$_2$, —OP(O)(OH)OP(O)(OH)$_2$, —OP(O)(OH)OP(O)(OH)OP(O)(OH)$_2$, —OP(O)(OH)(NH$_2$), an amino acid or an acyl group, and a pharmaceutically acceptable salt thereof, wherein the salt contains an alkali metal ion, an alkaline metal ion, an ammonium or an alkyl substituted ammonium ion; and wherein X, n, Y, $Z_1$, $Z_2$, $Z_3$, $Z_4$, $R_1$, $R_2$ and PBG are as defined in claim 10.

13. The compound according to claim 11, said compound having the structure of Formula (X):

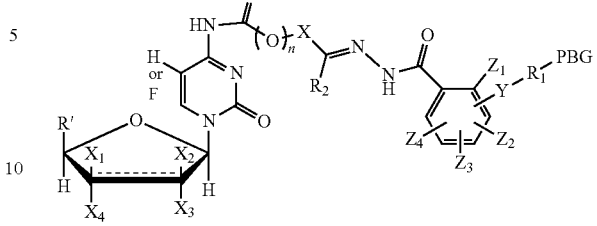

Formula (X)

or a pharmaceutically acceptable salt, hydrate, solvate, or isomer thereof;

wherein R' is —$R_3$ or —$CH_2R_3$; and $X_1$, $X_2$, $X_3$, $X_4$, $R_3$, X, n, Y, $Z_1$, $Z_2$, $Z_3$, $Z_4$, $R_1$ and $R_2$ are as defined in claim 11.

14. The compound according to claim 12, said compound having the structure of Formula (X):

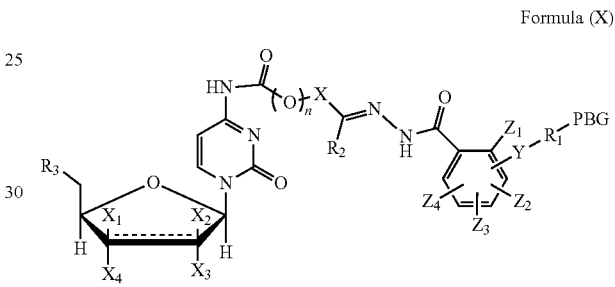

Formula (X)

or a pharmaceutically acceptable salt, hydrate, solvate, or isomer thereof; and wherein $X_1$, $X_2$, $X_3$, $X_4$, $R_3$, X, n, Y, $Z_1$, $Z_2$, $Z_3$, $Z_4$, $R_1$ and $R_2$ are as defined in claim 12.

15. The compound according to claim 1, wherein Agent is selected from the group consisting of N-nitrosoureas; doxorubicin, 2-pyrrolpyrrolinoanthracycline, morpholinoanthracycline, diacetatoxyalkylanthracycline, daunorubicin, epirubicin, idarubicin, nemorubicin, PNU-159682, mitoxantrone; ametantrone; chlorambucil, bendamustine, melphalan, oxazaphosphorines; 5-fluorouracil, 5'-deoxy-5-fluorocytidine, 2'-deoxy-5-fluoridine, cytarabine, cladribine, fludarabine, pentostatine, gemcitabine, 4-amino-1-(((2S,3R,4S,5R)-3,4-dihydroxy-5-methyltetrahydrofuran-2-yl)methyl)-5-fluoropyrimidin-2(1H)-one, thioguanine; methotrexate, raltitrexed, pemetrexed, plevitrexed; paclitaxel, docetaxel; topotecan, irinotecan, SN-38, 10-hydroxycamptothecin, GG211, lurtotecan, 9-aminocamptothecin, camptothecin, 7-formylcamptothecin, 7-acetylcamptothecin, 9-formylcamptothecin, 9-acetylcamptothecin, 9-formyl-10-hydroxycamptothecin, 10-formylcamptothecin, 10-acetylcamptothecin, 7-butyl-10-aminocamptothecin, 7-butyl-9-amino-10, 11-methylenedioxocamptothecin; vinblastine, vincristine, vindesine, vinorelbine; calicheamicins; maytansine, maytansinol; an auristatin selected from the group consisting of auristatin D, auristatin E, auristatin F, monomethyl auristatin D, monomethyl auristatin E, monomethyl auristatin F, monomethyl auristatin F nethylester, auristatin PYE, auristatin PHE, the related natural product dolastatin 10, and derivatives thereof; an amatoxin selected from the group consisting of α-amanitin, β-amanitin, γ-amanitin, F-amanitin, amanin, amaninamide, ainanullin, and amanullinic acid and derivatives thereof; duocarmycin A, duocarmycin B1, duocarmycin B2, duocarmycin C, duocarmycin SA, CC1065, adozelesin, bizelesin, carzelesin; eribulin; trabectedin; pyrrolobenzodiazepine, anthramycin, tomaymycin, sibiromycin, DC-81, DSB-120; epothilones; bleomycin; dactinomycin; plicamycin, mitomycin C and cis-configured platinum(II) complexes; or a derivative of any of the foregoing.

16. The compound according to claim 1, wherein:
(a) $Z_1$, $Z_2$, $Z_3$ and $Z_4$ are each independently selected from the group consisting of —H, halogen, —C(O)OH, —C(O)O—$C_1$-$C_6$ alkyl, —$NO_2$, haloalkyl, —S(O)$_2$—$C_1$-$C_6$ alkyl, and —CN, wherein at least one of $Z_1$, $Z_2$, $Z_3$ and $Z_4$ is not —H;
(b) $Z_1$, $Z_2$, $Z_3$ and $Z_4$ are each independently selected from the group consisting of —H, —Cl, —Br, —I, —F, —C(O)OH, —$NO_2$, —$CF_3$, and —CN;
(c) $Z_1$, $Z_2$, $Z_3$ and $Z_4$ are each independently selected from the group consisting of —H, —Cl, —F, —$NO_2$, and —$CF_3$;
(d) $Z_1$, $Z_2$, $Z_3$ and $Z_4$ are each independently selected from the group consisting of —OP(O)(OH)$_2$, —P(O)(OH)OP(O)(OH)$_2$, —OP(O)(OH)OP(O)(OH)OP(O)(OH)$_2$, —OP(O)(OH)(NH$_2$), —P(O)(OH)$_2$, —SO$_3$H, and a pharmaceutically acceptable salt thereof;
(e) $Z_1$ is selected from the group consisting of halogen, —C(O)OH, —C(O)O—$C_1$-$C_6$ alkyl, —$NO_2$, haloalkyl, —S(O)$_2$—$C_1$-$C_6$ alkyl, and —CN; and $Z_2$, $Z_3$ and $Z_4$ are each independently selected from —H, halogen, —C(O)OH, —C(O)O—$C_1$-$C_6$ alkyl, —$NO_2$, haloalkyl, —S(O)$_2$—$C_1$-$C_6$ alkyl, and —CN;
(f) $Z_1$ is selected from the group consisting of —Cl, —Br, —I, —F, —C(O)OH, —$NO_2$, —$CF_3$, and —CN; and $Z_2$, $Z_3$ and $Z_4$ are each independently selected from the group consisting of —H, —Cl, —Br, —I, —F, —C(O)OH, —$NO_2$, —$CF_3$, and —CN; or
(g) $Z_1$ is selected from the group consisting of —Cl, —F, and —$NO_2$; and $Z_2$, $Z_3$ and $Z_4$ are each independently selected from the group consisting of —H, —Cl, —F, —$NO_2$, and —$CF_3$.

17. A compound having a structure according to Formula (I):

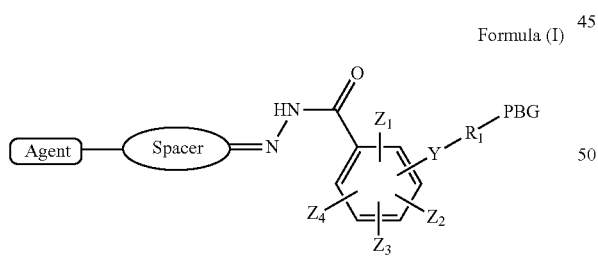

Formula (I)

or a pharmaceutically acceptable salt, hydrate, solvate, or isomer thereof;
wherein:
Agent is selected from the group consisting of a cytostatic agent, a cytotoxic agent, a cytokine, an immunosuppressive agent, an antirheumatic, an antiphlogistic, an antibiotic, an analgesic, a virostatic agent, an anti-inflammatory agent, an antimicotic agent, a transcription factor inhibitor, a cell cycle modulator, an MDR modulator, a proteasome or protease inhibitor, an apoptosis modulator, an enzyme inhibitor, a signal transduction inhibitor, a protease inhibitor, an angiogenesis inhibitor, a hormone or hormone derivative, an antibody or a fragment thereof, a therapeutically or diagnostically active peptide, a radioactive substance, a light emitting substance, a light absorbing substance, and a derivative of any of the foregoing;

Spacer is absent, or is selected from the group consisting of

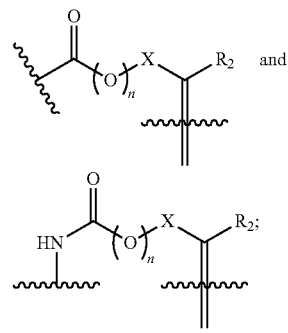

and n is 0 or 1;
X is selected from the group consisting of optionally substituted $C_1$-$C_{18}$ alkyl wherein optionally up to six carbon atoms in said $C_1$-$C_{18}$ alkyl are each independently replaced with —OCH$_2$CH$_2$—; optionally substituted $C_1$-$C_{18}$ alkyl-NH—C(O)—$R_5$— wherein optionally up to six carbon atoms in said $C_1$-$C_{18}$ alkyl are each independently replaced with —OCH$_2$CH$_2$—; optionally substituted $C_1$-$C_{18}$ alkyl-C(O)—NH—$R_5$— wherein optionally up to six carbon atoms in said $C_1$-$C_{18}$ alkyl are each independently replaced with —OCH$_2$CH$_2$—; optionally substituted aryl; optionally substituted heteroaryl; and optionally substituted cycloalkyl;
$R_5$ is selected from the group consisting of an optionally substituted aryl, optionally substituted heteroaryl, and optionally substituted cycloalkyl;

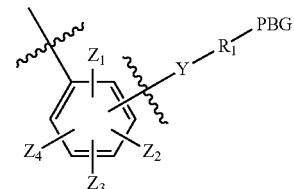

is:
(a) selected from the group consisting of:

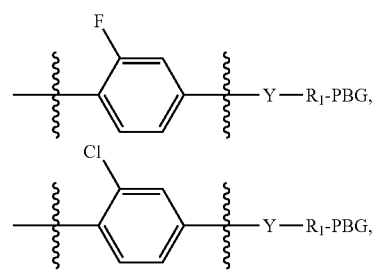

-continued
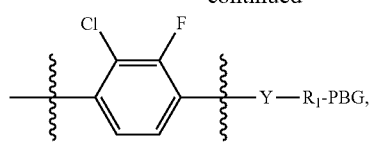
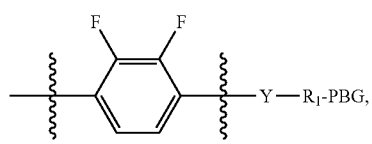
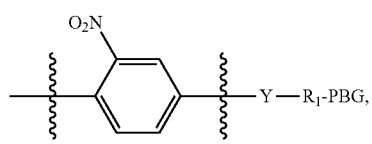
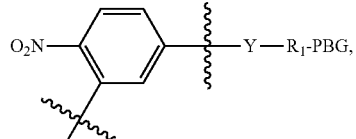
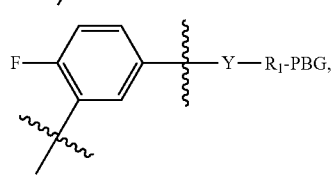
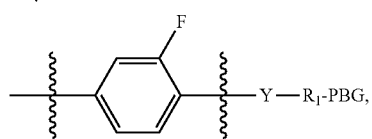
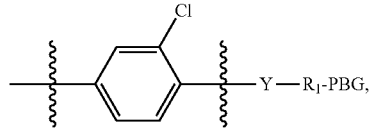
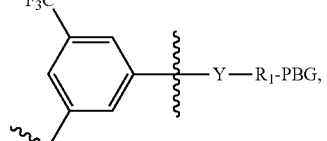
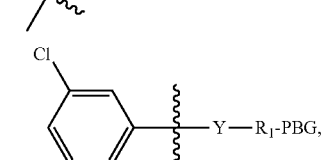
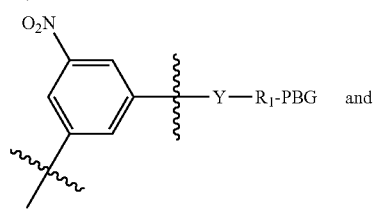 and
-continued
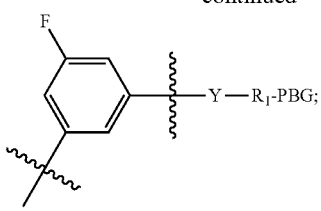
(b) selected from the group consisting of:
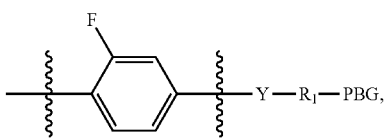
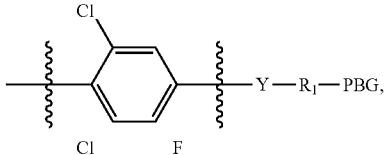
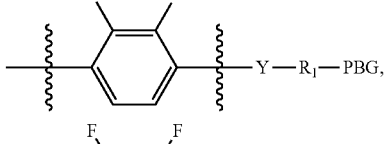
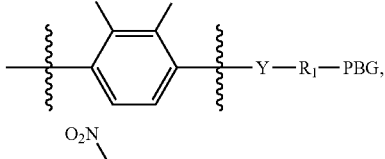
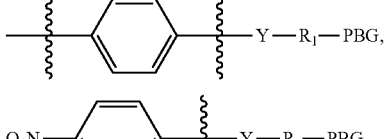
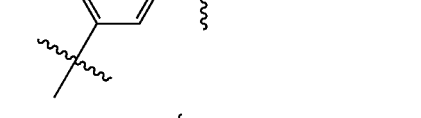 and
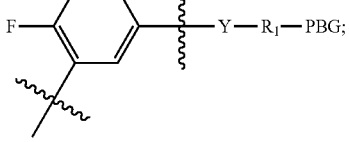
or
(c) selected from the group consisting of:
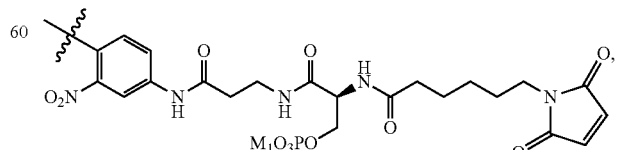
$M_1 = Mg^{2+}, 2Na^+, 2K^+, 2H^+, 2NH_4^+, Na^+, K^+, NH_4^+$ and/or $H^+$ 145
-continued

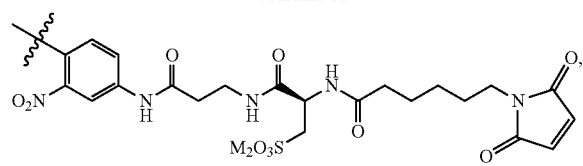

$M_2 = Na^+, K^+, H^+, NH_4^+$

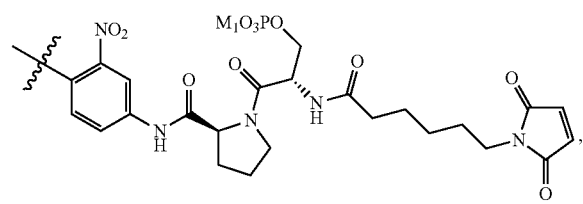

$M_1 = Mg^{2+}, 2Na^+, 2K^+, 2H^+, 2NH_4^+, Na^+, K^+, NH_4^+$ and/or $H^+$

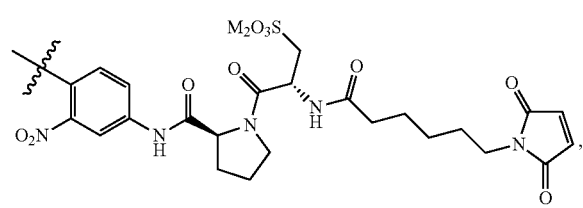

$M_2 = Na^+, K^+, H^+, NH_4^+$

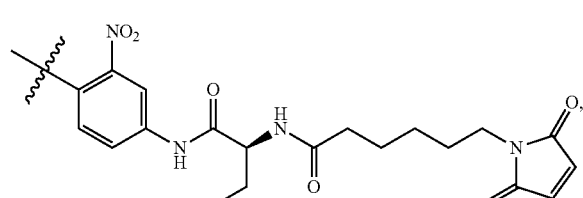

$M_1 = Mg^{2+}, 2Na^+, 2K^+, 2H^+, 2NH_4^+, Na^+, K^+, NH_4^+$ and/or $H^+$

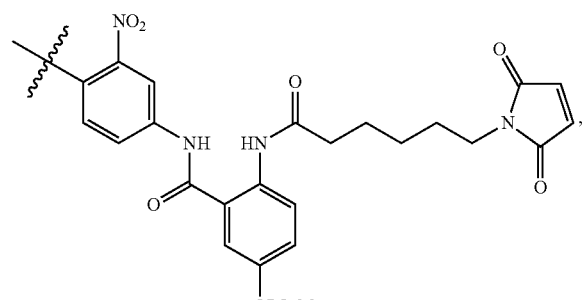

$M_1 = Mg^{2+}, 2Na^+, 2K^+, 2H^+, 2NH_4^+, Na^+, K^+, NH_4^+$ and/or $H^+$

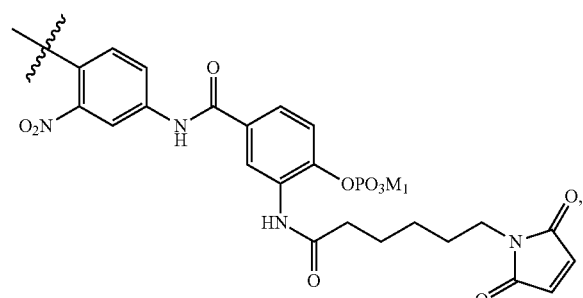

$M_1 = Mg^{2+}, 2Na^+, 2K^+, 2H^+, 2NH_4^+, Na^+, K^+, NH_4^+$ and/or $H^+$

146
-continued

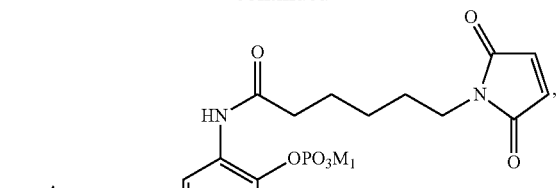

$M_1 = Mg^{2+}, 2Na^+, 2K^+, 2H^+, 2NH_4^+, Na^+, K^+, NH_4^+$ and/or $H^+$

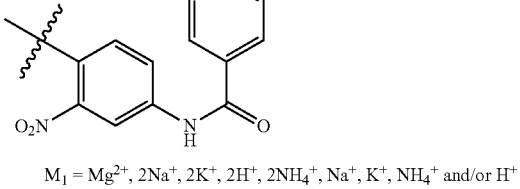

$M_1 = Mg^{2+}, 2Na^+, 2K^+, 2H^+, 2NH_4^+, Na^+, K^+, NH_4^+$ and/or $H^+$

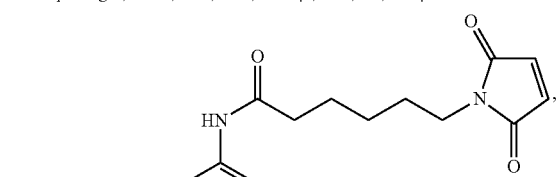

; and $M_2 = Na^+, K^+, H^+$ and/or $NH_4^+$

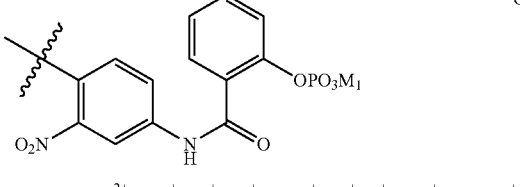

;

$M_2 = Na^+, K^+, H^+$ and/or $NH_4^+$ wherein Y is absent or selected from the group consisting of optionally substituted $C_1$-$C_6$ alkyl, —NH—C(O)—, —C(O)—NH—, —C(O)—O—, and —O—C(O)—;

$R_1$ is absent or selected from the group consisting of optionally substituted $C_1$-$C_{18}$ alkyl wherein optionally up to six carbon atoms in said $C_1$-$C_{18}$ alkyl are each independently replaced with —OCH$_2$CH$_2$—; optionally substituted $C_1$-$C_{18}$ alkyl-NH—C(O)R$_5$— wherein optionally up to six carbon atoms in said $C_1$-$C_{18}$ alkyl are each independently replaced with —OCH$_2$CH$_2$—; and optionally substituted $C_1$-$C_{18}$ alkyl-C(O)—NH—

R₅— wherein optionally up to six carbon atoms in said $C_1$-$C_{18}$ alkyl are each independently replaced with —OCH₂CH₂—,
or R₁ is a naturally or non-naturally occurring amino acid, or R₁ has the following formula:

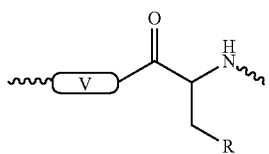

wherein:

[V] is absent, or is selected from the group consisting of:

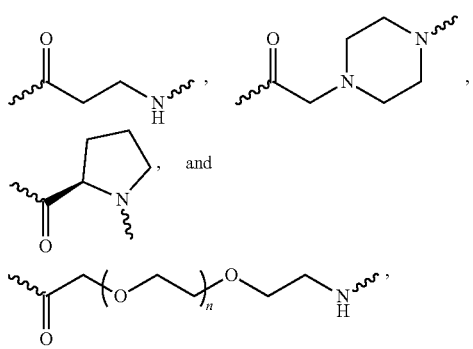

R is: ⌇⌇⌇OPO₃M₁ wherein $M_1$=Mg²⁺, 2Na⁺, 2K⁺ and/or 2NH₄⁺, or
⌇⌇⌇OSO₃M₂ wherein $M_2$=Na⁺, K⁺, H⁺, and/or NH₄⁺; and
PBG is

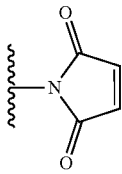

which may be optionally substituted.

18. The compound according to claim 1, wherein Y is:
(a) —C(O)—NH—;
(b) —C(O)—O—; or
(c) absent.

19. The compound according to claim 1, wherein R₁ is:
(a) selected from the group consisting of optionally substituted $C_1$-$C_{18}$ alkyl wherein optionally up to six carbon atoms in said $C_1$-$C_{18}$ alkyl are each independently replaced with —OCH₂CH₂—; optionally substituted $C_1$-$C_{18}$ alkyl-NH—C(O)—R₅— wherein optionally up to six carbon atoms in said $C_1$-$C_{18}$ alkyl are each independently replaced with —OCH₂CH₂—; and optionally substituted $C_1$-$C_{18}$ alkyl-C(O)—NH—R₅— wherein optionally up to six carbon atoms in said $C_1$-$C_{18}$ alkyl are each independently replaced with —OCH₂CH₂—;

(b)

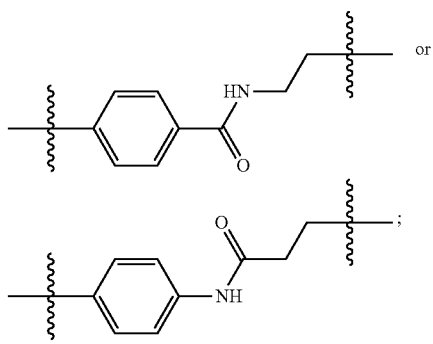

(c) absent;
(d) a naturally or non-naturally occurring amino acid; or
(e)

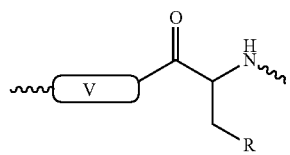

wherein:

[V] is absent, or is selected from the group consisting of:

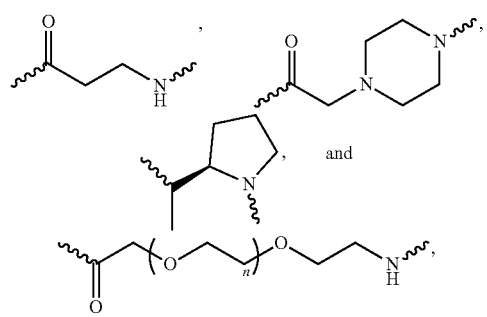

R is: ⌇⌇⌇OPO₃M₁ wherein $M_1$=Mg²⁺, 2Na⁺, 2K⁺ and/or 2NH₄⁺, or
⌇⌇⌇OSO₃M₂ wherein $M_2$=Na⁺, K⁺, H⁺, and/or NH₄⁺.

20. The compound according to claim 1, wherein Spacer is:
(a)

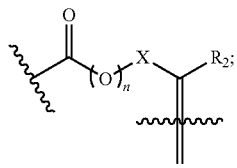

n is 0 or 1;
X is a selected from the group consisting of optionally substituted $C_1$-$C_{18}$ alkyl wherein optionally up to six carbon atoms in said $C_1$-$C_{18}$ alkyl are each independently replaced with —OCH$_2$CH$_2$—; optionally substituted aryl, optionally substituted heteroaryl, and optionally substituted cycloalkyl; and R$_2$ is as defined in claim 1;

(b)

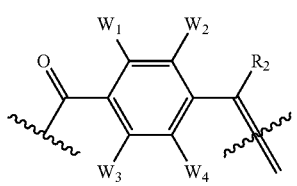

wherein R$_2$ is selected from the group consisting of —H, optionally substituted $C_1$-$C_{12}$ alkyl, optionally substituted aryl, and optionally substituted heteroaryl; and W$_1$, W$_2$, W$_3$ and W$_4$ are each independently selected from the group consisting of —H, halogen, —C(O)OH, —C(O)O—$C_1$-$C_6$ alkyl, —NO$_2$, haloalkyl, —S(O)$_2$—$C_1$-$C_6$ alkyl, and —CN;

(c)

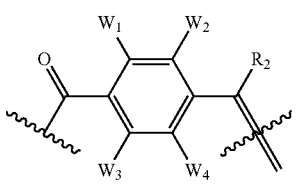

wherein R$_2$ is selected from the group consisting of —H, optionally substituted $C_1$-$C_{12}$ alkyl, optionally substituted aryl, and optionally substituted heteroaryl; and W$_1$, W$_2$, W$_3$ and W$_4$ are each independently selected from a phenoxy group, a primary, secondary or tertiary amine group, an ether group, a phenol group, an amide group, an ester group, an alkyl group, a substituted alkyl group, a phenyl group, and a vinyl group;

(d)

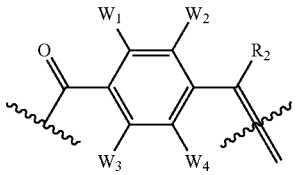

wherein R$_2$ is selected from the group consisting of —H, optionally substituted $C_1$-$C_{12}$ alkyl, optionally substituted aryl, and optionally substituted heteroaryl; and W$_1$, W$_2$, W$_3$ and W$_4$ are each independently selected from —OP(O)(OH)$_2$, —P(O)(OH)OP(O)(OH)$_2$, —OP(O)(OH)OP(O)(OH)OP(O)(OH)$_2$, —OP(O)(OH)(NH$_2$), —P(O)(OH)$_2$, —SO$_3$H, and a pharmaceutically acceptable salt thereof;

(e)

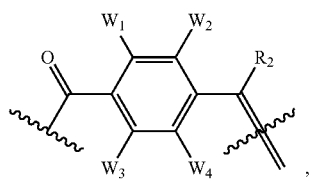

wherein R$_2$ is selected from the group consisting of —H, optionally substituted $C_1$-$C_{12}$ alkyl, optionally substituted aryl, and optionally substituted heteroaryl; W$_1$ is selected from the group consisting of halogen, —C(O)OH, —C(O)O—$C_1$-$C_6$ alkyl, —NO$_2$, haloalkyl, —S(O)$_2$—$C_1$-$C_6$ alkyl, and —CN; and W$_2$, W$_3$ and W$_4$ are each independently selected from the group consisting of —H, halogen, —C(O)OH, —C(O)O—$C_1$-$C_6$ alkyl, —NO$_2$, haloalkyl, —S(O)$_2$—$C_1$-$C_6$ alkyl, and —CN;

(f)

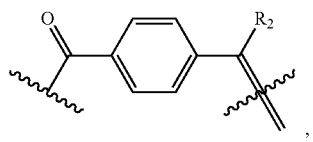

wherein R$_2$ is selected from the group consisting of —H, optionally substituted $C_1$-$C_{12}$ alkyl, optionally substituted aryl, and optionally substituted heteroaryl;

(g)

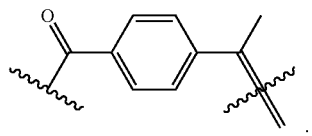 [SMILES: *C(=O)c1ccc(C(=*)C)cc1]

.

(h) is

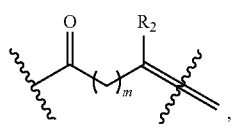

wherein m is 1, 2, 3, 4, 5, or 6; or (i)

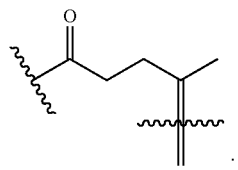 [SMILES: *C(=O)CCC(=*)C]

.

21. The compound according to claim 20, wherein W$_1$, W$_2$, W$_3$ and W$_4$ in subpart (b) are each independently selected from the group consisting of —H, —Cl, —Br, —I, —F, —C(O)OH, —NO$_2$, —CF$_3$, and —CN.

22. The compound according to claim 21, wherein $W_1$, $W_2$, $W_3$ and $W_4$ are each independently selected from the group consisting of —H, —Cl, —F, —NO$_2$, and —CF$_3$.

23. The compound according to claim 20, wherein $W_1$ in subpart (e) is selected from the group consisting of —Cl, —Br, —I, —F, —C(O)OH, —NO$_2$, —CF$_3$, and —CN; and $W_2$, $W_3$ and $W_4$ in subpart (e) are each independently selected from the group consisting of —H, —Cl, —Br, —I, —F, —C(O)OH, —NO$_2$, —CF$_3$, and —CN.

24. The compound according to claim 23, wherein $W_1$ is selected from the group consisting of —Cl, —F, and —NO$_2$; and $Z_2$, $Z_3$ and $Z_4$ are each independently selected from the group consisting of —H, —Cl, —F, —NO$_2$, and —CF$_3$.

25. The compound according to claim 6, wherein $X_1$, $X_2$, $X_3$, and $X_4$ are each independently selected from the group consisting of —H, —OH, —CH, —F, —Cl, —Br, —I, and —N$_3$.

26. A compound selected from the group consisting of:

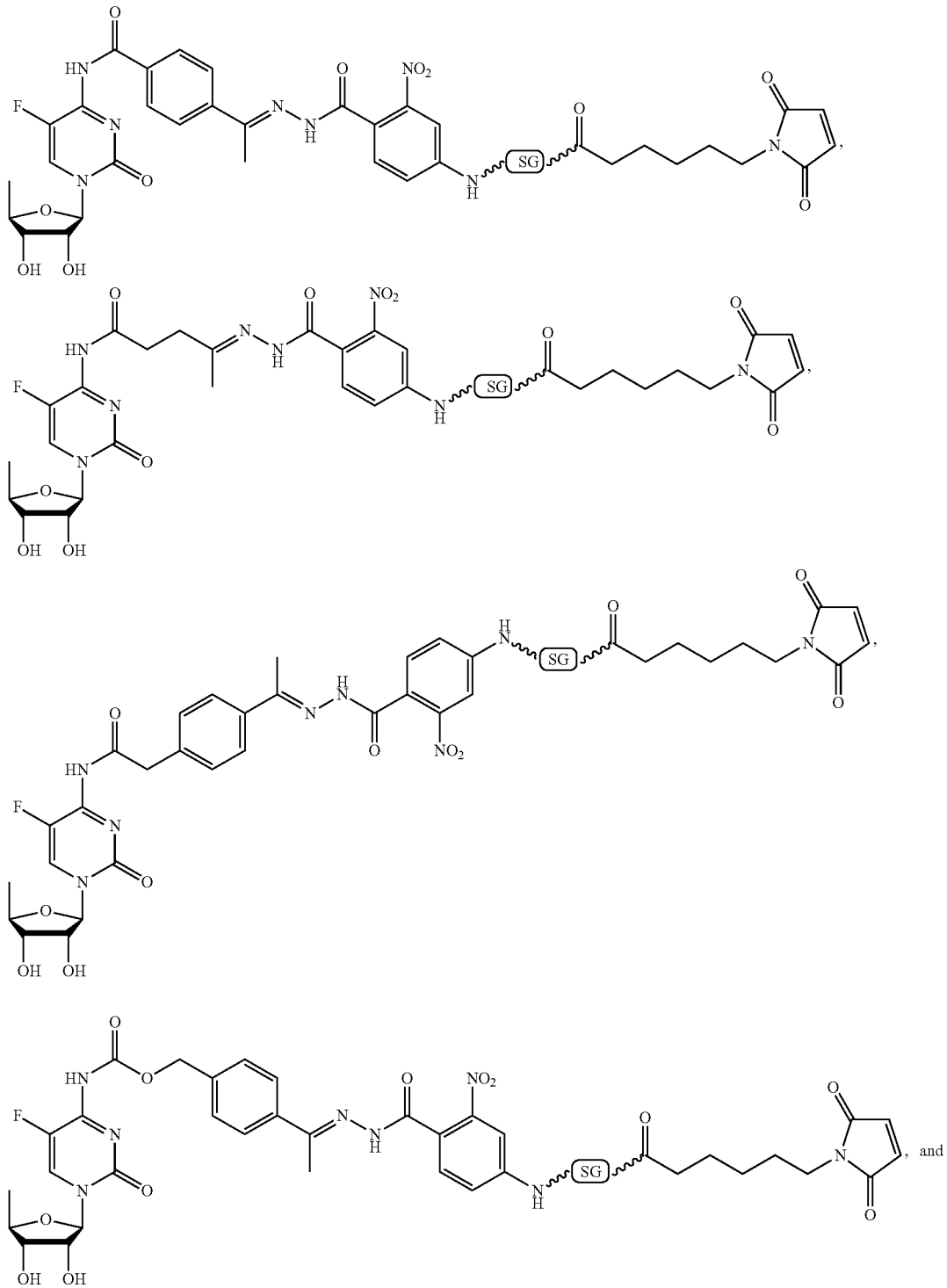

-continued

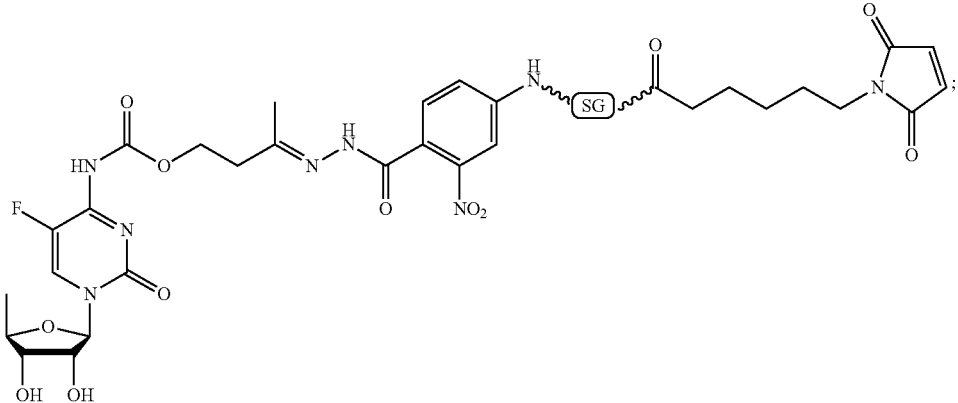

or a pharmaceutically acceptable salt, hydrate, solvate, or isomer thereof,
wherein:

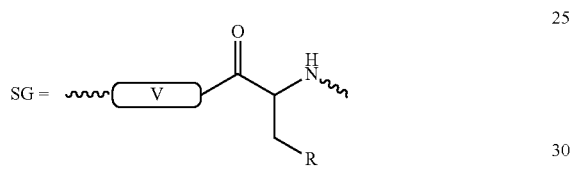

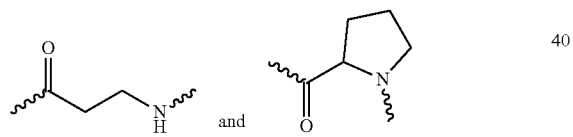 is absent, or is selected from the group consisting of:

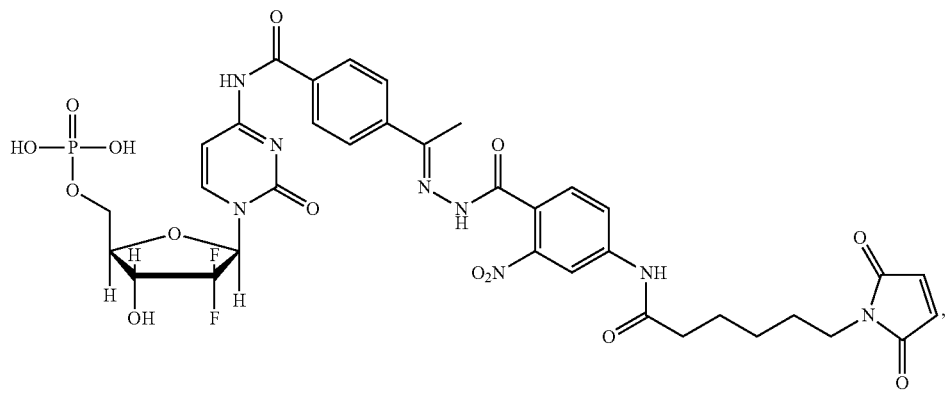

R is $\sim\!\!\sim\!\!\sim$ OPO$_3$M$_1$ wherein M$_1$=Mg$^{2+}$, 2Na$^+$, 2K$^+$, 2H$^+$, 2NH$_4^+$, Na$^+$, K$^+$, NH$_4^+$, and/or H$^+$ or
$\sim\!\!\sim\!\!\sim$ SO$_3$M$_2$ wherein M$_2$=Na$^+$, K$^+$, H$^+$, and/or NH$_4^+$.

27. A compound selected from the group consisting of:

-continued
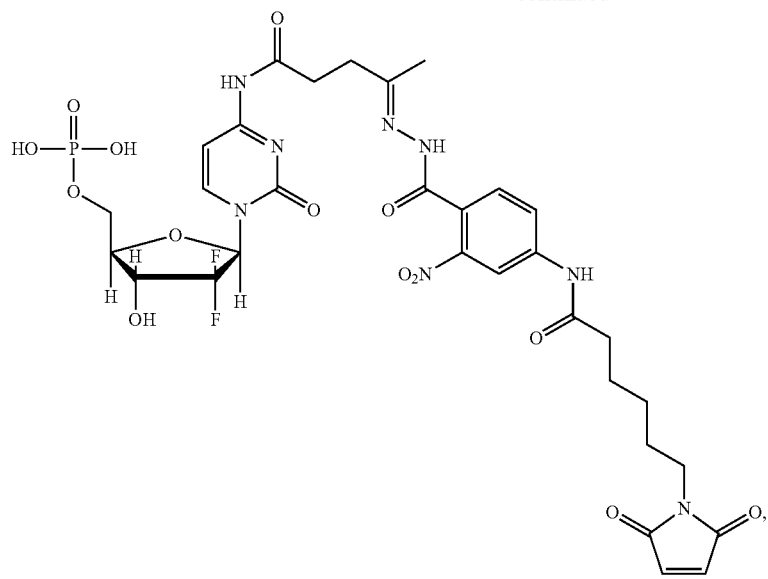
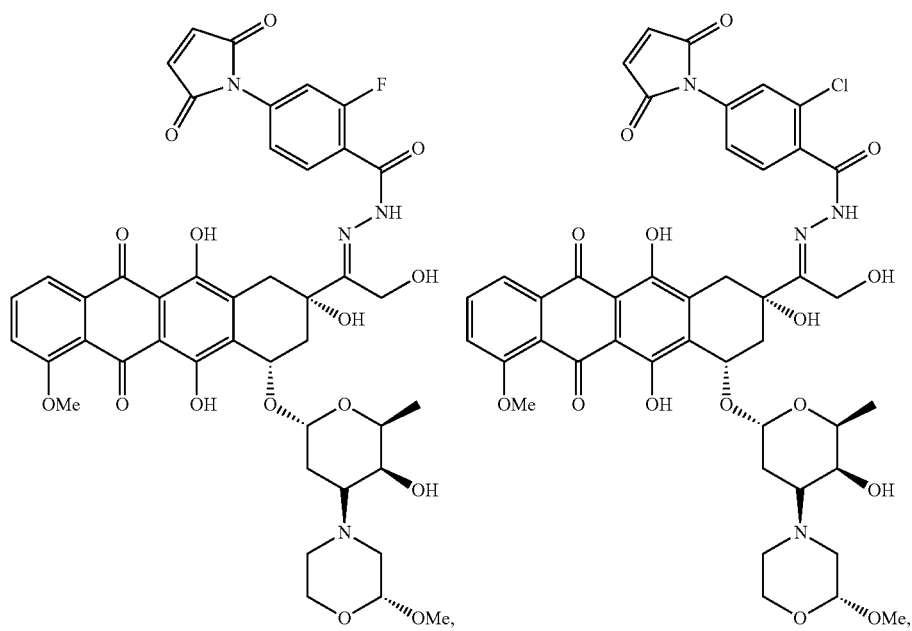

157
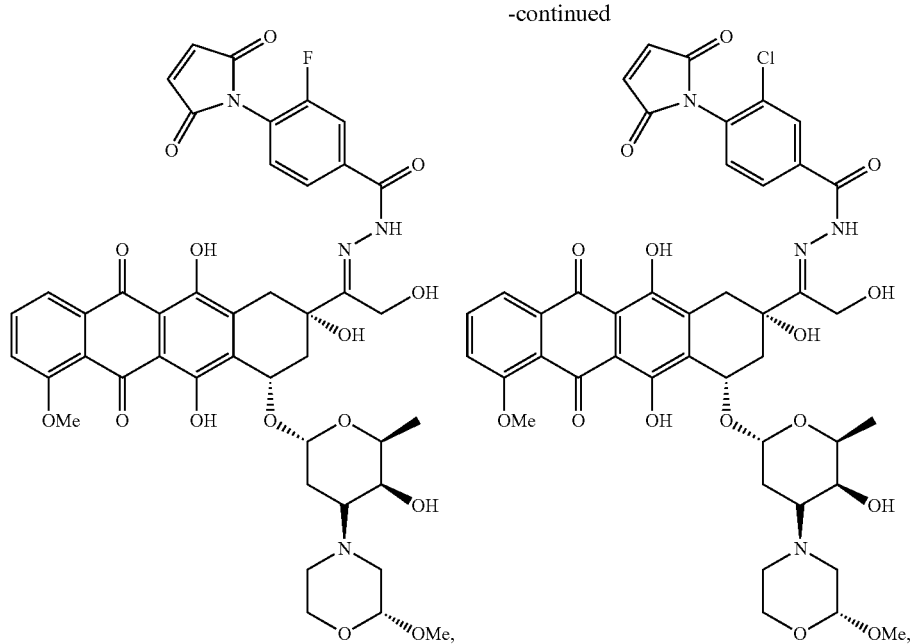
158
158
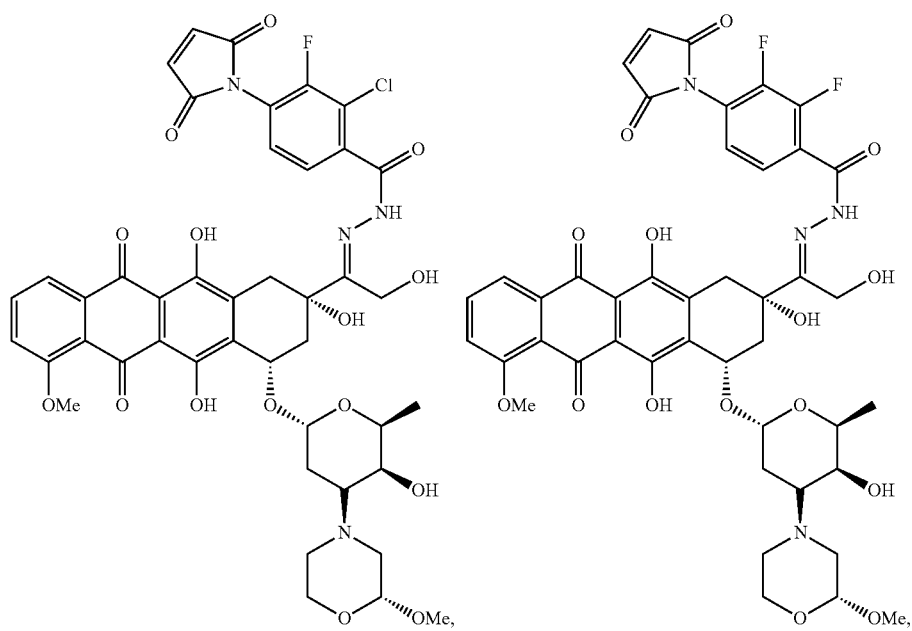

159 160
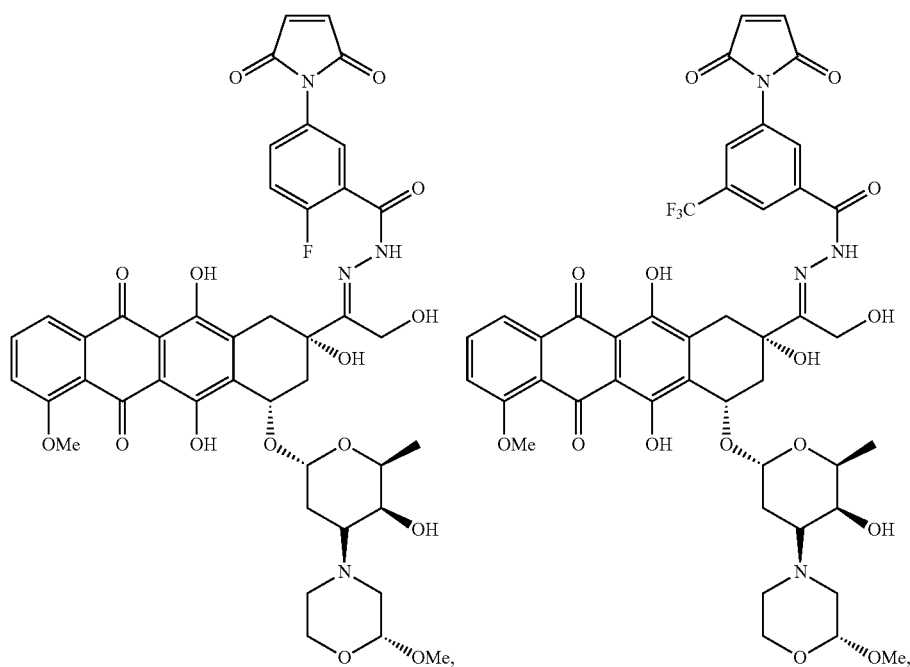
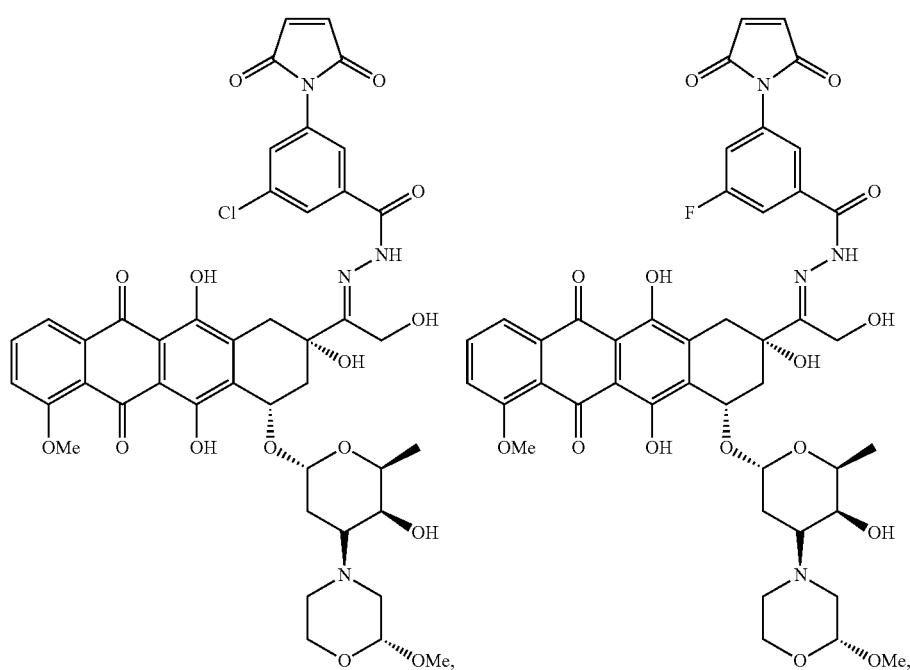

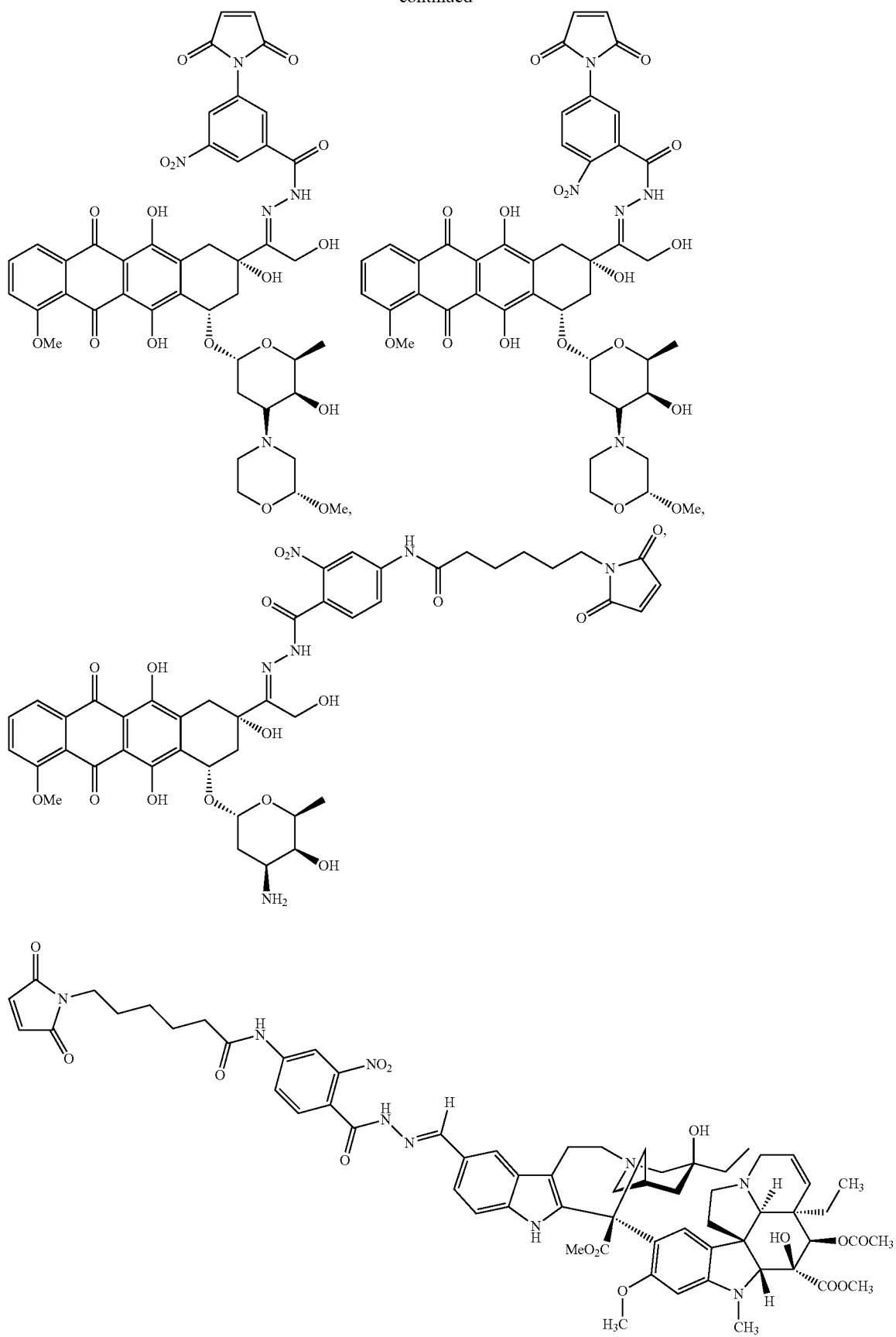

-continued
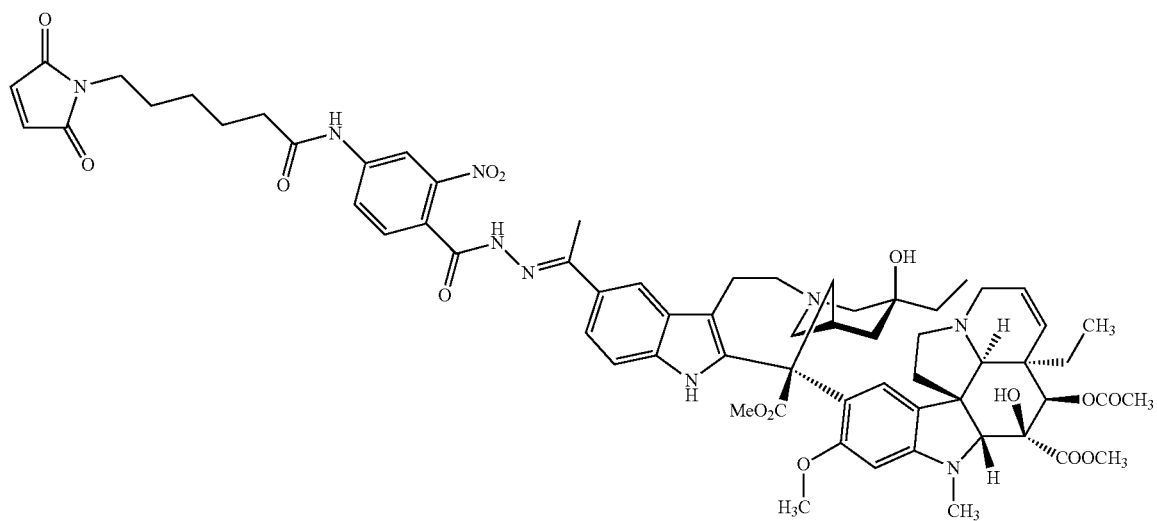
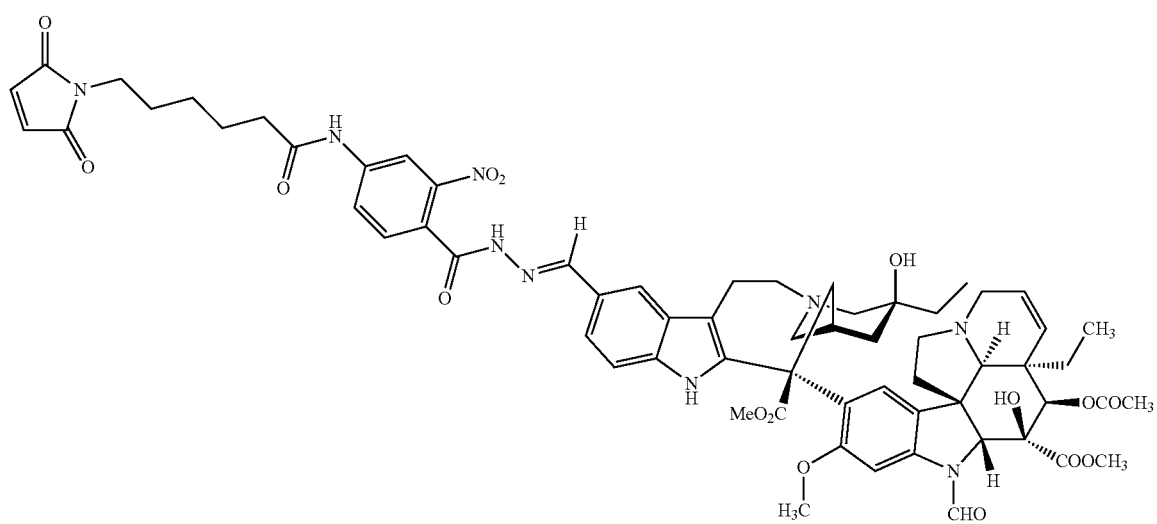
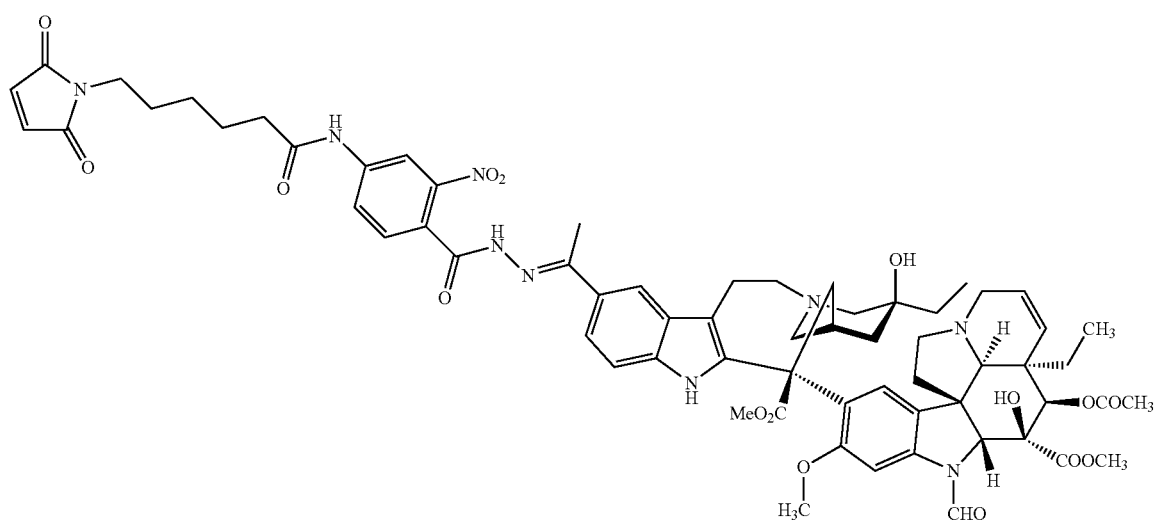

-continued
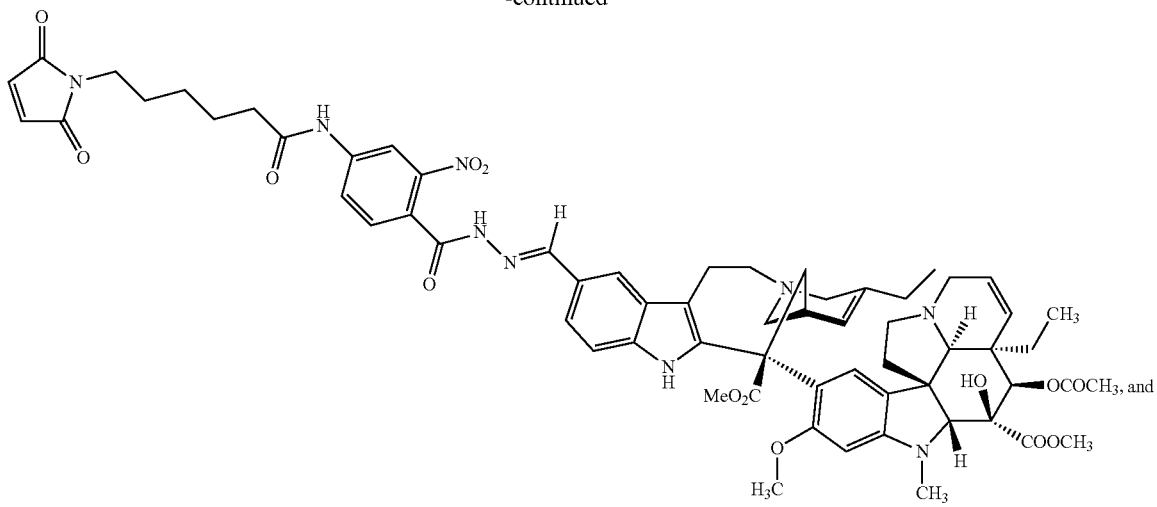
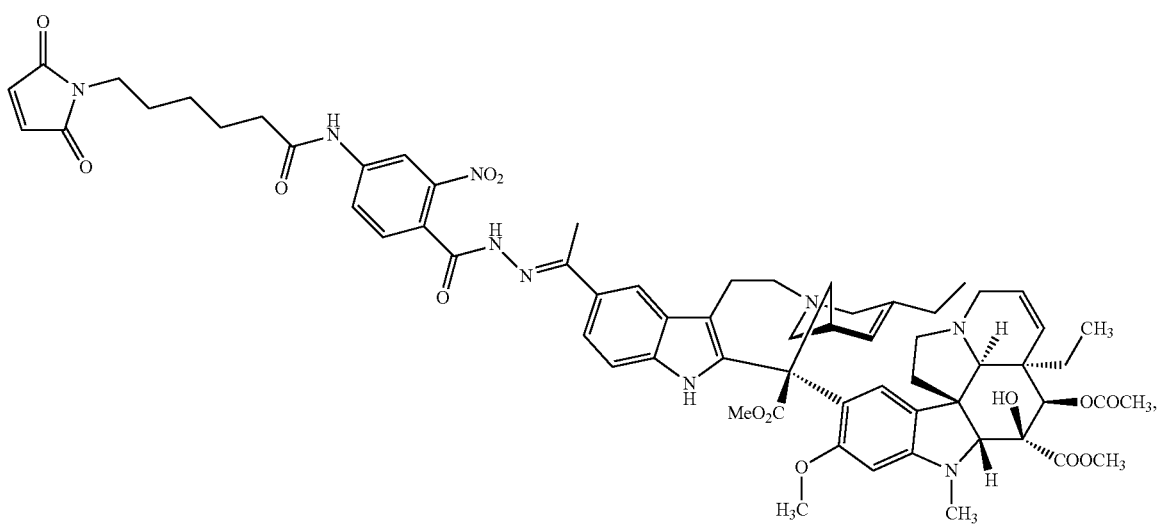
or a pharmaceutically acceptable salt, hydrate, solvate, or isomer thereof.
28. A compound selected from the group consisting of:
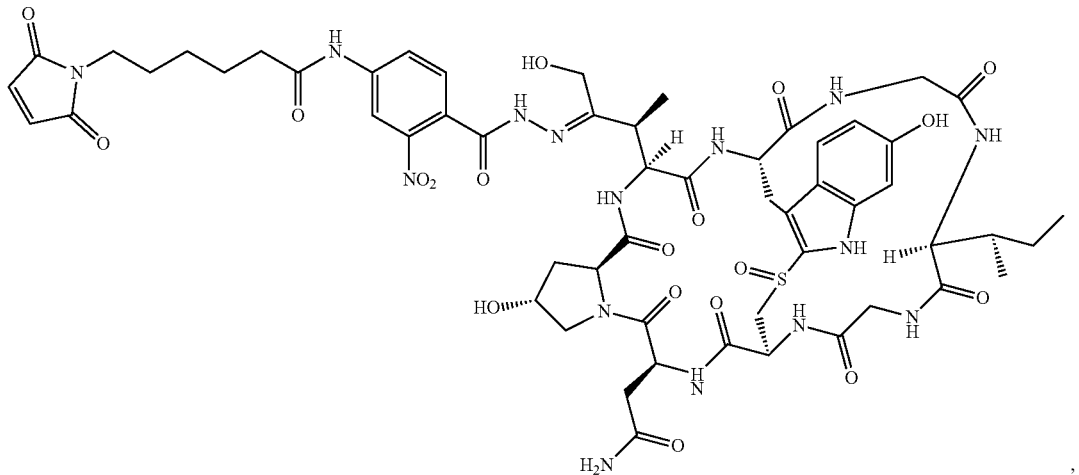

-continued
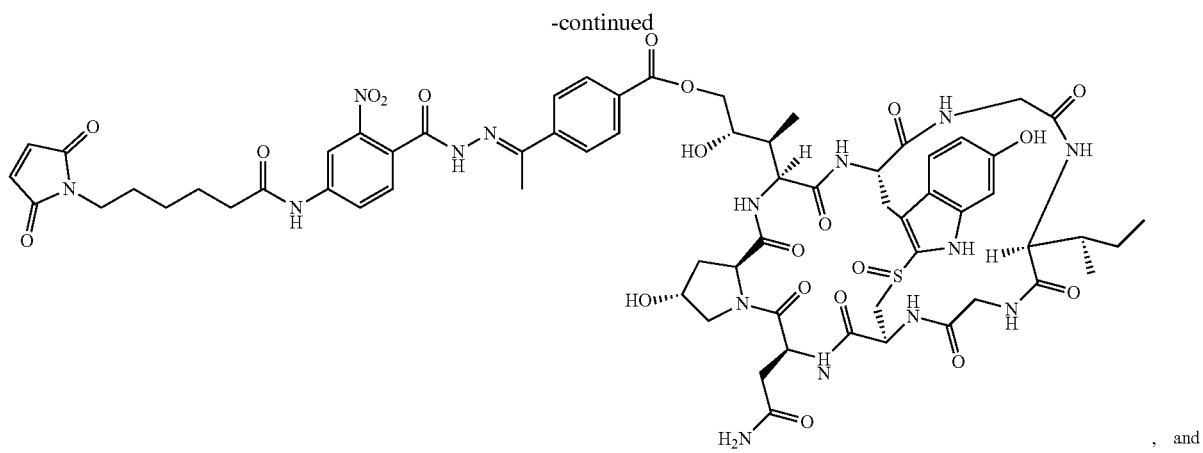
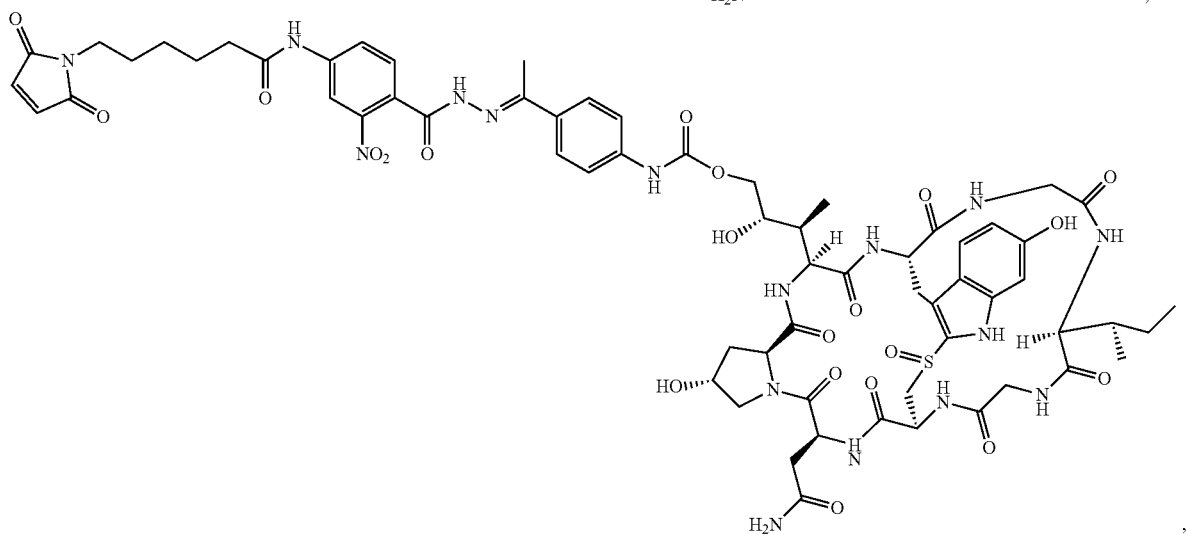
, and
or a pharmaceutically acceptable salt, hydrate, solvate, or isomer thereof.
29. A compound selected from the group consisting of:
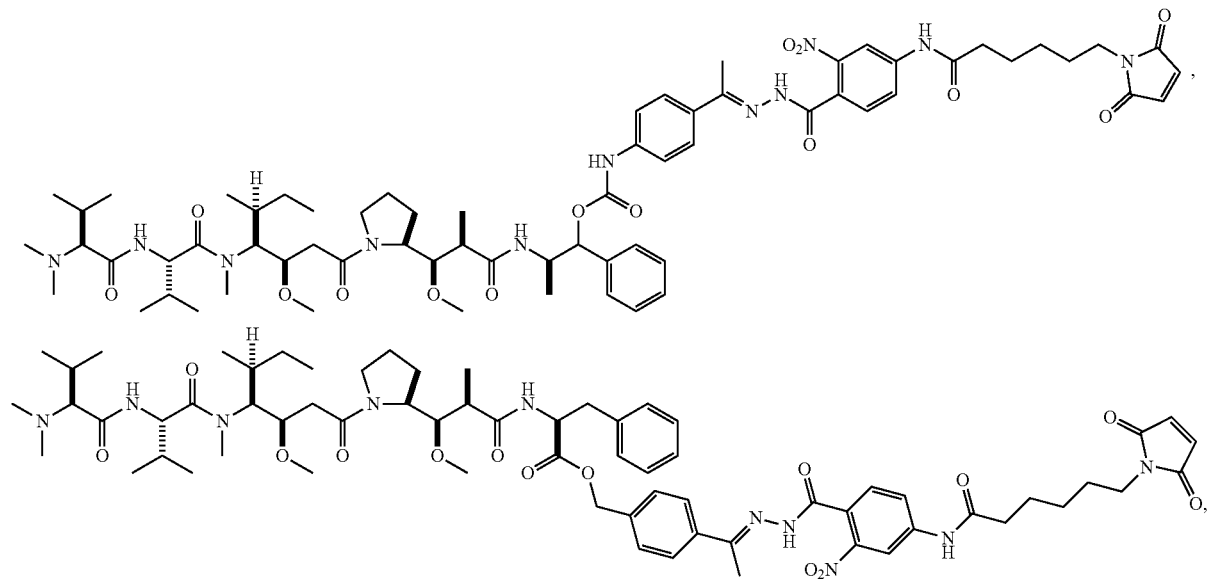

-continued

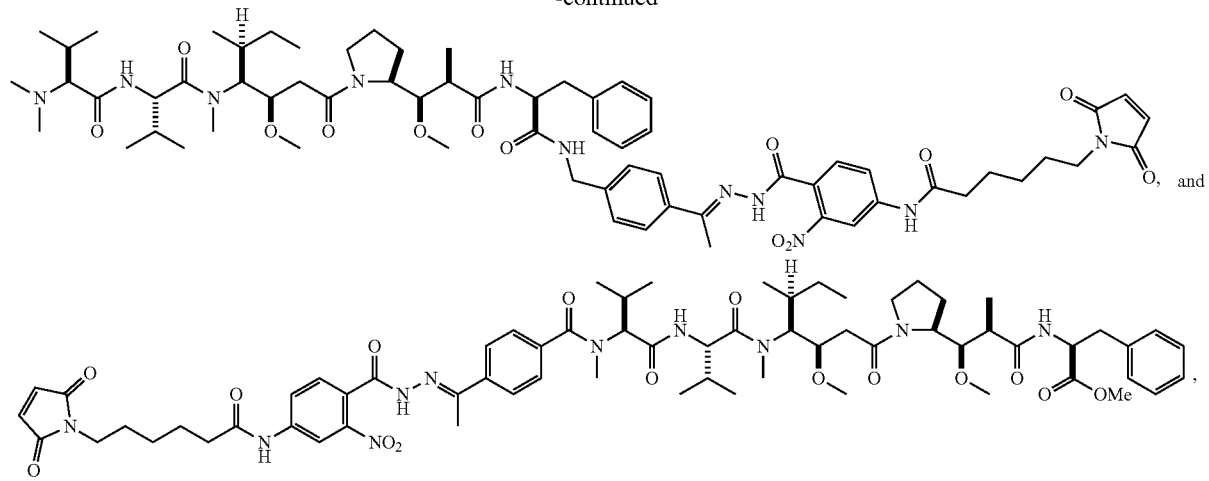

or a pharmaceutically acceptable salt, hydrate, solvate, or isomer thereof.

30. A pharmaceutical composition comprising a compound of claim 1, and a pharmaceutically acceptable carrier.

31. The compound according to claim 15, wherein Agent is selected from the group consisting of doxorubicin, 2-pyrrolpyrrolinoanthracycline, morpholinoanthracycline, diacetatoxyalkylanthracycline, daunorubicin, epirubicin, idarubicin, nemorubicin, PNU-159682, mitoxantrone or ametantrone, or a derivative of any of the foregoing.

32. The compound according to claim 15, wherein Agent is doxorubicin or a derivative thereof.

33. The compound according to claim 15, wherein Agent is selected from the group consisting of a maytansinoid, an auristatin, an epothilones, a bleomycin, dactinomycin, plicamycin, mitomycin C, a cis-configured platinum(II) complex, or a derivative of any of the foregoing.

34. A pharmaceutical composition comprising a compound according to claim 31, and a pharmaceutically acceptable carrier.

35. A pharmaceutical composition comprising a compound according to claim 32, and a pharmaceutically acceptable carrier.

36. A pharmaceutical composition comprising a compound according to claim 33, and a pharmaceutically acceptable carrier.

* * * * *

UNITED STATES PATENT AND TRADEMARK OFFICE
CERTIFICATE OF CORRECTION

| | | |
|---|---|---|
| PATENT NO. | : 11,384,104 B2 | Page 1 of 1 |
| APPLICATION NO. | : 15/735885 | |
| DATED | : July 12, 2022 | |
| INVENTOR(S) | : Felix Kratz et al. | |

It is certified that error appears in the above-identified patent and that said Letters Patent is hereby corrected as shown below:

In the Claims

In Claim 15, at Column 140, Line 63, delete "nethylester" and substitute therefor --methylester--.

In Claim 15, at Column 140, Lines 66-67, delete "F-amanitin" and substitute therefor --ε-amanitin--.

In Claim 15, at Column 140, Line 67, delete "ainanullin" and substitute therefor --amanullin--.

In Claim 25, at Column 152, Line 7, delete "-CH" and substitute therefor -- -CH$_3$--.

Signed and Sealed this
Eighth Day of November, 2022

Katherine Kelly Vidal
*Director of the United States Patent and Trademark Office*